US008053438B2

(12) United States Patent
Allen et al.

(10) Patent No.: US 8,053,438 B2
(45) Date of Patent: Nov. 8, 2011

(54) PYRAZINE COMPOUNDS AS PHOSPHODIESTERASE 10 INHIBITORS

(75) Inventors: Jennifer R. Allen, Newbury Park, CA (US); Matthew P. Bourbeau, Woodland Hills, CA (US); Ning Chen, Thousand Oaks, CA (US); Essa Hu, Camarillo, CA (US); Roxanne Kunz, Santa Monica, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/619,574

(22) Filed: Nov. 16, 2009

(65) Prior Publication Data

US 2010/0137278 A1    Jun. 3, 2010

Related U.S. Application Data

(60) Provisional application No. 61/114,567, filed on Nov. 14, 2008, provisional application No. 61/166,212, filed on Apr. 2, 2009.

(51) Int. Cl.
*A61K 31/4965* (2006.01)

(52) U.S. Cl. .................. 514/255.05; 544/408; 546/245; 548/309.4

(58) Field of Classification Search ............. 514/255.05; 544/408; 546/245; 548/309.4
See application file for complete search history.

(56) References Cited

U.S. PATENT DOCUMENTS

| 4,198,417 | A | 4/1980 | Ong et al. |
| 7,470,702 | B2 | 12/2008 | Staehle et al. |
| 2006/0281762 | A1 | 12/2006 | Staehle et al. |
| 2007/0021456 | A1 | 1/2007 | Mitjans et al. |
| 2008/0194605 | A1 | 8/2008 | Heinrich et al. |
| 2009/0082404 | A1 | 3/2009 | Staehle et al. |

FOREIGN PATENT DOCUMENTS

| WO | WO 2004/087155 A1 | 10/2004 |
| WO | WO 2005/019216 A1 | 3/2005 |
| WO | WO 2005/037829 A1 | 4/2005 |
| WO | WO 2005/042520 A1 | 5/2005 |
| WO | WO 2005/070920 A1 | 8/2005 |
| WO | WO 2007/016228 A2 | 2/2007 |
| WO | WO 2007/098169 A1 | 8/2007 |
| WO | WO 2007/100646 A1 | 9/2007 |
| WO | WO 2007/129183 A2 | 11/2007 |
| WO | WO 2008/057280 A1 | 5/2008 |
| WO | WO 2008/084299 A1 | 7/2008 |
| WO | WO 2009/081259 A1 | 7/2009 |
| WO | WO 2010/008739 A2 | 1/2010 |

OTHER PUBLICATIONS

Dounay et al., "Design, synthesis, and pharmacological evaluation of phenoxy pyridyl derivatives as dual norepinephrine reuptake inhibitors and 5-HT1A partial agonists," Bioorganic & Medicinal Chemistry Letters, 2010, 20(3):1114-1117.
Villani et al., "Benzopyranopyridine Derivatives. 1. Aminoalkyl Derivatives of the Azaxanthenes as Bronchodilating Agents," Journal of Medicinal Chemistry, 1975, 18(1):1-8.

*Primary Examiner* — James O Wilson
*Assistant Examiner* — Douglas M Willis
(74) *Attorney, Agent, or Firm* — Elsa D. Lemoine

(57) ABSTRACT

Pyrazine compounds, and compositions containing them, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

24 Claims, No Drawings

US 8,053,438 B2

PYRAZINE COMPOUNDS AS PHOSPHODIESTERASE 10 INHIBITORS

CROSS-REFERENCE TO RELATED APPLICATIONS

This application claims the benefit of U.S. Provisional Application No. 61/114,567, filed 14 Nov. 2008, and U.S. Provisional Application No. 61/166,212, filed 2 Apr. 2009, each of which is hereby incorporated by reference.

FIELD OF THE INVENTION

Provided herein are certain pyrazine compounds that are PDE10 inhibitors, pharmaceutical compositions containing such compounds, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

BACKGROUND

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kb, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

SUMMARY OF THE INVENTION

The present invention comprises a new class of pyrazine compounds useful in the treatment of diseases, such as PDE10-mediated diseases and other maladies, such as schizophrenia, bipolar disorder, or obsessive-compulsive disorder. Accordingly, the invention also comprises pharmaceutical compositions comprising the compounds, methods for the treatment of PDE10-mediated diseases and other maladies, such as schizophrenia, bipolar disorder, or obsessive-compulsive disorder, using the compounds and compositions of the invention, and intermediates and processes useful for the preparation of the compounds of the invention.

The compounds of the invention are represented by the following general structure:

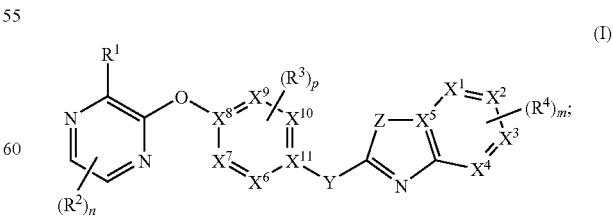

or a pharmaceutically acceptable salt thereof, wherein m, n, p, $R^1$, $R^2$, $R^3$, $R^4$, $X^1$, $X^2$, $X^3$, $X^4$, $X^5$, $X^6$, $X^7$, $X^8$, $X^9$, $X^{10}$, $X^{11}$, Y and Z are defined below.

Other compounds of the invention are represented by the following general structure:

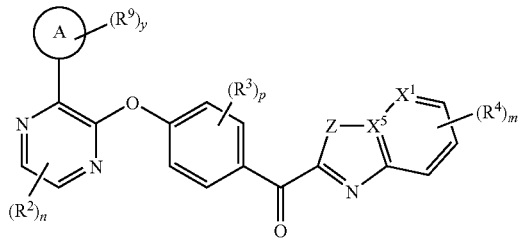

(II)

or a pharmaceutically acceptable salt thereof, wherein m, n, p, y, $R^2$, $R^3$, $R^4$, $R^9$, $X^1$, $X^5$, and Z are defined below.

Other compounds of the invention are represented by the following general structure:

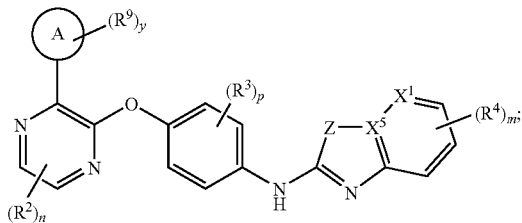

(III)

or a pharmaceutically acceptable salt thereof, wherein m, n, p, y, $R^2$, $R^3$, $R^4$, $R^9$, $X^1$, $X^5$, and Z are defined below.

Other compounds of the invention are represented by the following general structure:

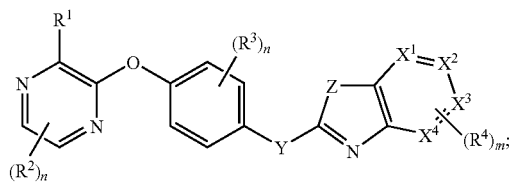

(IV)

or a pharmaceutically acceptable salt thereof, wherein m, n, $R^1$, $R^2$, $R^3$, $R^4$, $X^1$, $X^2$, $X^3$, $X^4$, Y and Z are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

One aspect of the current invention relates to compounds having the general structure of formula (I):

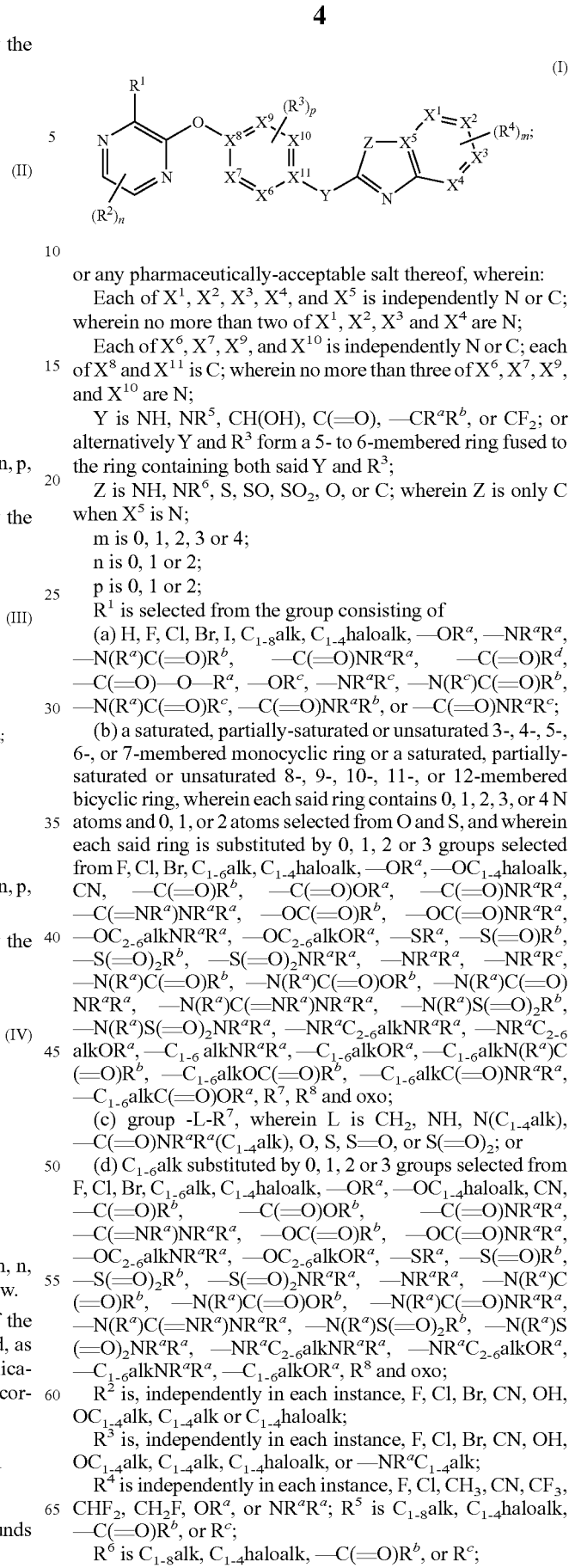

or any pharmaceutically-acceptable salt thereof, wherein:
Each of $X^1$, $X^2$, $X^3$, $X^4$, and $X^5$ is independently N or C; wherein no more than two of $X^1$, $X^2$, $X^3$ and $X^4$ are N;
Each of $X^6$, $X^7$, $X^9$, and $X^{10}$ is independently N or C; each of $X^8$ and $X^{11}$ is C; wherein no more than three of $X^6$, $X^7$, $X^9$, and $X^{10}$ are N;
Y is NH, $NR^5$, CH(OH), C(=O), —$CR^aR^b$, or $CF_2$; or alternatively Y and $R^3$ form a 5- to 6-membered ring fused to the ring containing both said Y and $R^3$;
Z is NH, $NR^6$, S, SO, $SO_2$, O, or C; wherein Z is only C when $X^5$ is N;
m is 0, 1, 2, 3 or 4;
n is 0, 1 or 2;
p is 0, 1 or 2;
$R^1$ is selected from the group consisting of
(a) H, F, Cl, Br, I, $C_{1-8}$alk, $C_{1-4}$haloalk, —$OR^a$, —$NR^aR^a$, —$N(R^a)C(=O)R^b$, —$C(=O)NR^aR^a$, —$C(=O)R^d$, —C(=O)—O—$R^a$, —$OR^c$, —$NR^aR^c$, —$N(R^c)C(=O)R^b$, —$N(R^a)C(=O)R^c$, —$C(=O)NR^aR^b$, or —$C(=O)NR^aR^c$;
(b) a saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O and S, and wherein each said ring is substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$NR^aR^c$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^7$, $R^8$ and oxo;
(c) group -L-$R^7$, wherein L is $CH_2$, NH, N($C_{1-4}$alk), —C(=O)$NR^aR^a$($C_{1-4}$alk), O, S, S=O, or S(=O)$_2$; or
(d) $C_{1-6}$alk substituted by 0, 1, 2 or 3 groups selected from F, Cl, Br, $C_{1-6}$alk, $C_{1-4}$haloalk, —$OR^a$, —$OC_{1-4}$haloalk, CN, —$C(=O)R^b$, —$C(=O)OR^b$, —$C(=O)NR^aR^a$, —$C(=NR^a)NR^aR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, $R^8$ and oxo;
$R^2$ is, independently in each instance, F, Cl, Br, CN, OH, $OC_{1-4}$alk, $C_{1-4}$alk or $C_{1-4}$haloalk;
$R^3$ is, independently in each instance, F, Cl, Br, CN, OH, $OC_{1-4}$alk, $C_{1-4}$alk, $C_{1-4}$haloalk, or —$NR^aC_{1-4}$alk;
$R^4$ is independently in each instance, F, Cl, $CH_3$, CN, $CF_3$, $CHF_2$, $CH_2F$, $OR^a$, or $NR^aR^a$; $R^5$ is $C_{1-8}$alk, $C_{1-4}$haloalk, —$C(=O)R^b$, or $R^c$;
$R^6$ is $C_{1-8}$alk, $C_{1-4}$haloalk, —$C(=O)R^b$, or $R^c$;

$R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo;

$R^8$ is a $C_{1-6}$alk substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk;

$R^c$ is a $C_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, which is substituted by 0, 1, 2 or 3 groups selected from F, Cl, Br, $C_{1-6}$alk, $C_{1-4}$haloalk, $R^7$, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, $SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo; and $R^d$ is a nitrogen-linked saturated, partially-saturated, or unsaturated 5-, 6- or 7-membered ring heterocycle containing the linking nitrogen and 0, 1 or 2 additional nitrogen atoms and containing 0 or 1 sulfur or oxygen atom, the heterocycle being substituted by 0, 1, 2 or 3 substituents selected from oxo, halo, $C_{1-4}$alk, $C_{1-3}$haloalk, —$OC_{1-4}$alk, —$NH_2$, —$NHC_{1-4}$alk, and —N($C_{1-4}$alk)$C_{1-4}$alk.

In another embodiment, the group:

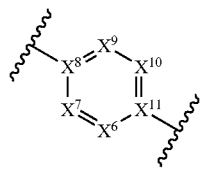

is selected from the group consisting of;

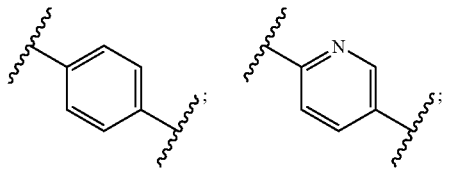

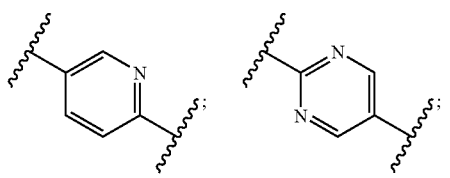

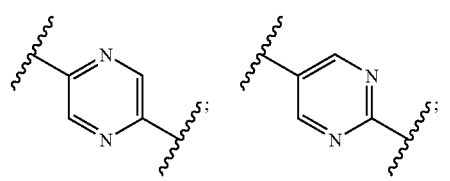

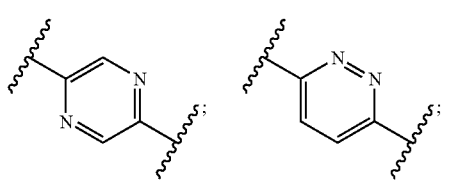

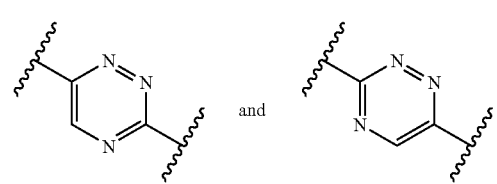

and

In another embodiment, the group

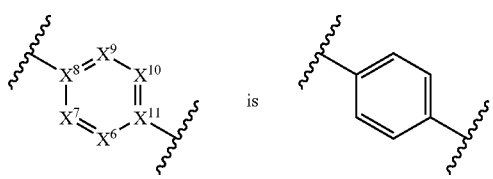

is

In another embodiment, the group

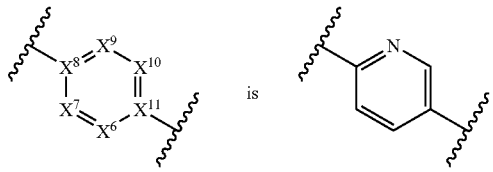

is

In another embodiment, the group

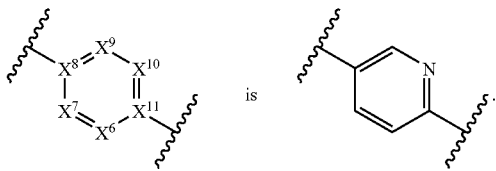 is 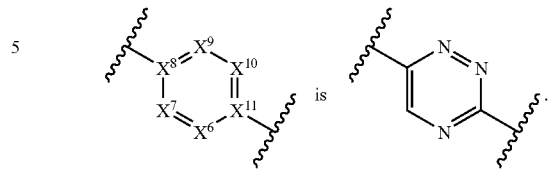

In another embodiment, the group

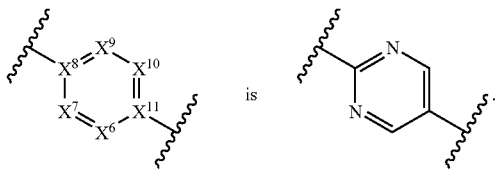 is 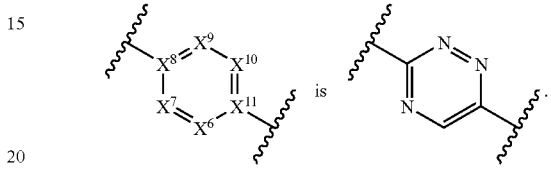

In another embodiment, the group

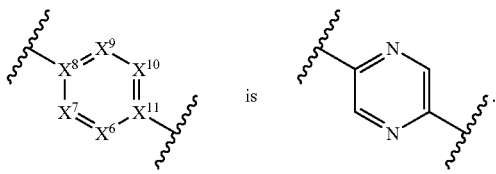 is .

In another embodiment, the group

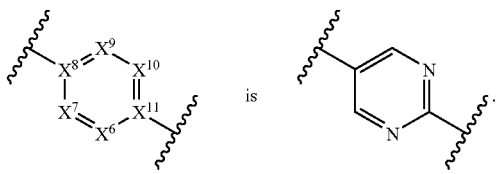 is .

In another embodiment, the group

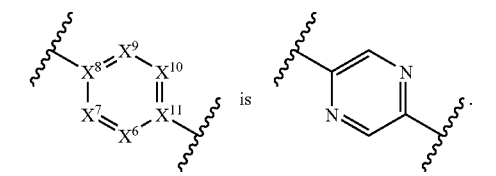 is .

In another embodiment, the group

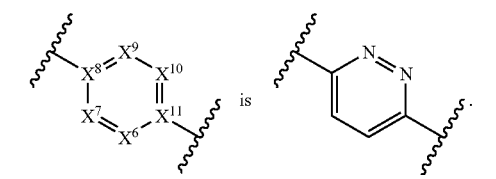 is .

In another embodiment, Y is NH, N—CH$_3$, CF$_2$, or —C(=O).

In another embodiment, Y is NH.

In another embodiment, Y is —C(=O).

In another embodiment, Y is —N—CH$_2$—C$_6$C$_5$—F.

In another embodiment, Y is —CH$_2$—.

In another embodiment, Y and R$^3$ form a 5- to 6-membered ring fused to the ring containing both said Y and R$^3$; wherein Y is NH, and R$^3$ is C$_{1-4}$alk or —NR$^a$C$_{1-4}$alk.

In another embodiment, X$^1$ is N or C, and each of X$^2$, X$^3$, X$^4$, and X$^5$ is C.

In another embodiment, X$^5$ is N.

In another embodiment, X$^5$ is C.

In another embodiment, Z is NH, N—C$_{1-4}$alk, N-haloC$_{1-4}$alk, S, or —C=.

In another embodiment, Z is N or —C=.

In another embodiment, m is 0 or 1.

In another embodiment, n is 0 or 1.

In another embodiment, p is 0 or 1.

In another embodiment, R$^1$ is selected from the group consisting of H, F, Cl, Br, I, —OR$^a$, C$_{1-8}$alk, C$_{1-4}$haloalk, —C(=O)—O—R$^a$, —C(=O)NR$^a$R$^a$, —OR$^c$, and —C(=O)NR$^a$R$^c$.

In another embodiment, R$^1$ is selected from the group consisting of H, F, Cl, Br, —OR$^a$, —C(=O)NR$^a$R$^a$, —OR$^c$, and —C(=O)NR$^a$R$^c$.

In another embodiment, R$^1$ is selected from the group consisting of a saturated, partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, 2 or 3 groups selected from F, Cl, Br, C$_{1-6}$alk, C$_{1-4}$haloalk, —OR$^a$, —OC$_{1-4}$ haloalk, CN, —C(=O)R$^b$, —C(=O)OR$^a$, —NR$^a$R$^a$, —NR$^a$R$^c$, R$^7$, R$^8$ and oxo.

In another embodiment, R$^1$ is selected from the group consisting of a saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 groups selected from F, Cl, Br, C$_{1-6}$alk, C$_{1-4}$haloalk, —OR$^a$, —OC$_{1-4}$ haloalk, CN, —C(=O)R$^b$, —C(=O)OR$^a$, —NR$^a$R$^a$, —NR$^a$R$^c$, R$^7$, R$^8$ and oxo.

In another embodiment, R$^1$ is selected from the group consisting of cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, dihydrotriazolo[4,3-a]pyrazinyl, pyrrolo[2,3-b]pyridinyl, all of which are substituted by 0, 1, 2 or 3 groups selected from all of which are substituted by 0, 1 or 2 groups selected from F, Cl, Br, $C_{1-6}$alk, $C_{1-4}$haloalk, —OR$^a$, CN, —C(=O)R$^b$, —C(=O)OR$^a$, —SR$^a$, R$^7$, and oxo.

In another embodiment, R$^1$ is -L-R$^7$ wherein L is —CH$_2$—.

In another embodiment, R$^1$ is $C_{1-6}$alk substituted by 0, 1, 2 or 3 groups selected from F, Cl, Br, $C_{1-6}$alk, $C_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, R$^8$ and oxo.

In another embodiment, R$^1$ is selected from the group consisting of: Cl, Br, I, COOH,

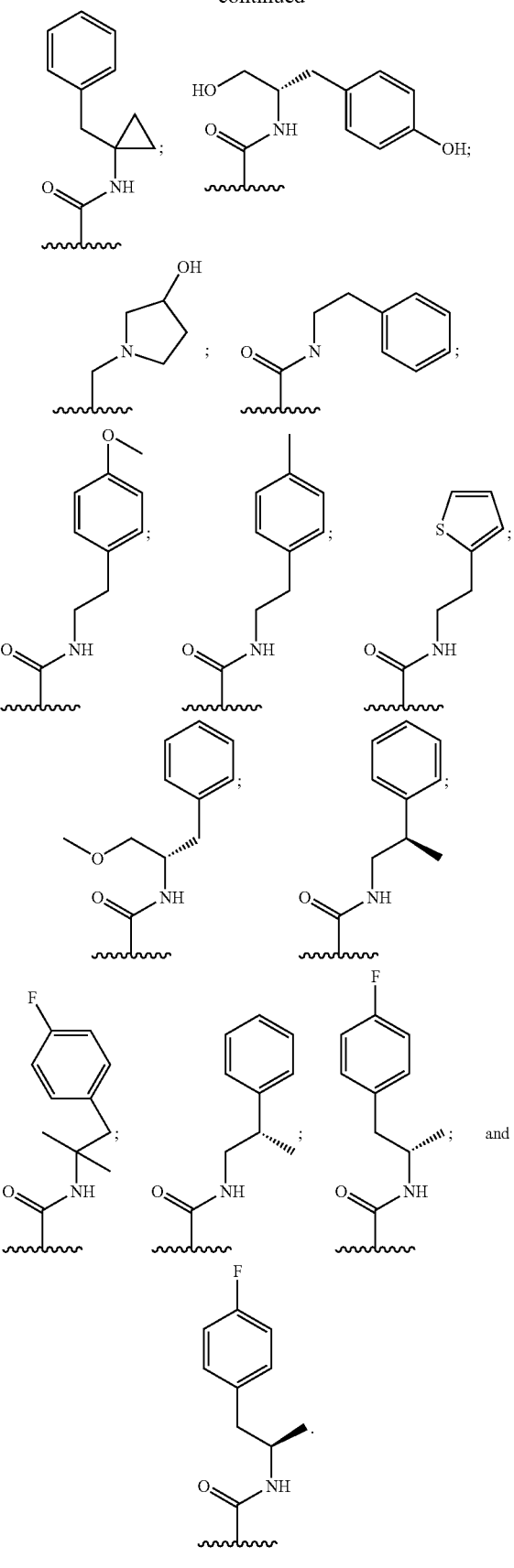

In another embodiment, R¹ is selected from the group consisting of:

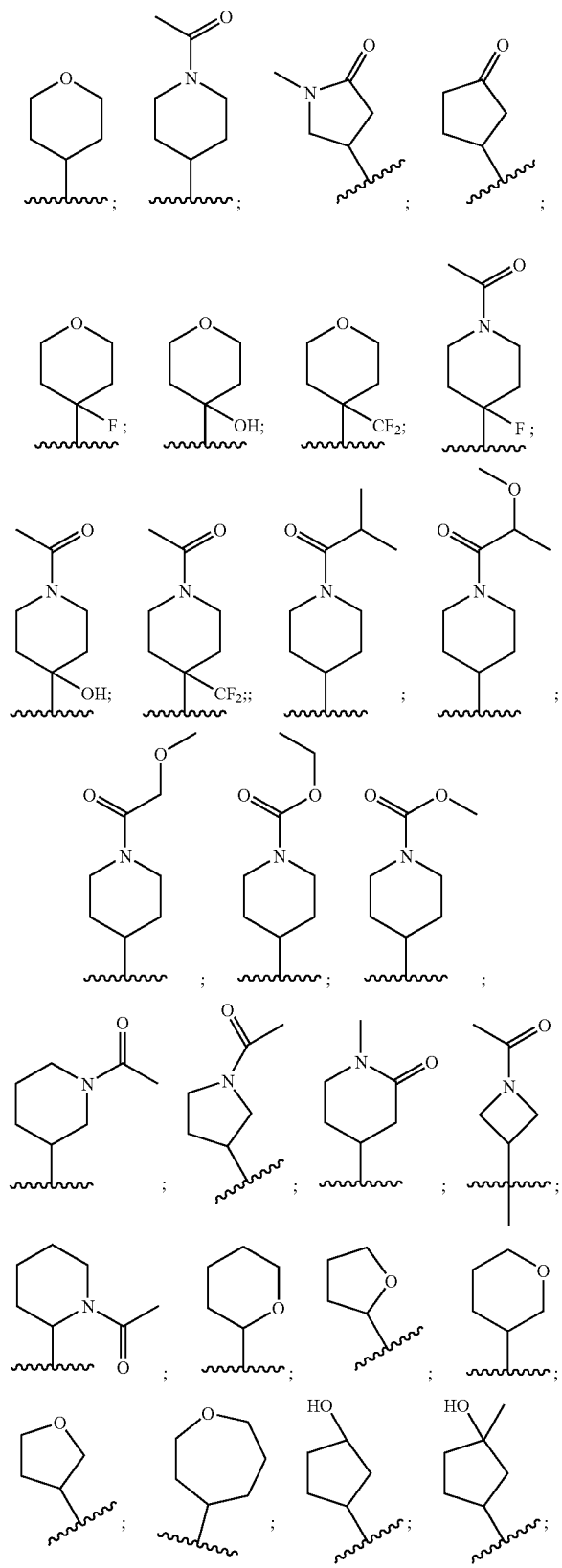

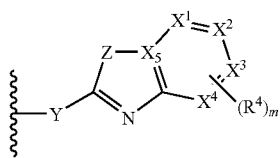

In another embodiment, R² is, independently in each instance, F, Cl, Br, CN, OH, OC$_{1-4}$alk, C$_{1-4}$alk or C$_{1-4}$haloalk.

In another embodiment, R³ is, independently in each instance, F, Cl, Br, CN, OH, OC$_{1-4}$alk, C$_{1-4}$alk or C$_{1-4}$haloalk.

In another embodiment, R⁴ is F.

In another embodiment, R⁵ is methyl.

In another embodiment, R⁶ is methyl.

In another embodiment, R⁷ is a saturated 3-, 4-, 5- or 6-membered monocyclic ring containing 0 or 1 N atom and 0 or 1 O atom, which is substituted by 0, 1, 2 or 3 groups selected from F, Cl, Br, C$_{1-6}$alk, C$_{1-4}$haloalk, —OR$^a$, —OC$_{1-4}$ haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, R⁸ and oxo.

In another embodiment, R⁸ is C$_{1-6}$alk substituted by 0 or 1 —OR$^a$.

In another embodiment, R$^a$ is H or C$_{1-6}$alk substituted by 0 or 1 —OH, —OC$_{1-4}$alk, —OC(=O) C$_{1-4}$alk, or —N(C$_{1-4}$alk)C$_{1-4}$alk.

In another embodiment, R$^c$ is a C$_{0-4}$alk-linked saturated, partially-saturated or unsaturated 3-, 5-, or 6-membered monocyclic ring containing 0 or 1 N atom and 0 or 1 atom selected from O and S, which is substituted by 0 or 1 groups selected from F, C$_{1-6}$alk, C$_{1-4}$haloalk, —OR$^a$, R⁷, or R⁸.

In another embodiment, the group of formula:

is selected from the group consisting of

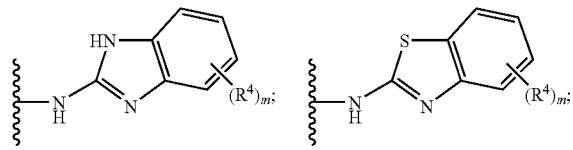

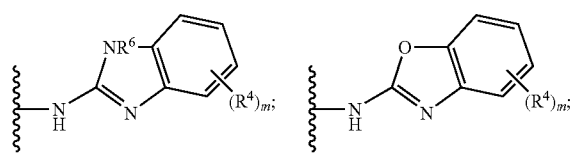

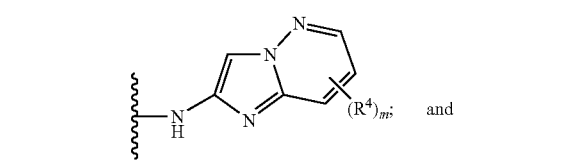

In another embodiment, the group of formula:

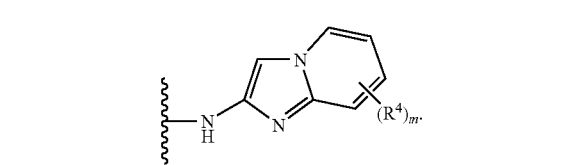

is selected from the group consisting of

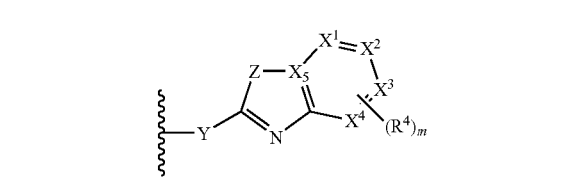

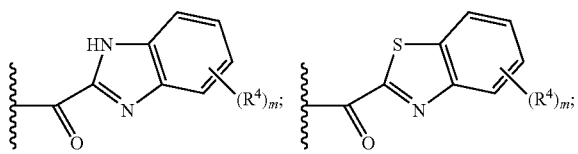

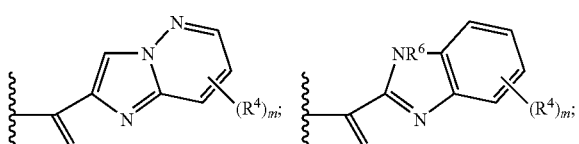

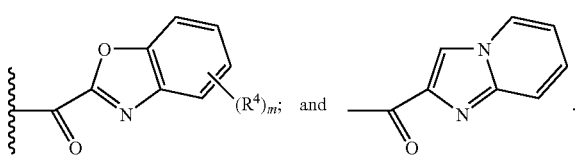

In another embodiment, the group of formula:

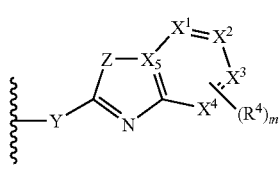

is selected from the group consisting of

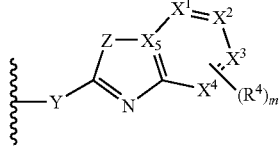

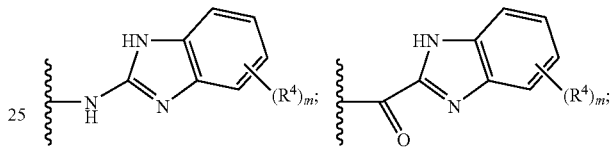

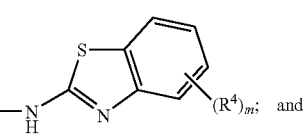

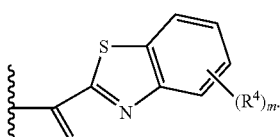

Another aspect of the invention relates to a method of treating conditions that may be treated with PDE10 inhibitors comprising the step of administering a compound of formula (I) of the present invention.

Another aspect of the invention relates to a method wherein said condition that may be treated with PDE10 inhibitors is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method wherein said condition that may be treated with PDE10 inhibitors is selected from the group consisting of schizophrenia, bipolar disorder, and obsessive-compulsive disorder.

Another aspect of the invention relates to a pharmaceutical composition comprising a compound of formula (I) and a pharmaceutically-acceptable diluent or carrier.

Another aspect of the current invention relates to compounds having the general structure of formula (II):

or any pharmaceutically-acceptable salt thereof, wherein:

Z is NH, $NR^6$, S or O;

m is 0, 1, 2, 3 or 4;

n is 0, 1 or 2;

p is 0, 1 or 2;

y is 0, 1, 2, 3 or 4;

$X^1$ is N or C;

$X^5$ is N or C;

Ring A is a carbon-linked-saturated, carbon-linked-partially-saturated, or carbon-linked-unsaturated 4-, 5-, 6-, 7-, 8-, 9-, 10-, 11-, or 12-membered carbocycle ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;

$R^2$ is, independently in each instance, F, Cl, Br, CN, OH, $OC_{1-4}$alk, $C_{1-4}$alk or $C_{1-4}$haloalk;

$R^3$ is, independently in each instance, F, Cl, Br, CN, OH, $OC_{1-4}$alk, $C_{1-4}$alk or $C_{1-4}$haloalk;

$R^4$ is independently in each instance, F, Cl, $CH_3$, CN, $CF_3$, $CHF_2$, $CH_2F$, $OR^a$, or $NR^aR^a$;

$R^5$ is $C_{1-8}$alk, $C_{1-4}$haloalk, —C(=O)$R^b$, or $R^c$;

$R^6$ is $C_{1-8}$alk, $C_{1-4}$haloalk, —C(=O)$R^b$, or $R^c$;

$R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2, 3, or 4 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$ alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo;

$R^8$ is a $C_{1-6}$alk substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$ alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo;

$R^9$ is independently selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —$NR^aR^c$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$ alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^7$, $R^8$ and oxo;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk; and $R^c$ is a $C_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, which is substituted by 0, 1, 2 or 3 groups selected from F, Cl, Br, $C_{1-6}$alk, $C_{1-4}$haloalk, $R^7$, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo.

In another embodiment, Z is NH, N—$C_{1-4}$alk, or S.

Another aspect of the current invention relates to compounds having the general structure of formula (IIa):

or a pharmaceutically acceptable salt thereof, wherein m, n, p, y, $R^2$, $R^3$, $R^4$, and $R^9$ are as defined in compounds of formula (II), and any other embodiments below.

In one embodiment of compounds of formula (IIa), ring A is bonded to the pyrazinyl ring via a carbon atom having an sp3 hybridization.

In one embodiment of compounds of formula (IIa), ring A is bonded to the pyrazinyl ring via a carbon atom having an sp2 hybridization.

In one embodiment of compounds of formula (IIa), ring A is bonded to the pyrazinyl ring via a carbon atom having an sp hybridization.

In one embodiment of compounds of formula (IIa), ring A is bonded to the pyrazinyl ring via a nitrogen atom having an sp3 hybridization.

In one embodiment of compounds of formula (IIa), ring A is bonded to the pyrazinyl ring via a nitrogen atom having an sp2 hybridization.

In another embodiment of compounds of formula (IIa), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIa), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

Another aspect of the current invention relates to compounds having the general structure of formula (IIb):

(IIb)

or a pharmaceutically acceptable salt thereof, wherein m, n, p, y, R$^2$, R$^3$, R$^4$, and R$^9$ are as defined in compounds of formula (II), and any other embodiments below.

In one embodiment of compounds of formula (IIb), ring A is bonded to the pyrazinyl ring via a carbon atom having an sp3 hybridization.

In one embodiment of compounds of formula (IIb), ring A is bonded to the pyrazinyl ring via a carbon atom having an sp2 hybridization.

In one embodiment of compounds of formula (IIb), ring A is bonded to the pyrazinyl ring via a carbon atom having an sp hybridization.

In one embodiment of compounds of formula (IIb), ring A is bonded to the pyrazinyl ring via a nitrogen atom having an sp3 hybridization.

In one embodiment of compounds of formula (IIb), ring A is bonded to the pyrazinyl ring via a nitrogen atom having an sp2 hybridization.

In another embodiment of compounds of formula (IIb), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment of compounds of formula (IIb), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$ alkN(R$^a$)C(=O)R$^b$, —C$_{1-6}$ alkOC(=O)R$^b$, —C$_{1-6}$ alkC(=O)NR$^a$R$^a$, —C$_{1-6}$ alkC(=O)OR$^a$, or oxo.

In another embodiment of compounds of formula (IIb), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, or oxo.

In another embodiment, the group of formula:

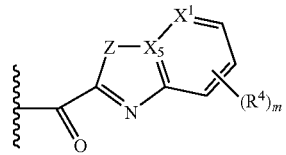

is selected from the group consisting of

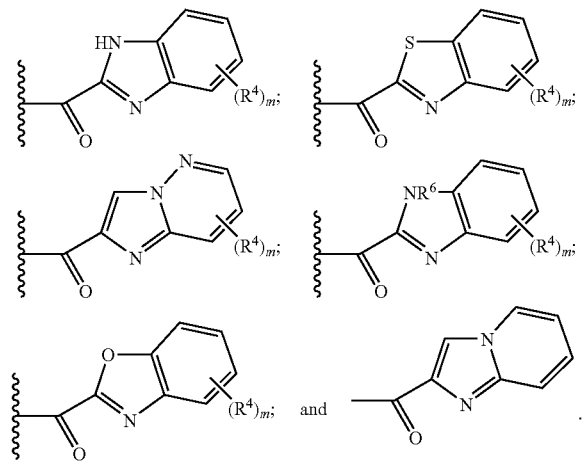

In another embodiment, ring A is a carbon-linked-saturated, partially-saturated, or unsaturated 4-, 5-, 6-, 7-, 8-, 9-, 10-, 11-, or 12-membered carbocycle ring containing 0, 1 or 2 N atoms and containing 0 or 1 S or O atom.

In another embodiment, ring A is a carbon-linked-saturated 4-, 5-, 6-, 7-, 8-, 9-, 10-, 11-, or 12-membered carbocycle ring containing 0, 1 or 2 N atoms and containing 0 or 1 S or O atom.

In another embodiment, ring A is a nitrogen-linked-saturated 4-, 5-, 6-, 7-membered carbocycle ring containing 0, 1 or 2 N atoms and containing 0 or 1 S or O atom.

In another embodiment, ring A is a nitrogen-linked-partially-saturated 4-, 5-, 6-, 7-, 8-, 9-, 10-membered carbocycle ring containing 0, 1 or 2 N atoms and containing 0 or 1 S or O atom.

In another embodiment, ring A is a nitrogen-linked-unsaturated 4-, 5-, 6-, 8-, 10-, or 12-membered carbocycle ring containing 0, 1 or 2 N atoms and containing 0 or 1 S or O atom.

In another embodiment, ring A is selected from the group consisting of cyclohexyl, cyclopentyl, cyclopentenyl, cyclohexenyl, and cycloheptyl.

In another embodiment, ring A is selected from the group consisting of azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, and tetrahydrothiopyranyl.

In another embodiment, ring A is selected from the group consisting of oxaspiro[3.5]nonyl, azepanyl, oxepanyl, and quinolinyl.

In another embodiment, ring A is selected from the group consisting of cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, dihydrotriazolo[4,3-a]pyrazinyl, pyrrolo[2,3-b]pyridinyl, all of which are substituted by 0, 1, 2 or 3 groups selected from all of which are substituted by 0, 1 or 2 groups selected from F, Cl, Br, $C_{1-6}$alk, $C_{1-4}$haloalk, —OR$^a$, CN, —C(=O)R$^b$, —C(=O)OR$^a$, —SR$^a$, R$^7$, and oxo.

In another embodiment, ring A is selected from the group consisting of

In another embodiment, ring A is selected from the group consisting of:

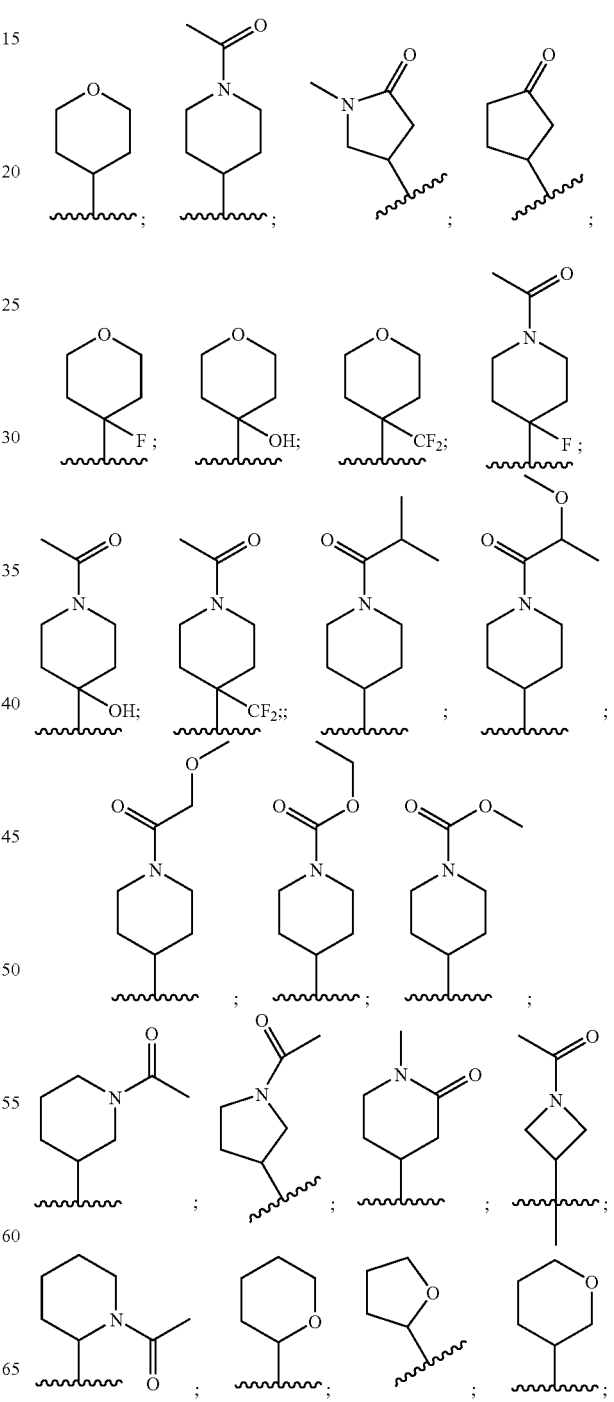

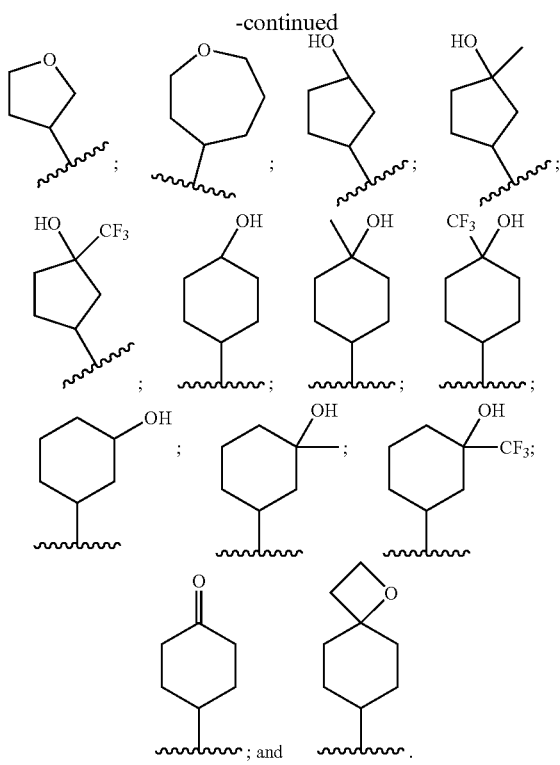

In another embodiment, m is 0 or 1.
In another embodiment, n is 0 or 1.
In another embodiment, p is 0 or 1.
In another embodiment, y is 0, 1, 2, or 3.
In another embodiment, $R^9$ is selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, —$NR^aR^c$, $R^7$, $R^8$ and oxo.

In another embodiment, $R^2$ is, independently in each instance, F, Cl, Br, CN, OH, $OC_{1-4}$alk, $C_{1-4}$alk or $C_{1-4}$haloalk.

In another embodiment, $R^3$ is, independently in each instance, F, Cl, Br, CN, OH, $OC_{1-4}$alk, $C_{1-4}$alk or $C_{1-4}$haloalk.
In another embodiment, $R^4$ is F.

In another embodiment, $R^6$ is methyl.

In another embodiment, $R^7$ is a saturated 5- or 6-membered monocyclic ring containing 0 or 1 N atom and 0 or 1 O atom, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alkN$R^aR^a$, —$OC_{2-6}$alkO$R^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alkN$R^aR^a$, —$NR^aC_{2-6}$alkO$R^a$, —$C_{1-6}$alkN$R^aR^a$, —$C_{1-6}$alkO$R^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo.

In another embodiment, $R^8$ is $C_{1-6}$alk substituted by 0 or 1 —$OR^a$.

In another embodiment, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

In another embodiment, $R^c$ is a $C_{0-4}$alk-linked saturated, partially-saturated or unsaturated 3-, 5-, or 6-membered monocyclic ring containing 0 or 1 N atom and 0 or 1 atom selected from O and S, which is substituted by 0 or 1 groups selected from $C_{1-6}$alk, $R^7$, or —$OR^a$.

Another aspect of the invention relates to a method of treating conditions that may be treated with PDE10 inhibitors comprising the step of administering a compound of formula (II).

Another aspect of the invention relates to a method of treating conditions that may be treated with PDE10 inhibitors comprising the step of administering a compound of formula (II); wherein said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering a compound of formula (II); wherein said condition is selected from the group consisting of schizophrenia, bipolar disorder, and obsessive-compulsive disorder.

Another aspect of the invention relates to a pharmaceutical composition comprising a compound of formula (II) and a pharmaceutically-acceptable diluent or carrier.

Another aspect of the current invention relates to compounds having the general structure of formula (III):

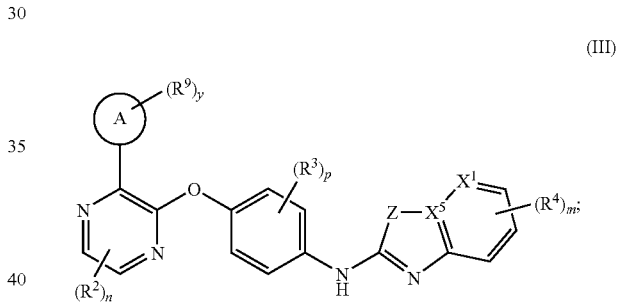

(III)

or any pharmaceutically-acceptable salt thereof, wherein:
Z is NH, $NR^6$, S or O;
m is 0, 1, 2, 3 or 4;
n is 0, 1 or 2;
p is 0, 1 or 2;
y is 0, 1, 2, 3 or 4;
$X^1$ is N or C;
$X^5$ is N or C;
Ring A is a carbon-linked-saturated, carbon-linked-partially-saturated, or carbon-linked-unsaturated 4-, 5-, 6-, 7-, 8-, 9-, 10-, 11-, or 12-membered carbocycle ring containing 0, 1 or 2 N atoms and containing 0 or 1 S or O atom; or a nitrogen-linked-saturated, nitrogen-linked-partially-saturated, or nitrogen-linked-unsaturated 4-, 5-, 6-, 7-, 8-, 9-, 10-, 11-, or 12-membered ring heterocycle containing the linking nitrogen and 0, 1 or 2 additional N atoms and containing 0 or 1 S or O atom;
$R^2$ is, independently in each instance, F, Cl, Br, CN, OH, $OC_{1-4}$alk, $C_{1-4}$alk or $C_{1-4}$haloalk;
$R^3$ is, independently in each instance, F, Cl, Br, CN, OH, $OC_{1-4}$alk, $C_{1-4}$alk or $C_{1-4}$haloalk;
$R^4$ is independently in each instance, F, Cl, $CH_3$, CN, $CF_3$, $CHF_2$, $CH_2F$, $OR^a$, or $NR^aR^a$;
$R^5$ is $C_{1-8}$alk, $C_{1-4}$haloalk, —C(=O)$R^b$, or $R^c$;
$R^6$ is $C_{1-8}$alk, $C_{1-4}$haloalk, —C(=O)$R^b$, or $R^c$;

R$^7$ is a saturated, partially-saturated or unsaturated 3-, 4-, 5-, 6-, or 7-membered monocyclic or 8-, 9-, 10-, 11-, or 12-membered bicyclic ring containing 0, 1, 2, 3, or 4 N atoms and 0 or 1 atoms selected from O and S, which is substituted by 0, 1, 2 or 3 groups selected from F, Cl, Br, C$_{1-6}$alk, C$_{1-4}$haloalk, —OR$^a$, —OC$_{1-4}$haloalk, CN, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$, R$^8$ and oxo;

R$^8$ is a C$_{1-6}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$ and oxo;

R$^9$ is independently selected from the group consisting of H, F, Cl, Br, C$_{1-6}$alk, C$_{1-4}$haloalk, —OR$^a$, —OC$_{1-4}$haloalk, CN, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —NR$^a$R$^c$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, C$_{1-6}$alkC(═O)NR$^a$R$^a$, —C$_{1-6}$alkC(═O)OR$^a$, R$^7$, R$^8$ and oxo;

R$^a$ is independently, at each instance, H or R$^b$;

R$^b$ is independently, at each instance, phenyl, benzyl or C$_{1-6}$alk, the phenyl, benzyl and C$_{1-6}$alk being substituted by 0, 1, 2 or 3 substituents selected from halo, C$_{1-4}$alk, C$_{1-3}$haloalk, —OH, —OC$_{1-4}$alk, —NH$_2$, —NHC$_{1-4}$alk, —OC(═O)C$_{1-4}$alk, or —N(C$_{1-4}$alk)C$_{1-4}$alk; and R$^c$ is a C$_{0-4}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atom selected from O and S, which is substituted by 0, 1, 2 or 3 groups selected from F, Cl, Br, C$_{1-6}$alk, C$_{1-4}$haloalk, R$^7$, —OR$^a$, —OC$_{1-4}$haloalk, CN, —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —OC$_{2-6}$alkNR$^a$R$^a$, —OC$_{2-6}$alkOR$^a$, —SR$^a$, —S(═O)R$^b$, —S(═O)$_2$R$^b$, —S(═O)$_2$NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$ and oxo.

In another embodiment, Z is NH, N—C$_{1-4}$alk, or S.

Another aspect of the current invention relates to compounds having the general structure of formula (IIIa):

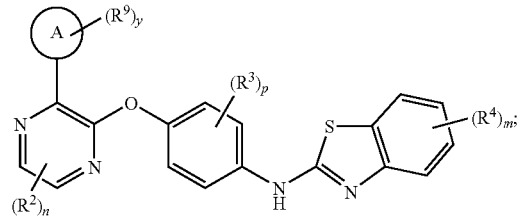

(IIIa)

or a pharmaceutically acceptable salt thereof, wherein m, n, p, y, R$^2$, R$^3$, R$^4$, and R$^9$ are as defined in compounds of formula (III), and any other embodiments below.

In one embodiment of compounds of formula (IIIa), ring A is bonded to the pyrazinyl ring via a carbon atom having an sp3 hybridization.

In one embodiment of compounds of formula (IIIa), ring A is bonded to the pyrazinyl ring via a carbon atom having an sp2 hybridization.

In one embodiment of compounds of formula (IIIa), ring A is bonded to the pyrazinyl ring via a carbon atom having an sp hybridization.

In one embodiment of compounds of formula (IIIa), ring A is bonded to the pyrazinyl ring via a nitrogen atom having an sp3 hybridization.

In one embodiment of compounds of formula (IIIa), ring A is bonded to the pyrazinyl ring via a nitrogen atom having an sp2 hybridization.

In another embodiment of compounds of formula (IIIa), ring A is a 5-membered ring saturated heterocycle, which is optionally substituted with —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —N(R$^a$)C(═O)R$^b$, —N(R$^a$)C(═O)OR$^b$, —N(R$^a$)C(═O)NR$^a$R$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$, and oxo.

In another embodiment of compounds of formula (IIIa), ring A is a 6-membered ring saturated heterocycle, which is optionally substituted with —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —N(R$^a$)C(═O)R$^b$, —N(R$^a$)C(═O)OR$^b$, —N(R$^a$)C(═O)NR$^a$R$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$, and oxo.

In another embodiment of compounds of formula (IIIa), ring A is a 4-membered ring saturated carbocycle, which is optionally substituted with —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —N(R$^a$)C(═O)R$^b$, —N(R$^a$)C(═O)OR$^b$, —N(R$^a$)C(═O)NR$^a$R$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$, and oxo.

In another embodiment of compounds of formula (IIIa), ring A is a 5-membered ring saturated carbocycle, which is optionally substituted with —C(═O)R$^b$, —C(═O)OR$^a$, —C(═O)NR$^a$R$^a$, —C(═NR$^a$)NR$^a$R$^a$, —OC(═O)R$^b$, —OC(═O)NR$^a$R$^a$, —N(R$^a$)C(═O)R$^b$, —N(R$^a$)C(═O)OR$^b$, —N(R$^a$)C(═O)NR$^a$R$^a$, —C$_{1-6}$alkN(R$^a$)C(═O)R$^b$, —C$_{1-6}$alkOC(═O)R$^b$, —C$_{1-6}$alkC(═O)NR$^a$R$^a$, —C$_{1-6}$alkC(═O)OR$^a$, and oxo.

In another embodiment of compounds of formula (IIIa), ring A is a 6-membered ring saturated carbocycle, which is optionally substituted with —C(═O)R$^b$, —C(═O)OR$^a$, —C(═O)NR$^a$R$^a$, —C(═NR$^a$)NR$^a$R$^a$, —OC(═O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo.

In another embodiment of compounds of formula (IIIa), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo.

Another aspect of the current invention relates to compounds having the general structure of formula (IIIb):

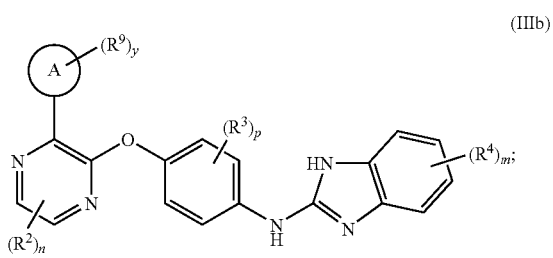

(IIIb)

or a pharmaceutically acceptable salt thereof, wherein m, n, p, y, R$^2$, R$^3$, R$^4$, and R$^9$ are as defined in compounds of formula (III), and any other embodiments below.

In one embodiment of compounds of formula (IIIb), ring A is bonded to the pyrazinyl ring via a carbon atom having an sp3 hybridization.

In one embodiment of compounds of formula (IIIb), ring A is bonded to the pyrazinyl ring via a carbon atom having an sp2 hybridization.

In one embodiment of compounds of formula (IIIb), ring A is bonded to the pyrazinyl ring via a carbon atom having an sp hybridization.

In one embodiment of compounds of formula (IIIb), ring A is bonded to the pyrazinyl ring via a nitrogen atom having an sp3 hybridization.

In one embodiment of compounds of formula (IIIb), ring A is bonded to the pyrazinyl ring via a nitrogen atom having an sp2 hybridization.

In another embodiment of compounds of formula (IIIb), ring A is a 5-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo.

In another embodiment of compounds of formula (IIIb), ring A is a 6-membered ring saturated heterocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo.

In another embodiment of compounds of formula (IIIb), ring A is a 4-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo.

In another embodiment of compounds of formula (IIIb), ring A is a 5-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo.

In another embodiment of compounds of formula (IIIb), ring A is a 6-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$, and oxo.

In another embodiment of compounds of formula (IIIb), ring A is a 7-membered ring saturated carbocycle, which is optionally substituted with —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —N(R$^a$)C(=O)R$^b$, —N(R$^a$)C(=O)OR$^b$, —N(R$^a$)C(=O)NR$^a$R$^a$, —C$_{1-6}$alkN(R$^a$)C(=O)R$^b$, —C$_{1-6}$alkOC(=O)R$^b$, C$_{1-6}$alkC(=O)NR$^a$R$^a$, —C$_{1-6}$alkC(=O)OR$^a$, and oxo.

In another embodiment, the group of formula:

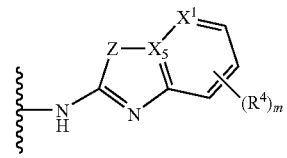

is selected from the group consisting of

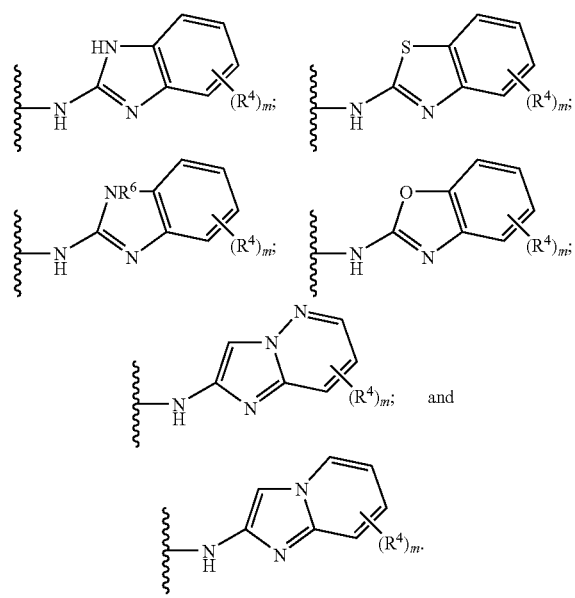

In another embodiment, ring A is a carbon-linked-saturated, partially-saturated, or unsaturated 4-, 5-, 6-, 7-, 8-, 9-, 10-, 11-, or 12-membered carbocycle ring containing 0, 1 or 2 N atoms and containing 0 or 1 S or O atom.

In another embodiment, ring A is a carbon-linked-saturated 4-, 5-, 6-, 7-, 8-, 9-, 10-, 11-, or 12-membered carbocycle ring containing 0, 1 or 2 N atoms and containing 0 or 1 S or O atom.

In another embodiment, ring A is a nitrogen-linked-saturated 4-, 5-, 6-, 7-membered carbocycle ring containing 0, 1 or 2 N atoms and containing 0 or 1 S or O atom.

In another embodiment, ring A is a nitrogen-linked-partially-saturated 4-, 5-, 6-, 7-, 8-, 9-, 10-membered carbocycle ring containing 0, 1 or 2 N atoms and containing 0 or 1 S or O atom.

In another embodiment, ring A is a nitrogen-linked-unsaturated 4-, 5-, 6-, 8-, 10-, or 12-membered carbocycle ring containing 0, 1 or 2 N atoms and containing 0 or 1 S or O atom.

In another embodiment, ring A is selected from the group consisting of cyclohexyl, cyclopentyl, cyclopentenyl, cyclohexenyl, and cycloheptyl.

In another embodiment, ring A is selected from the group consisting of azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, and tetrahydrothiopyranyl.

In another embodiment, ring A is selected from the group consisting of oxaspiro[3.5]nonyl, azepanyl, oxepanyl, and quinolinyl.

In another embodiment, ring A is selected from the group consisting of cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, quinolinyl, all of which are substituted by 0, 1, 2 or 3 groups selected from all of which are substituted by 0, 1 or 2 groups selected from F, Cl, Br, $C_{1-6}$alk, $C_{1-4}$haloalk, —OR$^a$, CN, —C(=O)R$^b$, —C(=O)OR$^a$, —SR$^a$, R$^7$, and oxo.

In another embodiment, ring A is selected from the group consisting of:

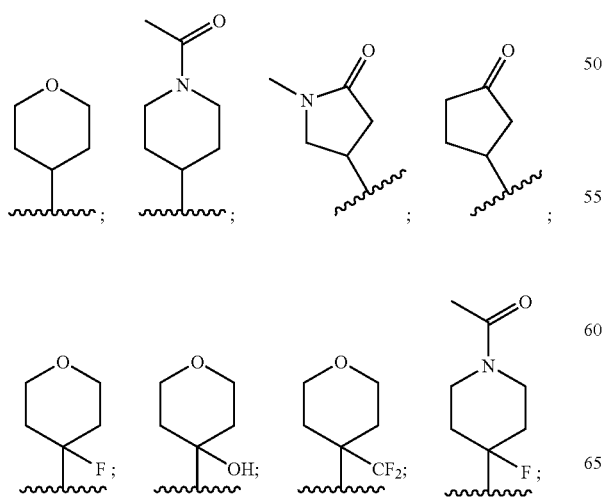

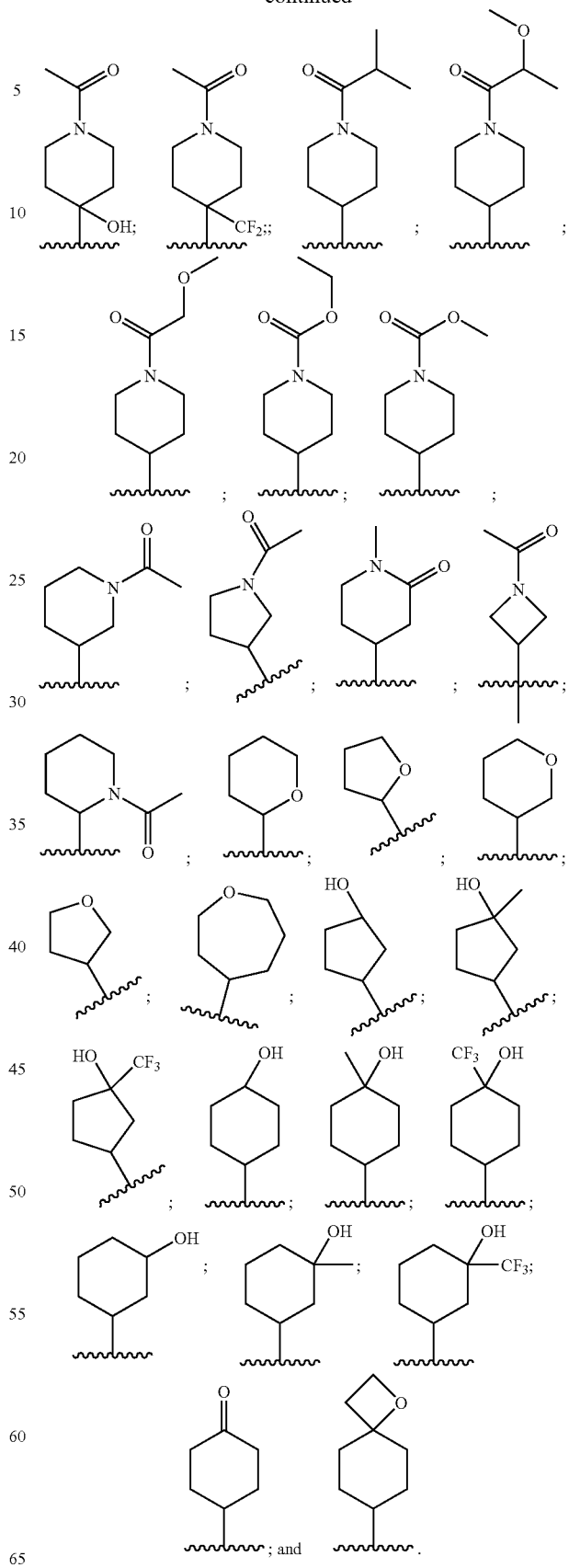

In another embodiment, m is 0 or 1.
In another embodiment, n is 0 or 1.
In another embodiment, p is 0 or 1.
In another embodiment, y is 0, 1, 2, or 3.
In another embodiment, $R^9$ is selected from the group consisting of H, F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, —$NR^aR^c$, $R^7$, $R^8$ and oxo.

In another embodiment, $R^2$ is, independently in each instance, F, Cl, Br, CN, OH, $OC_{1-4}$alk, $C_{1-4}$alk or $C_{1-4}$haloalk.

In another embodiment, $R^3$ is, independently in each instance, F, Cl, Br, CN, OH, $OC_{1-4}$alk, $C_{1-4}$alk or $C_{1-4}$haloalk.

In another embodiment, $R^4$ is F.

In another embodiment, $R^6$ is methyl.

In another embodiment, $R^7$ is a saturated 5- or 6-membered monocyclic ring containing 0 or 1 N atom and 0 or 1 O atom, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$, $R^8$ and oxo.

In another embodiment, $R^8$ is $C_{1-6}$alk substituted by 0 or 1 —$OR^a$.

In another embodiment, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

In another embodiment, $R^c$ is a $C_{0-4}$alk-linked saturated, partially-saturated or unsaturated 3-, 5-, or 6-membered monocyclic ring containing 0 or 1 N atom and 0 or 1 atom selected from O and S, which is substituted by 0 or 1 groups selected from $C_{1-6}$alk, $R^7$, or —$OR^a$.

Another aspect of the invention relates to a method of treating conditions that may be treated with PDE10 inhibitors comprising the step of administering a compound of formula (III).

Another aspect of the invention relates to a method of treating conditions that may be treated with PDE10 inhibitors comprising the step of administering a compound of formula (III); wherein said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering a compound of formula (III); wherein said condition is selected from the group consisting of schizophrenia, bipolar disorder, and obsessive-compulsive disorder.

Another aspect of the invention relates to a pharmaceutical composition comprising a compound of formula (III) and a pharmaceutically-acceptable diluent or carrier.

Another aspect of the current invention relates to compounds having the general structure of formula (IV):

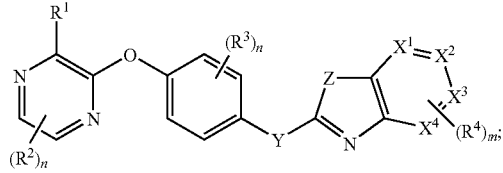

(IV)

or any pharmaceutically-acceptable salt thereof, wherein:

$X^1$ is N or C;
$X^2$ is N or C;
$X^3$ is N or C;
$X^4$ is N or C; wherein no more than two of $X^1$, $X^2$, $X^3$ and $X^4$ are N;
Y is NH, $NR^5$ or C(=O);
Z is NH, $NR^6$, S or O;
m is 0, 1 or 2;
n is independently in each instance 0, 1 or 2;
$R^1$ is selected from H, F, Cl, Br, $C_{1-8}$alk, $C_{1-4}$haloalk, —$OR^a$, —$NR^aR^a$, —N($R^a$)C(=O)$R^b$ and —C(=O)$NR^aR^a$, —C(=O)$R^d$, —$OR^c$, —$NR^aR^c$, —N($R^c$)C(=O)$R^b$, —N($R^a$)C(=O)$R^c$ and —C(=O)$NR^aR^c$; or $R^1$ is -L-$R^7$, wherein L is $CH_2$, NH, N($C_{1-4}$alk), O, S, S=O or S(=O)$_2$; and $R^7$ is a saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ and oxo;

$R^2$ is, independently in each instance, F, Cl, Br, CN, OH, $OC_{1-4}$alk, $C_{1-4}$alk or $C_{1-4}$haloalk;

$R^3$ is, independently in each instance, F, Cl, Br, CN, OH, $OC_{1-4}$alk, $C_{1-4}$alk or $C_{1-4}$haloalk;

$R^4$ is independently in each instance, F, Me or CN;

$R^5$ is $C_{1-8}$alk, $C_{1-4}$haloalk, or —C(=O)$R^b$;

$R^6$ is $C_{1-8}$alk, $C_{1-4}$haloalk, or —C(=O)$R^b$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —$OC_{1-4}$alk, —$NH_2$, —$NHC_{1-4}$alk, and —N($C_{1-4}$alk)$C_{1-4}$alk;

$R^c$ is a $C_{0-1}$alk-linked saturated, partially-saturated or unsaturated 3-, 4-, 5-, 6-, or 7-membered monocyclic or 8-, 9-, 10-, 11-, or 12-membered bicyclic ring containing 0, 1, 2 or 3 N atoms and 0 or 1 atoms selected from O and S, which is substituted by 0, 1, 2 or 3 groups selected from F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{2-6}$alk$NR^aR^a$, —$OC_{2-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$, —$NR^aC_{2-6}$alk$OR^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo; and R$^d$ is a nitrogen-linked saturated, partially-saturated or unsaturated 5-, 6- or 7-membered ring heterocycle containing the linking nitrogen and 0, 1 or 2 additional nitrogen atoms and containing 0 or 1 sulfur or oxygen atoms, the heterocycle being substituted by 0, 1, 2 or 3 substituents selected from oxo, halo, C$_{1-4}$alk, C$_{1-3}$haloalk, —OC$_{1-4}$alk, —NH$_2$, —NHC$_{1-4}$alk, and —N(C$_{1-4}$alk)C$_{1-4}$alk.

In another embodiment, Z is NH.
In another embodiment, Z is NR$^6$.
In another embodiment, Z is S.
In another embodiment, Z is O.
In another embodiment, Y is NH.
In another embodiment, Y is NR$^5$.
In another embodiment, Y is C(=O).
In another embodiment, X$^1$ is N.
In another embodiment, X$^2$ is N.
In another embodiment, X$^3$ is N.
In another embodiment, X$^4$ is N.
In another embodiment, X$^1$, X$^2$, X$^3$ and X$^4$ are all C.

In another embodiment, R$^1$ is C$_{3-4}$alk substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$ and oxo.

In another embodiment, R$^1$ is selected from piperidine, piperazine, pyrrolidine, morpholine, pyridine and pyrimidine, all of which are substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$ and oxo.

In another embodiment, R$^1$ is phenyl, all of which are substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$ and oxo.

In another embodiment, R$^1$ is selected from piperidine, piperazine, pyrrolidine and morpholine, all of which are substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$ and oxo.

In another embodiment, R$^1$ is selected from pyridine and pyrimidine, each of which are substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$ and oxo.

In another embodiment, R$^1$ is a saturated 5- or 6-membered carbocyclic ring substituted by 0, 1, 2 or 3 groups selected from F, Cl, Br, C$_{1-6}$alk, C$_{1-4}$haloalk, —OR$^a$, —OC$_{1-4}$haloalk, CN, —C(=O)R$^b$, —C(=O)OR$^b$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$ and oxo.

In another embodiment, R$^1$ is selected from

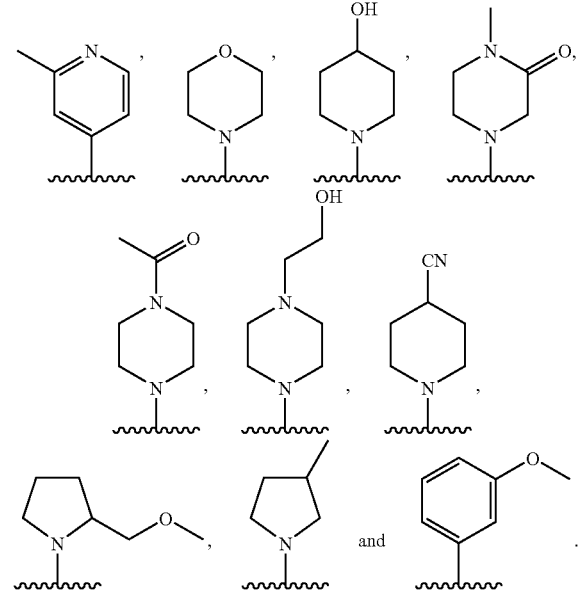

In another embodiment, m is 0.
In another embodiment, m is 1, and R$^4$ is F.
In another embodiment, m is 2; and R$^4$ is F.
In another embodiment, n is 0.

Another aspect of the invention relates to a method of treating schizophrenia, bipolar disorder, or obsessive-compulsive disorder using an effective amount of a compound of formula (IV).

Another aspect of the invention relates to a method of treating a disorder treatable by inhibition of PDE10 in a patient which method comprises administering to the patient a pharmaceutical composition comprising an effective amount of a compound of formula (IV).

Another aspect of the invention relates to a pharmaceutical composition comprising a compound of formula (IV) and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of schizophrenia, bipolar disorder, or obsessive-compulsive disorder.

Another aspect of the invention relates to compounds of selected from the group consisting of:

(1H-Benzo[d]imidazol-2-yl)(4-(3-morpholinopyrazin-2-yloxy)phenyl)methanone;
(S)-(1H-benzo[d]imidazol-2-yl)(4-(3-(4-(1,1,1-trifluoro-2-hydroxypropan-2-yl)piperidin-1-yl)pyrazin-2-yloxy)phenyl)methanone;
(1H-benzo[d]imidazol-2-yl)(4-(3-chloropyrazin-2-yloxy)phenyl)methanone;
[4-(3-Chloro-pyrazin-2-yloxy)-phenyl]-(6-fluoro-1H-benzoimidazol-2-yl)-methanone;
(1-Methyl-1H-benzo[d]imidazol-2-yl)(4-(3-morpholinopyrazin-2-yloxy)phenyl)-methanone;
(1-Isopropyl-1H-benzo[d]imidazol-2-yl)(4-(3-morpholinopyrazin-2-yloxy)phenyl)-methanone;
4-(3-(4-((1H-benzo[d]imidazol-2-yl)difluoromethyl)phenoxy)pyrazin-2-yl)morpholine
(1H-benzo[d]imidazol-2-yl)(4-(3-(4-(2-hydroxypropan-2-yl)piperidin-1-yl)pyrazin-2-yloxy)phenyl)methanone;
(1H-benzo[d]imidazol-2-yl)(4-(3-(4-hydroxypiperidin-1-yl)pyrazin-2-yloxy)phenyl)methanone;
(1H-benzo[d]imidazol-2-yl)(4-(3-(3-hydroxypiperidin-1-yl)pyrazin-2-yloxy)phenyl)methanone;
(1H-benzo[d]imidazol-2-yl)(4-(3-(4-methoxypiperidin-1-yl)pyrazin-2-yloxy)phenyl)methanone;
(1H-benzo[d]imidazol-2-yl)(4-(3-(pyrrolidin-1-yl)pyrazin-2-yloxy)phenyl)methanone;
(1H-benzo[d]imidazol-2-yl)(4-(3-(piperidin-1-yl)pyrazin-2-yloxy)phenyl)methanone;
(R)-(1H-benzo[d]imidazol-2-yl)(4-(3-(2-(methoxymethyl)pyrrolidin-1-yl)pyrazin-2-yloxy)phenyl)methanone;
(1H-benzo[d]imidazol-2-yl)(4-(3-(2,6-dimethylmorpholino)pyrazin-2-yloxy)phenyl)methanone;
(1H-benzo[d]imidazol-2-yl)(4-(3-(4-methylpiperazin-1-yl)pyrazin-2-yloxy)phenyl)methanone;
1-(4-(3-(4-(1H-benzo[d]imidazole-2-carbonyl)phenoxy)pyrazin-2-yl)piperazin-1-yl)ethanone;
1-(3-(4-(1H-benzo[d]imidazole-2-carbonyl)phenoxy)pyrazin-2-yl)piperidine-4-carbonitrile;
(1H-benzo[d]imidazol-2-yl)(4-(3-(tetrahydro-2H-pyran-4-ylamino)pyrazin-2-yloxy)phenyl)methanone;
(1H-benzo[d]imidazol-2-yl)(4-(3-(tetrahydro-2H-pyran-3-ylamino)pyrazin-2-yloxy)phenyl)methanone;
(4-(3-(1,4-oxazepan-4-yl)pyrazin-2-yloxy)phenyl)(1H-benzo[d]imidazol-2-yl)methanone;
(1H-benzo[d]imidazol-2-yl)(4-(3-(4-(methoxymethyl)piperidin-1-yl)pyrazin-2-yloxy)phenyl)methanone;
1-(3-(4-(1H-benzo[d]imidazole-2-carbonyl)phenoxy)pyrazin-2-yl)piperidin-4-one;
(1H-benzo[d]imidazol-2-yl)(4-(3-(4-(trifluoromethyl)piperidin-1-yl)pyrazin-2-yloxy)phenyl)methanone;
(1H-benzo[d]imidazol-2-yl)(4-(3-(4-(2-hydroxyethyl)piperazin-1-yl)pyrazin-2-yloxy)phenyl)methanone;
ethyl 2-(4-(3-(4-(1H-benzo[d]imidazole-2-carbonyl)phenoxy)pyrazin-2-yl)piperazin-1-yl)acetate;
(1H-benzo[d]imidazol-2-yl)(4-(3-(6,7-dihydro-1H-imidazo[4,5-c]pyridin-5(4H)-yl)pyrazin-2-yloxy)phenyl)methanone;
(1H-benzo[d]imidazol-2-yl)(4-(3-(4-methoxypiperidin-1-yl)pyrazin-2-yloxy)phenyl)methanone;
8-(3-(4-(1H-benzo[d]imidazole-2-carbonyl)phenoxy)pyrazin-2-yl)-2-methyl-2,8-diazaspiro[4.5]decan-1-one;
(1H-benzo[d]imidazol-2-yl)(4-(3-(4-morpholinopiperidin-1-yl)pyrazin-2-yloxy)phenyl)methanone;
(±)-(1H-benzo[d]imidazol-2-yl)(4-(3-(3-hydroxypyrrolidin-1-yl)pyrazin-2-yloxy)phenyl)methanone;
4-(3-(4-(1H-benzo[d]imidazole-2-carbonyl)phenoxy)pyrazin-2-yl)-1-methylpiperazin-2-one;
(S)-(1H-benzo[d]imidazol-2-yl)(4-(3-(2-(hydroxymethyl)pyrrolidin-1-yl)pyrazin-2-yloxy)phenyl)methanone;
(S)-(1H-benzo[d]imidazol-2-yl)(4-(3-(3-(hydroxymethyl)pyrrolidin-1-yl)pyrazin-2-yloxy)phenyl)methanone;
(1H-benzo[d]imidazol-2-yl)(4-(3-(3-methyl-5,6-dihydro-[1,2,4]triazolo[4,3-a]pyrazin-7(8H)-yl)pyrazin-2-yloxy)phenyl)methanone;
(R)-(1H-benzo[d]imidazol-2-yl)(4-(3-(3-(hydroxymethyl)pyrrolidin-1-yl)pyrazin-2-yloxy)phenyl)methanone;
(S)-(1H-benzo[d]imidazol-2-yl)(4-(3-(2-(methoxymethyl)pyrrolidin-1-yl)pyrazin-2-yloxy)phenyl)methanone;
(1H-benzo[d]imidazol-2-yl)(4-(3-(4-(2-hydroxyethyl)piperidin-1-yl)pyrazin-2-yloxy)phenyl)methanone;
(±)-1-(3-(4-(1H-benzo[d]imidazole-2-carbonyl)phenoxy)pyrazin-2-yl)piperidine-3-carbonitrile;
(±)-1-(3-(4-(1H-benzo[d]imidazole-2-carbonyl)phenoxy)pyrazin-2-yl)pyrrolidine-3-carbonitrile;
ethyl 1-(3-(4-(1H-benzo[d]imidazole-2-carbonyl)phenoxy)pyrazin-2-yl)piperidine-4-carboxylate;
(±)-methyl 1-(3-(4-(1H-benzo[d]imidazole-2-carbonyl)phenoxy)pyrazin-2-yl)pyrrolidine-3-carboxylate;
(±)-ethyl 1-(3-(4-(1H-benzo[d]imidazole-2-carbonyl)phenoxy)pyrazin-2-yl)piperidine-3-carboxylate;
(±)-(1H-benzo[d]imidazol-2-yl)(4-(3-(3-(3-methyl-1,2,4-oxadiazol-5-yl)pyrrolidin-1-yl)pyrazin-2-yloxy)phenyl)methanone;
(S)-(1H-benzo[d]imidazol-2-yl)(4-(3-3-hydroxypyrrolidin-1-yl)pyrazin-2-yloxy)phenyl)methanone;
(±)-(1H-benzo[d]imidazol-2-yl)(4-(3-(4-(1-hydroxyethyl)piperidin-1-yl)pyrazin-2-yloxy)phenyl)methanone;
1-(3-(4-(1H-benzo[d]imidazole-2-carbonyl)phenoxy)pyrazin-2-yl)piperidine-4-carboxylic acid;
(±)-(1H-benzo[d]imidazol-2-yl)(4-(3-(3-(2-hydroxyethyl)piperidin-1-yl)pyrazin-2-yloxy)phenyl)methanone;
(1H-benzo[d]imidazol-2-yl)(4-(3-(4-(hydroxymethyl)piperidin-1-yl)pyrazin-2-yloxy)phenyl)methanone;
(±)-(1H-benzo[d]imidazol-2-yl)(4-(3-(3-(2-hydroxypropan-2-yl)piperidin-1-yl)pyrazin-2-yloxy)phenyl)methanone;
(±)-4-(3-(4-(1H-benzo[d]imidazole-2-carbonyl)phenoxy)pyrazin-2-yl)-6-methylpiperazin-2-one;
(1H-imidazo[4,5-b]pyridin-2-yl)(4-(3-morpholinopyrazin-2-yloxy)phenyl)methanone;
(4-(3-chloropyrazin-2-yloxy)phenyl)(1H-imidazo[4,5-b]pyridin-2-yl)methanone;
(4-(3-chloropyrazin-2-yloxy)phenyl)(7-fluoro-1H-benzo[d]imidazol-2-yl)methanone;

(4-(3-chloropyrazin-2-yloxy)phenyl)(1-methyl-1H-benzo[d]imidazol-2-yl)methanone;
(1H-benzo[d]imidazol-2-yl)(4-(3-(3-hydroxyazetidin-1-yl)pyrazin-2-yloxy)phenyl)methanone;
(S)-N-(4-(3-(2-(Methoxymethyl)pyrrolidin-1-yl)pyrazin-2-yloxy)phenyl)benzo[d]thiazol-2-amine;
N-(4-(3-(Tetrahydro-2H-pyran-3-ylamino)pyrazin-2-yloxy)phenyl)benzo[d]thiazol-2-amine;
(S)-2-(1-(3-(4-(benzo[d]thiazol-2-ylamino)phenoxy)pyrazin-2-yl)pyrrolidin-2-yl)propan-2-ol;
1-(3-(4-(benzo[d]thiazol-2-ylamino)phenoxy)pyrazin-2-yl)-4-methylpiperidin-4-ol;
Benzo[d]thiazol-2-yl(4-(3-morpholinopyrazin-2-yloxy)phenyl)methanone;
N-(4-(3-Chloropyrazin-2-yloxy)phenyl)-6-fluorobenzo[d]thiazol-2-amine;
N-(4-(3-morpholinopyrazin-2-yloxy)phenyl)-1H-benzo[d]imidazol-2-amine;
5-fluoro-N-(4-(3-morpholinopyrazin-2-yloxy)phenyl)-1H-benzo[d]imidazol-2-amine;
N-(4-(3-morpholinopyrazin-2-yloxy)phenyl)benzo[d]thiazol-2-amine;
2-(1-(3-(4-(benzo[d]thiazol-2-ylamino)phenoxy)pyrazin-2-yl)piperidin-4-yl)propan-2-ol;
1-(3-(4-(benzo[d]thiazol-2-ylamino)phenoxy)pyrazin-2-yl)piperidin-4-ol;
N-(4-(3-(pyrrolidin-1-yl)pyrazin-2-yloxy)phenyl)benzo[d]thiazol-2-amine;
1-(3-(4-(benzo[d]thiazol-2-ylamino)phenoxy)pyrazin-2-yl)piperidin-3-ol;
1-(3-(4-(benzo[d]thiazol-2-ylamino)phenoxy)pyrazin-2-yl)piperidine-4-carbonitrile;
1-(4-(3-(4-(benzo[d]thiazol-2-ylamino)phenoxy)pyrazin-2-yl)piperazin-1-yl)ethanone;
N-(4-(3-(4-methylpiperazin-1-yl)pyrazin-2-yloxy)phenyl)benzo[d]thiazol-2-amine;
2-(1-(3-(4-(benzo[d]thiazol-2-ylamino)phenoxy)pyrazin-2-yl)piperidin-4-yl)-1,1,1-trifluoropropan-2-ol;
N-(4-(3-(2,6-dimethylmorpholino)pyrazin-2-yloxy)phenyl)benzo[d]thiazol-2-amine;
N-(4-((3-(1,1-dioxido-4-thiomorpholinyl)-2-pyrazinyl)oxy)phenyl)-1,3-benzothiazol-2-amine;
(S)-(1-(3-(4-(benzo[d]thiazol-2-ylamino)phenoxy)pyrazin-2-yl)pyrrolidin-2-yl)methanol;
N-(4-(3-(azetidin-1-yl)pyrazin-2-yloxy)phenyl)benzo[d]thiazol-2-amine;
1-(3-(4-(benzo[d]thiazol-2-ylamino)phenoxy)pyrazin-2-yl)azetidine-3-carboxylic acid;
2-(4-(3-(4-(benzo[d]thiazol-2-ylamino)phenoxy)pyrazin-2-yl)piperazin-1-yl)ethanol;
N-(4-(3-(6,7-dihydro-1H-imidazo[4,5-c]pyridin-5(4H)-yl)pyrazin-2-yloxy)phenyl)benzo[d]thiazol-2-amine;
1-(3-(4-(benzo[d]thiazol-2-ylamino)phenoxy)pyrazin-2-yl)piperidine-4-carboxamide;
N-(4-(3-(2-methyl-6,7-dihydro-1H-imidazo[4,5-c]pyridin-5(4H)-yl)pyrazin-2-yloxy)phenyl)benzo[d]thiazol-2-amine;
methyl 1-(3-(4-(benzo[d]thiazol-2-ylamino)phenoxy)pyrazin-2-yl)azetidine-3-carboxylate;
1-(3-(4-(benzo[d]thiazol-2-ylamino)phenoxy)pyrazin-2-yl)pyrrolidine-3-carbonitrile;
(R)-(1-(3-(4-(benzo[d]thiazol-2-ylamino)phenoxy)pyrazin-2-yl)pyrrolidin-3-yl)methanol;
2-(1-(3-(4-(benzo[d]thiazol-2-ylamino)phenoxy)pyrazin-2-yl)piperidin-4-yl)ethanol;
N-(4-(3-(4-(methoxymethyl)piperidin-1-yl)pyrazin-2-yloxy)phenyl)benzo[d]thiazol-2-amine;
N-(4-(3-(3-(methoxymethyl)pyrrolidin-1-yl)pyrazin-2-yloxy)phenyl)benzo[d]thiazol-2-amine;
(1-(3-(4-(benzo[d]thiazol-2-ylamino)phenoxy)pyrazin-2-yl)piperidin-4-yl)methanol;
4-(3-(4-(benzo[d]thiazol-2-ylamino)phenoxy)pyrazin-2-yl)piperazin-2-one;
4-(3-(4-(benzo[d]thiazol-2-ylamino)phenoxy)pyrazin-2-yl)-1-isopropylpiperazin-2-one;
N-(4-(3-(4-methoxypiperidin-1-yl)pyrazin-2-yloxy)phenyl)benzo[d]thiazol-2-amine;
1-(3-(4-(benzo[d]thiazol-2-ylamino)phenoxy)pyrazin-2-yl)azetidine-3-carbonitrile;
4-(3-(4-(benzo[d]thiazol-2-ylamino)phenoxy)pyrazin-2-yl)-6-methylpiperazin-2-one;
1-(1-(3-(4-(benzo[d]thiazol-2-ylamino)phenoxy)pyrazin-2-yl)piperidin-4-yl)ethanol;
methyl 1-(3-(4-(benzo[d]thiazol-2-ylamino)phenoxy)pyrazin-2-yl)pyrrolidine-3-carboxylate;
(1-(3-(4-(benzo[d]thiazol-2-ylamino)phenoxy)pyrazin-2-yl)piperidin-2-yl)methanol;
N-(4-(3-(3-(methoxymethyl)piperidin-1-yl)pyrazin-2-yloxy)phenyl)benzo[d]thiazol-2-amine;
N-(4-(3-(1,4-dioxa-8-azaspiro[4.5]decan-8-yl)pyrazin-2-yloxy)phenyl)benzo[d]thiazol-2-amine;
N-(4-(3-chloropyrazin-2-yloxy)phenyl)-7-fluorobenzo[d]thiazol-2-amine;
N-(4-(3-chloropyrazin-2-yloxy)phenyl)-6-fluorobenzo[d]thiazol-2-amine;
N-(4-(3-chloropyrazin-2-yloxy)phenyl)-5-fluorobenzo[d]thiazol-2-amine;
N-(4-(3-chloropyrazin-2-yloxy)-2-fluorophenyl)benzo[d]thiazol-2-amine;
(1H-benzo[d]imidazol-2-yl)(4-(3-(2-(trifluoromethyl)pyridin-4-yl)pyrazin-2-yloxy)phenyl)methanone;
(1H-benzo[d]imidazol-2-yl)(4-(3-(2-(4-methoxybenzyloxy)pyridin-3-yl)pyrazin-2-yloxy)phenyl)methanone;
3-(3-(4-(1H-benzo[d]imidazole-2-carbonyl)phenoxy)pyrazin-2-yl)pyridin-2(1H)-one;
(1H-benzo[d]imidazol-2-yl)(4-(3-(2-methylpyridin-4-yl)pyrazin-2-yloxy)phenyl)methanone;
4-(3-(4-(1H-benzo[d]imidazole-2-carbonyl)phenoxy)pyrazin-2-yl)benzonitrile;
(1H-benzo[d]imidazol-2-yl)(4-(3-(2-methylpyridin-3-yl)pyrazin-2-yloxy)phenyl)methanone;
(1-methyl-1H-benzo[d]imidazol-2-yl)(4-(3-(2-methylpyridin-3-yl)pyrazin-2-yloxy)phenyl)methanone;
(1H-benzo[d]imidazol-2-yl)(4-(3-(2,6-dimethoxypyridin-3-yl)pyrazin-2-yloxy)phenyl)methanone;
(1H-benzo[d]imidazol-2-yl)(4-(3-(4-methoxypyridin-3-yl)pyrazin-2-yloxy)phenyl)methanone;
(1H-benzo[d]imidazol-2-yl)(4-(3-(3-methoxypyridin-4-yl)pyrazin-2-yloxy)phenyl)methanone;
(1H-benzo[d]imidazol-2-yl)(4-(3-(2-methoxyphenyl)pyrazin-2-yloxy)phenyl)methanone;
(1H-benzo[d]imidazol-2-yl)(4-(3-(2-methoxyquinolin-3-yl)pyrazin-2-yloxy)phenyl)methanone;
(1H-benzo[d]imidazol-2-yl)(4-(3-(5-fluoro-2-methoxypyridin-3-yl)pyrazin-2-yloxy)phenyl)methanone;
(5-fluoro-1H-benzo[d]imidazol-2-yl)(4-(3-(2-methoxypyridin-3-yl)pyrazin-2-yloxy)phenyl)methanone;
(1H-benzo[d]imidazol-2-yl)(4-(3-(5-methoxypyridin-3-yl)pyrazin-2-yloxy)phenyl)methanone;
(4-(3-(2-methoxypyridin-3-yl)pyrazin-2-yloxy)phenyl)(1-methyl-1H-benzo[d]imidazol-2-yl)methanone;
(1H-benzo[d]imidazol-2-yl)(4-(3-(2-methoxypyridin-4-yl)pyrazin-2-yloxy)phenyl)methanone;

(1H-benzo[d]imidazol-2-yl)(4-(3-(6-methoxypyridin-3-yl)pyrazin-2-yloxy)phenyl)methanone;
(1H-benzo[d]imidazol-2-yl)(4-(3-(2-methoxypyridin-3-yl)pyrazin-2-yloxy)phenyl)methanone;
(1H-benzo[d]imidazol-2-yl)(4-(3-(pyridin-3-yl)pyrazin-2-yloxy)phenyl)methanone;
(1H-benzo[d]imidazol-2-yl)(4-(3-(pyridin-4-yl)pyrazin-2-yloxy)phenyl)methanone;
3-(3-(4-(1H-benzo[d]imidazole-2-carbonyl)phenoxy)pyrazin-2-yl)benzonitrile;
methyl 4-(3-(4-(1H-benzo[d]imidazole-2-carbonyl)phenoxy)pyrazin-2-yl)benzoate;
4-(3-(4-(1H-benzo[d]imidazole-2-carbonyl)phenoxy)pyrazin-2-yl)benzoic acid;
(1H-benzo[d]imidazol-2-yl)(4-(3-(3-methoxyphenyl)pyrazin-2-yloxy)phenyl)methanone;
(1H-benzo[d]imidazol-2-yl)(4-(3-(quinolin-4-yl)pyrazin-2-yloxy)phenyl)methanone;
(1H-benzo[d]imidazol-2-yl)(4-(3-(quinolin-5-yl)pyrazin-2-yloxy)phenyl)methanone;
(4-(3-(3,6-dihydro-2H-pyran-4-yl)pyrazin-2-yloxy)phenyl)(1H-imidazo[4,5-b]pyridin-2-yl)methanone;
2-(3-(4-(1H-benzo[d]imidazole-2-carbonyl)phenoxy)pyrazin-2-yl)-4,4-dimethylcyclohex-2-enone;
1-(4-(3-(4-(1H-benzo[d]imidazole-2-carbonyl)phenoxy)pyrazin-2-yl)-5,6-dihydropyridin-1(2H)-yl)ethanone;
(1-(2-fluoroethyl)-1H-benzo[d]imidazol-2-yl)(4-(3-(2-methoxypyridin-3-yl)pyrazin-2-yloxy)phenyl)methanone;
N-(4-(3-(2-methylpyridin-4-yl)pyrazin-2-yloxy)phenyl)benzo[d]thiazol-2-amine;
3-(3-(4-(benzo[d]thiazol-2-ylamino)-3-fluorophenoxy)pyrazin-2-yl)cyclohex-2-enone;
(rac)-3-(3-(4-(benzo[d]thiazol-2-ylamino)-3-fluorophenoxy)pyrazin-2-yl)cyclohex-2-enol;
N-(4-(3-(6-morpholinopyridin-3-yl)pyrazin-2-yloxy)phenyl)benzo[d]thiazol-2-amine;
N-(4-(3-(4-morpholinophenyl)pyrazin-2-yloxy)phenyl)benzo[d]thiazol-2-amine;
N-(4-(3-(6-methylpyridin-3-yl)pyrazin-2-yloxy)phenyl)benzo[d]thiazol-2-amine;
N-(4-(3-(1H-pyrrolo[2,3-b]pyridin-5-yl)pyrazin-2-yloxy)phenyl)benzo[d]thiazol-2-amine;
5-(3-(4-(benzo[d]thiazol-2-ylamino)phenoxy)pyrazin-2-yl)picolinonitrile
N-(4-(3-(pyrimidin-5-yl)pyrazin-2-yloxy)phenyl)benzo[d]thiazol-2-amine;
N-(4-(3-(2-methoxypyrimidin-5-yl)pyrazin-2-yloxy)phenyl)benzo[d]thiazol-2-amine;
N-(4-(3-(6-chloropyridin-3-yl)pyrazin-2-yloxy)phenyl)benzo[d]thiazol-2-amine;
(5-(3-(4-(benzo[d]thiazol-2-ylamino)phenoxy)pyrazin-2-yl)pyridin-2-yl)methanol;
N-(4-(3-(quinolin-5-yl)pyrazin-2-yloxy)phenyl)benzo[d]thiazol-2-amine;
N-(4-(3-(pyridin-3-yl)pyrazin-2-yloxy)phenyl)benzo[d]thiazol-2-amine;
N-(4-(3-(3-methoxypyridin-4-yl)pyrazin-2-yloxy)phenyl)benzo[d]thiazol-2-amine;
N-(4-(3-(3-methoxyphenyl)pyrazin-2-yloxy)phenyl)benzo[d]thiazol-2-amine;
7-fluoro-N-(4-(3-(2-methoxypyridin-3-yl)pyrazin-2-yloxy)phenyl)benzo[d]thiazol-2-amine;
N-(4-(3-(2-methoxypyridin-4-yl)pyrazin-2-yloxy)phenyl)benzo[d]thiazol-2-amine;
6-fluoro-N-(4-(3-(2-methoxypyridin-3-yl)pyrazin-2-yloxy)phenyl)benzo[d]thiazol-2-amine;
5-fluoro-N-(4-(3-(2-methoxypyridin-3-yl)pyrazin-2-yloxy)phenyl)benzo[d]thiazol-2-amine;
N-(4-(3-(2-methoxypyridin-3-yl)pyrazin-2-yloxy)phenyl)benzo[d]thiazol-2-amine;
N-(4-(3-(5-methoxypyridin-3-yl)pyrazin-2-yloxy)phenyl)benzo[d]thiazol-2-amine;
N-(2-fluoro-4-(3-(2-methoxypyridin-3-yl)pyrazin-2-yloxy)phenyl)benzo[d]thiazol-2-amine;
N-(2-fluoro-4-(3-(2-fluoropyridin-4-yl)pyrazin-2-yloxy)phenyl)benzo[d]thiazol-2-amine;
tert-butyl 4-(3-(4-(benzo[d]thiazol-2-ylamino)-3-fluorophenoxy)pyrazin-2-yl)-5,6-dihydropyridine-1(2H)-carboxylate;
(1H-benzo[d]imidazol-2-yl)(4-(3-methoxypyrazin-2-yloxy)phenyl)methanone;
(1H-benzo[d]imidazol-2-yl)(4-(3-isopropoxypyrazin-2-yloxy)phenyl)methanone;
(1H-benzo[d]imidazol-2-yl)(4-(3-isobutoxypyrazin-2-yloxy)phenyl)methanone;
(1H-benzo[d]imidazol-2-yl)(4-(3-(cyclopropylmethoxy)pyrazin-2-yloxy)phenyl)methanone;
(1H-benzo[d]imidazol-2-yl)(4-(3-(2,2,2-trifluoroethoxy)pyrazin-2-yloxy)phenyl)methanone;
(1H-benzo[d]imidazol-2-yl)(4-(3-(2-methoxyethoxy)pyrazin-2-yloxy)phenyl)methanone;
(1H-benzo[d]imidazol-2-yl)(4-(3-(pyridin-2-ylmethoxy)pyrazin-2-yloxy)phenyl)methanone;
(1H-benzo[d]imidazol-2-yl)(4-(3-phenoxypyrazin-2-yloxy)phenyl)methanone;
(1H-benzo[d]imidazol-2-yl)(4-(3-(pyridin-3-yloxy)pyrazin-2-yloxy)phenyl)methanone;
(1H-benzo[d]imidazol-2-yl)(4-(3-(but-2-ynyloxy)pyrazin-2-yloxy)phenyl)methanone;
(1H-benzo[d]imidazol-2-yl)(4-(3-(2-(4-methylthiazol-5-yl)ethoxy)pyrazin-2-yloxy)phenyl)methanone;
(1H-benzo[d]imidazol-2-yl)(4-(3-((tetrahydrofuran-3-yl)methoxy)pyrazin-2-yloxy)phenyl)methanone;
(1H-benzo[d]imidazol-2-yl)(4-(3-(2-morpholino ethoxy)pyrazin-2-yloxy)phenyl)methanone;
(1H-benzo[d]imidazol-2-yl)(4-(3-(2-(pyrrolidin-1-yl)ethoxy)pyrazin-2-yloxy)phenyl)methanone;
(1H-benzo[d]imidazol-2-yl)(4-(3-(2-(dimethylamino)ethoxy)pyrazin-2-yloxy)phenyl)methanone;
(1H-benzo[d]imidazol-2-yl)(4-(3-(2-(1-methylpyrrolidin-2-yl)ethoxy)pyrazin-2-yloxy)phenyl)methanone;
(1H-benzo[d]imidazol-2-yl)(4-(3-(pyridin-4-ylmethoxy)pyrazin-2-yloxy)phenyl)methanone;
(1H-benzo[d]imidazol-2-yl)(4-(3-(2-(pyridin-2-yl)ethoxy)pyrazin-2-yloxy)phenyl)methanone;
(1H-benzo[d]imidazol-2-yl)(4-(3-(3-(pyridin-3-yl)propoxy)pyrazin-2-yloxy)phenyl)methanone;
(1H-benzo[d]imidazol-2-yl)(4-(3-(pyridin-3-ylmethoxy)pyrazin-2-yloxy)phenyl)methanone;
(1H-benzo[d]imidazol-2-yl)(4-(3-propoxypyrazin-2-yloxy)phenyl)methanone;
(1H-benzo[d]imidazol-2-yl)(4-(3-(tetrahydro-2H-pyran-4-yl)pyrazin-2-yloxy)phenyl)methanone;
(1H-imidazo[4,5-b]pyridin-2-yl)(4-(3-(tetrahydro-2H-pyran-4-yl)pyrazin-2-yloxy)phenyl)methanone;
(6-fluoro-1H-benzo[d]imidazol-2-yl)(4-(3-(tetrahydro-2H-pyran-4-yl)pyrazin-2-yloxy)phenyl)methanone;
(1-methyl-1H-benzo[d]imidazol-2-yl)(4-(3-(tetrahydro-2H-pyran-4-yl)pyrazin-2-yloxy)phenyl)methanone;
(6-fluoro-1-methyl-1H-benzo[d]imidazol-2-yl)(4-(3-(tetrahydro-2H-pyran-4-yl)pyrazin-2-yloxy)phenyl)methanone;

(5-fluoro-1-methyl-1H-benzo[d]imidazol-2-yl)(4-(3-(tetrahydro-2H-pyran-4-yl)pyrazin-2-yloxy)phenyl)methanone;
1H-benzimidazol-2-yl(4-((3-(tetrahydro-2H-pyran-3-yl)-2-pyrazinyl)oxy)-phenyl)methanone;
1H-Benzimidazol-2-yl(4-((3-(4-methoxy-1-cyclohexen-1-yl)-2-pyrazinyl) oxy)phenyl)methanone;
1H-benzimidazol-2-yl(4-((3-(cis-4-hydroxycyclohexyl)-2-pyrazinyl)oxy)phenyl)methanone; and 1H-benzimidazol-2-yl(4-((3-(trans-4-hydroxycyclohexyl)-2-pyrazinyl)oxy)phenyl)methanone;
(rac)-cis-(1H-benzo[d]imidazol-2-yl)(4-(3-(3-hydroxycyclohexyl)pyrazin-2-yloxy)phenyl)methanone;
(rac)-trans-(1H-benzo[d]imidazol-2-yl)(4-(3-(3-hydroxycyclohexyl)pyrazin-2-yloxy)phenyl)methanone;
(rac)-cis-3-(3-(4-(benzo[d]thiazol-2-ylamino)phenoxy)pyrazin-2-yl)cyclohexanol;
(rac)-trans-3-(3-(4-(benzo[d]thiazol-2-ylamino)phenoxy)pyrazin-2-yl)cyclohexanol;
N-(4-(3-(Tetrahydro-2H-pyran-3-yl)pyrazin-2-yloxy)phenyl)benzo[d]thiazol-2-amine;
(rac)-3-(3-(4-(benzo[d]thiazol-2-ylamino)phenoxy)pyrazin-2-yl)cyclohexanone;
4-(2-(4-(1H-Benzo[d]imidazole-2-carbonyl)phenoxy)pyridin-3-yl)cyclohexanone;
(1H-Benzo[d]imidazol-2-yl)(4-(3-((1s,4s)-4-hydroxy-4-methylcyclohexyl)pyridin-2-yloxy)phenyl)methanone;
(1H-Benzo[d]imidazol-2-yl)(4-(3-((1r,4r)-4-hydroxy-4-methylcyclohexyl)pyridin-2-yloxy)phenyl)methanone;
(1H-Benzo[d]imidazol-2-yl)(4-(3-(oxepan-4-yl)pyrazin-2-yloxy)phenyl)methanone;
(1H-benzo[d]imidazol-2-yl)(4-(3-(4,4-difluorocyclohex-1-enyl)pyrazin-2-yloxy)phenyl)methanone;
4-(3-(4-(benzo[d]thiazol-2-ylamino)phenoxy)pyrazin-2-yl)tetrahydro-2H-pyran-4-carbonitrile;
N-methyl-N-(4-(3-(tetrahydro-2H-pyran-4-yl)pyrazin-2-yloxy)phenyl)benzo[d]thiazol-2-amine;
4-(3-(4-(benzo[d]thiazol-2-ylamino)phenoxy)pyrazin-2-yl)tetrahydro-2H-pyran-4-ol;
(1H-benzo[d]imidazol-2-yl)(4-(3-(4-fluorotetrahydro-2H-pyran-4-yl)pyrazin-2-yloxy)phenyl)methanone;
N-(4-(3-(4-fluorotetrahydro-2H-pyran-4-yl)pyrazin-2-yloxy)phenyl)benzo[d]thiazol-2-amine;
1-tert-butyl 4-methyl 4-(4-(benzo[d]thiazol-2-ylamino)phenoxy)pyrazin-2-yl)piperidine-1,4-dicarboxylate;
tert-butyl 4-(3-(4-(benzo[d]thiazol-2-ylamino)phenoxy)pyrazin-2-yl)-4-(hydroxymethyl)piperidine-1-carboxylate;
N-(4-(3-(Tetrahydro-2H-pyran-4-yl)pyrazin-2-yloxy)phenyl)-1H-benzo[d]imidazol-2-amine;
N-(4-(3-(Tetrahydro-2H-pyran-4-yl)pyrazin-2-yloxy)phenyl)benzo[d]thiazol-2-amine;
7-M ethoxy-N-(4-(3-(tetrahydro-2H-pyran-4-yl)pyrazin-2-yloxy)phenyl)-1H-benzo[d]imidazol-2-amine;
(rac)-3-(3-(4-(1H-benzo[d]imidazole-2-carbonyl)phenoxy)pyrazin-2-yl)cyclohexanone;
4-(3-(4-(1H-benzo[d]imidazole-2-carbonyl)phenoxy)pyrazin-2-yl)tetrahydro-2H-pyran-4-carbonitrile;
methyl 4-(3-(4-(benzo[d]thiazol-2-ylamino)phenoxy)pyrazin-2-yl)tetrahydro-2H-pyran-4-carboxylate;
(1H-benzo[d]imidazol-2-yl)(4-(3-(4-hydroxytetrahydro-2H-pyran-4-yl)pyrazin-2-yloxy)phenyl)methanone;
6-fluoro-N-(4-(3-(tetrahydro-2H-pyran-4-yl)pyrazin-2-yloxy)phenyl)benzo[d]thiazol-2-amine;
N-(2-fluoro-4-(3-(tetrahydro-2H-pyran-4-yl)pyrazin-2-yloxy)phenyl)benzo[d]thiazol-2-amine;
N-(2-fluoro-4-(pyrazin-2-yloxy)phenyl)benzo[d]thiazol-2-amine;
7-fluoro-N-(4-(pyrazin-2-yloxy)phenyl)benzo[d]thiazol-2-amine;
5-fluoro-N-(4-(3-(tetrahydro-2H-pyran-4-yl)pyrazin-2-yloxy)phenyl)benzo[d]thiazol-2-amine;
5-fluoro-N-(4-(pyrazin-2-yloxy)phenyl)benzo[d]thiazol-2-amine;
(1H-benzo[d]imidazol-2-yl)(4-(3-cyclopentylpyrazin-2-yloxy)phenyl)methanone;
N-(4-(3-(tetrahydrofuran-3-yl)pyrazin-2-yloxy)phenyl)benzo[d]thiazol-2-amine;
1H-benzo[d]imidazole-2-yl(4-(3-(tetrahydro-2H-thiopyran-4-yl)pyrazin-2-yloxy)phenyl)methanone;
N-(4-(3-cyclopentylpyrazin-2-yloxy)phenyl)benzo[d]thiazol-2-amine;
1-(4-(3-(4-(1H-benzo[d]imidazole-2-carbonyl)phenoxy)pyrazin-2-yl)piperidin-1-yl)ethanone;
1-(4-(3-(4-(benzo[d]thiazol-2-ylamino)phenoxy)pyrazin-2-yl)piperidin-1-yl)ethanone;
(1H-benzo[d]imidazol-2-yl)(4-(3-(1-(2-fluoroethyl)piperidin-4-yl)pyrazin-2-yloxy)phenyl)methanone;
methyl 4-(3-(4-(1H-benzo[d]imidazole-2-carbonyl)phenoxy)pyrazin-2-yl)piperidine-1-carboxylate;
1-(4-(3-(4-((1H-benzo[d]imidazol-2-yl)(hydroxy)methyl)phenoxy)pyrazin-2-yl)piperidin-1-yl)ethanone;
(1H-benzo[d]imidazol-2-yl)(4-(3-(2-methoxypyridin-3-yl)pyrazin-2-yloxy)phenyl)methanol;
(1H-benzo[d]imidazol-2-yl)(4-(3-(piperidin-4-yl)pyrazin-2-yloxy)phenyl)methanone;
1-(4-(3-(4-(1H-benzo[d]imidazole-2-carbonyl)phenoxy)pyrazin-2-yl)piperidin-1-yl)perdeuteroethanone;
1-(4-(3-(4-(1H-benzo[d]imidazole-2-carbonyl)phenoxy)pyrazin-2-yl)piperidin-1-yl)-2-methoxyethanone;
1-(4-(3-(4-(benzo[d]thiazol-2-ylamino)phenoxy)pyrazin-2-yl)piperidin-1-yl)-2-methoxyethanone;
1-(4-(3-(4-(1H-benzo[d]imidazole-2-carbonyl)phenoxy)pyrazin-2-yl)piperidin-1-yl)-2-fluoropropan-1-one;
1-(4-(3-(4-(benzo[d]thiazol-2-ylamino)phenoxy)pyrazin-2-yl)piperidin-1-yl)-2-fluoropropan-1-one;
N-(4-(3-(1-(2-fluoroethyl)piperidin-4-yl)pyrazin-2-yloxy)phenyl)benzo[d]thiazol-2-amine;
N-(4-(3-(1-methylpiperidin-4-yl)pyrazin-2-yloxy)phenyl)benzo[d]thiazol-2-amine;
1-(4-(3-(4-(1H-benzo[d]imidazole-2-carbonyl)phenoxy)pyrazin-2-yl)piperidin-1-yl)-1-oxopropan-2-yl acetate;
1-(4-(3-(4-(benzo[d]thiazol-2-ylamino)phenoxy)pyrazin-2-yl)piperidin-1-yl)-2-hydroxypropan-1-one;
1-(3-(3-(4-(1H-benzo[d]imidazole-2-carbonyl)phenoxy)pyrazin-2-yl)pyrrolidin-1-yl)ethanone;
1-(3-(3-(4-(benzo[d]thiazol-2-ylamino)phenoxy)pyrazin-2-yl)pyrrolidin-1-yl)ethanone;
1-(4-(3-(4-(1-methyl-1H-benzo[d]imidazole-2-carbonyl)phenoxy)pyrazin-2-yl)piperidin-1-yl)ethanone;
2-methoxy-1-(4-(3-(4-(1-methyl-1H-benzo[d]imidazole-2-carbonyl)phenoxy)pyrazin-2-yl)piperidin-1-yl)ethanone;
2-(4-(3-(4-(1H-benzo[d]imidazole-2-carbonyl)phenoxy)pyrazin-2-yl)piperidin-1-yl)-2-oxoethyl acetate;
1-(4-(3-(4-(1H-benzo[d]imidazole-2-carbonyl)phenoxy)pyrazin-2-yl)piperidin-1-yl)-2-(dimethylamino)ethanone;
1-(4-(3-(4-(benzo[d]thiazol-2-ylamino)phenoxy)pyrazin-2-yl)piperidin-1-yl)-2-(dimethylamino)ethanone;
3-(4-(3-(4-(1H-benzo[d]imidazole-2-carbonyl)phenoxy)pyrazin-2-yl)piperidin-1-yl)-3-oxopropanenitrile;

1-(4-(3-(4-(benzo[d]thiazol-2-ylamino)-2-fluorophenoxy)pyrazin-2-yl)piperidin-1-yl)ethanone;
1-(4-(3-(6-(benzo[d]thiazol-2-ylamino)pyridin-3-yloxy)pyrazin-2-yl)piperidin-1-yl)ethanone;
1-(3-(3-(4-(1H-benzo[d]imidazole-2-carbonyl)phenoxy)pyrazin-2-yl)azetidin-1-yl)ethanone;
1-(3-(3-(4-(1H-benzo[d]imidazole-2-carbonyl)phenoxy)pyrazin-2-yl)piperidin-1-yl)ethanone;
4-(3-(4-(1H-Benzo[d]imidazole-2-carbonyl)phenoxy)pyrazin-2-yl)-1-methyl-5,6-dihydropyridin-2(1H)-one;
4-(3-(4-(1H-Benzo[d]imidazole-2-carbonyl)phenoxy)pyrazin-2-yl)-1-methylpiperidin-2-one;
3-(4-(1H-benzo[d]imidazole-2-carbonyl)phenoxy)-N-phenethylpyrazine-2-carboxamide;
3-(4-(1H-benzo[d]imidazole-2-carbonyl)phenoxy)-N-(4-(trifluoromethyl)phenethyl)pyrazine-2-carboxamide;
(S)-3-(4-(1H-benzo[d]imidazole-2-carbonyl)phenoxy)-N-(1-methoxypropan-2-yl)pyrazine-2-carboxamide;
3-(4-(1H-benzo[d]imidazole-2-carbonyl)phenoxy)-N-(2-(pyridin-2-yl)ethyl)pyrazine-2-carboxamide;
3-(4-(1H-benzo[d]imidazole-2-carbonyl)phenoxy)-N-(2-hydroxyethyl)pyrazine-2-carboxamide;
(rac)-3-(4-(1H-benzo[d]imidazole-2-carbonyl)phenoxy)-N-(1-(pyridin-2-yl)propan-2-yl)pyrazine-2-carboxamide;
3-(4-(1H-benzo[d]imidazole-2-carbonyl)phenoxy)-N-(1-benzylcyclopropyl)pyrazine-2-carboxamide;
(R)-1-(3-(4-(1H-benzo[d]imidazole-2-carbonyl)phenoxy)pyrazin-2-yl)pyrrolidine-3-carbonitrile;
(S)-1-(3-(4-(1H-benzo[d]imidazole-2-carbonyl)phenoxy)pyrazin-2-yl)pyrrolidine-3-carbonitrile;
(R)-ethyl 1-(3-(4-(1H-benzo[d]imidazole-2-carbonyl)phenoxy)pyrazin-2-yl)piperidine-3-carboxylate;
(S)-ethyl 1-(3-(4-(1H-benzo[d]imidazole-2-carbonyl)phenoxy)pyrazin-2-yl)piperidine-3-carboxylate;
(S)-methyl 1-(3-(4-(1H-benzo[d]imidazole-2-carbonyl)phenoxy)pyrazin-2-yl)pyrrolidine-3-carboxylate;
(R)-methyl 1-(3-(4-(1H-benzo[d]imidazole-2-carbonyl)phenoxy)pyrazin-2-yl)pyrrolidine-3-carboxylate;
(R)-4-(3-(4-(benzo[d]thiazol-2-ylamino)phenoxy)pyrazin-2-yl)-6-methylpiperazin-2-one;
(S)-4-(3-(4-(benzo[d]thiazol-2-ylamino)phenoxy)pyrazin-2-yl)-6-methylpiperazin-2-one;
(1H-benzo[d]imidazol-2-yl)(4-(3-((1R,3S)-3-hydroxycyclohexyl)pyrazin-2-yloxy)phenyl)methanone;
(1H-benzo[d]imidazol-2-yl)(4-(3-((1S,3R)-3-hydroxycyclohexyl)pyrazin-2-yloxy)phenyl)methanone;
(1S,3R)-3-(3-(4-(benzo[d]thiazol-2-ylamino)phenoxy)pyrazin-2-yl)cyclohexanol;
(1R,3S)-3-(3-(4-(benzo[d]thiazol-2-ylamino)phenoxy)pyrazin-2-yl)cyclohexanol;
(1H-benzo[d]imidazol-2-yl)(4-(3-((1S,3S)-3-hydroxycyclohexyl)pyrazin-2-yloxy)phenyl)methanone;
(1H-benzo[d]imidazol-2-yl)(4-(3-((1R,3R)-3-hydroxycyclohexyl)pyrazin-2-yloxy)phenyl)methanone;
(1S,3S)-3-(3-(4-(benzo[d]thiazol-2-ylamino)phenoxy)pyrazin-2-yl)cyclohexanol;
(1R,3R)-3-(3-(4-(benzo[d]thiazol-2-ylamino)phenoxy)pyrazin-2-yl)cyclohexanol;
(R)-1-(4-(3-(4-(1H-benzo[d]imidazole-2-carbonyl)phenoxy)pyrazin-2-yl)piperidin-1-yl)-2-fluoropropan-1-one;
(S)-1-(4-(3-(4-(1H-benzo[d]imidazole-2-carbonyl)phenoxy)pyrazin-2-yl)piperidin-1-yl)-2-fluoropropan-1-one;
(R)-1-(4-(3-(4-(benzo[d]thiazol-2-ylamino)phenoxy)pyrazin-2-yl)piperidin-1-yl)-2-fluoropropan-1-one;
(S)-1-(4-(3-(4-(benzo[d]thiazol-2-ylamino)phenoxy)pyrazin-2-yl)piperidin-1-yl)-2-fluoropropan-1-one;
(R)-3-(3-(4-(benzo[d]thiazol-2-ylamino)phenoxy)pyrazin-2-yl)cyclohexanone;
(S)-3-(3-(4-(benzo[d]thiazol-2-ylamino)phenoxy)pyrazin-2-yl)cyclohexanone; or
any pharmaceutically-acceptable salt thereof.

The compounds of this invention may have in general several asymmetric centers and are typically depicted in the form of racemic mixtures. This invention is intended to encompass racemic mixtures, partially racemic mixtures and separate enantiomers and diasteromers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^{2}H$ and $^{3}H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

"$C_{\alpha-\beta}$alk" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0$alk indicates a direct bond. Examples of $C_{1-6}$alkyl include, but are not limited to the following:

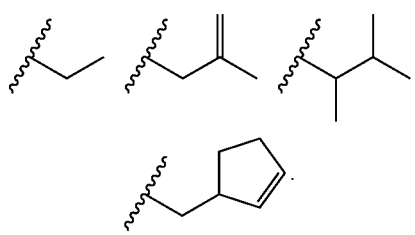

"Benzo group", alone or in combination, means the divalent radical C$_4$H$_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I.

"C$_{\alpha-\beta}$haloalk" means an alk group, as described above, wherein any number—at least one—of the hydrogen atoms attached to the alk chain are replaced by F, Cl, Br or I.

The group N(R$^a$)R$^a$ and the like include substituents where the two R$^a$ groups together form a ring, optionally including a N, O or S atom, and include groups such as:

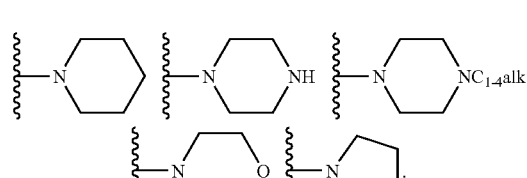

The group N(C$_{\alpha-\beta}$alk) C$_{\alpha-\beta}$alk, wherein α and β are as defined above, include substituents where the two C$_{\alpha-\beta}$alk groups together form a ring, optionally including a N, O or S atom, and include groups such as:

"Carbocycle" means a ring comprising by itself or in combination with other terms, represents, unless otherwise stated, cyclic version of "C$_{\alpha-\beta}$alk". Thus, the term "carbocycle" is meant to be included in the terms "C$_{\alpha-\beta}$alk". Examples of carbocycle include cyclopentyl, cyclohexyl, 1-cyclohexenyl, 3-cyclohexenyl, cycloheptyl, cyclobutylene, cyclohexylene and the like.

"Heterocycle" means a ring comprising at least one carbon atom and at least one other atom selected from N, O and S. Examples of heterocycles that may be found in the claims include, but are not limited to, the following:

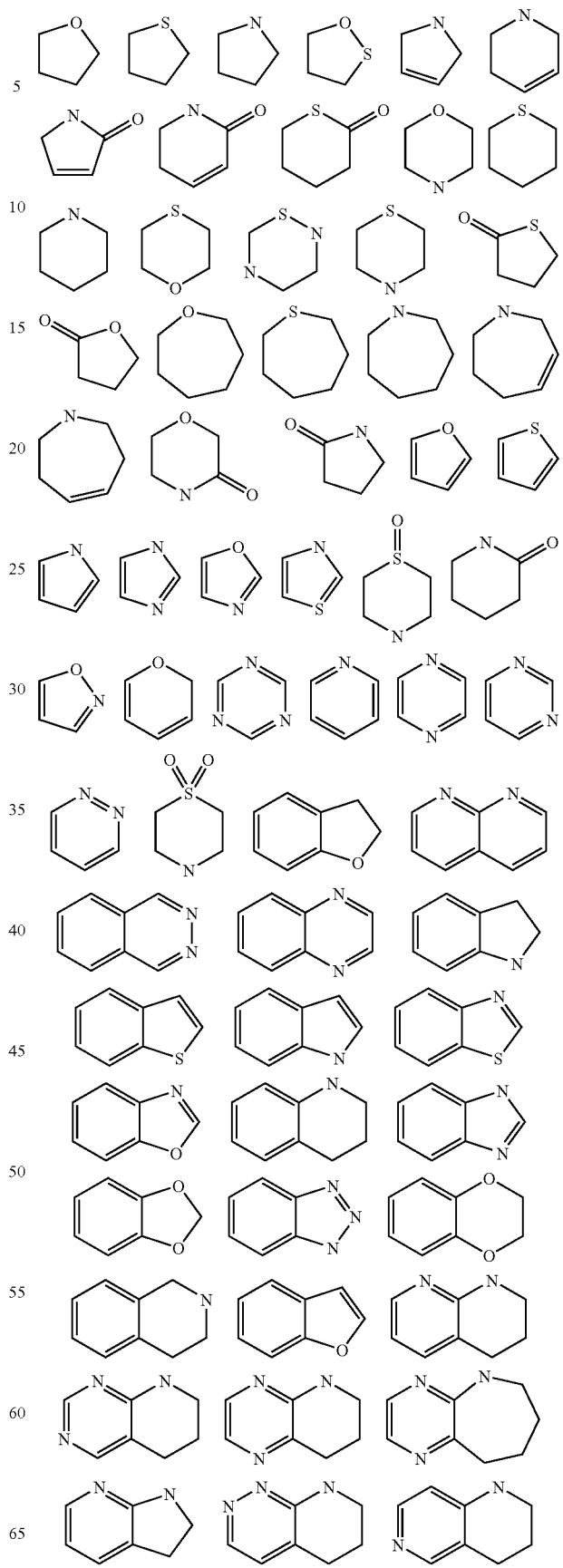

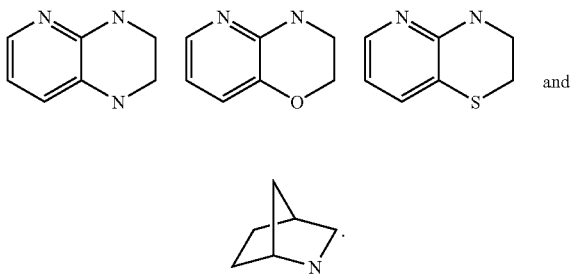

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Sylilation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

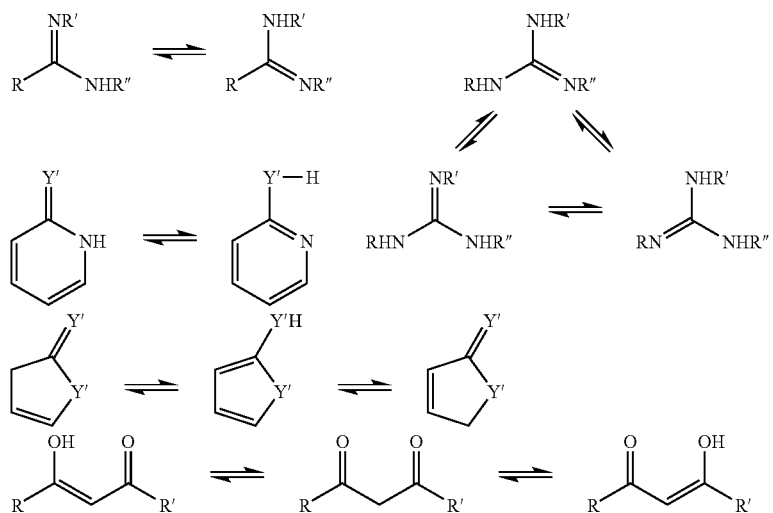

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . ." and "is . . . or . . ." (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Utility and Methods of Use

Provided herein are methods for treating a disorder or disease by inhibiting PDE10 enzyme. The methods, in general, comprises the step of administering a therapeutically effective amount of a compounds of the present invention, or an individual stereoisomer, a mixture of stereoisomers, or a pharmaceutically acceptable salt or solvate thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-10A, intracellular levels of cAMP are increased, thereby increasing the release of insulin-containing secretory granules and, therefore, increasing insulin secretion. See, for example, WO 2005/012485, which is hereby incorporated by reference in its entirety. The compounds of Formula (I) can also be used to treat diseases disclosed in US Patent application publication No. 2006/019975, the disclosure of which is incorporated herein by reference in its entirety.

Testing

The PDE10 inhibitory activities of the compounds of the present invention can be tested, for example, using the in vitro and in vivo assays described in the Biological Examples below.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

EXPERIMENTAL

In the following schemes, the compounds of the invention, along with their definitions, such as m, n, p, $R^1$, $R^2$, $R^3$, $R^4$, $X^1$, $X^2$, $X^3$, $X^4$, $X^5$, $X^6$, $X^7$, $X^8$, $X^9$, $X^{10}$, $X^{11}$, Y and Z, are as described above.

Unless otherwise noted, all materials were obtained from commercial suppliers and used without further purification. All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

The following abbreviations are used:
DCM—dichloromethane
DMSO—dimethyl sulfoxide
DMF—N,N-dimethylformamide
THF—tetrahydrofuran
Et$_2$O—diethyl ether
EtOAc—ethyl acetate
MeOH—methyl alcohol
EtOH—ethyl alcohol
IPA—isopropyl alcohol
Me—methyl
MeCN—acetonitrile
MeI—iodomethane
NMP—1-methyl-2-pyrrolidinone
DCM—dichloromethane
TFA—trifluoroacetic acid
MTBE—methyl tert-butyl ether
DIPEA—diisopropylethyl amine
HBTU—2-(1H-Benzotriazole-1-yl)-1,1,3,3-tetramethylaminium hexafluorophosphate
HATU—O-(7-Azobenzotriazol-1-yl)-1,1,3,3-tetramethyluronium hexafluorophosphate
Sat.—saturated
h—hour
min—minutes
mL—milliliters
g—grams
mg—milligrams All compounds were divided in five classes based on their IC50 values against PDE10. The range of the IC50 in each class is as follows:

"+" designates an $IC_{50}$ value in the range beginning from 1.0 uM and ending at 5.0 uM;

"++" designates an $IC_{50}$ value in the range beginning from 250 nM and ending at 1.0 uM;

"+++" designates an $IC_{50}$ value in the range beginning from 100 nM and ending at 250 nM;

"++++" designates an $IC_{50}$ value in the range beginning from 25 nM and ending at 100 nM; and "+++++" designates an $IC_{50}$ value of less than 25 nM.

SCHEME 7

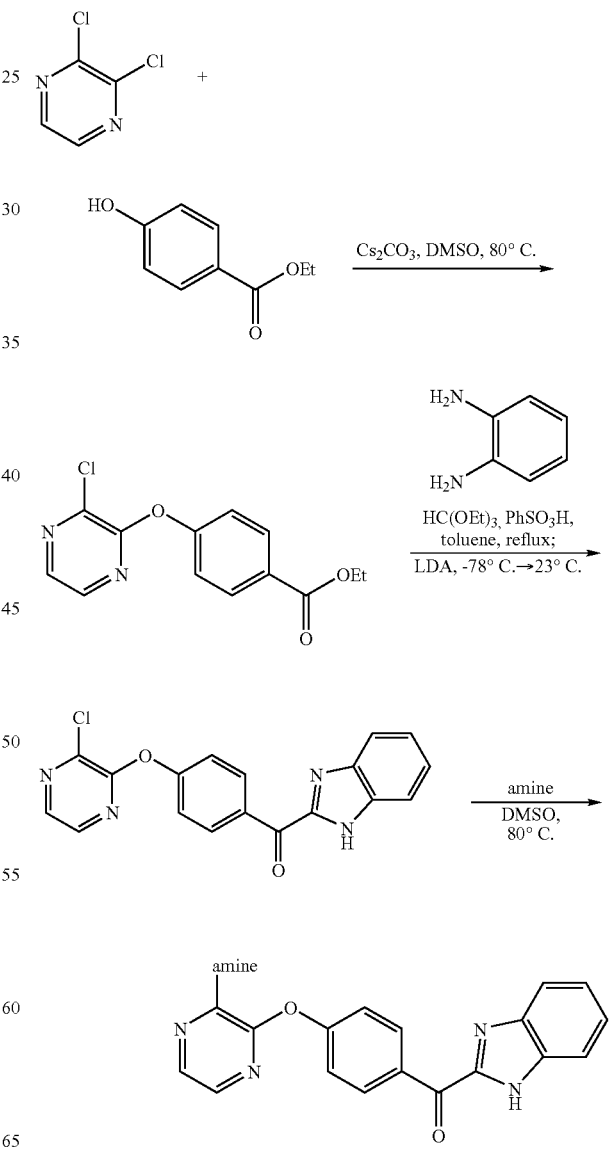

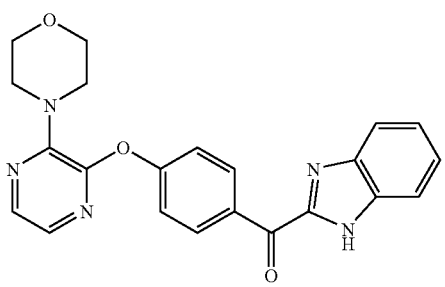

Example 1

(1H-BENZO[D]IMIDAZOL-2-YL)(4-(3-MOR-PHOLINOPYRAZIN-2-YLOXY)-PHENYL)METHANONE

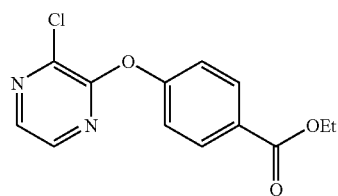

STEP 1. ETHYL 4-(3-CHLOROPYRAZIN-2-YLOXY) BENZOATE

To a solution of 4-hydroxybenzoic acid ethyl ester (55.21 g, 332.3 mmol) and 2,3-dichloropyrazine (49.50 g, 332.3 mmol) in DMSO (300 mL) was added cesium carbonate (129.9 g, 398.7 mmol). The mixture was heated to 70° C. until the starting material was consumed. The mixture was cooled to RT, diluted with water and DCM, the layers were separated and the aqueous layer was extracted with DCM (2×). The combined organics were washed with brine, dried over $Na_2SO_4$, filtered and concentrated. The crude material was washed with copious amounts of methanol and dried to give ethyl 4-(3-chloropyrazin-2yloxy)benzoate.

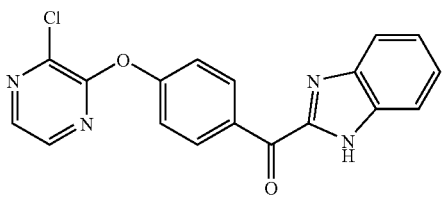

STEP 2. (1H-BENZO[D]IMIDAZOL-2-YL)(4-(3-CHLOROPYRAZIN-2-YLOXY)PHENYL)-METHANONE

A solution of benzene-1,2-diamine (1.5 g, 14 mmol), triethyl orthoformate (5.7 mL, 37 mmol), and benzenesulfonic acid (0.075 g, 0.47 mmol) in toluene (15 mL) was heated to reflux for 4 h and then slowly distilled to remove half of the solvent. The mixture was then cooled to RT and neutralized with diisopropyl amine, followed by addition of a solution of ethyl 4-(3-chloropyrazin-2-yloxy)benzoate (4.3 g, 15 mmol) in THF (15 mL). The mixture was cooled to −78° C. and 1.2 equiv of LDA (9.2 mL, 17 mmol) was added. After aging at −78° C. for 1.5 h, the mixture was warmed to RT after 1.5 h and then 2N HCl was added and the mixture was agitated for 30 min. Following that, the mixture was adjusted to pH 9 with 1N NaOH. Ethyl acetate was added and the layers were separated, the aqueous was extracted with ethyl acetate (3×), and the combined organics were washed with brine, dried over $Na_2SO_4$, filtered and concentrated. Upon treatment with MeOH, a yellow solid crashed out which was filtered and collected to give (1H-benzo[d]imidazol-2-yl)(4-(3-chloropyrazin-2-yloxy)phenyl)methanone.

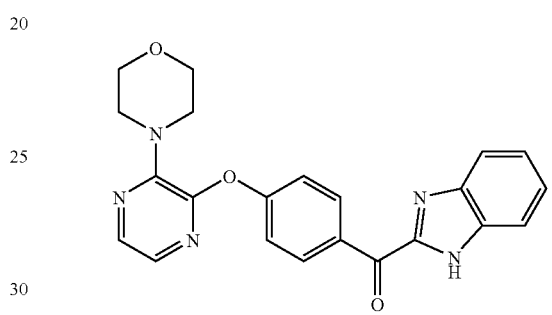

STEP 3. (1H-BENZO[D]IMIDAZOL-2-YL)(4-(3-MORPHOLINOPYRAZIN-2-YLOXY)-PHENYL)METHANONE

A solution of (1H-benzo[d]imidazol-2-yl)(4-(3-chloropyrazin-2-yloxy)phenyl)-methanone (23.00 g, 65.6 mmol) and morpholine (17.2 mL, 197 mmol) was heated to 90° C. in DMSO (165 mL). After complete consumption of the starting material, the hot solution was dripped into ice water which caused a yellow solid to precipitate. The solid was slurried in boiling EtOH (600 mL) and enough tetrahydrofuran was added to completely dissolve the solids. The solution was transferred to the freezer for crystallization. The solid was collected by filtration and air-dried to give (1H-benzo[d]imidazol-2-yl)(4-(3-morpholinopyrazin-2-yloxy)phenyl)methanone. MS (ESI, pos. ion) m/z: 402.1 (M+1). IC50 (uM) ++++.

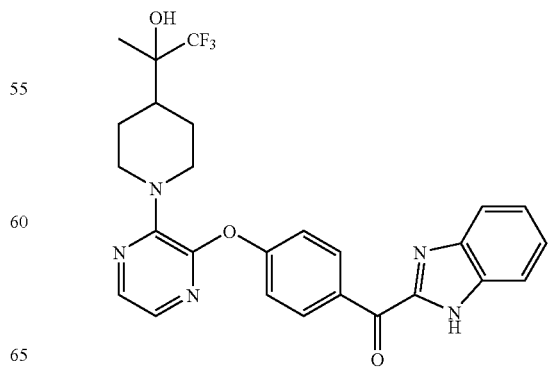

Example 2

(S)-(1H-BENZO[D]IMIDAZOL-2-YL)(4-(3-(4-(1,1,1-TRIFLUORO-2-HYDROXYPROPAN-2-YL)PIPERID IN-1-YL)PYRAZIN-2-YLOXY)PHENYL)METHANONE

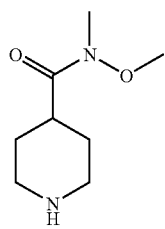

STEP 1. N-METHOXY-N-METHYLPIPERIDINE-4-CARBOXAMIDE

To a mixture of piperidine-4-carboxylic acid (100 g, 775 mmol) in 1,4-dioxane (400 mL) and water (100 mL), triethylamine (135 mL, 969 mmol) was added at 25-30° C. and stirred for 15 min. Then 110 g of boc anhydride was added. It was stirred for overnight at the same temperature. After completion of the reaction, the solvent was removed under vacuum. The residue was purified by dilution with EtOAc and washing with H₂O (1000 mL). The organic layer was dried over anhydrous sodium sulfate and concentrated under vacuum to afford 1-(tert-butoxycarbonyl)piperidine-4-carboxylic acid product.

To a solution of 1-(tert-butoxycarbonyl)piperidine-4-carboxylic acid (50 g, 218 mmol) in DCM (500 mL), 1,1-carbonyldiimidazole (46 g, 284 mmol) was added and the reaction mixture was stirred for 1 h at 25-30° C. N,O-Dimethylamine hydrochloride (30 g, 306 mmol) was then added and the resulting mixture was stirred for 15 h at 25-30° C. After completion of the reaction, the reaction mixture was diluted with DCM and washed with water, saturated NaHCO₃ solution, and 10% NaOH solution. The organic layer was dried over anhydrous sodium sulfate and concentrated under vacuum to afford pure tert-butyl 4-(methoxy(methyl)carbamoyl)-piperidine-1-carboxylate product.

To a solution of tert-butyl 4-(methoxy(methyl)carbamoyl) piperidine-1-carboxylate (50 g, 182 mmol) in DCM (400 mL) was added trifluoroacetic acid (150 mL) and the resulting mixture was stirred for 6 h at 25-30° C. After completion of the reaction, the solvent was removed under reduced pressure to afford 40 g of N-methoxy-N-methylpiperidine-4-carboxamide product. [M+1]=173.04

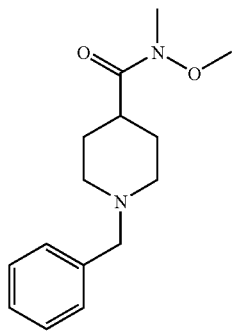

STEP 2. 1-BENZYL-N-METHOXY-N-METHYLPIPERIDINE-4-CARBOXAMIDE

To the solution of N-methoxy-N-methylpiperidine-4-carboxamide (40 g, 232 mmol) in acetone (400 mL) was added benzyl bromide (42 mL, 349 mmol) and K₂CO₃ (64 g, 465 mmol) and the reaction mixture was stirred at 80° C. under reflux for 16 h. After completion of the reaction, the reaction mixture was filtered and acetone was removed under reduced pressure. The residue was purified by silica gel column chromatography (eluting with 50% ethyl acetate in hexane) to afford 1-benzyl-N-methoxy-N-methylpiperidine-4-carboxamide product. [M+1]=263.15

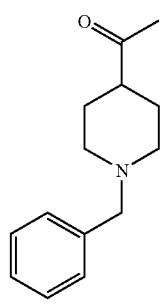

STEP 3. 1-(1-BENZYLPIPERIDIN-4-YL)ETHANONE

To a stirred solution of 1-benzyl-N-methoxy-N-methylpiperidine-4-carboxamide (11.5 g, 44 mmol) in diethyl ether (150 mL) at 0° C. was added methyl magnesium bromide (15.7 g, 132 mmol), drop-wise over 10 min. The resulting mixture was stirred at 25-30° C. for 2 h. After completion of the reaction, the mixture was treated with EtOAc and saturated NH₄Cl solution. The separated organic layer was washed with brine and dried over anhydrous sodium sulfate and concentrated under vacuum to afford 1-(1-benzylpiperidin-4-yl)ethanone product. [M+1]=218.1

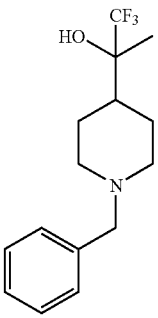

STEP 4. 2-(1-BENZYLPIPERIDIN-4-YL)-1,1,1-TRIFLUOROPROPAN-2-OL

To a stirred solution of potassium acetate (0.19 g, 1 mmol) in dimethylformamide (2 mL) was added a solution of 1-(1-benzylpiperidin-4-yl)ethanone (0.5 g, 2.3 mmol) in dimethylformamide (2 mL) and CF₃SiMe₃ (0.67 mL, 4.6 mmol). The reaction mixture was stirred for 1 h at RT. After completion of the reaction, the reaction mixture was quenched with saturated aqueous NH₄Cl solution. The mixture was extracted with ethyl acetate and dried over anhydrous sodium sulfate and concentrated under vacuum. The residue was purified by silica gel column chromatography to afford 1-benzyl-4-(1,1,1-trifluoro-2-(trimethylsilyloxy)propan-2-yl)piperidine product.

To a stirred solution of 1-benzyl-4-(1,1,1-trifluoro-2-(trimethylsilyloxy)propan-2-yl)piperidine (3 g, 8.3 mmol) in THF (30 mL), tetrabutylammonium fluoride (3.2 g, 12.4 mmol) was added slowly at RT. The reaction mixture was stirred for 3 h. After completion of the reaction, the mixture was quenched with saturated ammonium chloride solution, extracted with ethyl acetate. The organic layer was washed with brine solution and dried over anhydrous sodium sulfate and concentrated under vacuum to afford 2-(1-benzylpiperidin-4-yl)-1,1,1-trifluoropropan-2-ol product. [M+1]=288.15

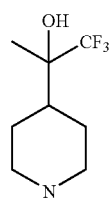

STEP 5. 1,1,1-TRIFLUORO-2-(PIPERIDIN-4-YL)PROPAN-2-OL

To a stirred solution of 2-(1-benzylpiperidin-4-yl)-1,1,1-trifluoropropan-2-ol in methanol (25 mL), palladium on carbon (150 mg, 3.26 mmol) was added under hydrogen atmosphere. The resulting mixture was stirred under reflux for 6 h at 65 C. After completion of the reaction, the mixture was filtered and concentrated under vacuum to afford 1,1,1-trifluoro-2-(piperidin-4-yl)propan-2-ol. [M+H]=198.06

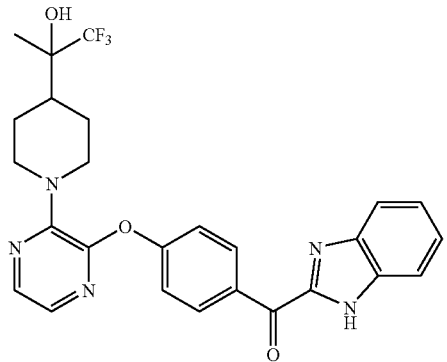

STEP 6. (S)-(1H-BENZO[D]IMIDAZOL-2-YL)(4-(3-(4-(1,1,1-TRIFLUORO-2-HYDROXYPROPAN-2-YL)PIPERIDIN-1-YL)PYRAZIN-2-YLOXY)PHENYL)METHANONE

Same as step 3 of example 1 to provide product. MS (ESI, pos. ion) m/z: 512 (M+1). IC50 (uM) ++++.

SCHEME 2

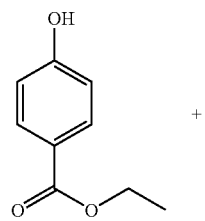

+

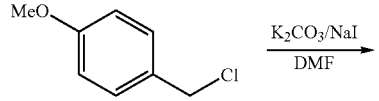

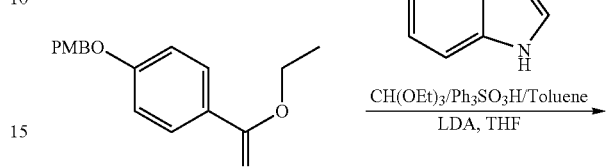

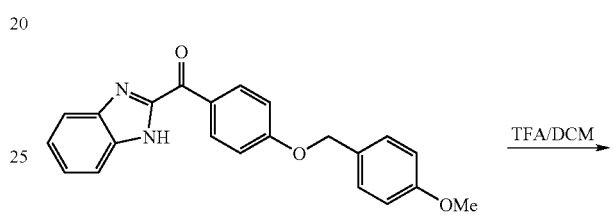

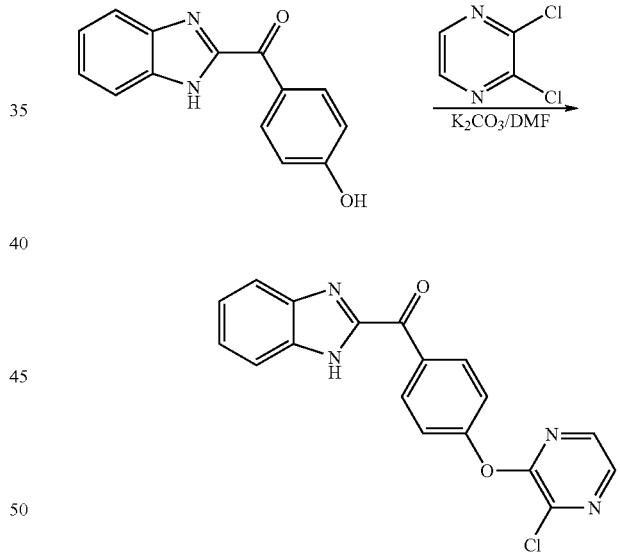

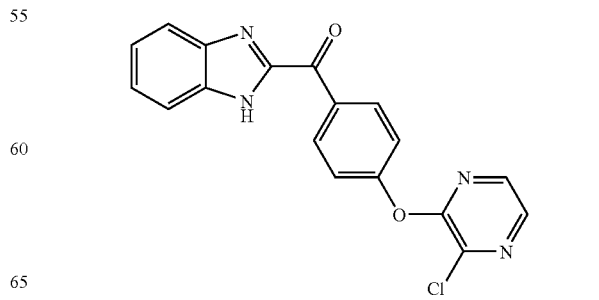

Example 3

(1H-BENZO[D]IMIDAZOL-2-YL)(4-(3-CHLORO-PYRAZIN-2-YLOXY)PHENYL)METHANONE

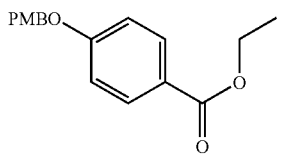

STEP 1: ETHYL 4-(4-METHOXYBENZYLOXY)BENZOATE

To a stirred solution of ethyl 4-hydroxybenzoate (530 g, 3.19 mol) in DMF (6 L) were added $K_2CO_3$ powder (1102 g, 7.97 mol, 2.5 eq.), NaI (1195 g, 7.97 mol, 2.5 eq.) and PMB-Cl (599.4 g, 3.83 mol, 1.2 eq.) at ambient temperature. The reaction mixture was heated at 50° C. overnight under nitrogen atmosphere. The reaction mixture was cooled to ambient temperature and ice-water (9 L) was added to the reaction mixture. The resulting solid was filtered and washed with water (5 L), dried at 40° C. under vacuum to obtain product.

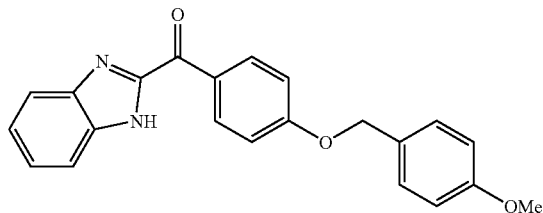

STEP 2: (1H-BENZO[D]IMIDAZOL-2-YL)(4-(4-METHOXYBENZYLOXY)PHENYL)METHANONE

A solution of benzimidazole (450 g, 3.81 mol), triethyl orthoformate (1129.3 g, 7.62 mol, 2.0 eq.) and benzenesulphonic acid (16 g) in toluene (4 L) was heated to reflux, and half of the solvent was removed by distillation. Toluene (3 L) was added again and 2 L was removed by slow distillation. The reaction mixture was cooled, was neutralized with diisopropylamine (55 mL), and to it were added THF (4 L) and 2 (1200 g, 4.2 mol, 1.1 eq.). The mixture was cooled to −78° C. and to it was added LDA (2.32 L, 2M in THF/hexane/ethylbenzene, 4.5 mol, 1.2 eq.) drop wise over 3 h. After the addition, the reaction mixture was stirred at −78° C. for 2 h. It was then warmed to ambient temperature, 2N aqueous HCl (3.9 L) was added and the mixture was stirred for 2 h. The layers were separated, organic layer was washed with 10% aqueous $NaHCO_3$ solution and brine, dried over $Na_2SO_4$, filtered and concentrated to give 2177 g crude as an oil. To this crude were added MTBE (3 L) and hexanes (250 ml) and left overnight in cold room. The resulting solid was filtered and washed with MTBE, followed by 10% EtOAC/Hexanes to give product.

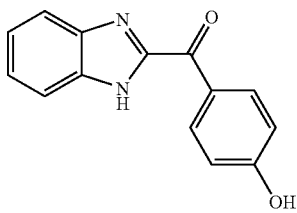

STEP 3: (1H-BENZO[D]IMIDAZOL-2-YL)(4-HYDROXYPHENYL)METHANONE

To a slurry of compound (1H-benzo[d]imidazol-2-yl)(4-(4-methoxybenzyloxy)phenyl)methanone (268 g, 0.75 mol) in dichloromethane (2.7 L) at ambient temperature was added TFA (289 mL, 3.75 mol, 5.0 eq.) slowly using an addition funnel. The reaction was stirred at ambient temp for 16 h. LCMS analysis of the reaction mixture revealed that the reaction was complete. The reaction mixture was neutralized with satd. aqueous $NaHCO_3$ to pH=7-8, and stirred for 20 minutes. The resulting solid was filtered and washed with water and dried under vacuum oven at 45° C. to give product.

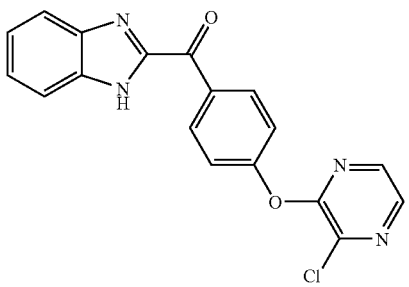

STEP 4: (1H-BENZO[D]IMIDAZOL-2-YL)(4-(3-CHLOROPYRAZIN-2-YLOXY)PHENYL)METHANONE

To a solution of compound (1H-benzo[d]imidazol-2-yl)(4-hydroxyphenyl)methanone (100 g, 0.42 mol) in anhydrous DMF (1.1 L) was added $K_2CO_3$ (145 g, 1.05 mol, 2.5 eq.) and 2,3-dichloropyrazine (75.08 g, 0.50 mol, 1.2 eq.). The reaction was stirred at 90° C. for 18 h. LCMS analysis of the reaction mixture showed that the reaction was complete. The reaction mixture was cooled to ambient temperature and ice-water (3 L) was added, stirred for 30 minutes. The resulting solid was filtered and washed with water (3 L) followed by MTBE (2×500 mL) and dried under vacuum. The solid was treated with 50% MTBE/DCM at 50° C. for 1 h and filtered hot, washed with 50% MTBE/DCM and dried under vacuum overnight to obtain product. Mother liquor was refluxed with 50% MTBE/DCM for 2 h and filtered hot and washed with 50% MTBE/DCM to get another batch of product. MS (ESI, pos. ion) m/z: 351.0 (M+1). IC50 (uM) +.

SCHEME 3

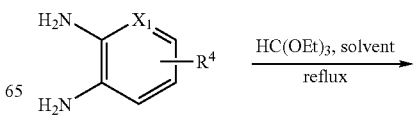

-continued

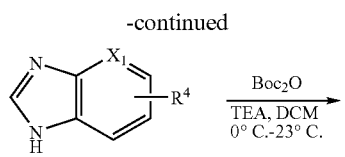

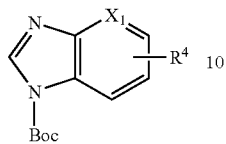

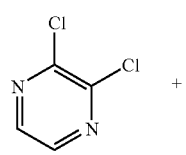

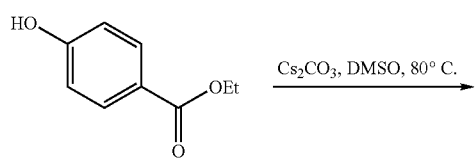

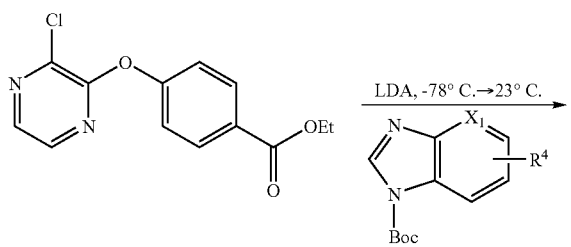

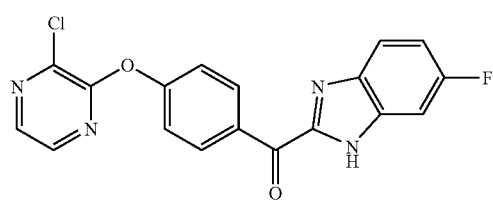

Example 4: [4-(3-CHLORO-PYRAZIN-2-YLOXY)-PHENYL]-(6-FLUORO-1H-BENZOIMIDAZOL-2-YL)-METHANONE

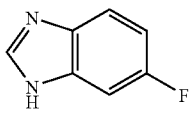

STEP 1. 6-FLUORO-1H-BENZOIMIDAZOLE

To the solution of 4-fluoro-benzene-1,2-diamine (10 g, 79.4 mmol) and triethylorthoformate (117 mL, 793 mmol) was added few drop of ethanol and the reaction mixture was refluxed at 150° C. overnight. The reaction mixture was concentrated and the residue was directly taken to the next step. [M+H]=137.

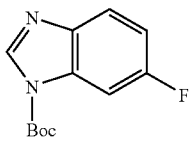

STEP 2. 6-FLUORO-BENZOIMIDAZOLE-1-CARBOXYLIC ACID TERT-BUTYL ESTER

To the solution of 6-fluoro-1H-benzoimidazole (21.5 g, 159 mmol) and triethylamine (34.2 mL, 237 mmol) in DCM (200 mL) was added di-tert-butyl dicarbonate (41.3 mL, 190 mmol) at 5° C. The reaction mixture was stirred at RT overnight. The reaction was then diluted with DCM (100 mL) and washed with water (3×50 ml). The organic layer was dried (Na$_2$SO$_4$) and concentrated. The crude product was purified by silica gel (100-200 mesh) column using 5-10% ethyl acetate-hexane as eluent to obtain the title compound. [M+H]= 237.

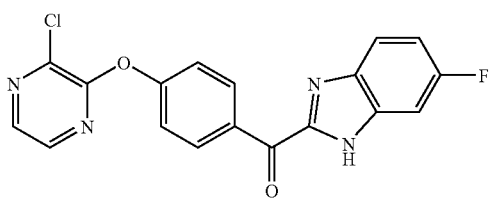

STEP 3. [4-(3-CHLORO-PYRAZIN-2-YLOXY)-PHENYL]-(6-FLUORO-1H-BENZOIMIDAZOL-2-YL)-METHANONE

A solution of 4-(3-Chloro-pyrazin-2-yloxy)-benzoic acid ethyl ester (20 g, 84.7 mmol) and 6-fluoro benzoimidazole-1-carboxylic acid tert-butyl ester (21.2 g, 76.3 mmol) in freshly dried THF (150 mL) was cooled to −78° C. LiHMDS (106 mL, 106 mmol) was added slowly to it over 1.2 h. The reaction mixture was stirred at the same temperature for 3.5 h. The reaction was brought to −20° C. and slowly quenched with addition of 2N HCl until pH 3-4. The resulting mixture was stirred at RT for 1 h, extracted with ethyl acetate (3×200 mL), and washed with water (2×100 mL). The organic layer was dried (Na$_2$SO$_4$) and concentrated. To the crude product was added methanol (70 mL). After stirring for 1 h, the solid was collected by filtration to give the title compound. MS (ESI, pos. ion) m/z: 369.2 (M+1). IC50 (uM) +.

SCHEME 4

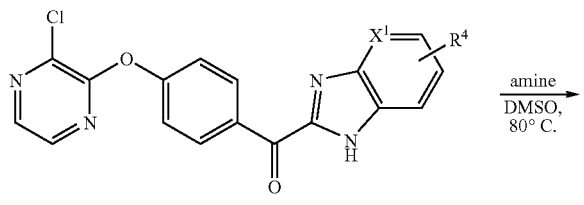

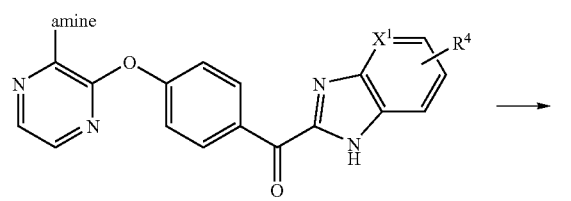

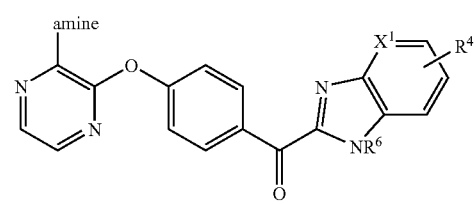

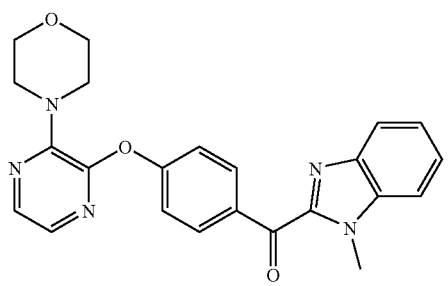

Example 5

(1-METHYL-1H-BENZO[D]IMIDAZOL-2-YL)(4-(3-MORPHOLINOPYRAZIN-2-YLOXY)PHENYL)METHANONE

To a suspension of (1H-benzo[d]imidazol-2-yl)(4-(3-morpholinopyrazin-2-yloxy)-phenyl)methanone as prepared according to Scheme 3, (0.2 g, 0.5 mmol) in DMF (1 mL) was added cesium carbonate (0.2 g, 0.7 mmol) and iodomethane (0.04 mL, 0.6 mmol). The resulting mixture was stirred at RT overnight. LC/MS showed complete conversion. Compound crashed out in MeOH. Filtered the resulting orange solid and rinse with copious amounts of MeOH. Solids were dried by vacuum pump overnight to afford (1-methyl-1H-benzo[d]imidazol-2-yl)(4-(3-morpholinopyrazin-2-yloxy)phenyl)methanone. MS (ESI, pos. ion) m/z: 416.1.(M+1). IC50 (uM) ++++.

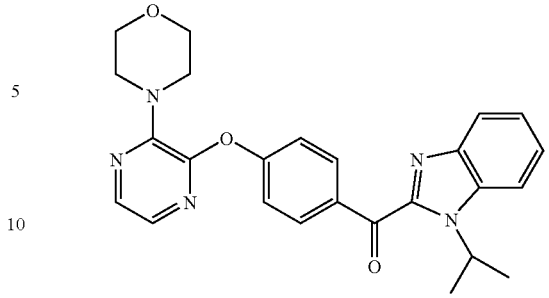

Example 6

(1-ISOPROPYL-1H-BENZO[D]IMIDAZOL-2-YL)(4-(3-MORPHOLINOPYRAZIN-2-YLOXY)PHENYL)METHANONE

A mixture of (1H-benzo[d]imidazol-2-yl)(4-(3-morpholinopyrazin-2-yloxy)-phenyl)methanone (115 mg, 286 µmol), potassium carbonate (79.2 mg, 573 µmol) and 2-iodopropane (97.4 mg, 573 µmol) in DMF (2 mL) was stirred overnight. Additional isopropyl iodide was added until the starting material was consumed. The mixture was diluted with water and ethyl acetate. The layers were separated and the aqueous layer was extracted with ethyl acetate and the combined organics were washed with brine, dried over Na$_2$SO$_4$, filtered and concentrated. The residue was purified by Biotage™, 10-30% acetone/hexanes gradient, to give (1-isopropyl-1H-benzo[d]imidazol-2-yl) (4-(3-morpholinopyrazin-2-yloxy) phenyl)methanone. MS (ESI, pos. ion) m/z: 444.1 (M+1). IC50 (uM) ++++.

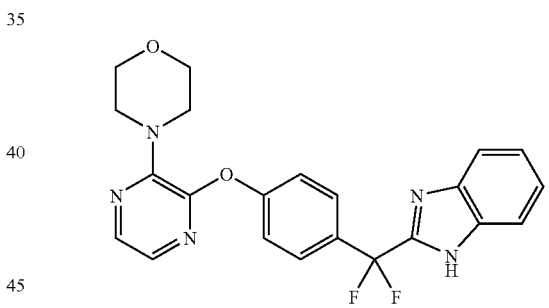

Example 7

4-(3-(4-(((1H-BENZO[D]IMIDAZOL-2-YL)DIFLUOROMETHYL)PHENOXY)PYRAZIN-2-YL)MORPHOLINE

A solution of (1H-benzo[d]imidazol-2-yl)(4-(3-(tetrahydro-2H-pyran-4-yl)pyrazin-2-yloxy)phenyl)methanone (155 mg, 0.387 mmol) in Chloroform (15.500 ml) was cooled to 0° C. and DAST (1.023 ml, 7.74 mmol) was added. The ice bath was removed and the reaction was allowed to warm to room temperature. The reaction was quenched with water and the mixture was diluted with dichloromethane. After separation of the layers, the aqueous layer was extracted with DCM. The combined organic layers were washed with brine, dried over Na2SO4, filtered and concentrated. The residue was purified by silica gel chromatography to give 4-(3-(4-((1H-benzo[d]imidazol-2-yl)difluoromethyl)phenoxy)pyrazin-2-yl)morpholine. MS (ESI, pos. ion) m/z: 423.0 (M+1). IC50 (uM) +++.

TABLE (IA)

EXAMPLES 8 to 56 ARE TABULATED BELOW:

| Ex # | Structure | IUPAC names | MS |
|---|---|---|---|
| 8 | 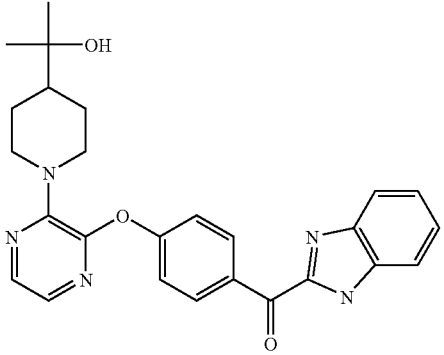 | (1H-benzo[d]imidazol-2-yl)(4-(3-(4-(2-hydroxypropan-2-yl)piperidin-1-yl)pyrazin-2-yloxy)phenyl)methanone | 458 |
| 9 | 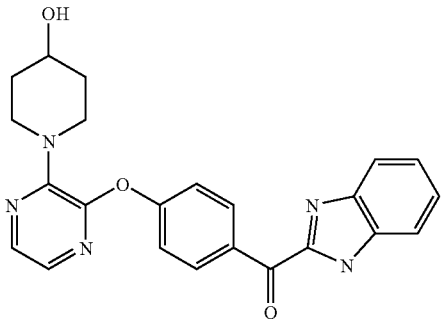 | (1H-benzo[d]imidazol-2-yl)(4-(3-(4-hydroxypiperidin-1-yl)pyrazin-2-yloxy)phenyl)methanone | 416 |
| 10 | 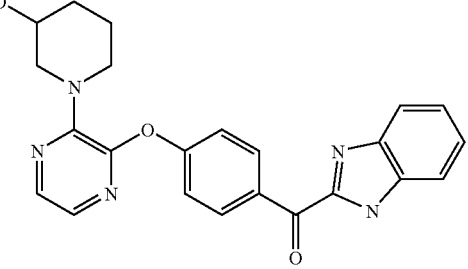 | (1H-benzo[d]imidazol-2-yl)(4-(3-(3-hydroxypiperidin-1-yl)pyrazin-2-yloxy)phenyl)methanone | 416 |
| 11 | 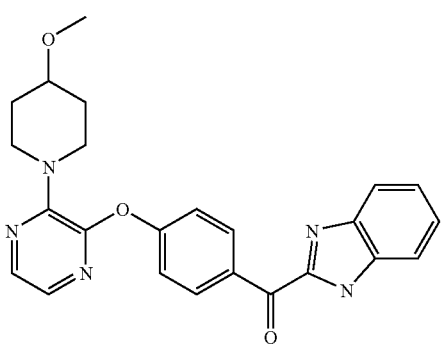 | (1H-benzo[d]imidazol-2-yl)(4-(3-(4-methoxypiperidin-1-yl)pyrazin-2-yloxy)phenyl)methanone | 430 |

TABLE (IA)-continued

EXAMPLES 8 to 56 ARE TABULATED BELOW:

| Ex # | Structure | IUPAC names | MS |
|---|---|---|---|
| 12 | 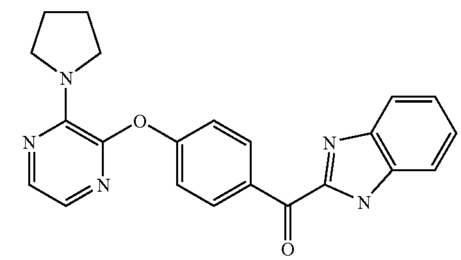 | (1H-benzo[d]imidazol-2-yl)(4-(3-(pyrrolidin-1-yl)pyrazin-2-yloxy)phenyl)methanone | 386 |
| 13 | 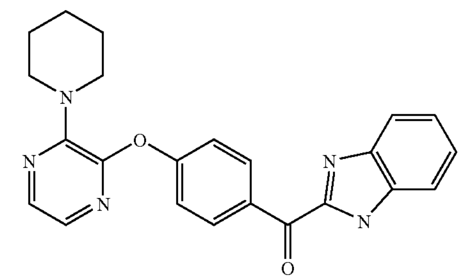 | (1H-benzo[d]imidazol-2-yl)(4-(3-(piperidin-1-yl)pyrazin-2-yloxy)phenyl)methanone | 400 |
| 14 | 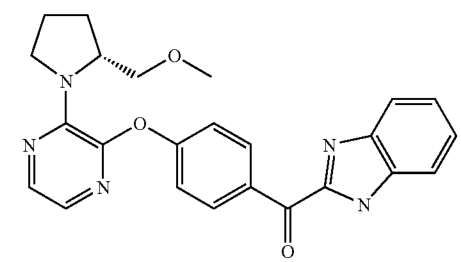 | (R)-(1H-benzo[d]imidazol-2-yl)(4-(3-(2-(methoxymethyl)pyrrolidin-1-yl)pyrazin-2-yloxy)phenyl)methanone | 430 |
| 15 | 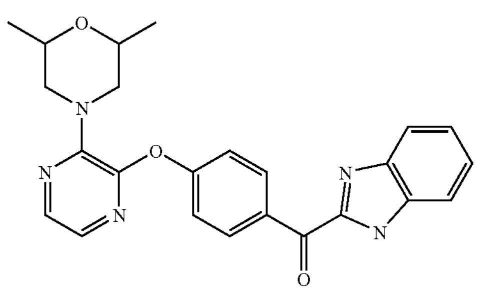 | (1H-benzo[d]imidazol-2-dimethylmorpholino)-pyrazin-2-yloxy)phenyl)methanone | 430 |
| 16 | 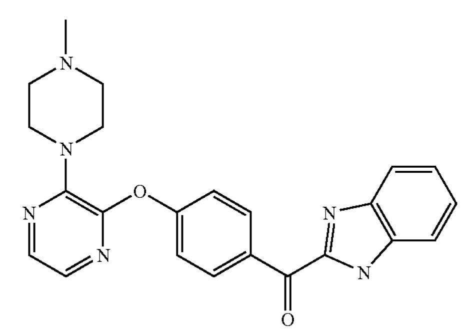 | (1H-benzo[d]imidazol-2-yl)(4-(3-(4-methylpiperazin-1-yl)pyrazin-2-yloxy)phenyl)methanone | 415 |

TABLE (IA)-continued

EXAMPLES 8 to 56 ARE TABULATED BELOW:

| Ex # | Structure | IUPAC names | MS |
|---|---|---|---|
| 17 | 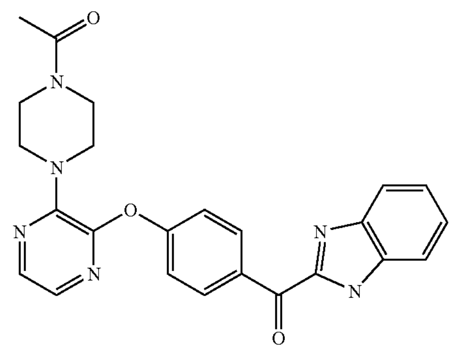 | 1-(4-(3-(4-(1H-benzo[d]imidazole-2-carbonyl)phenoxy)pyrazin-2-yl)piperazin-1-yl)ethanone | 443 |
| 18 | 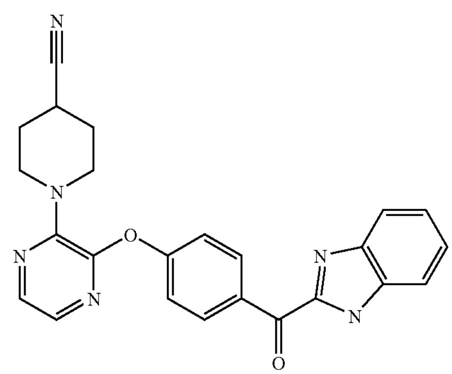 | 1-(3-(4-(1H-benzo[d]imidazole-2-carbonyl)phenoxy)pyrazin-2-yl)piperidine-4-carbonirile | 425 |
| 19 | 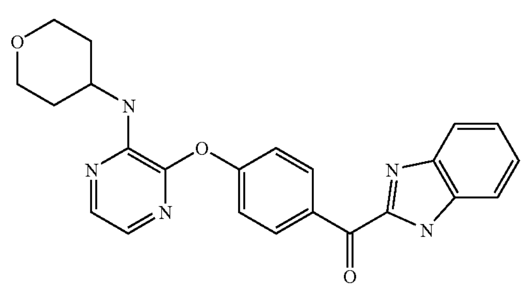 | (1H-benzo[d]imidazol-2-yl)(4-(3-(tetrahydro-2H-pyran-4-ylamino)pyrazin-2-yloxy)phenyl)methanone | 416 |
| 20 | 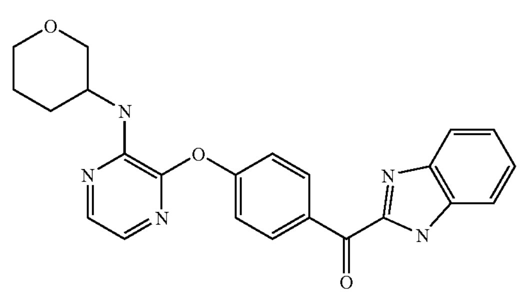 | (1H-benzo[d]imidazol-2-yl)(4-(3-(tetrahydro-2H-pyran-3-ylamino)pyrazin-2-yloxy)phenyl)methanone | 416 |

TABLE (IA)-continued

EXAMPLES 8 to 56 ARE TABULATED BELOW:

| Ex # | Structure | IUPAC names | MS |
|---|---|---|---|
| 21 | 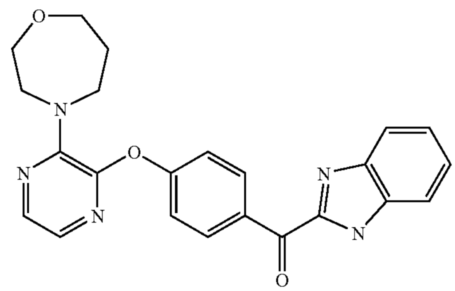 | (4-(3-(1,4-oxazepan-4-yl)pyrazin-2-yloxy)phenyl)(1H-benzo[d]imidazol-2-yl)methanone | 416 |
| 22 | 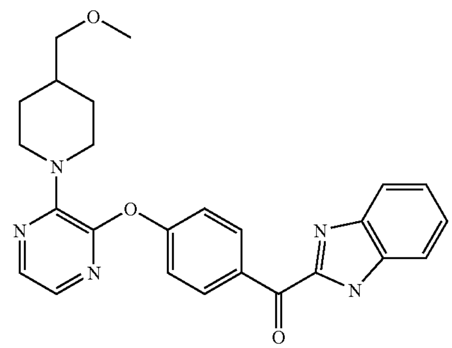 | (1H-benzo[d]imidazol-2-yl)(4-(3-(4-(methoxymethyl)piperidin-1-yl)pyrazin-2-yloxy)phenyl)methanone | 444 |
| 23 | 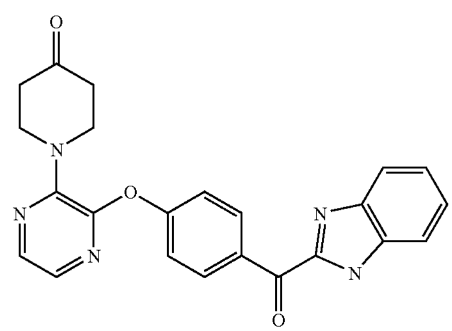 | 1-(3-(4-(1H-benzo[d]imidazole-2-carbonyl)phenoxy)pyrazin-2-yl)piperidin-4-one | 414 |
| 24 | 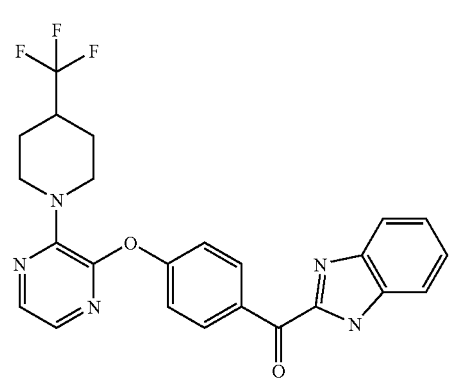 | (1H-benzo[d]imidazol-2-yl)(4-(3-(4-(trifluoromethyl)piperidin-1-yl)pyrazin-2-yloxy)phenyl)methanone | 468 |

TABLE (IA)-continued

EXAMPLES 8 to 56 ARE TABULATED BELOW:

| Ex # | Structure | IUPAC names | MS |
|---|---|---|---|
| 25 | 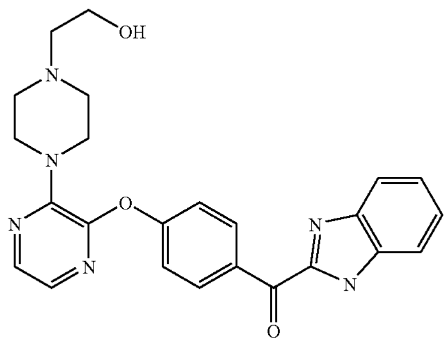 | (1H-benzo[d]imidazol-2-yl)(4-(3-(4-(2-hydroxyethyl)piperazin-1-yl)pyrazin-2-yloxy)phenyl)methanone | 445 |
| 26 | 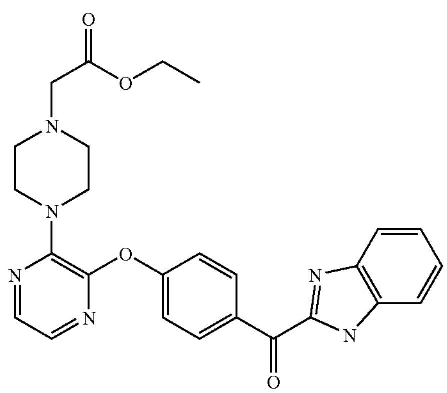 | ethyl 2-(4-(3-(4-(1H-benzo[d]imidazole-2-carbonyl)phenoxy)pyrazin-2-yl)piperazin-1-yl)acetate | 487 |
| 27 | 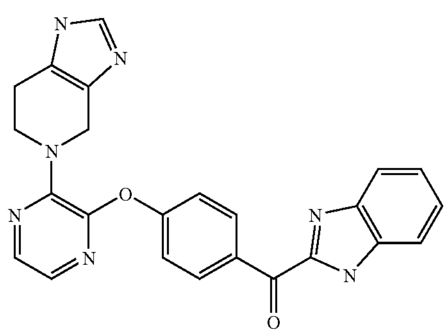 | (1H-benzo[d]imidazol-2-yl)(4-(3-(6,7-dihydro-1H-imidazo[4,5-c]pyridin-5(4H)-yl)pyrazin-2-oyloxy)phenyl)methanone | 438 |
| 28 | 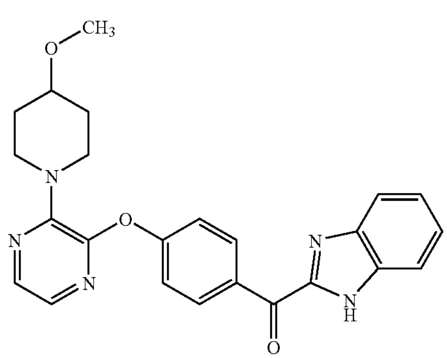 | (1H-benzo[d]imidazol-2-yl)(4-(3-(4-methoxypiperidin-1-yl)pyrazin-2-yloxy)phenyl)methanone | 430 |

TABLE (IA)-continued

EXAMPLES 8 to 56 ARE TABULATED BELOW:

| Ex # | Structure | IUPAC names | MS |
|---|---|---|---|
| 29 | 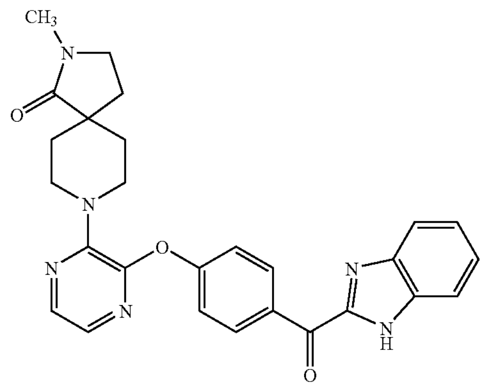 | 8-(3-(4-(1H-benzo[d]imidazole-2-carbonyl)phenoxy)pyrazin-2-yl)-2-methyl-2,8-diazaspiro[4.5]decan-1-one | 483 |
| 30 | 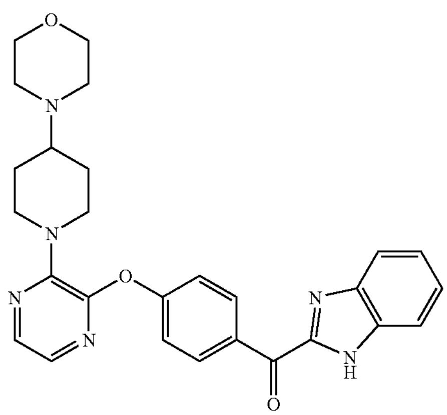 | (1H-benzo[d]imidazol-2-yl)(4-(3-(4-morpholinopiperidin-1-yl)pyrazin-2-yloxy)phenyl)methanone | 485 |
| 31 | | (±)-(1H-benzo[d]imidazol-2-yl)(4-(3-(3-hydroxypyrrolidin-1-yl)pyrazin-2-yloxy)phenyl)methanone | 402 |

TABLE (IA)-continued

EXAMPLES 8 to 56 ARE TABULATED BELOW:

| Ex # | Structure | IUPAC names | MS |
|---|---|---|---|
| 32 | 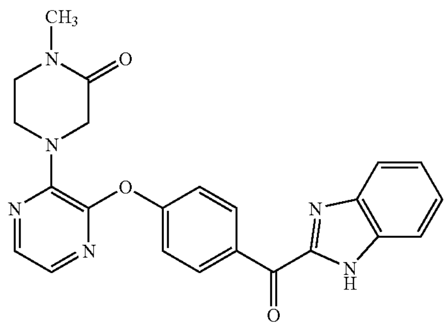 | 4-(3-(4-(1H-benzo[d]imidazole-2-carbonyl)phenoxy)pyrazin-2-yl)-1-methylpiperazin-2-one | 429 |
| 33 | 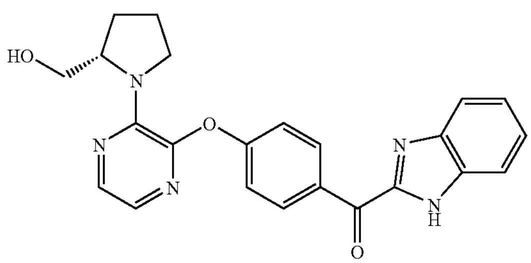 | (S)-(1H-benzo[d]imidazol-2-yl)(4-(3-(2-(hydroxymethyl)pyrrolidin-1-yl)pyrazin-2-yloxy)phenyl)methanone | 416 |
| 34 | 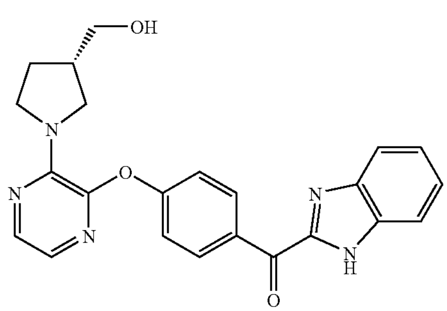 | (S)-(1H-benzo[d]imidazol-2-yl)(4-(3-(3-(hydroxymethyl)pyrrolidin-1-yl)pyrazin-2-yloxy)phenyl)methanone | 416 |
| 35 | 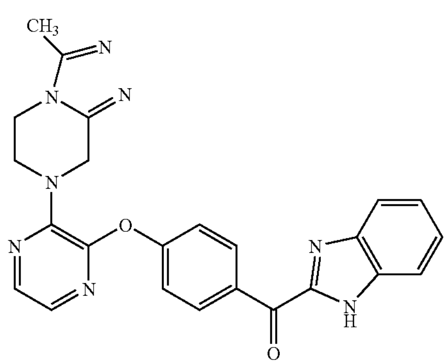 | (1H-benzo[d]imidazol-2-yl)(4-(3-(3-methyl-5,6-dihydro-[1,2,4]triazolo[4,3-a]pyrazin-7(8H)-yl)pyrazin-2-yloxy)phenyl)methanone | 453 |

TABLE (IA)-continued

EXAMPLES 8 to 56 ARE TABULATED BELOW:

| Ex # | Structure | IUPAC names | MS |
|---|---|---|---|
| 36 | 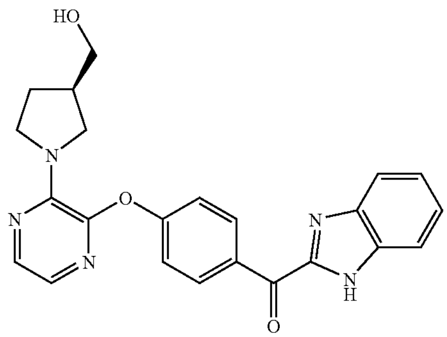 | (R)-(1H-benzo[d]imidazol-2-yl)(4-(3-(3-(hydroxymethyl)pyrrolidin-1-yl)pyrazin-2-yloxy)phenyl)methanone | 416 |
| 37 | 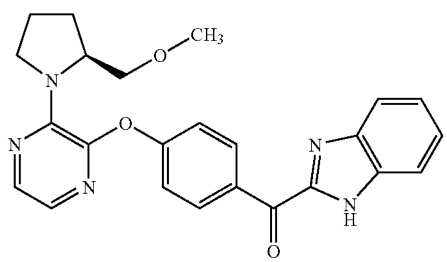 | (S)-(1H-benzo[d]imidazol-2-yl)(4-(3-(2-(methoxymethyl)pyrrolidin-1-yl)pyrazin-2-yloxy)phenyl)methanone | 430 |
| 38 | 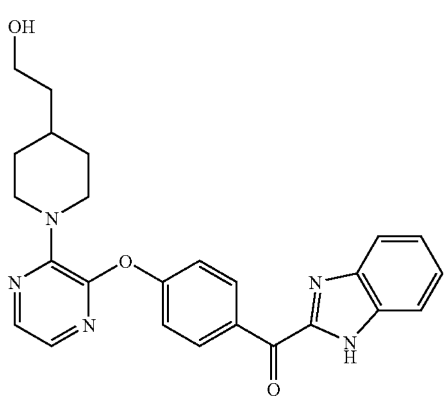 | (1H-benzo[d]imidazol-2-yl)(4-(3-(4-(2-hydroxyethyl)piperidin-1-yl)pyrazin-2-yloxy)phenyl)methanone | 444 |

TABLE (IA)-continued

EXAMPLES 8 to 56 ARE TABULATED BELOW:

| Ex # | Structure | IUPAC names | MS |
|---|---|---|---|
| 39 | 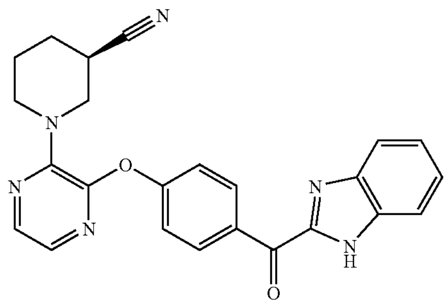 | (±)-1-(3-(4-(1H-benzo[d]imidazole-2-carbonyl)phenoxy)pyrazin-2-yl)piperidine-3-carbonitrile | 425 |
| | Chiral | | |
| 40 | 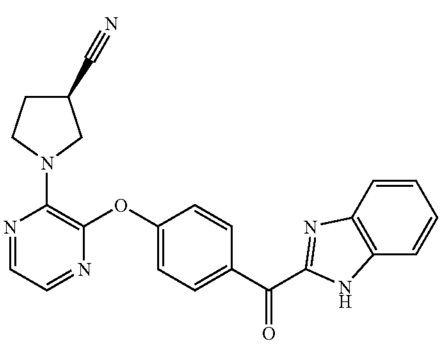 | (±)-1-(3-(4-(1H-benzo[d]imidazole-2-carbonyl)phenoxy)pyrazin-2-yl)pyrrolidine-3-carbonitrile | 411 |

TABLE (IA)-continued
EXAMPLES 8 to 56 ARE TABULATED BELOW:
| Ex # | Structure | IUPAC names | MS |
|---|---|---|---|
| 41 | 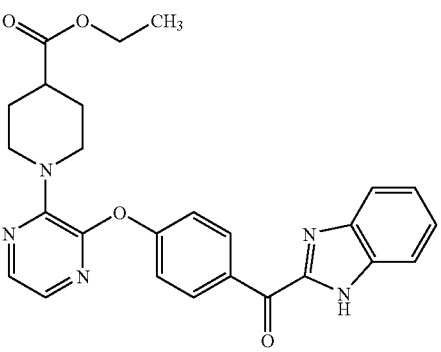 | ethyl 1-(3-(4-(1H-benzo[d]imidazole-2-carbonyl)phenoxy)pyrazin-2-yl)piperidine-4-carboxylate | 472 |
| 42 | 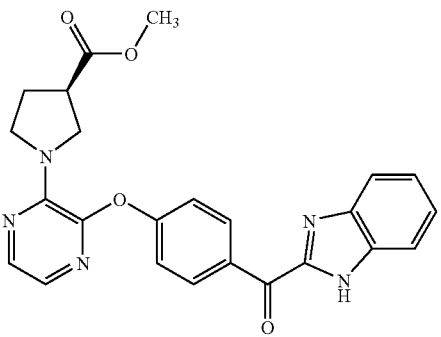<br>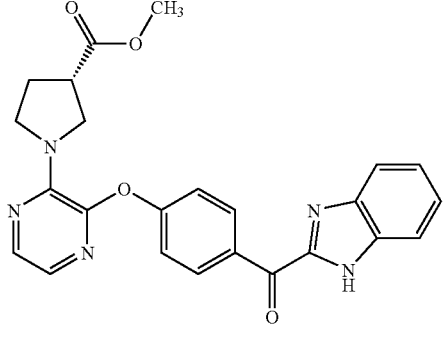 | (±)-methyl 1-(3-(4-(1H-benzo[d]imidazole-2-carbonyl)phenoxy)pyrazin-2-yl)pyrrolidine-3-carboxylate | 444 |

TABLE (IA)-continued
EXAMPLES 8 to 56 ARE TABULATED BELOW:
| Ex # | Structure | IUPAC names | MS |
|---|---|---|---|
| 43 | | (±)-ethyl 1-(3-(4-(1H-benzo[d]imidazole-2-carbonyl)phenoxy)pyrazin-2-yl)piperidine-3-carboxylate | 472 |
| 44 | | (±)-(1H-benzo[d]imidazol-2-yl)(4-(3-(3-(3-methyl-1,2,4-oxadiazol-5-yl)pyrrolidin-1-yl)pyrazin-2-yloxy)phenyl)methanone | 468 |
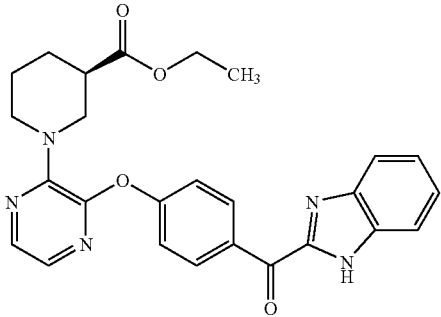
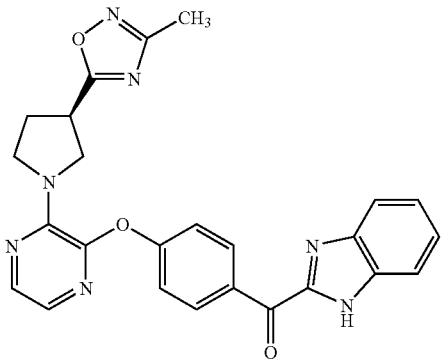

TABLE (IA)-continued

EXAMPLES 8 to 56 ARE TABULATED BELOW:

| Ex # | Structure | IUPAC names | MS |
|---|---|---|---|
| 45 | 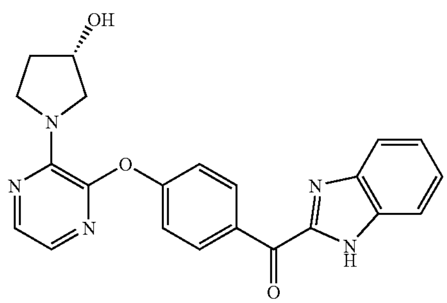 | (S)-(1H-benzo[d]imidazol-2-yl)(4-(3-(3-hydroxypyrrolidin-1-yl)pyrazin-2-yloxy)phenyl)methanone | 402 |
| 46 | | (±)-(1H-benzo[d]imidazol-2-yl)(4-(3-(4-(1-hydroxyethyl)piperidin-1-yl)pyrazin-2-yloxy)phenyl)methanone | 444 |
| 47 | 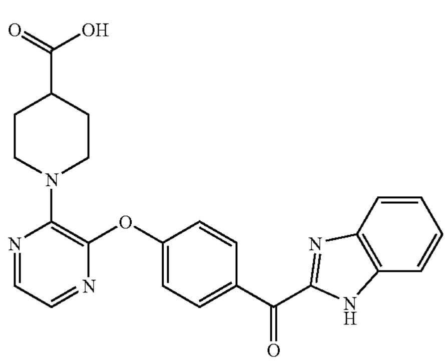 | 1-(3-(4-(1H-benzo[d]imidazole-2-carbonyl)phenoxy)pyrazin-2-yl)piperidine-4-carboxylic acid | 444 |

TABLE (IA)-continued

EXAMPLES 8 to 56 ARE TABULATED BELOW:

| Ex # | Structure | IUPAC names | MS |
|---|---|---|---|
| 48 | 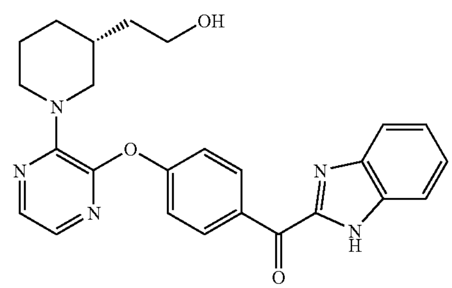 | (±)-(1H-benzo[d]imidazol-2-yl)(4-(3-(3-(2-hydroxyethyl)piperidin-1-yl)pyrazin-2-yloxy)phenyl)methanone | 444 |
| 49 | 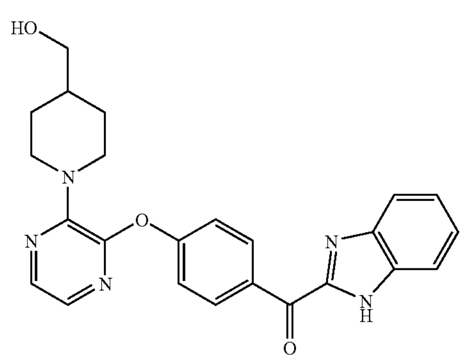 | (1H-benzo[d]imidazol-2-yl)(4-(3-(4-(hydroxymethyl)piperidin-1-yl)pyrazin-2-yloxy)phenyl)methanone | 430 |

TABLE (IA)-continued

EXAMPLES 8 to 56 ARE TABULATED BELOW:

| Ex # | Structure | IUPAC names | MS |
|---|---|---|---|
| 50 | 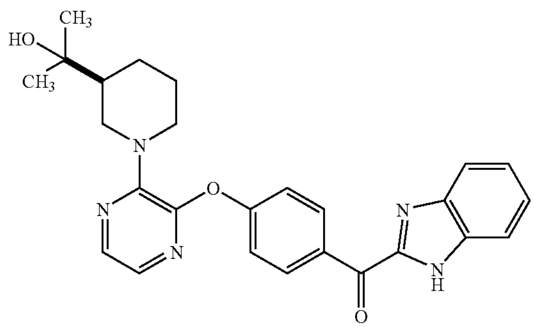 | (±)-(1H-benzo[d]imidazol-2-yl)(4-(3-(3-(2-hydroxypropan-2-yl)piperidin-1-yl)pyrazin-2-yloxy)phenyl)methanone | 458 |
| 51 | 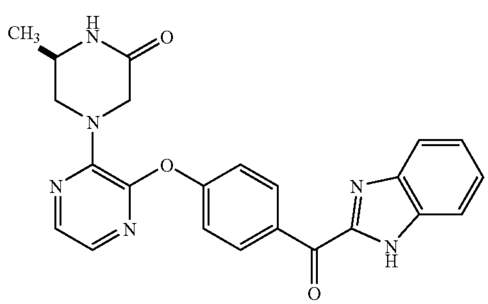 | (±)-4-(3-(4-(1H-benzo[d]imidazole-2-carbonyl)phenoxy)pyrazin-2-yl)-6-methylpiperazin-2-one | 429 |

TABLE (IA)-continued

EXAMPLES 8 to 56 ARE TABULATED BELOW:

| Ex # | Structure | IUPAC names | MS |
|---|---|---|---|
| 52 | 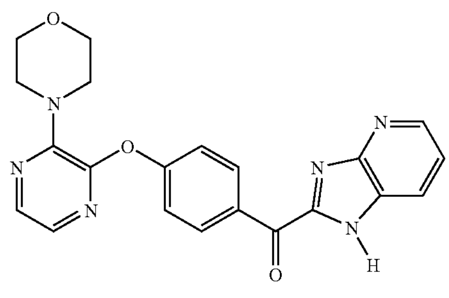 | (1H-imidazo[4,5-b]pyridin-2-yl)(4-(3-morpholinopyrazin-2-yloxy)phenyl)methanone | 403 |
| 53 | 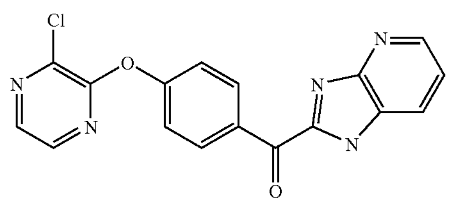 | (4-(3-chloropyrazin-2-yloxy)phenyl)(1H-imidazo[4,5-b]pyridin-2-yl)methanone | 352 |
| 54 | 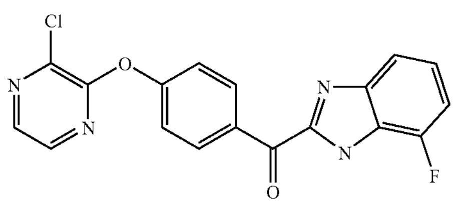 | (4-(3-chloropyrazin-2-yloxy)phenyl)(7-fluoro-1H-benzo[d]imidazol-2-yl)methanone | 369 |
| 55 | 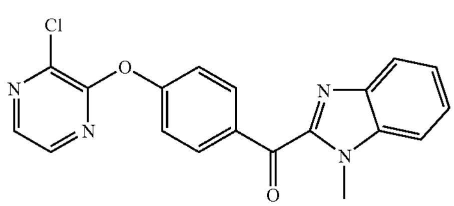 | (4-(3-chloropyrazin-2-yloxy)phenyl)(1-methyl-1H-benzo[d]imidazol-2-yl)methanone | 365 |
| 56 | 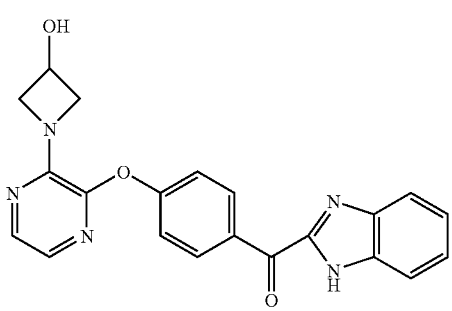 | (1H-benzo[d]imidazol-2-yl)(4-(3-(3-hydroxyazetidin-1-yl)pyrazin-2-yloxy)phenyl)methanone | 388 |

TABLE (1B)

| | | | |
|---|---|---|---|
| PREPARATION OF EXAMPLES 8 TO 56 ARE TABULATED BELOW: | | | |
| Ex# | Synthetic Scheme | How different from main route | Reagent difference |
| 8 | 1 | Same | 2-(piperidin-4-yl)propan-2-ol |
| 9 | 1 | Same | piperidin-4-ol |
| 10 | 1 | Same | piperidin-3-ol |
| 11 | 1 | 1 eq TEA, 90° C., 1.5 h, not sealed | 4-methoxypiperidine |
| 12 | 1 | Same | pyrrolidine |
| 13 | 1 | Same | piperidine |
| 14 | 1 | 70° C., 5 h, not sealed | 2-(methoxymethyl)pyrrolidine |
| 15 | 1 | 90° C., 9 h, not sealed | 2,6-dimethylmorpholine |
| 16 | 1 | Same | 1-methylpiperazine |
| 17 | 1 | Same | 1-acetylpiperazine |

TABLE (1B)-continued

PREPARATION OF EXAMPLES 8 TO 56 ARE TABULATED BELOW:

| Ex# | Synthetic Scheme | How different from main route | Reagent difference |
|---|---|---|---|
| 18 | 1 | Same | 4-cyanopiperidine |
| 19 | 1 | iPr₂NEt, 200° C., microwave | 4-aminotetrahydropyran |
| 20 | 1 | K₂CO₃, 200° C., microwave | 3-aminotetrahydropyran |
| 21 | 1 | 70° C., 5 h, not sealed | 1,4-oxazepane |
| 22 | 1 | 70° C., 5 h, not sealed | 4-(methoxymethyl)piperidine |
| 23 | 1 | (1) Cs₂CO₃, 90° C. (2) TFA | 4-piperidone + 1,4-dioxa-8-azaspiro[4.5]decane |
| 24 | 1 | Same | 4-(trifluoromethyl)piperidine |
| 25 | 1 | Same | 2-(piperazin-1-yl)ethanol |

TABLE (1B)-continued

PREPARATION OF EXAMPLES 8 TO 56 ARE TABULATED BELOW:

| Ex# | Synthetic Scheme | How different from main route | Reagent difference |
|---|---|---|---|
| 26 | 1 | Same | 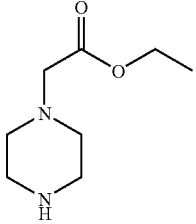 |
| 27 | 1 | Same | 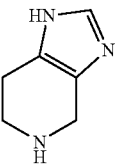 |
| 28 | 1 | 1.0 equivalents of triethylamine was added to the reaction | 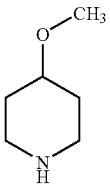 |
| 29 | 1 | 3.0 equivalents of cesium carbonate was added to the reaction | 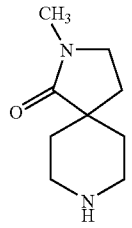 |
| 30 | 1 | 3.0 equivalents of cesium carbonate was added to the reaction | 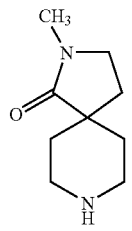 |
| 31 | 1 | Same | 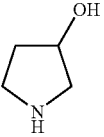 |
| 32 | 1 | 1.0 equivalents of triethylamine was added to the reaction | 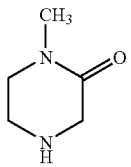 |
| 33 | 1 | 1.0 equivalents of triethylamine was added to the reaction | 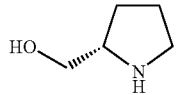 |

TABLE (1B)-continued

PREPARATION OF EXAMPLES 8 TO 56 ARE TABULATED BELOW:

| Ex# | Synthetic Scheme | How different from main route | Reagent difference |
|---|---|---|---|
| 34 | 1 | 4.5 equivalents of triethylamine was added to the reaction | (S)-3-(hydroxymethyl)pyrrolidine |
| 35 | 1 | 1.0 equivalents of triethylamine was added to the reaction | 3-methyl-5,6,7,8-tetrahydro-[1,2,4]triazolo[4,3-a]pyrazine |
| 36 | 1 | 1.0 equivalents of triethylamine was added to the reaction | (R)-3-(hydroxymethyl)pyrrolidine |
| 37 | 1 | 1.0 equivalents of triethylamine was added to the reaction | (S)-2-(methoxymethyl)pyrrolidine |
| 38 | 1 | 1.0 equivalents of triethylamine was added to the reaction | 2-(piperidin-4-yl)ethanol |
| 39 | 1 | Same | piperidine-3-carbonitrile |
| 40 | 1 | 1.0 equivalents of triethylamine was added to the reaction | pyrrolidine-3-carbonitrile |
| 41 | 1 | 3.0 equivalents of triethylamine was added to the reaction | ethyl piperidine-4-carboxylate |

TABLE (1B)-continued
PREPARATION OF EXAMPLES 8 TO 56 ARE TABULATED BELOW:
| Ex# | Synthetic Scheme | How different from main route | Reagent difference |
|---|---|---|---|
| 42 | 1 | 3.0 equivalents of triethylamine was added to the reaction | 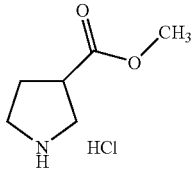 |
| 43 | 1 | Same | 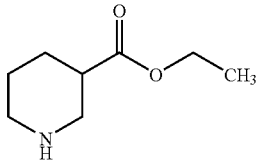 |
| 44 | 1 | Same | 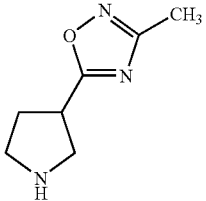 |
| 45 | 1 | Same | 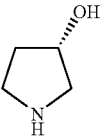 |
| 46 | 1 | Same | 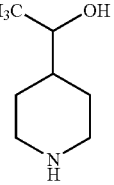 |
| 47 | 1 | Workup: HCl | 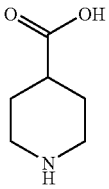 |
| 48 | 1 | Same | 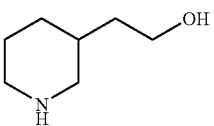 |
| 49 | 1 | Same | 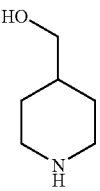 |

TABLE (1B)-continued

PREPARATION OF EXAMPLES 8 TO 56 ARE TABULATED BELOW:

| Ex# | Synthetic Scheme | How different from main route | Reagent difference |
|---|---|---|---|
| 50 | 1 | 6.0 equivalents of triethylamine was added to the reaction | 3-(2-hydroxypropan-2-yl)piperidine |
| 51 | 1 | Same | 5-methylpiperazin-2-one |
| 52 | 1 | Same | pyridine-2,3-diamine |
| | | | morpholine |
| 53 | 1 | Same | pyridine-2,3-diamine |
| 54 | 1 | Same | 3-fluorobenzene-1,2-diamine |
| 55 | 4 | Same | (2-(4-((3-chloropyrazin-2-yl)oxy)phenyl)(1H-benzo[d]imidazol-2-yl)methanone |
| 56 | 1 | Cs₂CO₃, NMP, 135° C. | azetidin-3-ol HCl |

SCHEME 5

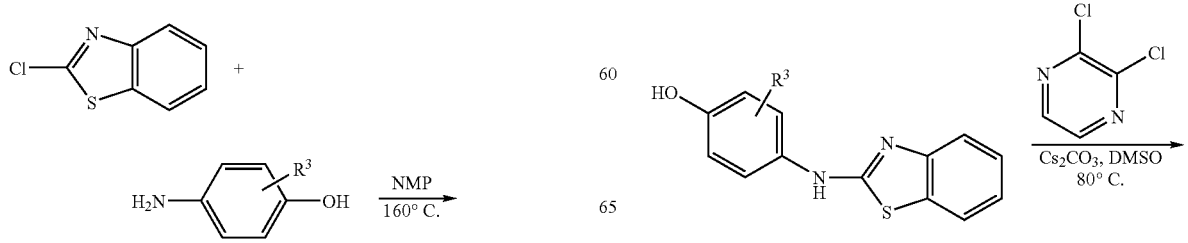

-continued

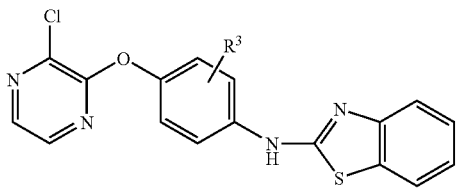

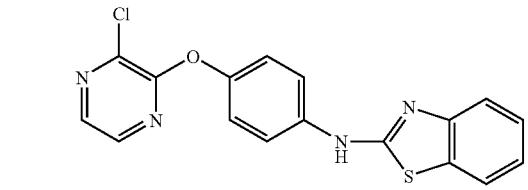

STEP 2. N-(4-(3-CHLOROPYRAZIN-2-YLOXY)PHENYL)BENZO[D]THIAZOL-2-AMINE

To a solution of 4-(benzo[d]thiazol-2-ylamino)phenol (3.1 g, 12.8 mmol) and 2,3-dichloropyrazine (2.29 g, 15.4 mmol) in DMSO (35 mL) was added cesium carbonate (5.0 g, 15.4 mmol). The reaction mixture was heated to 80° C. for 2 h. The mixture was cooled to RT, diluted with EtOAc and brine. The aqueous layer was extracted with EtOAc (2×) and the combined organics were dried over Na2SO4, filtered and concentrated. The crude product was chromatographed through a Redi-Sep® pre-packed silica gel column (120 g), eluting with a gradient of 0% to 100% EtOAc in hexane, to provide N-(4-(3-chloropyrazin-2-yloxy)phenyl)benzo[d]thiazol-2-amine as light-tan solid.

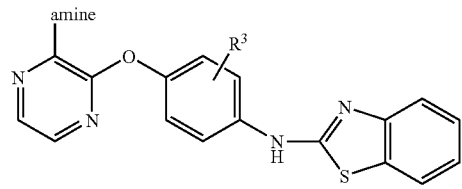

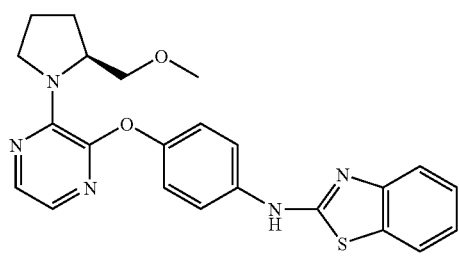

Example 57

(S)-N-(4-(3-(2-(METHOXYMETHYL)PYRROLIDIN-1-YL)PYRAZIN-2-YLOXY)PHENYL)BENZO[D]THIAZOL-2-AMINE

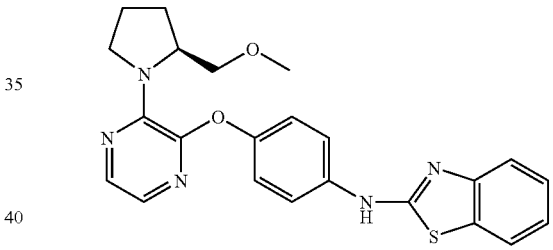

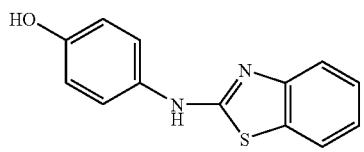

STEP 1. 4-(BENZO[D]THIAZOL-2-YLAMINO)PHENOL

The solution of 2-chlorobenzothiazole (2.47 mL, 20 mmol) and 4-aminophenol (2.18 g, 20.0 mmol) in N-methylpyrrolidone (16 mL) was heated at 160° C. for 7 h. The reaction mixture was quenched with aqueous 2N NaOH and then extracted with EtOAc. The organic layer was washed with 2N NaOH. To the combined aqueous layer was added aqueous 5N HCl until pH 6, then the product was extracted with EtOAc (2×), dried (Na$_2$SO$_4$) and concentrated. The crude product was dissolved in MeOH and treated with Soothed 2. Chromatograph through a Redi-Sep® pre-packed silica gel column (120 g), eluting with a gradient of 0% to 50% EtOAc in hexane, provided 4-(benzo[d]thiazol-2-ylamino)phenol as a tan solid.

STEP 3. (S)—N-(4-(3-(2-(METHOXYMETHYL)PYRROLIDIN-1-YL)PYRAZIN-2-YLOXY)PHENYL)BENZO[D]THIAZOL-2-AMINE

To a solution of N-(4-(3-chloropyrazin-2-yloxy)phenyl)benzo[d]thiazol-2-amine (180 mg, 0.51 mmol) in DMSO (2 mL) was added (s)-(+)-2-(methoxymethyl)-pyrrolidine (0.29 mL, 2.55 mmol). The reaction mixture was heated at 80° C. for 16 h. The reaction mixture was partitioned between EtOAc and brine. The aqueous layer was back extracted with EtOAc (2×) and the combined organics were dried (Na$_2$SO$_4$) and concentrated. The crude product was chromatographed through a Redi-Sep® pre-packed silica gel column (40 g), eluting with a gradient of 0% to 40% EtOAc in hexanes, followed by reverse-phase preparative HPLC using a Phenomena Gemini™ column (10 micron, C18, 110 Å, 150×30 mm), 0.1% TFA in CH$_3$CN/H$_2$O as mobile phase, gradient 10% to 90% over 15 min., then treated with Si-carbonate resin to provide (S)—N-(4-(3-(2-(methoxymethyl)pyrrolidin-1-yl)pyrazin-2-yloxy)phenyl)benzo[d]thiazol-2-amine as off-white solid. MS (ESI, pos. ion) m/z: 434.1 (M+1). IC50 (uM) +++++.

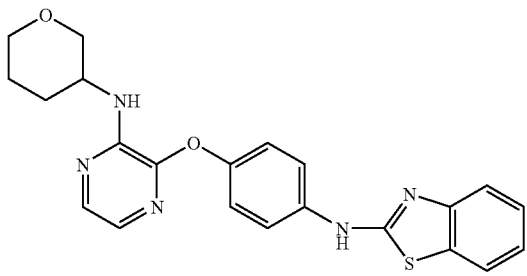

Example 58

N-(4-(3-(TETRAHYDRO-2H-PYRAN-3-YLAMINO)PYRAZIN-2-YLOXY)PHENYL)BENZO[D]THIAZOL-2-AMINE

To a microwave vial was charged with N-(4-(3-chloropyrazin-2-yloxy)phenyl)benzo[d]thiazol-2-amine (0.25 g, 0.71 mmol), tetrahydro-2H-pyran-3-amine hydrochloride (0.19 g, 1.4 mmol), and DIPEA (0.49 mL, 2.8 mmol) in isopropyl alcohol (2 mL). The reaction was stirred and heated in a Discover® model microwave reactor (CEM, Matthews, N.C.) at 200° C. for 30 min (200 watts, Powermax™ feature on), then at the same temperature for another 15 min. The reaction mixture was partitioned between EtOAc and brine. The aqueous layer was extracted with EtOAc (3×) and the combined organics was dried (Na₂SO₄) and concentrated. The crude product was chromatographed through a Redi-Sep® pre-packed silica gel column (40 g), eluting with a gradient of 0% to 50% EtOAc in hexane, to provide N-(4-(3-(tetrahydro-2H-pyran-3-ylamino)pyrazin-2-yloxy)phenyl)benzo[d]thiazol-2-amine as off-white solid. MS (ESI, pos. ion) m/z: 420.0 (M+1). IC50 (uM) ++++.

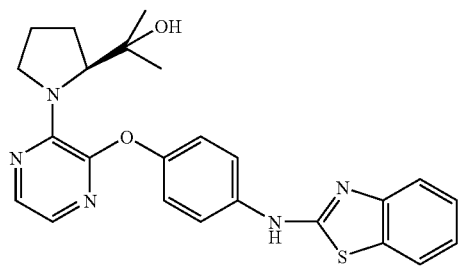

STEP 1. (S)-METHYL 1-BENZYLPYRROLIDINE-2-CARBOXYLATE.

l-praline methyl ester hydrochloride (5.8 g, 35 mmol) was suspended in DCM (40 mL), to it was added triethylamine (12 ml, 84 mmol). After stirring for 10 min, the precipitate formed was filtered off and washed with DCM (5 mL). To the filtrate was added benzyl bromide (5.0 ml, 42 mmol). The reaction mixture was stirred at RT for 16 h. The reaction mixture was diluted with EtOAc and washed with water and brine, dried (Na2SO4) and concentrated. The crude product was chromatographed through a Redi-Sep® pre-packed silica gel column (120 g), eluting with a gradient of 0% to 25% EtOAc in hexane, to provide (S)-methyl 1-benzylpyrrolidine-2-carboxylate as colorless oil. MS (ESI, pos. ion) m/z: 220.0 (M+1).

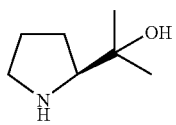

STEP 2. (S)-2-(PYRROLIDIN-2-YL)PROPAN-2-OL.

Methylmagnesium chloride, 3.0 m solution in tetrahydrofuran (24 ml, 71 mmol) was slowly injected into a solution of (S)-methyl 1-benzylpyrrolidine-2-carboxylate (3.87 g, 18 mmol) in dry THF (50 mL) at 0° C. The reaction mixture was stirred at that temperature for 3.5 h. The reaction was quenched with saturated NH₄Cl and extracted with EtOAc (3×). The combined organic layers were washed with water and brine, dried (Na₂SO₄) and concentrated. The residue was chromatographed through a Redi-Sep® pre-packed silica gel column (120 g), eluting with a gradient of 0% to 50% EtOAc in hexane, to provide (S)-2-(1-benzylpyrrolidin-2-yl)propan-2-ol as clear oil.

To a solution of (S)-2-(1-benzylpyrrolidin-2-yl)propan-2-ol (1.38 g, 6.29 mmol) in MeOH (50 mL) was added palladium hydroxide, 20 wt % pd (dry basis) on carbon, wet, degussa type e101 ne/w (230 mg, 1.64 mmol) and acetic acid glacial (690 μl, 12.0 mmol). The reaction mixture was stirred at RT under 1 atm of H₂ for 24 h. The reaction mixture was filtered through a pad of celite and washed with MeOH. The solvent was evaporated and the residue was partitioned between 2 N NaOH and EtOAc. The aqueous layer was extracted with EtOAc (2×) and the combined organic layer was dried (Na₂SO₄) and concentrated. The crude product was chromatographed through a Redi-Sep® pre-packed silica gel column (40 g), eluting with a gradient of 50% to 100% MeOH in EtOAc, to provide (S)-2-(pyrrolidin-2-yl)propan-2-ol as an orange oil.

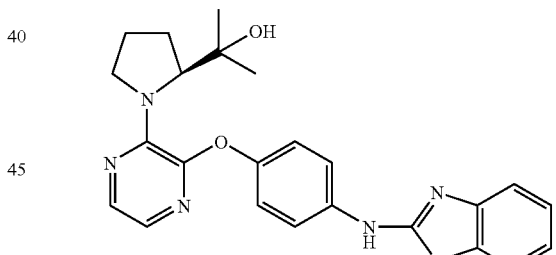

STEP 3. (S)-2-(1-(3-(4-(BENZO[D]THIAZOL-2-YLAMINO)PHENOXY)PYRAZIN-2-YL)PYRROLIDIN-2-YL)PROPAN-2-OL.

To a solution of N-(4-(3-chloropyrazin-2-yloxy)phenyl)benzo[d]thiazol-2-amine (180 mg, 507 μmol) in DMSO (2 mL) was added (S)-2-(pyrrolidin-2-yl)propan-2-ol (216 mg, 1674 μmol). The reaction mixture was heated at 80° C. for 16 h, then at 100° C. for 72 h.

The reaction mixture was partitioned between EtOAc and brine. The aqueous layer was back extracted with EtOAc (2×) and the combined organics were dried (Na₂SO₄) and concentrated. The crude product was chromatographed through a Redi-Sep® pre-packed silica gel column (40 g), eluting with a gradient of 0% to 40% EtOAc in hexane to provide (S)-2-(1-(3-(4-(benzo[d]thiazol-2-ylamino)phenoxy)pyrazin-2-yl)pyrrolidin-2-yl)propan-2-ol as tan solid. MS (ESI, pos. ion) m/z: 448.1 (M+1). IC50 (uM) +++++.

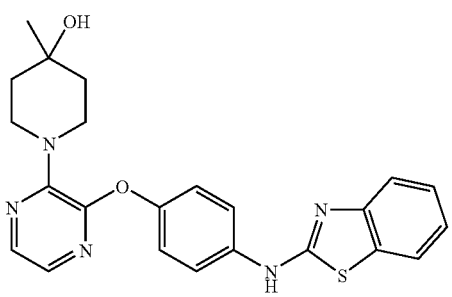

Example 60

1-(3-(4-(BENZO[D]THIAZOL-2-YLAMINO)PHE-NOXY)PYRAZIN-2-YL)-4-METHYLPIPERIDIN-4-OL

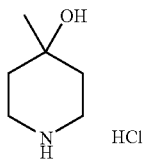

STEP 1. 4-METHYLPIPERIDIN-4-OL HYDROCHLORIDE.

To tert-butyl 4-hydroxy-4-methylpiperidine-1-carboxylate (1.0 g, 4.6 mmol) was added hydrogen chloride, 1.0 M solution in diethyl ether (4.6 ml, 4.6 mmol). The reaction mixture was stirred at RT for 4 h. The reaction mixture was concentrated down to give a yellow oil which was used directly in the following step.

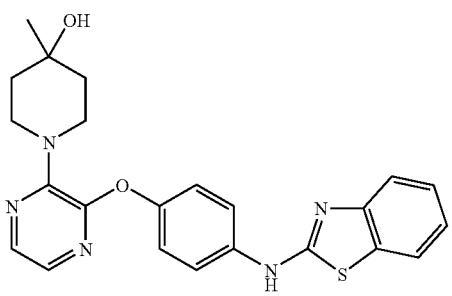

STEP 2: 1-(3-(4-(BENZO[D]THIAZOL-2-YLAMINO)PHENOXY)PYRAZIN-2-YL)-4-METHYLPIPERIDIN-4-OL.

The crude material from previous step was triturated with ether/DCM. The solvent was decanted and the residue was concentrated to give a light-yellow solid. To it was added N-(4-(3-chloropyrazin-2-yloxy)phenyl)benzo[d]thiazol-2-amine (180 mg, 0.507 mmol), cesium carbonate (496 mg, 1.522 mmol) and DMSO (2.0 mL). The reaction mixture was stirred at 80° C. for 16 h. The reaction mixture was partitioned between EtOAc and brine. The aqueous layer was back extracted with EtOAc (2×) and the combined EtOAc layer was dried (Na$_2$SO$_4$) and concentrated. The crude material was dissolved in DCM and purified by chromatography through a Redi-Sep® pre-packed silica gel column (40 g), eluting with a gradient of 0% to 70% EtOAc in hexane, to provide 1-(3-(4-(benzo[d]thiazol-2-ylamino)phenoxy)pyrazin-2-yl)-4-methylpiperidin-4-ol as light-yellow solid. MS (ESI, pos. ion) m/z: 434.1 (M+1) . . . IC50 (uM) +++++.

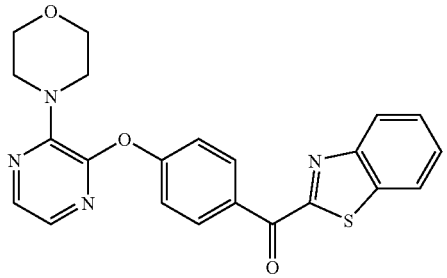

Example 61

BENZO[D]THIAZOL-2-YL(4-(3-MORPHOLINOPYRAZIN-2-YLOXY)PHENYL)METHANONE

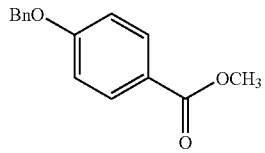

STEP 1. 4-BENZYLOXY-BENZOIC ACID METHYL ESTER.

In a 2 L two-necked round bottom flask was charged methyl 4-hydroxybenzoate (100 g, 0.657 mol) and 500 mL of DMF. Potassium carbonate (180 g, 1.3 mol) was added and the mixture was cooled to 0° C. Benzylbromide (77 mL, 0.66 mol) was added dropwise to the reaction mixture with vigorous stirring for 30 min. After the addition was complete, the reaction mixture was stirred for 8 h at RT, then diluted with 500 ml water. The solid precipitated was collected by filtration and washed with water. Drying in a vacuum oven overnight provided the title compound.

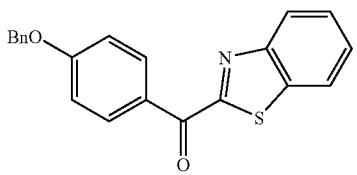

STEP 2. BENZO[D]THIAZOL-2-YL(4-(BENZYLOXY)PHENYL)METHANONE.

In a 100 ml round bottom flask were added 4-benzyloxy-benzoic acid methyl ester (0.8 g, 3.1 mmol) and benzothiozole (312 mg, 3.1 mmol), followed by dry THF. After cooling the reaction mixture to −70° C., LDA (15.2 mL 1.6 M, 18.6 mmol) was added slowly for 5 min. The reaction mixture was stirred −70° C. for 2 h. The reaction was quenched with 1N HCl and extracted with ethyl acetate. The aqueous was back extracted with EtOAc and the combined organics was washed with brine and dried (Na₂SO₄) and concentrated to give benzo[d]thiazol-2-yl(4-(benzyloxy)phenyl)methanone.

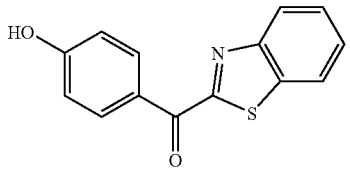

STEP 3. BENZO[D]THIAZOL-2-YL(4-HYDROXYPHENYL)METHANONE.

In a 1 L round bottom flask was charged in a solution of boron trifluride diethyl etherate (101.2 g, 312 mmol) and dimethylsulfide (112 g, 809 mmol) in dry methylenedichloride (300 ml). Benzo[d]thiazol-2-yl(4-(benzyloxy)phenyl) methanone (30 g, 86.9 mmol) was added slowly to the mixture and the resulting solution was stirred at room temperature for 72 h. The reaction mixture was then quenched with water and diluted with CH₂Cl₂. The organic phase was washed with brine, dried (Na2SO4) and concentrated. The crude product was purified by silica gel column chromatography with hexane and ethyl acetate to give benzo[d]thiazol-2-yl(4-hydroxyphenyl)methanone. [M+H]=256.

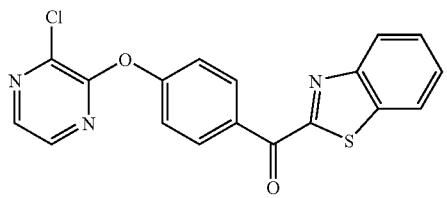

STEP 4: BENZO[D]THIAZOL-2-YL(4-(3-CHLOROPYRAZIN-2-YLOXY)PHENYL)METHANONE

In 250 mL round bottom flask were charged benzo[d]thiazol-2-yl(4-hydroxyphenyl)methanone (6.0 g, 23.5 mmol), 2,3-dichloro-pyrazine (3.48 g, 23.5 mmol), DMSO (60 mL), and cesium carbonate (15 g, 47 mmol). The reaction mixture was stirred at 90° C. for 6 h. The reaction mixture was diluted with cold water and the precipitate was collected by filtration. The crude product was purified by silica gel column chromatography with hexane and ethyl acetate to give the title compound. [M+H]=368.

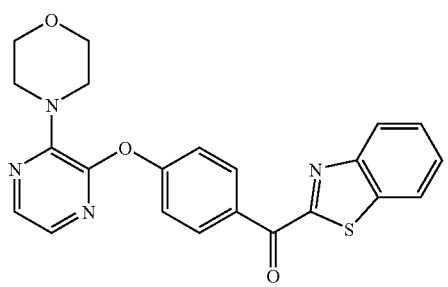

STEP 5. BENZO[D]THIAZOL-2-YL(4-(3-MORPHOLINOPYRAZIN-2-YLOXY)PHENYL)METHANONE

To a solution of benzo[d]thiazol-2-yl(4-(3-chloropyrazin-2-yloxy)phenyl)methanone (185 mg, 0.503 mmol) in DMSO (2 mL) was added morpholine (219 μl, 2.52 mmol). The reaction mixture was heated at 100° C. for 2 h. The reaction mixture was partitioned between EtOAc and brine. The precipitate formed was collected by filtration, washed with EtOAc and water, dried to provide benzo[d]thiazol-2-yl(4-(3-morpholinopyrazin-2-yloxy)phenyl)methanone as light-yellow solid. MS (ESI, pos. ion) m/z: 419.0. IC50 (uM) ++.

SCHEME 6

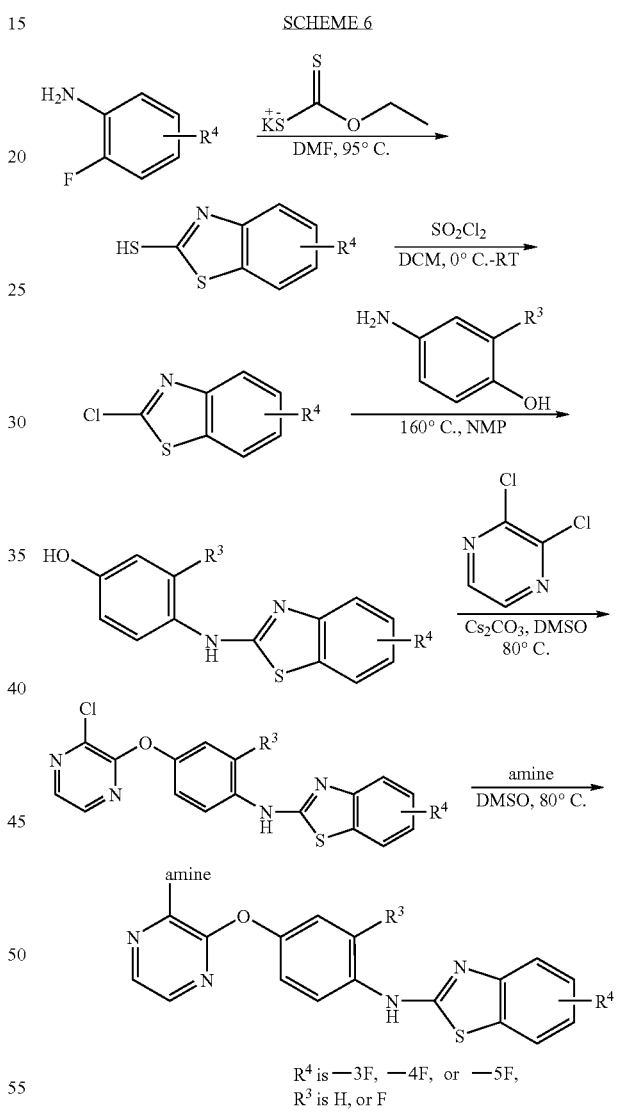

R⁴ is —3F, —4F, or —5F,
R³ is H, or F

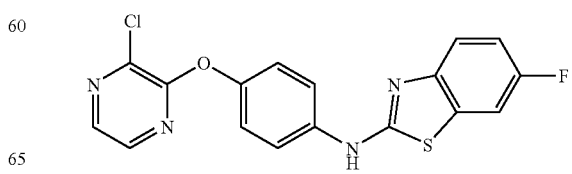

Example 62

N-(4-(3-CHLOROPYRAZIN-2-YLOXY)PHENYL)-6-FLUOROBENZO[D]THIAZOL-2-AMINE

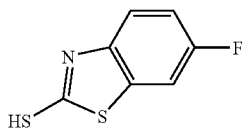

STEP-1. 6-FLUOROBENZO[D]THIAZOLE-2-THIOL

4-Fluorobenzene-1,2-diamine (10.0 g, 0.077 mol) and potassium O-ethyl carbonodithioate (37.1 g, 0.234 mol) were dissolved in dry DMF (150 mL) under nitrogen and heated to 95° C. for 12 h. The reaction was cooled to RT and 200 mL water was added followed by addition of 5N HCl to get precipitates. After stirring for 1 h, the precipitates were collected by filtration, washed with water and dried under vacuum for 2 h. The crude compound was then washed with chloroform and dried to give 6-fluorobenzo[d]thiazole-2-thiol as yellow solid.

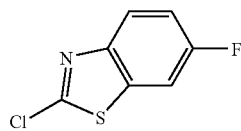

STEP-2. 2-CHLORO-6-FLUOROBENZO[D]THIAZOLE 6-fluorobenzo[d]thiazole-2-thiol (14.0 g, 0.075 mol) was suspended in dry DCM (100 mL) under nitrogen and cooled to 0° C. Sulfuryl chloride (18.5 mL) was then added dropwise and the reaction was allowed to warm to RT and stirred for 1 h. The reaction mixture was then poured on to crushed ice and extracted with DCM (4×300 mL). The combined organic extract was given brine wash (2×150 mL), dried (Na$_2$SO$_4$) and concentrated. The crude compound was purified by column chromatography (Silica 100-200 mesh; 3-7% ethyl acetate in hexane) to provide 2-chloro-6-fluorobenzo[d]thiazole as a white solid.

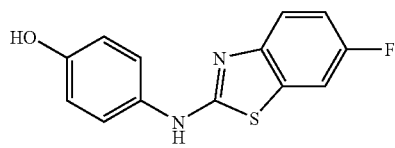

STEP-3. 4-(6-FLUOROBENZO[D]THIAZOL-2-YLAMINO)PHENOL

2-Chloro-6-fluorobenzo[d]thiazole (7.0 g, 0.037 mol) and 4-aminophenol (4.0 g, 0.037 mol) in NMP (50 mL) was heated at 160° C. for 7 h. The reaction was quenched with 2N NaOH (100 mL) and then extracted with EtOAc (2×100 mL). The organic layer was washed with 2 N NaOH (50 mL) and to the combined aqueous layer was added 5 N HCl until pH 6 and then extracted with EtOAc (3×200 mL). The combined organic extracts were washed with brine, dried (Na$_2$SO$_4$) and concentrated. The crude was purified by column chromatography (silica gel 100-200 mesh; 80% ethyl acetate in hexanes) to afford 4-(6-fluorobenzo[d]thiaol-2-ylamino)phenol as a white solid.

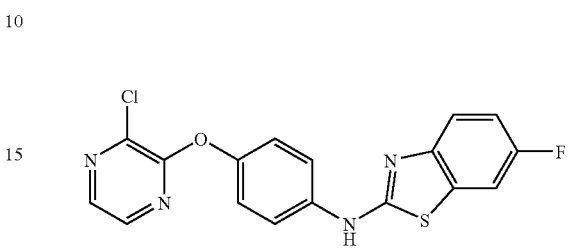

STEP-4. N-(4-(3-CHLOROPYRAZIN-2-YLOXY)PHENYL)-6-FLUOROBENZO[D]THIAZOL-2-AMINE

To a solution of 4-(6-fluorobenzo[d]thiazol-2-ylamino) phenol (7.5 g, 0.028 mol) and 2,3-dichloropyrazine (5.0 g, 0.034 mol) in DMSO (35 mL) was added cesium carbonate (11.0 g, 0.034 mol). The mixture was heated to 80° C. for 2 h. The reaction mixture was cooled to RT and diluted with water (350 mL). The aqueous layer was extracted with EtOAc (4×300 mL). The combined organic extract was washed with brine, dried (Na$_2$SO$_4$) and concentrated. The crude product was purified by column chromatography (silica 100-200 mesh; 30-60% ethyl acetate in hexane) to give N-(4-(3-chloropyrazin-2-yloxy)phenyl)-6-fluorobenzo[d]thiazol-2-amine as a white solid. [M+H]=372.8. IC50 (uM) +.

SCHEME 7

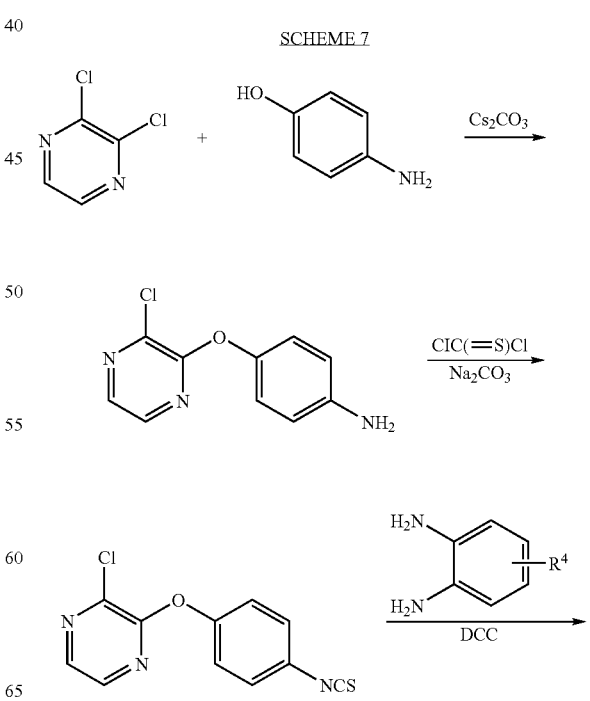

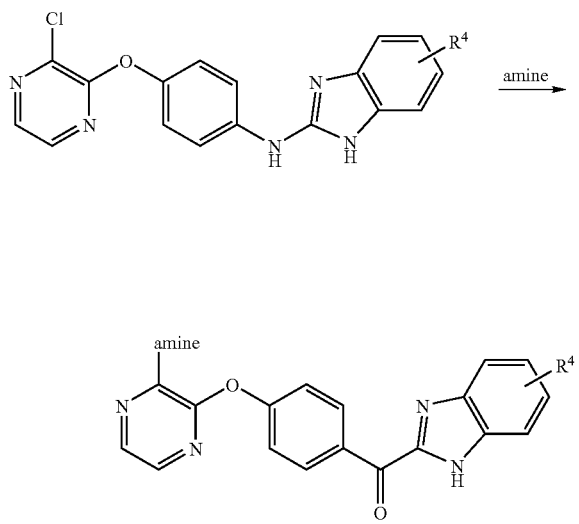 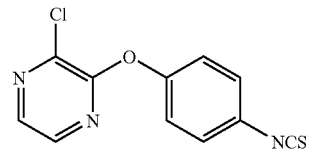

STEP 2. CHLORO-3-(4-ISOTHIOCYANATOPHENOXY) PYRAZINE

To a mixtre of 4-(3-chloropyrazin-2-yloxy)benzenamine (620 mg, 2797 μmol) and sodium carbonate (652 mg, 6154 μmol) in chloroform (10 ml) was added thiophosgene (236 μl, 3077 μmol). The solution turned cloudy and was stirred overnight at room temperature. The solvent had evaporated so the residue was taken back up in chloroform and the solids were removed by filtration. The filtrate was collected and the solvent was removed by roto-vap to give the desired product as a brown solid which was used without further purification.

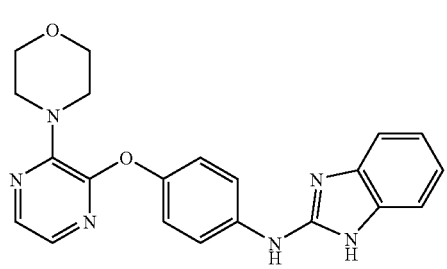

Example 63

N-(4-(3-MORPHOLINOPYRAZIN-2-YLOXY)PHENYL)-1H-BENZO[D]IMIDAZOL-2-AMINE

STEP 3. N-(4-(3-CHLOROPYRAZIN-2-YLOXY)PHENYL)-1H-BENZO[D]IMIDAZOL-2-AMINE

The mixture of 2-chloro-3-(4-isothiocyanatophenoxy)pyrazine (190 mg, 721 mmol), benzene-1,2-diamine (93.5 mg, 865 μmol) and N,N'-dicyclohexylcarbodiimide (223 mg, 1081 μmol) in THF (1.5 ml) was heated at 75° C. for 1.5 hrs. The mixture was cooled to room temperature, diluted with DCM and absorbed onto silica for purification using a 20-100% EtOAc/hexanes gradient to give the desired product.

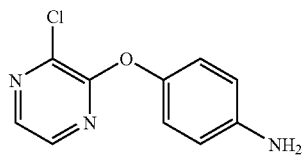 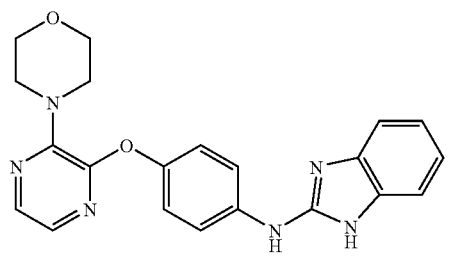

STEP 1. 4-(3-CHLOROPYRAZIN-2-YLOXY)BENZENAMINE 2,3-dichloropyrazine (470 mg, 3155 μmol) was combined with 4-aminophenol (344 mg, 3155 μmol) and cesium carbonate (1233 mg, 3786 μmol) in DMSO (5 ml) and heated to 70 C. After 3 hours, the mixture was cooled to room temperature, transferred to a separatory funnel rinsing with ethyl acetate and water, the layers were separated and the aqueous was extracted with ethyl acetate (3×). The combined organics were rinsed with brine, dried over sodium sulfate, filtered and concentrated to yield a brown solid which was carried forward without purification.

STEP 4. N-(4-(3-MORPHOLINOPYRAZIN-2-YLOXY)PHENYL)-1H-BENZO[D]IMIDAZOL-2-AMINE

N-(4-(3-chloropyrazin-2-yloxy)phenyl)-1H-benzo[d]imidazol-2-amine (191 mg, 565 μmol) and morpholine (74 μL, 848 μmol) in DMSO was heated to 80° C. After 3 h, starting material remained so additional morpholine (74 uL, 848 umol) was added and the mixture was heated overnight. The hot solution was then poured onto ice water which caused a brown solid to precipitate. The solid was collected by filtration, washed and dried to give the desired product. MS (ESI, pos. ion) m/z: 389.1 (M+1). IC50 (uM) +++++.

TABLE (IIA)

EXAMPLES 64 TO 103 ARE TABULATED BELOW:

| Ex# | Structure | IC50 (uM) | IUPAC names | MS |
|---|---|---|---|---|
| 64 | 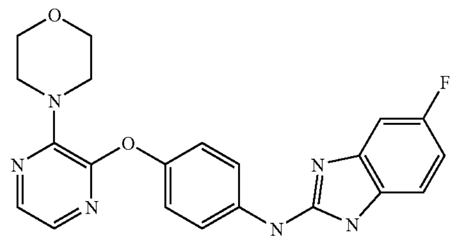 | ++++ | 5-fluoro-N-(4-(3-morpholinopyrazin-2-yloxy)phenyl)-1H-benzo[d]imidazol-2-amine | 407 |
| 65 | 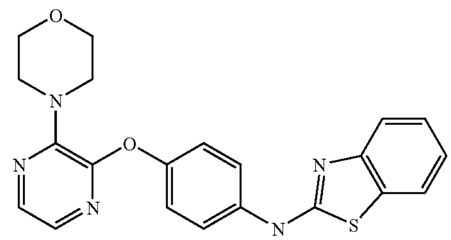 | +++++ | N-(4-(3-morpholinopyrazin-2-yloxy)phenyl)benzo[d]thiazol-2-amine | 406 |
| 66 | 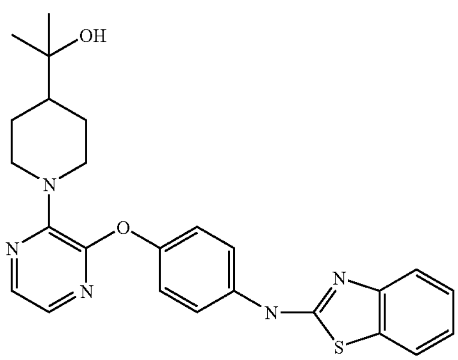 | +++++ | 2-(1-(3-(4-(benzo[d]thiazol-2-ylamino)phenoxy)pyrazin-2-yl)piperidin-4-yl)propan-2-ol | 462 |
| 67 | 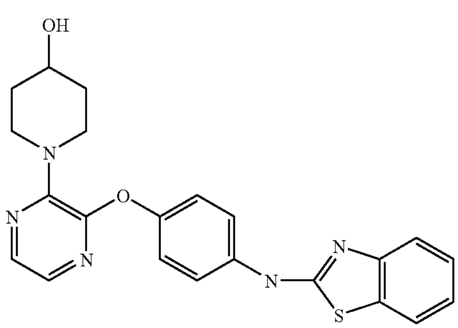 | +++++ | 1-(3-(4-(benzo[d]thiazol-2-ylamino)phenoxy)pyrazin-2-yl)piperidin-4-ol | 420 |
| 68 | 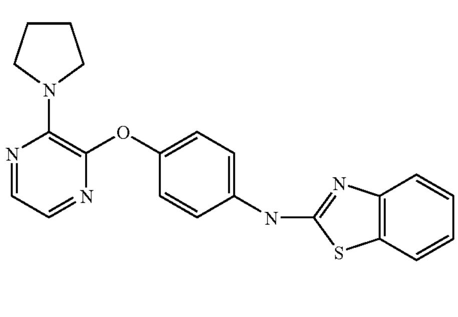 | ++++ | N-(4-(3-(pyrrolidin-1-yl)pyrazin-2-yloxy)phenyl)benzo[d]thiazol-2-amine | 390 |

TABLE (IIA)-continued

EXAMPLES 64 TO 103 ARE TABULATED BELOW:

| Ex# | Structure | IC50 (uM) | IUPAC names | MS |
|---|---|---|---|---|
| 69 | 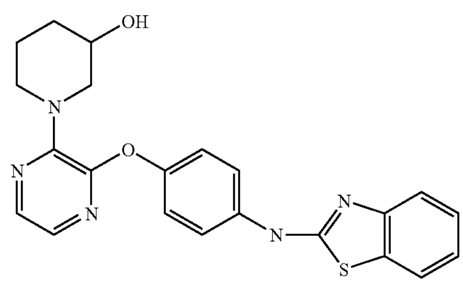 | +++++ | 1-(3-(4-(benzo[d]thiazol-2-ylamino)phenoxy)pyrazin-2-yl)piperidin-3-ol | 420 |
| 70 | 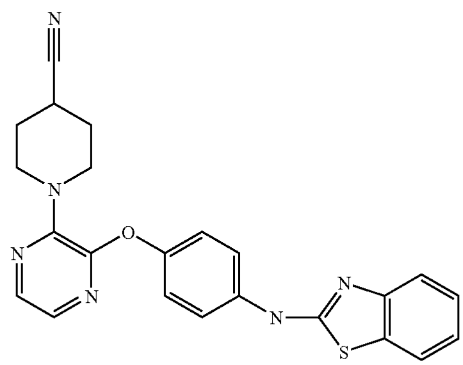 | +++++ | 1-(3-(4-(benzo[d]thiazol-2-ylamino)phenoxy)pyrazin-2-yl)piperidine-4-carbonitrile | 429 |
| 71 | 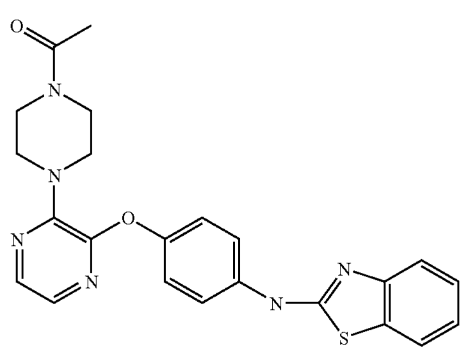 | ++++ | 1-(4-(3-(4-(benzo[d]thiazol-2-ylamino)phenoxy)pyrazin-2-yl)piperazin-1-yl)ethanone | 447 |
| 72 | 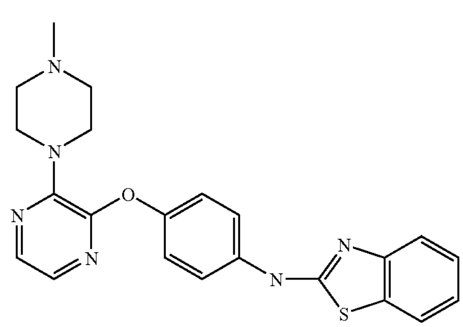 | ++++ | N-(4-(3-(4-methylpiperazin-1-yl)pyrazin-2-yloxy)phenyl)benzo[d]thiazol-2-amine | 419 |

TABLE (IIA)-continued

EXAMPLES 64 TO 103 ARE TABULATED BELOW:

| Ex# | Structure | IC50 (uM) | IUPAC names | MS |
|---|---|---|---|---|
| 73 | 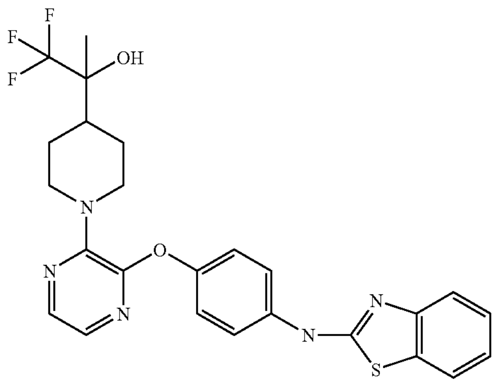 | ++ | 2-(1-(3-(4-(benzo[d]thiazol-2-ylamino)phenoxy)pyrazin-2-yl)piperidin-4-yl)-1,1,1-trifluoropropan-2-ol | 516 |
| 74 | 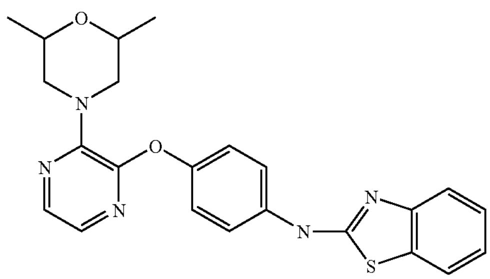 | ++++ | N-(4-(3-(2,6-dimethylmorpholino)pyrazin-2-yloxy)phenyl)benzo[d]thiazol-2-amine | 434 |
| 75 | 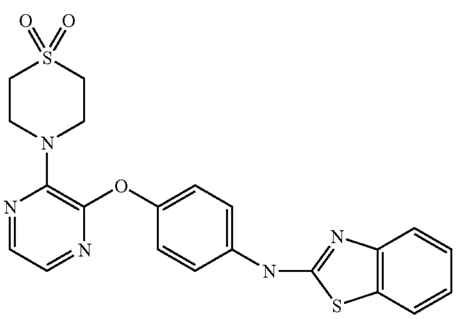 | ++ | N-(4-((3-(1,1-dioxido-4-thiomorpholinyl)-2-pyrazinyl)oxy)phenyl)-1,3-benzothiazol-2-amine | 454 |
| 76 | 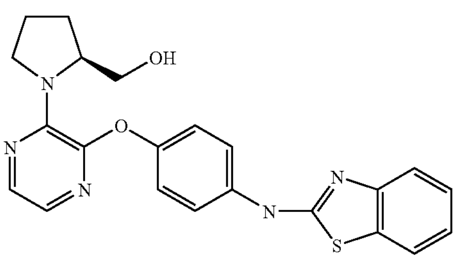 | +++++ | (S)-(1-(3-(4-(benzo[d]thiazol-2-ylamino)phenoxy)pyrazin-2-yl)pyrrolidin-2-yl)methanol | 420 |
| 77 | 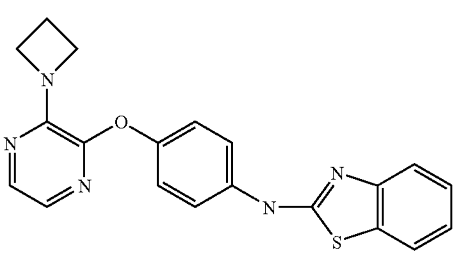 | ++++ | N-(4-(3-(azetidin-1-yl)pyrazin-2-yloxy)phenyl)benzo[d]thiazol-2-amine | 376 |

TABLE (IIA)-continued

EXAMPLES 64 TO 103 ARE TABULATED BELOW:

| Ex# | Structure | IC50 (uM) | IUPAC names | MS |
|---|---|---|---|---|
| 78 | 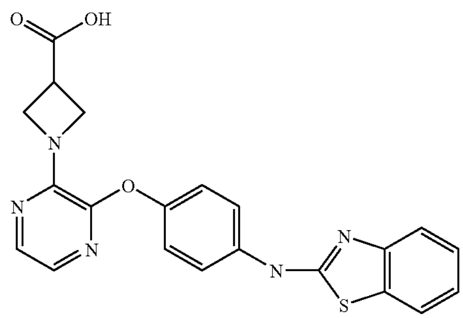 | +++++ | 1-(3-(4-(benzo[d]thiazol-2-ylamino)phenoxy)pyrazin-2-yl)azetidine-3-carboxylic acid | 420 |
| 79 | 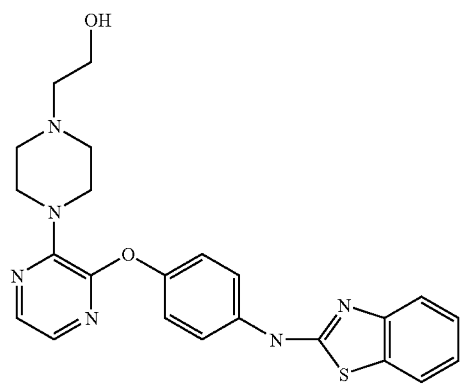 | +++++ | 2-(4-(3-(4-(benzo[d]thiazol-2-ylamino)phenoxy)pyrazin-2-yl)piperazin-1-yl)ethanol | 449 |
| 80 | 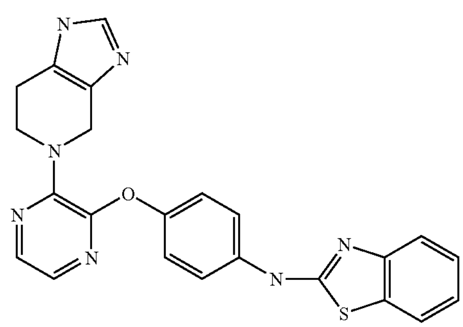 | ++++ | N-(4-(3-(6,7-dihydro-1H-imidazo[4,5-c]pyridin-5(4H)-yl)pyrazin-2-yloxy)phenyl)benzo[d]thiazol-2-amine | 442 |
| 81 | 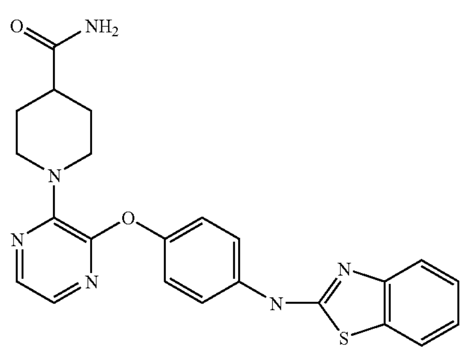 | +++++ | 1-(3-(4-(benzo[d]thiazol-2-ylamino)phenoxy)pyrazin-2-yl)piperidine-4-carboxamide | 447 |

TABLE (IIA)-continued

EXAMPLES 64 TO 103 ARE TABULATED BELOW:

| Ex# | Structure | IC50 (uM) | IUPAC names | MS |
|---|---|---|---|---|
| 82 | 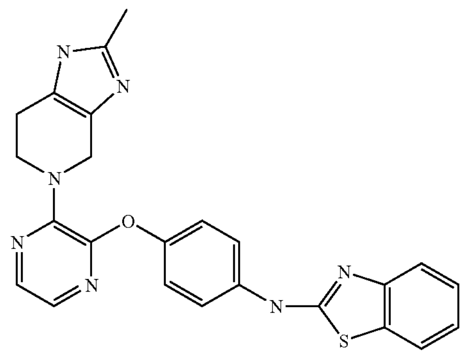 | +++ | N-(4-(3-(2-methyl-6,7-dihydro-1H-imidazo[4,5-c]pyridin-5(4H)-yl)pyrazin-2-yloxy)phenyl)benzo[d]thiazol-2-amine | 456 |
| 83 | 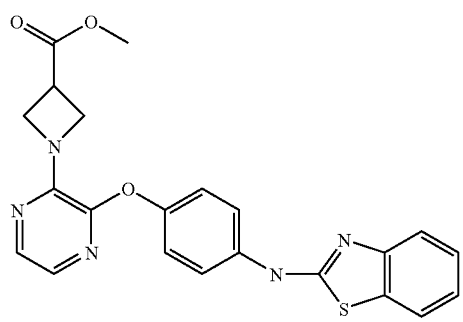 | +++++ | methyl 1-(3-(4-(benzo[d]thiazol-2-ylamino)phenoxy)pyrazin-2-yl)azetidine-3-carboxylate | 434 |
| 84 | 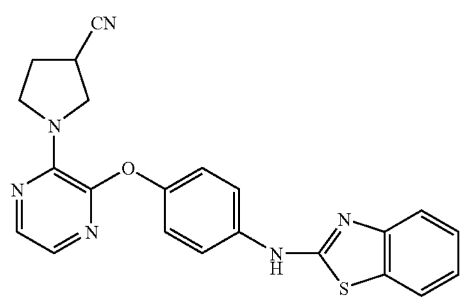 | +++++ | 1-(3-(4-(benzo[d]thiazol-2-ylamino)phenoxy)pyrazin-2-yl)pyrrolidine-3-carbonitrile | 415 |
| 85 | 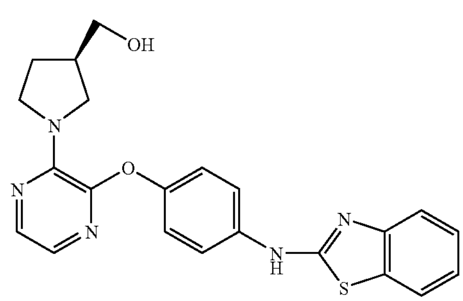 | +++++ | (R)-(1-(3-(4-(benzo[d]thiazol-2-ylamino)phenoxy)pyrazin-2-yl)pyrrolidin-3-yl)methanol | 420 |

TABLE (IIA)-continued

EXAMPLES 64 TO 103 ARE TABULATED BELOW:

| Ex# | Structure | IC50 (uM) | IUPAC names | MS |
|---|---|---|---|---|
| 86 | 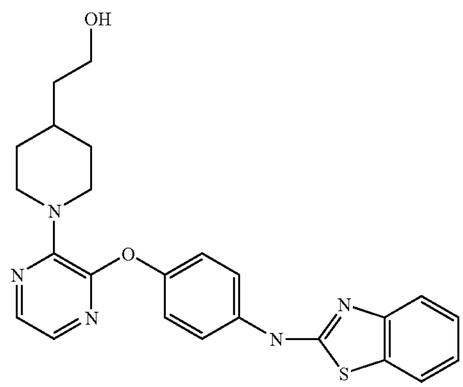 | ++++ | 2-(1-(3-(4-(benzo[d]thiazol-2-ylamino)phenoxy)pyrazin-2-yl)piperidin-4-yl)ethanol | 448 |
| 87 | 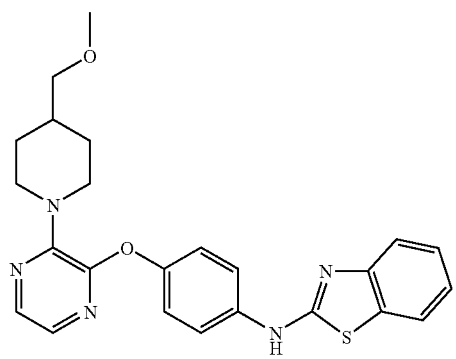 | ++++ | N-(4-(3-(4-(methoxymethyl)piperidin-1-yl)pyrazin-2-yloxy)phenyl)benzo[d]thiazol-2-amine | 448 |
| 88 | | +++++ | N-(4-(3-(3-(methoxymethyl)pyrrolidin-1-yl)pyrazin-2-yloxy)phenyl)benzo[d]thiazol-2-amine | 434 |

TABLE (IIA)-continued

EXAMPLES 64 TO 103 ARE TABULATED BELOW:

| Ex# | Structure | IC50 (uM) | IUPAC names | MS |
|---|---|---|---|---|
| 89 | 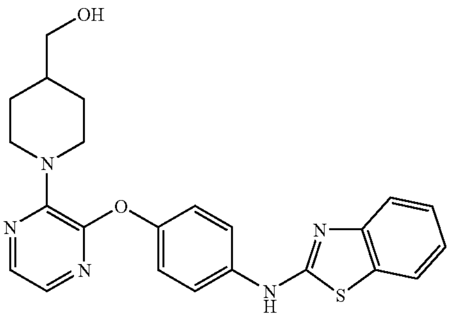 | +++++ | (1-(3-(4-(benzo[d]thiazol-2-ylamino)phenoxy)pyrazin-2-yl)piperidin-4-yl)methanol | 434 |
| 90 | 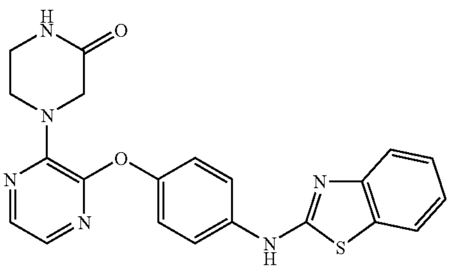 | +++++ | 4-(3-(4-(benzo[d]thiazol-2-ylamino)phenoxy)pyrazin-2-yl)piperazin-2-one | 434 |
| 91 | 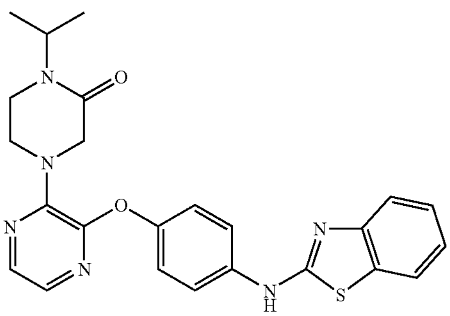 | ++++ | 4-(3-(4-(benzo[d]thiazol-2-ylamino)phenoxy)pyrazin-2-yl)-1-isopropylpiperazin-2-one | 461 |
| 92 | 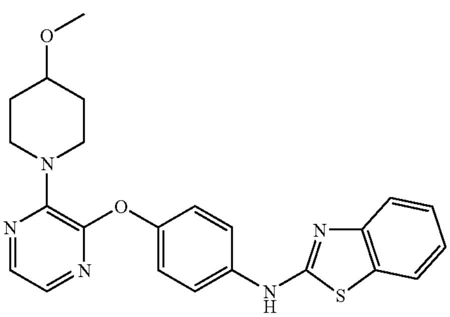 | +++++ | N-(4-(3-(4-methoxypiperidin-1-yl)pyrazin-2-yloxy)phenyl)benzo[d]thiazol-2-amine | 434 |
| 93 | 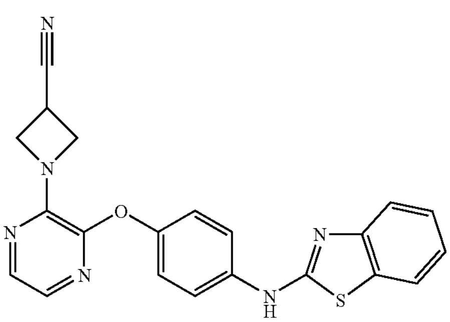 | ++++ | 1-(3-(4-(benzo[d]thiazol-2-ylamino)phenoxy)pyrazin-2-yl)azetidine-3-carbonitrile | 401 |

TABLE (IIA)-continued

EXAMPLES 64 TO 103 ARE TABULATED BELOW:

| Ex# | Structure | IC50 (uM) | IUPAC names | MS |
|---|---|---|---|---|
| 94 | | +++++ | 4-(3-(4-(benzo[d]thiazol-2-ylamino)phenoxy)pyrazin-2-yl)-6-methylpiperazin-2-one | 433 |
| 95 | 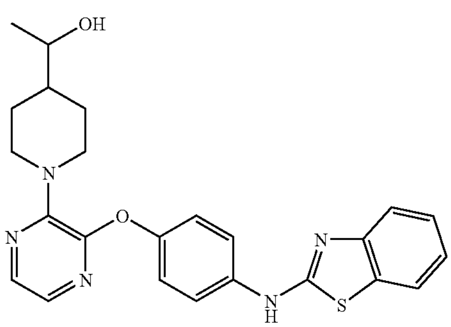 | ++++ | 1-(1-(3-(4-(benzo[d]thiazol-2-ylamino)phenoxy)pyrazin-2-yl)piperidin-4-yl)ethanol | 448 |
| 96 | 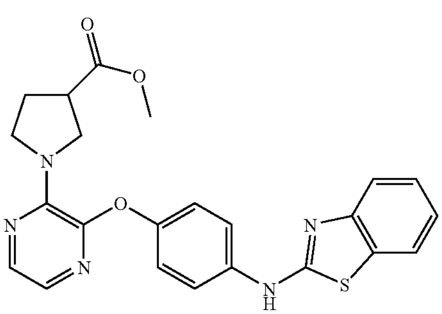 | +++++ | methyl 1-(3-(4-(benzo[d]thiazol-2-ylamino)phenoxy)pyrazin-2-yl)pyrrolidine-3-carboxylate | 448 |
| 97 | 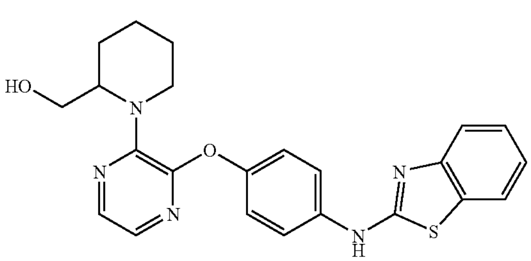 | +++++ | (1-(3-(4-(benzo[d]thiazol-2-ylamino)phenoxy)pyrazin-2-yl)piperidin-2-yl)methanol | 434 |

TABLE (IIA)-continued

EXAMPLES 64 TO 103 ARE TABULATED BELOW:

| Ex# | Structure | IC50 (uM) | IUPAC names | MS |
|---|---|---|---|---|
| 98 | 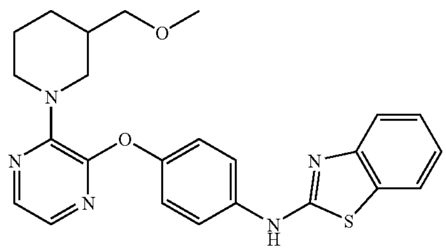 | ++++ | N-(4-(3-(3-(methoxymethyl)piperidin-1-yl)pyrazin-2-yloxy)phenyl)benzo[d]thiazol-2-amine | 448 |
| 99 | 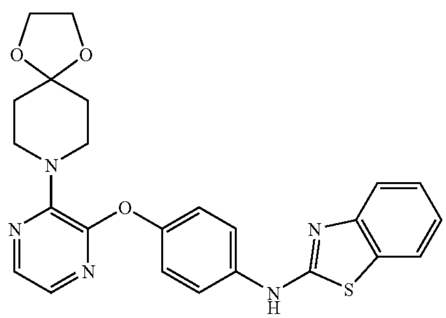 | ++++ | N-(4-(3-(1,4-dioxa-8-azaspiro[4.5]decan-8-yl)pyrazin-2-yloxy)phenyl)benzo[d]thiazol-2-amine | 462 |
| 100 | 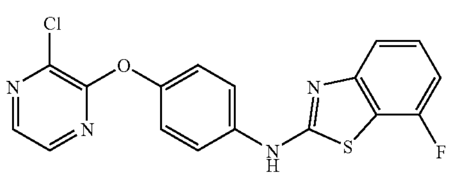 | + | N-(4-(3-chloropyrazin-2-yloxy)phenyl)-7-fluorobenzo[d]thiazol-2-amine | 372 |
| 101 | 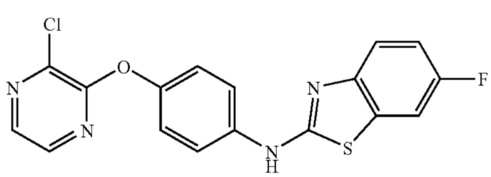 | + | N-(4-(3-chloropyrazin-2-yloxy)phenyl)-6-fluorobenzo[d]thiazol-2-amine | 372 |
| 102 | 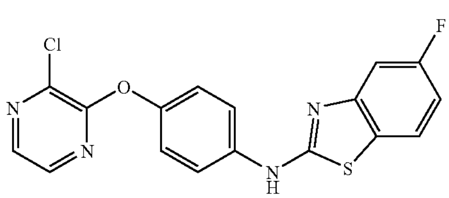 | + | N-(4-(3-chloropyrazin-2-yloxy)phenyl)-5-fluorobenzo[d]thiazol-2-amine | 372 |
| 103 | 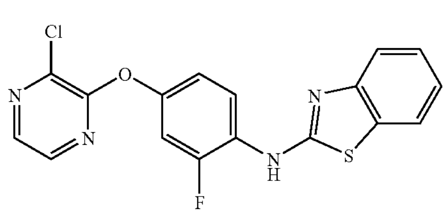 | + | N-(4-(3-chloropyrazin-2-yloxy)-2-fluorophenyl)benzo[d]thiazol-2-amine | 372 |

TABLE (IIB)
PREPARATION OF EXAMPLES 64 TO 103 ARE TABULATED BELOW:
| Ex# | Synthetic Scheme | How Different from Main Route | Reagent Difference |
|---|---|---|---|
| 64 | 7 | Same | 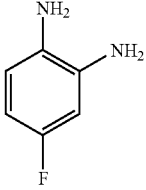 |
| 65 | 5 | Same |  |
| 66 | 5 | Same | 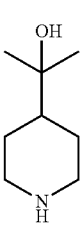 |
| 67 | 5 | Same | 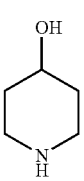 |
| 68 | 5 | Same |  |
| 69 | 5 | Same | 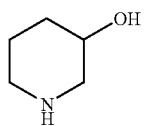 |
| 70 | 5 | Same | 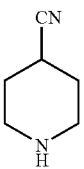 |
| 71 | 5 | Same | 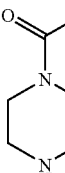 |
| 72 | 5 | Same | 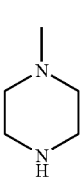 |
| 73 | 5 | Same | 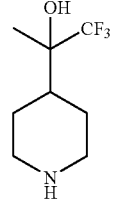 |
| 74 | 5 | Same | 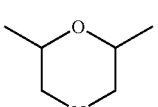 |
| 75 | 5 | Same | 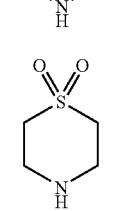 |
| 76 | 5 | Same | 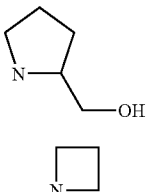 |
| 77 | 5 | Same | 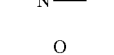 |
| 78 | 5 | Same | 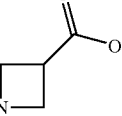 |
| 79 | 5 | Same | 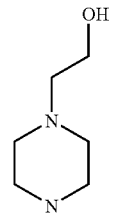 |
| 80 | 5 | Same | 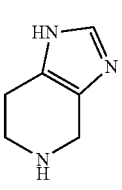 |
| 81 | 5 | Same | 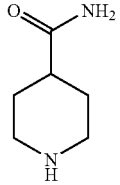 |

TABLE (IIB)-continued
PREPARATION OF EXAMPLES 64
TO 103 ARE TABULATED BELOW:
| Ex# | Synthetic Scheme | How Different from Main Route | Reagent Difference |
|---|---|---|---|
| 82 | 5 | Same | 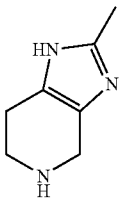 |
| 83 | 5 | Cs₂CO₃ | 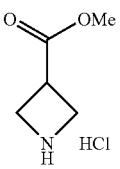 |
| 84 | 5 | Cs₂CO₃ | 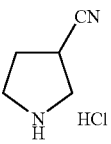 |
| 85 | 5 | Cs₂CO₃ | 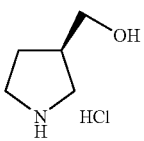 |
| 86 | 5 | Same | 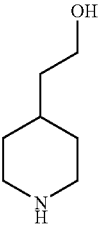 |
| 87 | 5 | Cs₂CO₃ | 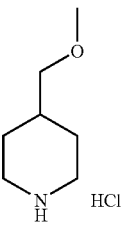 |
| 88 | 5 | Cs₂CO₃ | 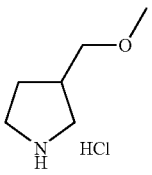 |
| 89 | 5 | Same | 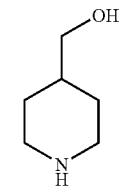 |
| 90 | 5 | Same | 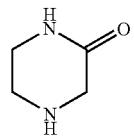 |
| 91 | 5 | Cs₂CO₃ | 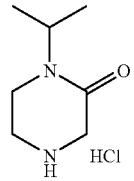 |
| 92 | 5 | Same | 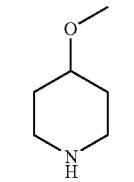 |
| 93 | 5 | Cs₂CO₃ | 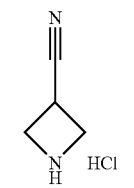 |
| 94 | 5 | Same | 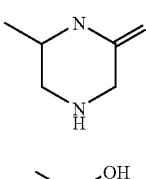 |
| 95 | 5 | Same | 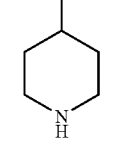 |
| 96 | 5 | Cs₂CO₃ | 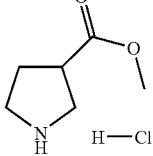 |

TABLE (IIB)-continued

PREPARATION OF EXAMPLES 64 TO 103 ARE TABULATED BELOW:

| Ex# | Synthetic Scheme | How Different from Main Route | Reagent Difference |
|---|---|---|---|
| 97 | 5 | Same | 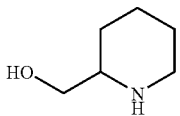 |
| 98 | 5 | Same | 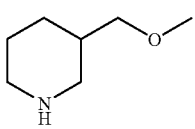 |
| 99 | 5 | Same | 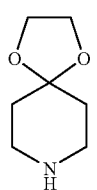 |
| 100 | 6 | Same |  |
| 101 | 6 | Same | 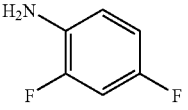 |
| 102 | 6 | Same | 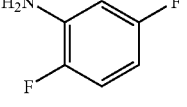 |
| 103 | 6 | Same | 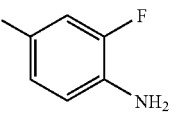 |

SCHEME 8

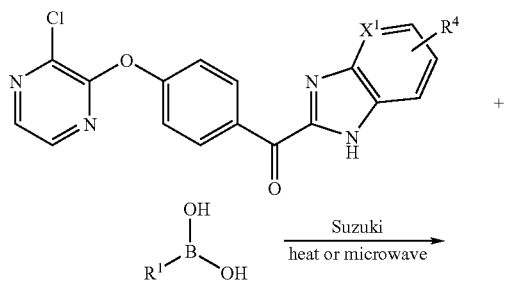

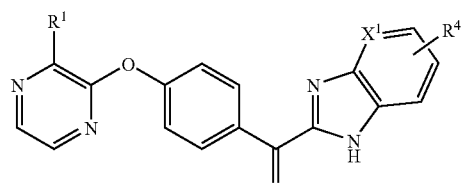

X¹ is CH or N

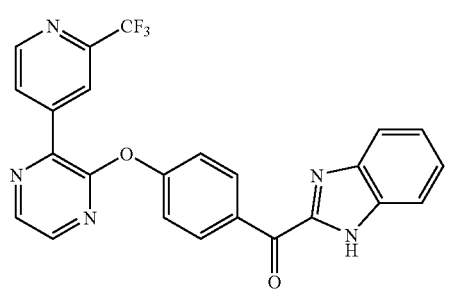

EXAMPLE 104: (1H-BENZO[D]IMIDAZOL-2-YL)(4-(3-(2-(TRIFLUOROMETHYL)PYRIDIN-4-YL)PYRAZIN-2-YLOXY)PHENYL)METHANONE

A mixture of (1H-benzo[d]imidazol-2-yl)(4-(3-chloropyrazin-2-yloxy)phenyl)methanone (300 mg, 0.855 mmol), potassium phosphate (545 mg, 2.57 mmol), 2-(trifluoromethyl)pyridin-4-ylboronic acid (490 mg, 2.57 mmol), and Bis-[4-(di-tert-butylphosphino)-N,N-dimethylbenzenamine] palladium dichloride (121 mg, 0.171 mmol) in dimethoxyethane was heated to 80° C. Following complete reaction, the mixture was cooled to room temperature which caused a solid to precipitate which was collected by filtration and dried to give (1H-benzo[d]imidazol-2-yl)(4-(3-(2-(trifluoromethyl)pyridin-4-yl)pyrazin-2-yloxy)phenyl)methanone. MS (ESI, pos. ion) m/z: 461.0 (M+1). IC50 (uM) +++++.

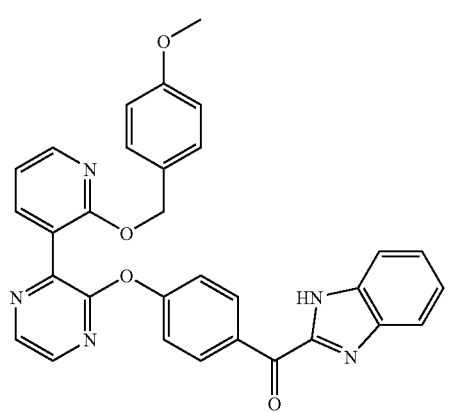

EXAMPLE 105

(1H-BENZO[D]IMIDAZOL-2-YL)(4-(3-(2-(4-METHOXYBENZYLOXY)PYRIDIN-3-YL)PYRAZIN-2-YLOXY)PHENYL)METHANONE

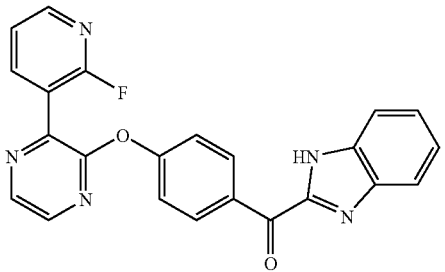

STEP 1. (5-FLUORO-1H-BENZO[D]IMIDAZOL-2-YL)(4-(3-(2-METHOXY PYRIDIN-3-YL)PYRAZIN-2-YLOXY)PHENYL)METHANONE

To a microwave safe 30 ml tubes were charged with (1H-benzo[d]imidazol-2-yl)(4-(3-chloropyrazin-2-yloxy)phenyl)methanone (0.500 g, 1.43 mmol), 2-fluoropyridin-3-yl-boronic acid (0.241 g, 1.71 mmol), tetrakis(triphenylphosphine)palladium(0) (0.165 g, 0.143 mmol) and a 2M solution of sodium carbonate monohydrate (2.14 mL, 4.28 mmol) in 1,4-dioxane. The flasks were sealed and heated to 150° C. for 45 min in a microwave. The reaction mixture was diluted with DCM (75 mL), washed with water and brine. It was dried over magnesium sulfate, concentrated and dried in vacuo. It was suspended in DCM/MeOH and stirred. The insoluble material was collected by filtration, recrystallized overnight from boiling MeOH and hexane, then dried in a vacuum oven to give (1H-benzo[d]imidazol-2-yl)(4-(3-(2-fluoropyridin-3-yl)pyrazin-2-yloxy)phenyl)methanone as yellow solid. LC/MS: MS (ESI, pos. ion) m/z: 412.1 (M+1).

STEP. 2. (1H-BENZO[D]IMIDAZOL-2-YL)(4-(3-(2-(4-METHOXYBENZYLOXY)PYRIDIN-3-YL)PYRAZIN-2-YLOXY)PHENYL)METHANONE

To a mixture of (1H-benzo[d]imidazol-2-yl)(4-(3-(2-fluoropyridin-3-yl)pyrazin-2-yloxy)phenyl)methanone (200 mg, 0.486 mmol) and 4-methoxybenzyl alcohol (0.905 mL, 7.29 mmol) in toluene in a 6 mL tube was added potassium tert-butoxide, 1.0 m solution in 2-methyl-2-propanol (2.431 mL, 2.431 mmol). The reaction was heated to 80° C. After 7 min a mixture of products was observed by LC/MS. The mixture was diluted with DCM (30 mL), and washed with water (3×25 mL) and brine (30 mL). It was dried over magnesium sulfate, concentrated and dried in vacuo. It was purified by flash chromatography (40 g SiliaSep pre-packed silica gel column, eluent: 0-40% EtOAc in hexane) to give (1H-benzo[d]imidazol-2-yl)(4-(3-(2-(4-methoxybenzyloxy)pyridin-3-yl)pyrazin-2-yloxy)phenyl)methanone. MS (ESI, pos. ion) m/z: 532.0 (M+1).

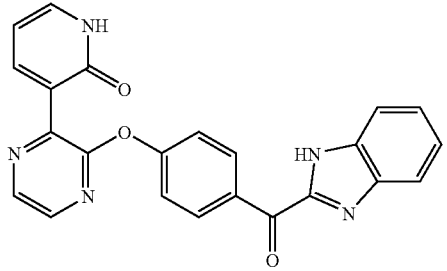

EXAMPLE 106

3-(3-(4-(1H-BENZO[D]IMIDAZOLE-2-CARBONYL)PHENOXY)PYRAZIN-2-YL)PYRIDIN-2(1H)-ONE

To a suspension of (1H-benzo[d]imidazol-2-yl)(4-(3-(2-(4-methoxybenzyloxy)pyridin-3-yl)pyrazin-2-yloxy)phenyl)methanone (0.050 g, 0.094 mmol) in DCM/water in a 50 mL round bottom flask was added DDQ (0.026 g, 0.113 mmol) and dioxane (1 mL). The mixture was stirred at 60° C. for 16 h. The mixture was diluted with saturated NaHCO$_3$ and extracted with DCM (3×25 mL). The combined organic layer was washed with saturated NaHCO$_3$ and brine. The insoluble material was collected, washed with ethanol, filtered and dried in vacuo to give 3-(3-(4-(1H-benzo[d]imidazole-2-carbonyl)phenoxy)pyrazin-2-yl)pyridin-2(1H)-one. MS (ESI, pos. ion) m/z: 410.2 (M+1). IC50 (uM) +++++.

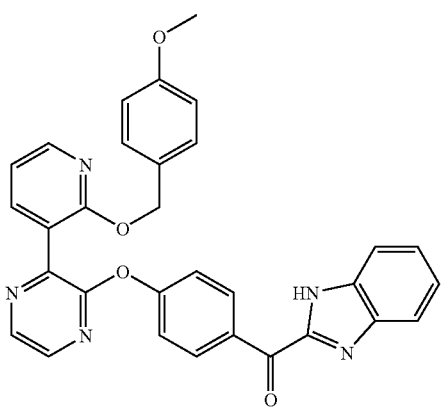

TABLE (IIIA)

EXAMPLES 107 TO 134 ARE TABULATED BELOW:

| Ex# | Structure | IC50 (uM) | IUPAC names | MS |
|---|---|---|---|---|
| 107 | 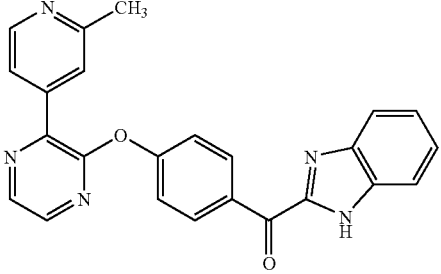 | +++++ | (1H-benzo[d]imidazol-2-yl)(4-(3-(2-methylpyridin-4-yl)pyrazin-2-yloxy)phenyl)methanone | 408 |
| 108 | 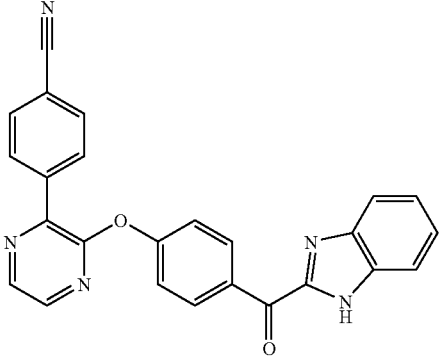 | +++++ | 4-(3-(4-(1H-benzo[d]imidazole-2-carbonyl)phenoxy)pyrazin-2-yl)benzonitrile | 418 |
| 109 | 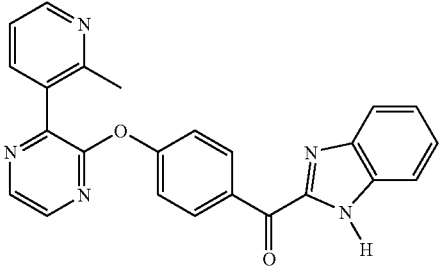 | ++++ | (1H-benzo[d]imidazol-2-yl)(4-(3-(2-methylpyridin-3-yl)pyrazin-2-yloxy)phenyl)methanone | 408 |
| 110 | 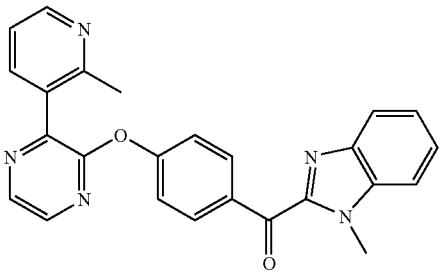 | ++++ | (1-methyl-1H-benzo[d]imidazol-2-yl)(4-(3-(2-methylpyridin-3-yl)pyrazin-2-yloxy)phenyl)methanone | 422 |

TABLE (IIIA)-continued

EXAMPLES 107 TO 134 ARE TABULATED BELOW:

| Ex# | Structure | IC50 (uM) | IUPAC names | MS |
|---|---|---|---|---|
| 111 | 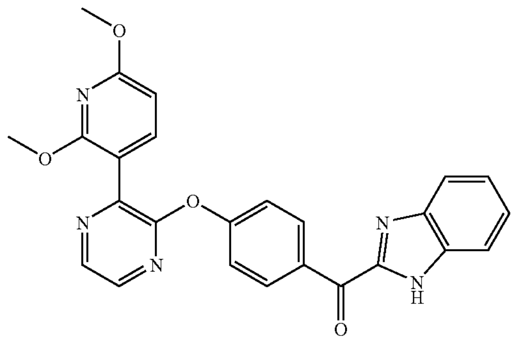 | ++++ | (1H-benzo[d]imidazol-2-yl)(4-(3-(2,6-dimethoxypyridin-3-yl)pyrazin-2-yloxy)phenyl)methanone | 454 |
| 112 | 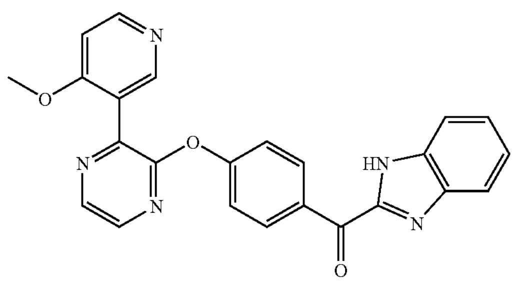 | ++++ | (1H-benzo[d]imidazol-2-yl)(4-(3-(4-methoxypyridin-3-yl)pyrazin-2-yloxy)phenyl)methanone | 424 |
| 113 | 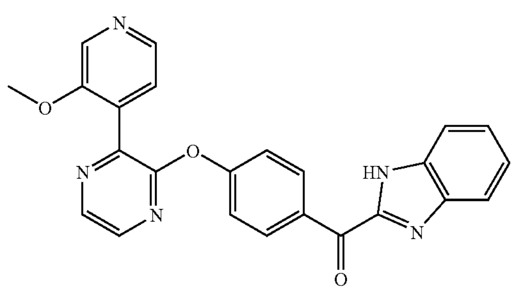 | ++++ | (1H-benzo[d]imidazol-2-yl)(4-(3-(3-methoxypyridin-4-yl)pyrazin-2-yloxy)phenyl)methanone | 424 |
| 114 | 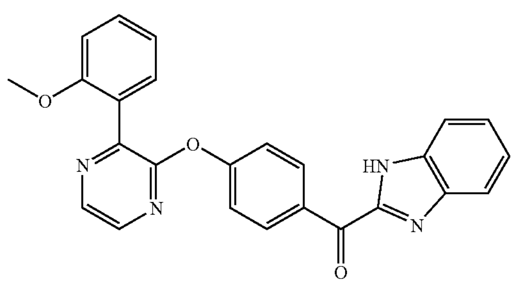 | ++++ | (1H-benzo[d]imidazol-2-yl)(4-(3-(2-methoxyphenyl)pyrazin-2-yloxy)phenyl)methanone | 423 |
| 115 | 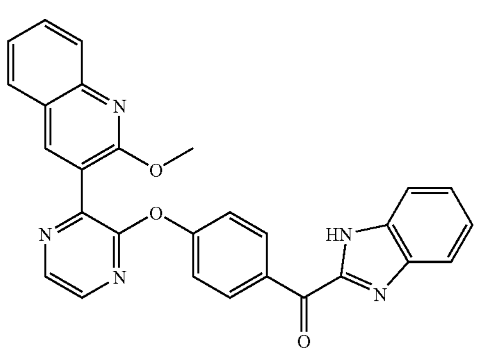 | +++++ | (1H-benzo[d]imidazol-2-yl)(4-(3-(2-methoxyquinolin-3-yl)pyrazin-2-yloxy)phenyl)methanone | 474 |

TABLE (IIIA)-continued

EXAMPLES 107 TO 134 ARE TABULATED BELOW:

| Ex# | Structure | IC50 (uM) | IUPAC names | MS |
|---|---|---|---|---|
| 116 | 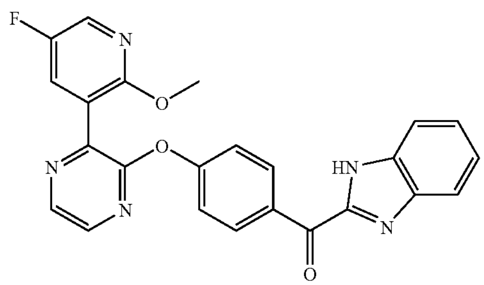 | +++++ | (1H-benzo[d]imidazol-2-yl)(4-(3-(5-fluoro-2-methoxypyridin-3-yl)pyrazin-2-yloxy)phenyl)methanone | 442 |
| 117 | 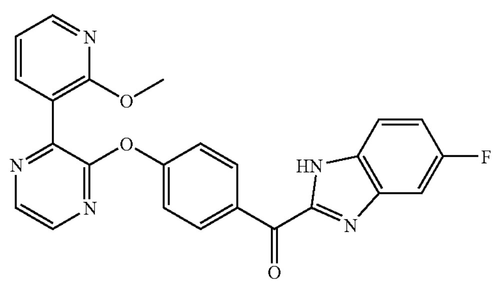 | ++++ | (5-fluoro-1H-benzo[d]imidazol-2-yl)(4-(3-(2-methoxypyridin-3-yl)pyrazin-2-yloxy)phenyl)methanone | 442 |
| 118 | 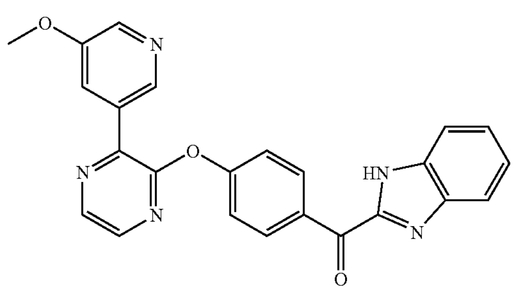 | +++++ | (1H-benzo[d]imidazol-2-yl)(4-(3-(5-methoxypyridin-3-yl)pyrazin-2-yloxy)phenyl)methanone | 424 |
| 119 | 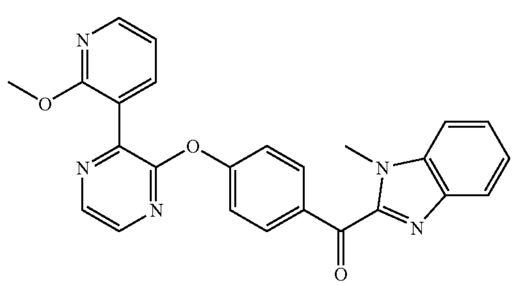 | +++++ | (4-(3-(2-methoxypyridin-3-yl)pyrazin-2-yloxy)phenyl)(1-methyl-1H-benzo[d]imidazol-2-yl)methanone | 438 |
| 120 | 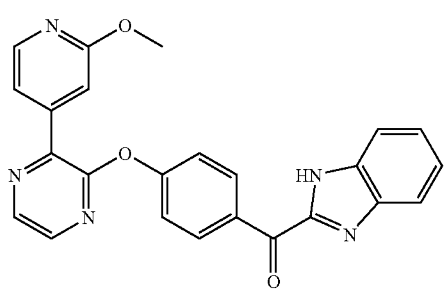 | +++++ | (1H-benzo[d]imidazol-2-yl)(4-(3-(2-methoxypyridin-4-yl)pyrazin-2-yloxy)phenyl)methanone | 424 |

TABLE (IIIA)-continued

EXAMPLES 107 TO 134 ARE TABULATED BELOW:

| Ex# | Structure | IC50 (uM) | IUPAC names | MS |
|---|---|---|---|---|
| 121 | 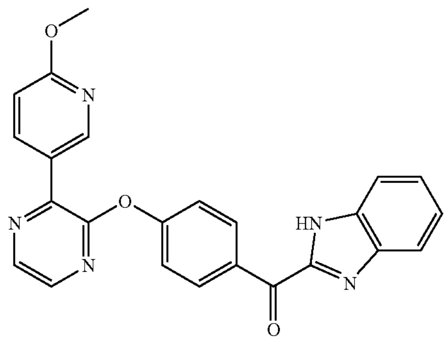 | +++++ | (1H-benzo[d]imidazol-2-yl)(4-(3-(6-methoxypyridin-3-yl)pyrazin-2-yloxy)phenyl)methanone | 424 |
| 122 | 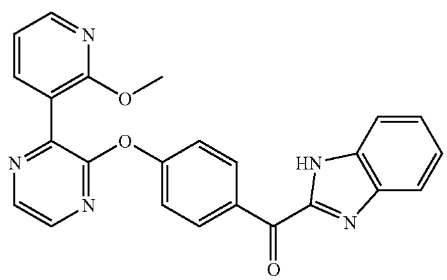 | +++++ | (1H-benzo[d]imidazol-2-yl)(4-(3-(2-methoxypyridin-3-yl)pyrazin-2-yloxy)phenyl)methanone | 424 |
| 123 | 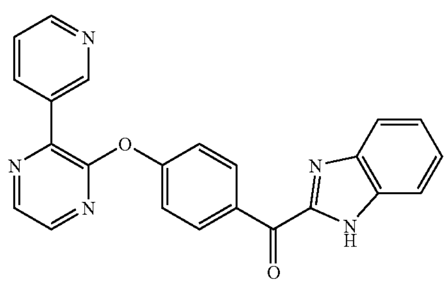 | +++++ | (1H-benzo[d]imidazol-2-yl)(4-(3-(pyridin-3-yl)pyrazin-2-yloxy)phenyl)methanone | 394 |
| 124 | 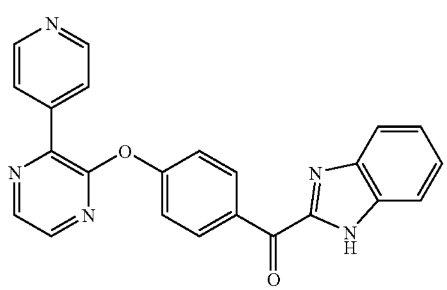 | +++++ | (1H-benzo[d]imidazol-2-yl)(4-(3-(pyridin-4-yl)pyrazin-2-yloxy)phenyl)methanone | 394 |
| 125 | 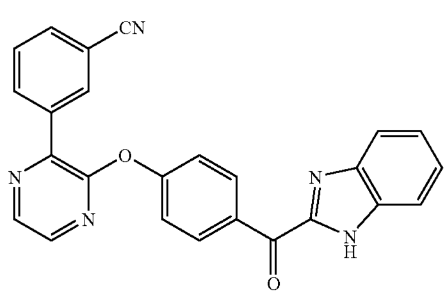 | +++++ | 3-(3-(4-(1H-benzo[d]imidazole-2-carbonyl)phenoxy)pyrazin-2-yl)benzonitrile | 418 |

TABLE (IIIA)-continued

EXAMPLES 107 TO 134 ARE TABULATED BELOW:

| Ex# | Structure | IC50 (uM) | IUPAC names | MS |
|---|---|---|---|---|
| 126 | 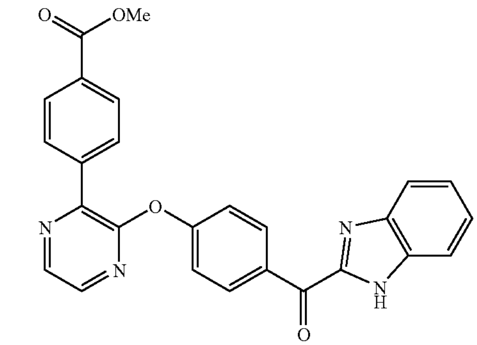 | +++++ | methyl 4-(3-(4-(1H-benzo[d]imidazole-2-carbonyl)phenoxy)pyrazin-2-yl)benzoate | 451 |
| 127 | 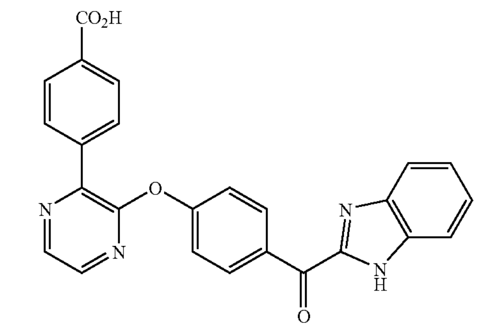 | +++++ | 4-(3-(4-(1H-benzo[d]imidazole-2-carbonyl)phenoxy)pyrazin-2-yl)benzoic acid | 437 |
| 128 | 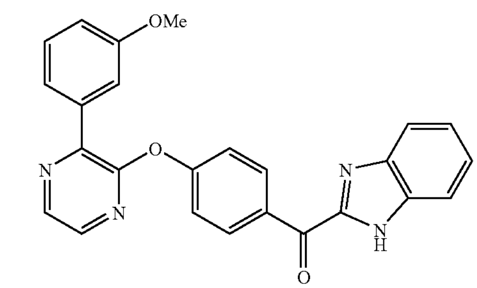 | +++++ | (1H-benzo[d]imidazol-2-yl)(4-(3-(3-methoxyphenyl)pyrazin-2-yloxy)phenyl)methanone | 423 |
| 129 | 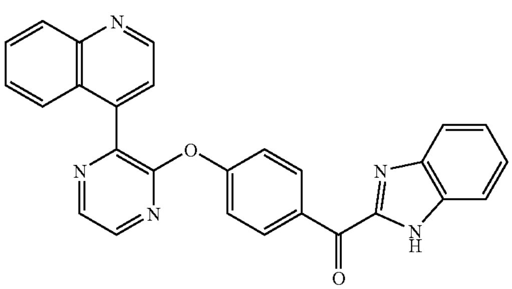 | ++++ | (1H-benzo[d]imidazol-2-yl)(4-(3-(quinolin-4-yl)pyrazin-2-yloxy)phenyl)methanone | 444 |
| 130 | 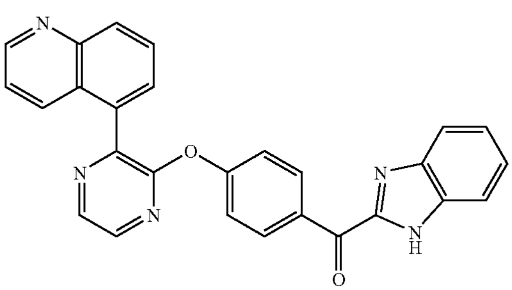 | ++++ | (1H-benzo[d]imidazol-2-yl)(4-(3-(quinolin-5-yl)pyrazin-2-yloxy)phenyl)methanone | 444 |

TABLE (IIIA)-continued

EXAMPLES 107 TO 134 ARE TABULATED BELOW:

| Ex# | Structure | IC50 (uM) | IUPAC names | MS |
|---|---|---|---|---|
| 131 | 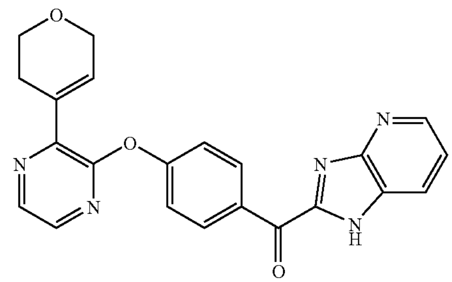 | ++++ | (4-(3-(3,6-dihydro-2H-pyran-4-yl)pyrazin-2-yloxy)phenyl)(1H-imidazo[4,5-b]pyridin-2-yl)methanone | 400 |
| 132 | 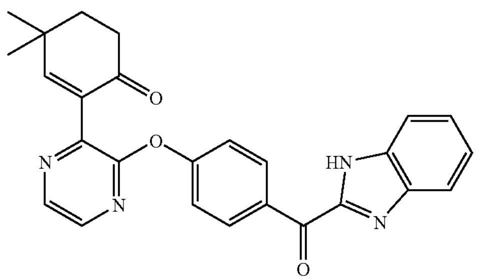 | ++++ | 2-(3-(4-(1H-benzo[d]imidazole-2-carbonyl)phenoxy)pyrazin-2-yl)-4,4-dimethylcyclohex-2-enone | 49 |
| 133 | 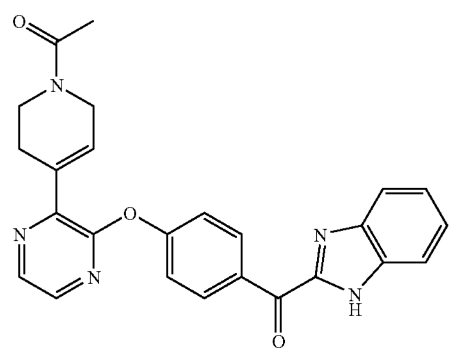 | +++++ | 1-(4-(3-(4-(1H-benzo[d]imidazole-2-carbonyl)phenoxy)pyrazin-2-yl)-5,6-dihydropyridin-1(2H)-yl)ethanone | 440 |
| 134 | 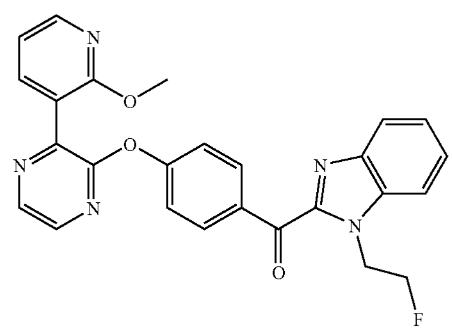 | +++++ | (1-(2-fluoroethyl)-1H-benzo[d]imidazol-2-yl)(4-(3-(2-methoxypyridin-3-yl)pyrazin-2-yloxy)phenyl)methanone | 470 |

TABLE (IIIB)

PREPARATION OF EXAMPLES 107 TO 134 ARE TABULATED BELOW:

| Ex# | Synthetic Scheme | How different from main route | Reagent difference |
|---|---|---|---|
| 107 | 8 | Same | 2-methylpyridin-4-yl boronic acid |
| 108 | 8 | Same | 4-cyanophenyl boronic acid |
| 109 | 8 | Same | 2-methylpyridin-3-yl boronic acid |
| 110 | 4 | Same | (4-((3-(2-methylpyridin-3-yl)pyrazin-2-yl)oxy)phenyl)(1H-benzimidazol-2-yl)methanone |
| 111 | 8 | $PdCl_2(PPh_3)_2$, $Na_2CO_3$ 140° C., microwave | 2,6-dimethoxypyridin-3-yl boronic acid |
| 112 | 8 | $PdCl_2(PPh_3)_2$, $K_2CO_3$ 140° C., microwave | 4-methoxypyridin-3-yl boronic acid · HCl |
| 113 | 8 | T: 130° C. | 3-methoxypyridin-4-yl boronic acid |
| 114 | 8 | $K_3PO_4$, A-Phos, 150° C., microwave | 2-methoxyphenyl boronic acid |

TABLE (IIIB)-continued

PREPARATION OF EXAMPLES 107 TO 134 ARE TABULATED BELOW:

| Ex# | Synthetic Scheme | How different from main route | Reagent difference |
|---|---|---|---|
| 115 | 8 | K₃PO₄, A-Phos, 150° C. microwave | 2-methoxyquinoline-3-boronic acid |
| 116 | 8 | K₃PO₄, A-Phos, 150° C., microwave | 5-fluoro-2-methoxypyridine-3-boronic acid |
| 117 | 8 | K₃PO₄, A-Phos, 150° C., microwave | 2-methoxypyridine-3-boronic acid, Different ketobenzimidazole |
| 118 | 8 | K₃PO₄, A-Phos, 150° C., microwave | 5-methoxypyridine-3-boronic acid pinacol ester |
| 119 | 8 | K₃PO₄, A-Phos, 150° C., microwave | 2-methoxypyridine-3-boronic acid, Different ketobenzimidazole |
| 120 | 8 | K₃PO₄, A-Phos, 150° C., microwave | 2-methoxypyridine-4-boronic acid |

TABLE (IIIB)-continued
PREPARATION OF EXAMPLES 107 TO 134 ARE TABULATED BELOW:
| Ex# | Synthetic Scheme | How different from main route | Reagent difference |
|---|---|---|---|
| 121 | 8 | $K_3PO_4$, A-Phos, 150° C., microwave | 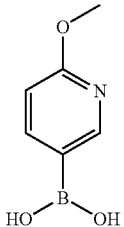 |
| 122 | 8 | $K_3PO_4$, A-Phos, 150° C., microwave | 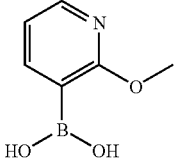 |
| 123 | 8 | $PdCl_2(^tBu_2PhP)_2$, KOAc, 100° C. | 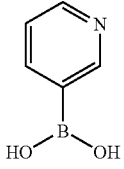 |
| 124 | 8 | $PdCl_2(^tBu_2PhP)_2$, KOAc, 100° C. | 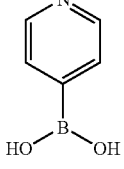 |
| 125 | 8 | $PdCl_2(^tBu_2PhP)_2$, KOAc, 100° C. | 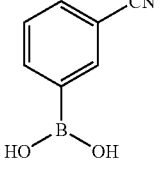 |
| 126 | 8 | $PdCl_2(^tBu_2PhP)_2$, KOAc, 100° C. | 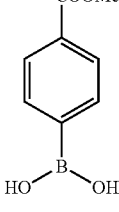 |
| 127 | 8 | LiOH, THF/$H_2O$ | 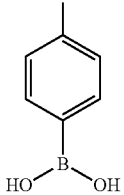 |

TABLE (IIIB)-continued

PREPARATION OF EXAMPLES 107 TO 134 ARE TABULATED BELOW:

| Ex# | Synthetic Scheme | How different from main route | Reagent difference |
|---|---|---|---|
| 128 | 8 | PdCl$_2$($^t$Bu$_2$PhP)$_2$, KOAc, 100° C. | 3-methoxyphenylboronic acid |
| 129 | 8 | PdCl$_2$($^t$Bu$_2$PhP)$_2$, KOAc, 100° C. | quinoline-4-boronic acid |
| 130 | 8 | PdCl$_2$($^t$Bu$_2$PhP)$_2$, KOAc, 100° C. | quinoline-5-boronic acid |
| 131 | 8 | PdCl$_2$(PPh$_3$)$_2$, Na$_2$CO$_3$, | 3,6-dihydro-2H-pyran-4-boronic acid pinacol ester |
| 132 | 8 | PdCl$_2$($^t$Bu$_3$P)$_2$, K$_2$CO$_3$, 150° C., microwave | 4,4-dimethyl-2-(4,4,5,5-tetramethyl-1,3,2-dioxaborolan-2-yl)cyclohex-2-enone |

TABLE (IIIB)-continued

PREPARATION OF EXAMPLES 107 TO 134 ARE TABULATED BELOW:

| Ex# | Synthetic Scheme | How different from main route | Reagent difference |
|---|---|---|---|
| 133 | 8 | PdCl$_2$($^t$Bu$_2$PhP)$_2$, KOAc, 100° C., | 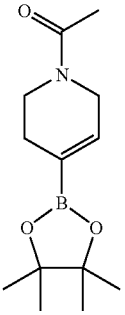 |
| 134 | 4 | Same | 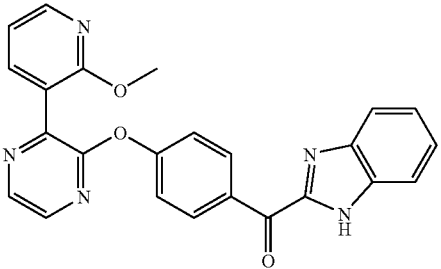 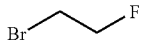 |

SCHEME 9

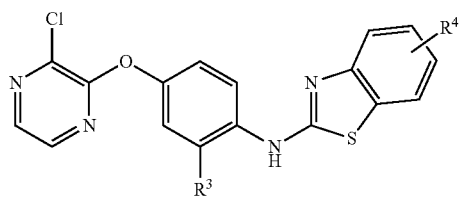

+

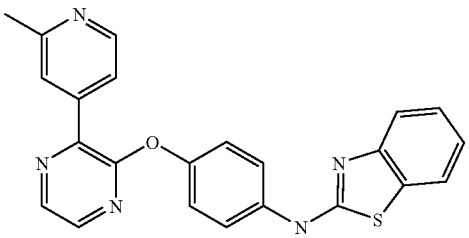

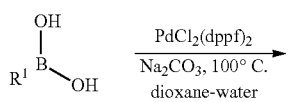

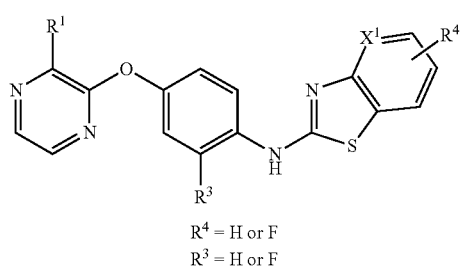

R$^4$ = H or F
R$^3$ = H or F

EXAMPLE 135

N-(4-(3-(2-METHYLPYRIDIN-4-YL)PYRAZIN-2-YLOXY)PHENYL)BENZO[D]THIAZOL-2-AMINE

A suspension of N-(4-(3-chloropyrazin-2-yloxy)phenyl)benzo[d]thiazol-2-amine (180 mg, 0.507 mmol), 2-methylpyridin-4-ylboronic acid (278 mg, 2.03 mmol), PdCl$_2$(dppf)-CH$_2$Cl$_2$ adduct (41.4 mg, 0.051 mmol), and sodium carbonate (323 mg, 3.04 mmol) in 1,4-dioxane (3 mL) and water (2 mL) was sparged with argon for 5 min, then heated to 100° C. for 2 h. The reaction mixture was partitioned between EtOAc and 1M NaOH. The aqueous layer was extracted with EtOAc (2×) and the combined organics was dried over Na$_2$SO$_4$ and concentrated. The crude material was absorbed on Silica gel and purified by chromatography through a Redi-Sep pre-packed silica gel column (40 g), eluting with a gradient of 0% to 70% EtOAc in hexane, to provide N-(4-(3-(2-methylpyridin-4-yl)pyrazin-2-yloxy)phenyl)benzo[d]thiazol-2-amine as white solid. MS (ESI, pos. ion) m/z: 412.0 (M+1). IC50 (uM) +++++.

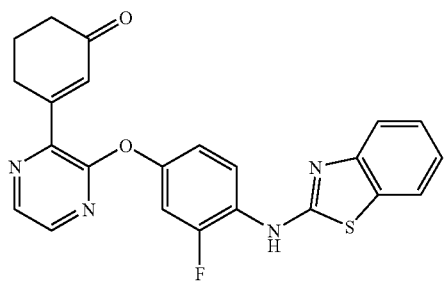

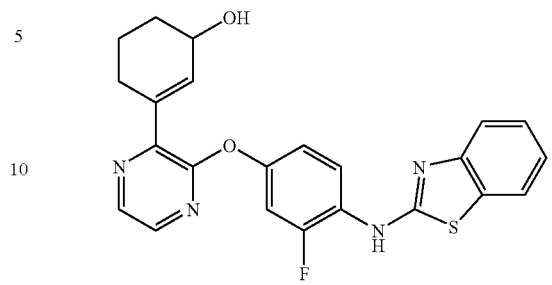

EXAMPLE 136

3-(3-(4-(BENZO[D]THIAZOL-2-YLAMINO)-3-FLUOROPHENOXY)PYRAZIN-2-YL)CYCLO-HEX-2-ENONE

A mixture of N-(4-(3-chloropyrazin-2-yloxy)-2-fluorophenyl)benzo[d]thiazol-2-amine (2098 mg, 5.63 mmol), 3-(4,4,5,5-tetramethyl-1,3,2-dioxaborolan-2-yl)cyclohex-2-enone (1000 mg, 4.50 mmol), dichlorobis(triphenylphosphine)palladium(ii) (316 mg, 0.450 mmol), and sodium carbonate (1432 mg, 13.51 mmol) in DME/H$_2$O/EtOH (7:3:2, 36 ml) was heated to 140° C. for 3 h. Water (100 ml) was added and the reaction mixture was extracted with EtAOc (3×100 ml). The combined organic layers were washed with brine and dried over sodium sulfate. Filtration and concentration under reduced pressure afforded 3-(3-(4-(benzo[d]thiazol-2-ylamino)-3-fluorophenoxy)pyrazin-2-yl)cyclohex-2-enone. MS (ESI, pos. ion) m/z: 433.0 (M+1). IC50 (uM) +++++.

EXAMPLE 137

(RAC)-3-(3-(4-(BENZO[D]THIAZOL-2-YLAMINO)-3-FLUOROPHENOXY)PYRAZIN-2-YL)CYCLOHEX-2-ENOL

Sodium tetrahydroborate (157 mg, 4.16 mmol) was added to a suspension of 3-(3-(4-(benzo[d]thiazol-2-ylamino)-3-fluorophenoxy)pyrazin-2-yl)cyclohex-2-enone (600 mg, 1.387 mmol) in MeOH (20 ml) at RT. The mixture was stirred at RT for 1 h, and was then cooled in an ice-water bath. Saturated aqueous ammonium chloride (5 ml) was added along with distilled water (100 ml). The resulting mixture was extracted with EtOAc (2×100 ml), and the combined organic layers were washed with brine and dried over sodium sulfate. Filtration and concentration under reduced pressure, followed by flash chromatography on silica gel (30% to 60% EtOAc in hexanes) afforded (rac)-3-(3-(4-(benzo[d]thiazol-2-ylamino)-3-fluorophenoxy)pyrazin-2-yl)cyclohex-2-enol as a white solid. MS (ESI, pos. ion) m/z: 435.0 (M+1). IC50 (uM) +++++.

TABLE (IVA)

EXAMPLES 138 TO 159 ARE TABULATED BELOW:

| Ex# | Structure | IC50 (uM) | IUPAC names | MS |
|---|---|---|---|---|
| 138 | (structure) | +++ | N-(4-(3-(6-morpholinopyridin-3-yl)pyrazin-2-yloxy)phenyl)benzo[d]thiazol-2-amine | 483 |

TABLE (IVA)-continued

EXAMPLES 138 TO 159 ARE TABULATED BELOW:

| Ex# | Structure | IC50 (uM) | IUPAC names | MS |
|---|---|---|---|---|
| 139 | 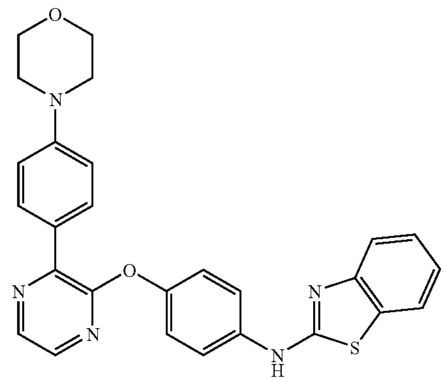 | +++ | N-(4-(3-(4-morpholinophenyl)pyrazin-2-yloxy)phenyl)benzo[d]thiazol-2-amine | 482 |
| 140 | 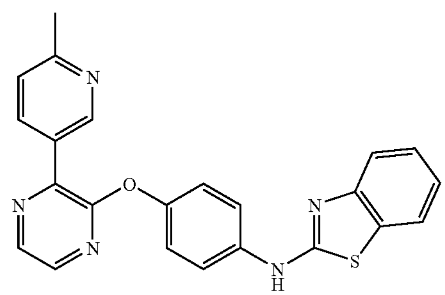 | +++++ | N-(4-(3-(6-methylpyridin-3-yl)pyrazin-2-yloxy)phenyl)benzo[d]thiazol-2-amine | 412 |
| 141 | 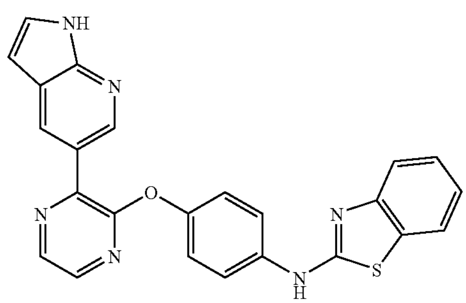 | ++++ | N-(4-(3-(1H-pyrrolo[2,3-b]pyridin-5-yl)pyrazin-2-yloxy)phenyl)benzo[d]thiazol-2-amine | 437 |
| 142 | 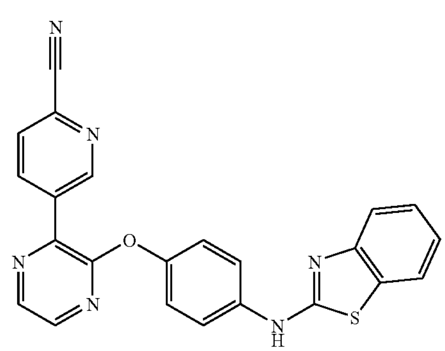 | +++++ | 5-(3-(4-(benzo[d]thiazol-2-ylamino)phenoxy)pyrazin-2-yl)picolinonitrile | 423 |

TABLE (IVA)-continued

EXAMPLES 138 TO 159 ARE TABULATED BELOW:

| Ex# | Structure | IC50 (uM) | IUPAC names | MS |
|---|---|---|---|---|
| 143 | 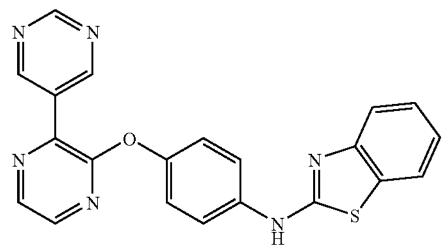 | +++++ | N-(4-(3-(pyrimidin-5-yl)pyrazin-2-yloxy)phenyl)benzo[d]thiazol-2-amine | 399 |
| 144 | 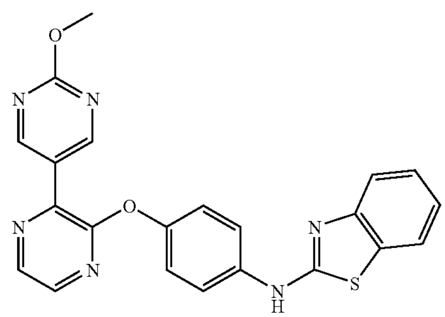 | +++++ | N-(4-(3-(2-methoxypyrimidin-5-yl)pyrazin-2-yloxy)phenyl)benzo[d]thiazol-2-amine | 429 |
| 145 | 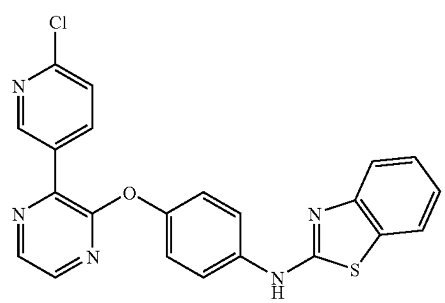 | +++++ | N-(4-(3-(6-chloropyridin-3-yl)pyrazin-2-yloxy)phenyl)benzo[d]thiazol-2-amine | 432 |
| 146 | 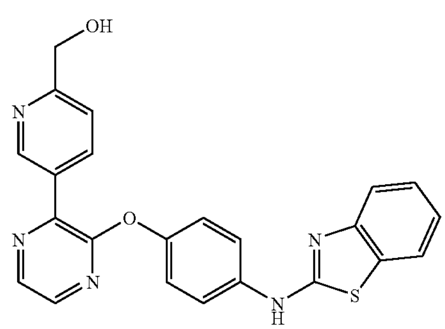 | ++++ | (5-(3-(4-(benzo[d]thiazol-2-ylamino)phenoxy)pyrazin-2-yl)pyridin-2-yl)methanol | 428 |
| 147 | 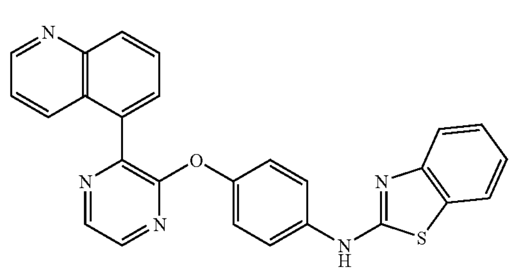 | ++++ | N-(4-(3-(quinolin-5-yl)pyrazin-2-yloxy)phenyl)benzo[d]thiazol-2-amine | 448 |

TABLE (IVA)-continued

EXAMPLES 138 TO 159 ARE TABULATED BELOW:

| Ex# | Structure | IC50 (uM) | IUPAC names | MS |
|---|---|---|---|---|
| 148 | 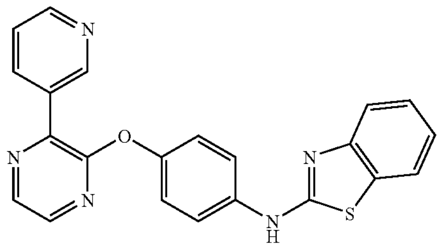 | +++++ | N-(4-(3-(pyridin-3-yl)pyrazin-2-yloxy)phenyl)benzo[d]thiazol-2-amine | 398 |
| 149 | 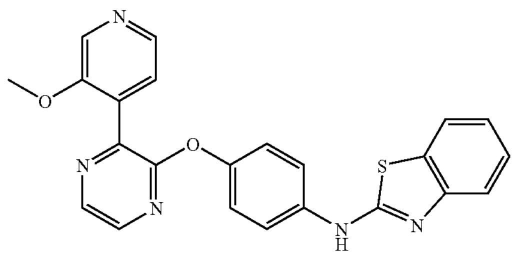 | +++++ | N-(4-(3-(3-methoxypyridin-4-yl)pyrazin-2-yloxy)phenyl)benzo[d]thiazol-2-amine | 428 |
| 150 | 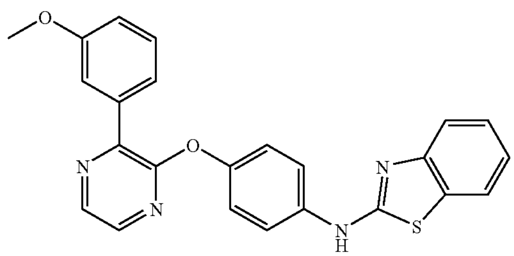 | ++++ | N-(4-(3-(3-methoxyphenyl)pyrazin-2-yloxy)phenyl)benzo[d]thiazol-2-amine | 427 |
| 151 | 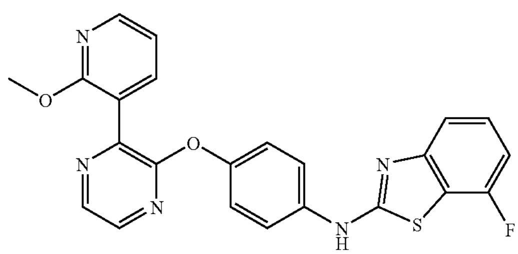 | ++++ | 7-fluoro-N-(4-(3-(2-methoxypyridin-3-yl)pyrazin-2-yloxy)phenyl)benzo[d]thiazol-2-amine | 446 |
| 152 | 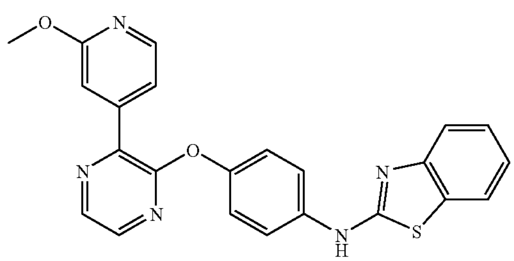 | +++++ | N-(4-(3-(2-methoxypyridin-4-yl)pyrazin-2-yloxy)phenyl)benzo[d]thiazol-2-amine | 428 |
| 153 | 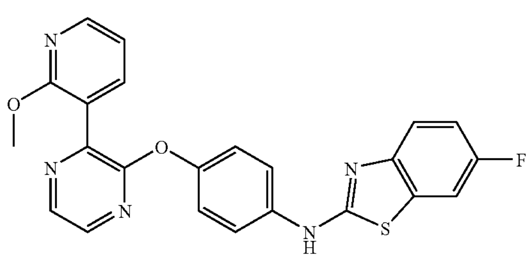 | ++++ | 6-fluoro-N-(4-(3-(2-methoxypyridin-3-yl)pyrazin-2-yloxy)phenyl)benzo[d]thiazol-2-amine | 446 |

TABLE (IVA)-continued

EXAMPLES 138 TO 159 ARE TABULATED BELOW:

| Ex# | Structure | IC50 (uM) | IUPAC names | MS |
|---|---|---|---|---|
| 154 | 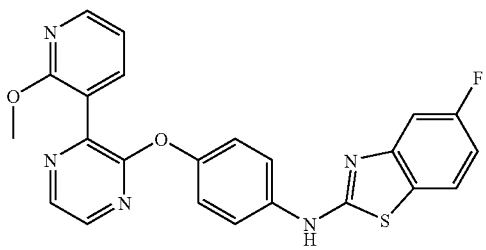 | ++++ | 5-fluoro-N-(4-(3-(2-methoxypyridin-3-yl)pyrazin-2-yloxy)phenyl)benzo[d]thiazol-2-amine | 446 |
| 155 | 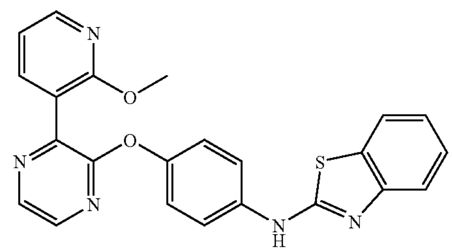 | +++++ | N-(4-(3-(2-methoxypyridin-3-yl)pyrazin-2-yloxy)phenyl)benzo[d]thiazol-2-amine | 428 |
| 156 | 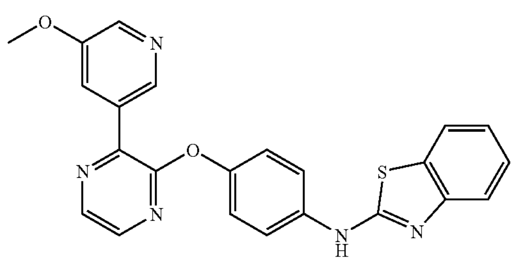 | ++++ | N-(4-(3-(5-methoxypyridin-3-yl)pyrazin-2-yloxy)phenyl)benzo[d]thiazol-2-amine | 428 |
| 157 | 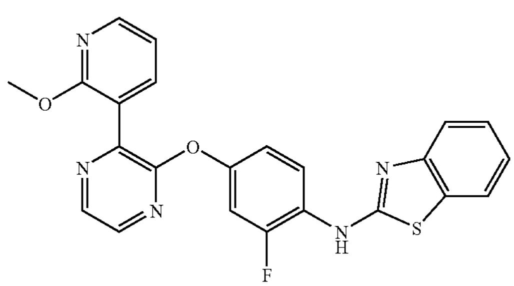 | ++++ | N-(2-fluoro-4-(3-(2-methoxypyridin-3-yl)pyrazin-2-yloxy)phenyl)benzo[d]thiazol-2-amine | 446 |
| 158 | 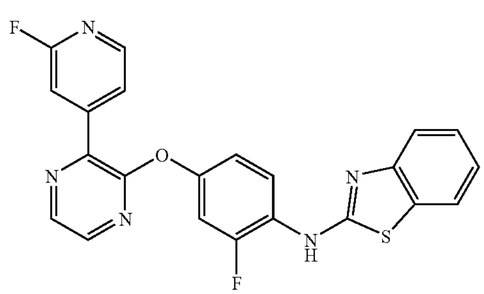 | ++++ | N-(2-fluoro-4-(3-(2-fluoropyridin-4-yl)pyrazin-2-yloxy)phenyl)benzo[d]thiazol-2-amine | 434 |

TABLE (IVA)-continued
EXAMPLES 138 TO 159 ARE TABULATED BELOW:
| Ex# | Structure | IC50 (uM) | IUPAC names | MS |
|---|---|---|---|---|
| 159 | 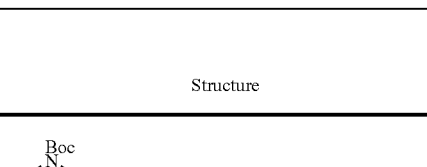 | +++++ | tert-butyl 4-(3-(4-(benzo[d]thiazol-2-ylamino)-3-fluorophenoxy)pyrazin-2-yl)-5,6-dihydropyridine-1(2H)-carboxylate | 520 |
TABLE (IVB)
PREPARATION OF EXAMPLES 138 TO 159 ARE TABULATED BELOW:
| Ex# | Synthetic Scheme | How Different from Main Route | Reagent Difference |
|---|---|---|---|
| 138 | 9 | Same | 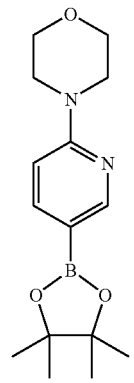 |
| 139 | 9 | Same | 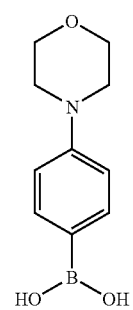 |
| 140 | 9 | Same | 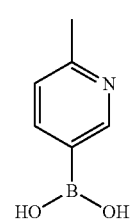 |

TABLE (IVB)-continued

PREPARATION OF EXAMPLES 138 TO 159 ARE TABULATED BELOW:

| Ex# | Synthetic Scheme | How Different from Main Route | Reagent Difference |
|---|---|---|---|
| 141 | 9 | Same | 7-azaindole-5-boronic acid pinacol ester |
| 142 | 9 | Same | 2-cyanopyridine-5-boronic acid pinacol ester |
| 143 | 9 | Same | pyrimidine-5-boronic acid pinacol ester |
| 144 | 9 | Same | 2-methoxypyrimidine-5-boronic acid |
| 145 | 9 | Same | 2-chloropyridine-5-boronic acid |

TABLE (IVB)-continued
PREPARATION OF EXAMPLES 138 TO 159 ARE TABULATED BELOW:
| Ex# | Synthetic Scheme | How Different from Main Route | Reagent Difference |
|---|---|---|---|
| 146 | 9 | Same | 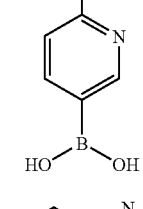 |
| 147 | 9 | Same |  |
| 148 | 9 | Same |  |
| 149 | 9 | KOAc, A-Phos, 130° C. | 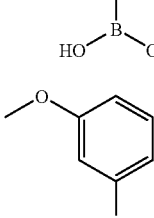 |
| 150 | 9 | Same | 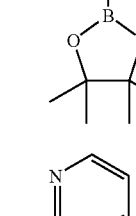 |
| 151 | 9 | Same | 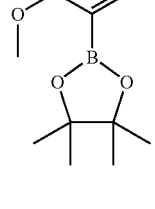 |

TABLE (IVB)-continued

PREPARATION OF EXAMPLES 138 TO 159 ARE TABULATED BELOW:

| Ex# | Synthetic Scheme | How Different from Main Route | Reagent Difference |
|---|---|---|---|
| 152 | 9 | Same | [2-methoxypyridin-4-yl boronic acid pinacol ester] |
| 153 | 9 | Same | [2-methoxypyridin-3-yl boronic acid pinacol ester] |
| 154 | 9 | Same | [2-methoxypyridin-3-yl boronic acid pinacol ester] |
| 155 | 9 | K₃PO₄, A-Phos, 150° C., microwave | [2-methoxypyridin-3-yl boronic acid] |
| 156 | 9 | K₃PO₄, A-Phos, 150° C., microwave | [5-methoxypyridin-3-yl boronic acid] |

TABLE (IVB)-continued

PREPARATION OF EXAMPLES 138 TO 159 ARE TABULATED BELOW:

| Ex# | Synthetic Scheme | How Different from Main Route | Reagent Difference |
|---|---|---|---|
| 157 | 9 | (Ph₃P)₂PdCl₂, 120° C., microwave | |
| 158 | 9 | (Ph₃P)₂PdCl₂, 100° C., microwave | |
| 159 | 9 | (Ph₃P)₂PdCl₂, 140° C., microwave | |

SCHEME 10

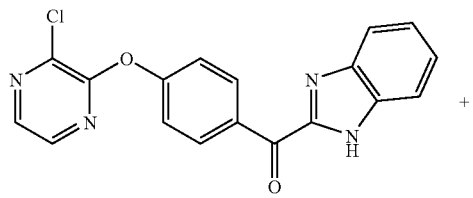

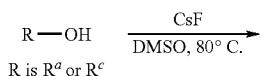

R is R$^a$ or R$^c$

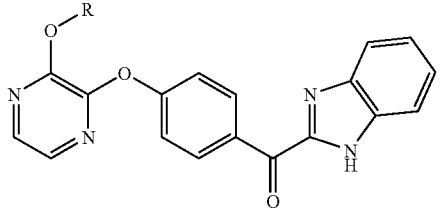

General Procedure:

Into 8 mL vial was added alcohol (4 eq., 2 mmol), CsF (304 mg, 4 eq., 2 mmol) and a solution of (1H-benzo[d]imidazol-2-yl)(4-(3-chloropyrazin-2-yloxy)phenyl)methanone (175 mg, 500 umol) in 6 mL of anhydrous DMSO. The vial was capped and heated at 80° C. for 12 h. The reaction mixture was cooled to room temperature and filtered to remove insoluble material. The compounds were purified by HPLC.

TABLE (VA)

EXAMPLES 160 TO 180 ARE TABULATED BELOW:

| Ex # | Structure | IC50 (uM) | IUPAC names | MS (M + 1) |
|---|---|---|---|---|
| 160 | 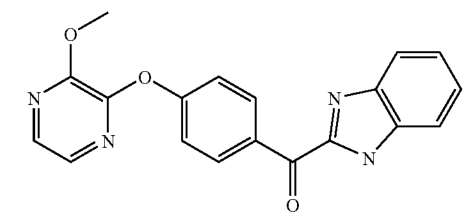 | + | (1H-benzo[d]imidazol-2-yl)(4-(3-methoxypyrazin-2-yloxy)phenyl)methanone | 347 |
| 161 | 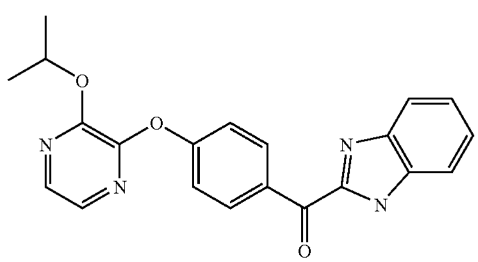 | + | (1H-benzo[d]imidazol-2-yl)(4-(3-isopropoxypyrazin-2-yloxy)phenyl)methanone | 375 |
| 162 | 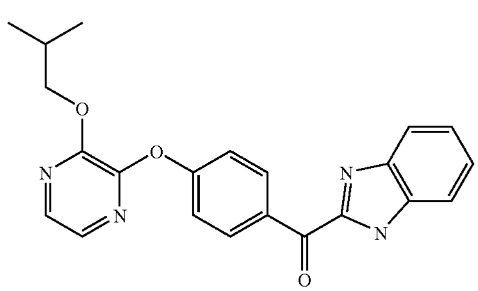 | + | (1H-benzo[d]imidazol-2-yl)(4-(3-isobutoxypyrazin-2-yloxy)phenyl)methanone | 389 |

TABLE (VA)-continued

EXAMPLES 160 TO 180 ARE TABULATED BELOW:

| Ex # | Structure | IC50 (uM) | IUPAC names | MS (M + 1) |
|---|---|---|---|---|
| 163 | 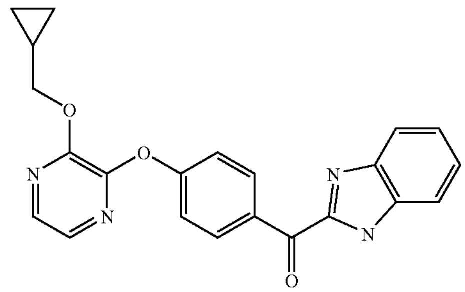 | ++ | (1H-benzo[d]imidazol-2-yl)(4-(3-(cyclopropylmethoxy)pyrazin-2-yloxy)phenyl)methanone | 387 |
| 164 | 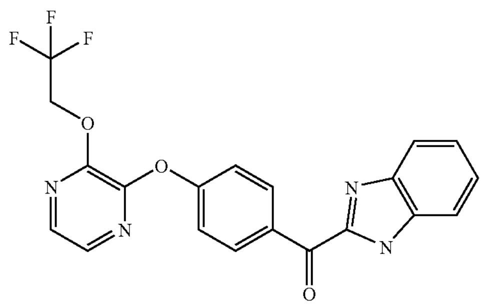 | ++ | (1H-benzo[d]imidazol-2-yl)(4-(3-(2,2,2-trifluoroethoxy)pyrazin-2-yloxy)phenyl)methanone | 415 |
| 165 | 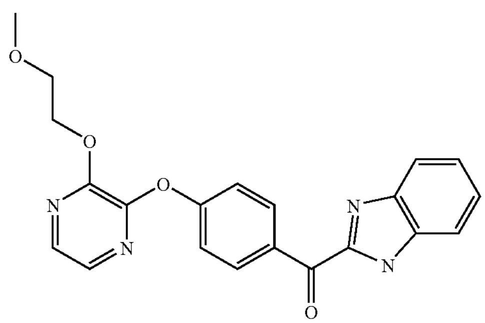 | ++ | (1H-benzo[d]imidazol-2-yl)(4-(3-(2-methoxyethoxy)pyrazin-2-yloxy)phenyl)methanone | 391 |
| 166 | 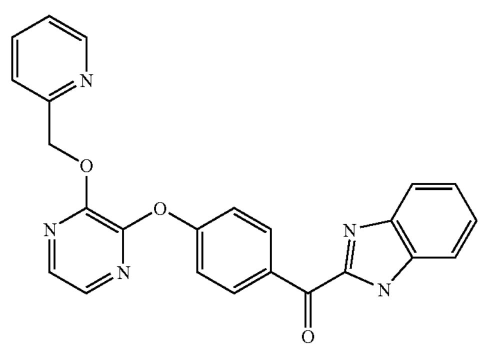 | ++++ | (1H-benzo[d]imidazol-2-yl)(4-(3-(pyridin-2-ylmethoxy)pyrazin-2-yloxy)phenyl)methanone | 424 |
| 167 | 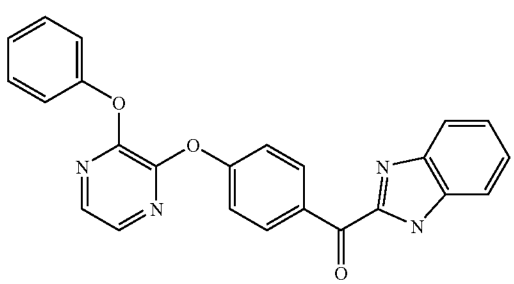 | +++ | (1H-benzo[d]imidazol-2-yl)(4-(3-phenoxypyrazin-2-yloxy)phenyl)methanone | 409 |

TABLE (VA)-continued

EXAMPLES 160 TO 180 ARE TABULATED BELOW:

| Ex # | Structure | IC50 (uM) | IUPAC names | MS (M + 1) |
|---|---|---|---|---|
| 168 | 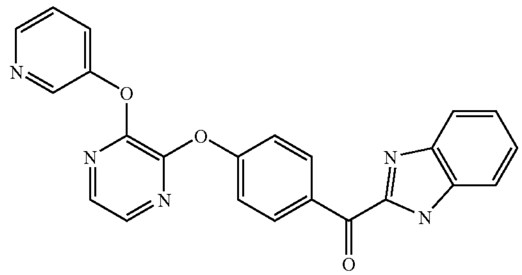 | +++ | (1H-benzo[d]imidazol-2-yl)(4-(3-(pyridin-3-yloxy)pyrazin-2-yloxy)phenyl)methanone | 410 |
| 169 | 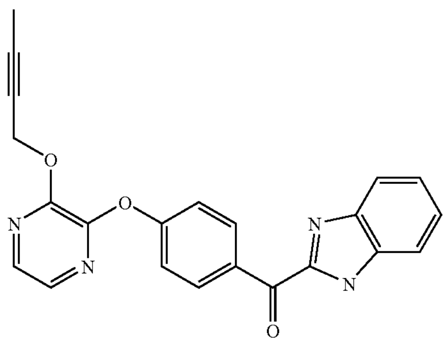 | +++ | (1H-benzo[d]imidazol-2-yl)(4-(3-(but-2-ynyloxy)pyrazin-2-yloxy)phenyl)methanone | 385 |
| 170 | 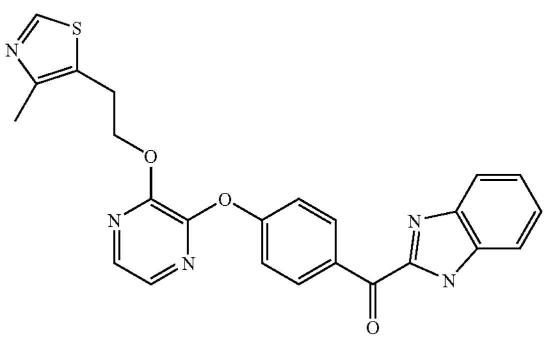 | +++ | (1H-benzo[d]imidazol-2-yl)(4-(3-(2-(4-methylthiazol-5-yl)ethoxy)pyrazin-2-yloxy)phenyl)methanone | 458 |
| 171 | 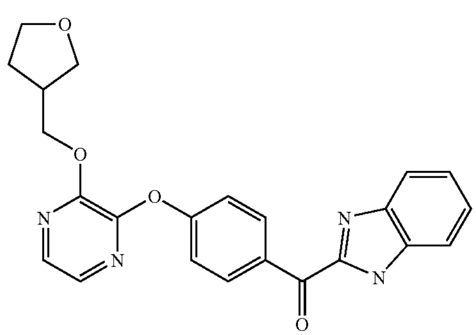 | +++ | (1H-benzo[d]imidazol-2-yl)(4-(3-((tetrahydrofuran-3-yl)methoxy)pyrazin-2-yloxy)phenyl)methanone | 417 |

TABLE (VA)-continued

EXAMPLES 160 TO 180 ARE TABULATED BELOW:

| Ex # | Structure | IC50 (uM) | IUPAC names | MS (M + 1) |
|---|---|---|---|---|
| 172 | 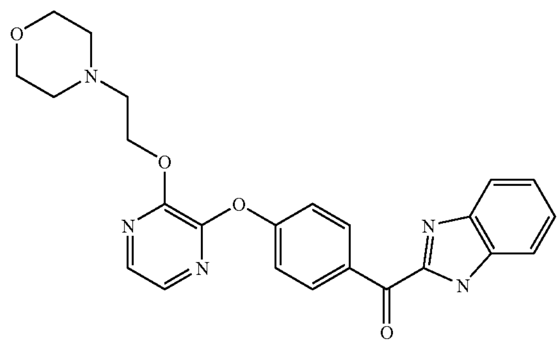 | +++ | (1H-benzo[d]imidazol-2-yl)(4-(3-(2-morpholinoethoxy)pyrazin-2-yloxy)phenyl)methanone | 446 |
| 173 | 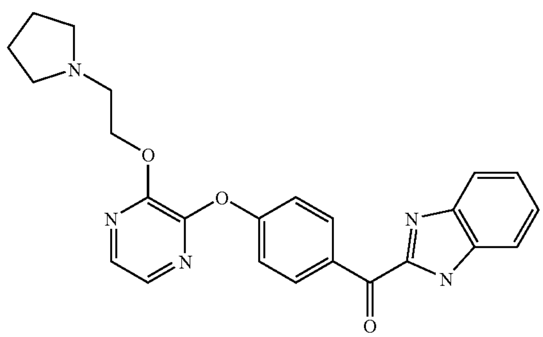 | +++ | (1H-benzo[d]imidazol-2-yl)(4-(3-(2-(pyrrolidin-1-yl)ethoxy)pyrazin-2-yloxy)phenyl)methanone | 430 |
| 174 | 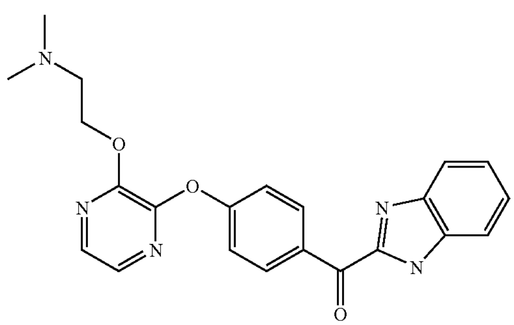 | +++ | (1H-benzo[d]imidazol-2-yl)(4-(3-(2-(dimethylamino)ethoxy)pyrazin-2-yloxy)phenyl)methanone | 404 |
| 175 | 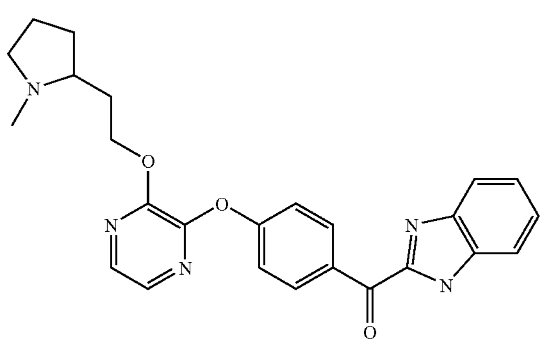 | +++ | (1H-benzo[d]imidazol-2-yl)(4-(3-(2-(1-methylpyrrolidin-2-yl)ethoxy)pyrazin-2-yloxy)phenyl)methanone | 444 |

TABLE (VA)-continued

EXAMPLES 160 TO 180 ARE TABULATED BELOW:

| Ex # | Structure | IC50 (uM) | IUPAC names | MS (M + 1) |
|---|---|---|---|---|
| 176 | 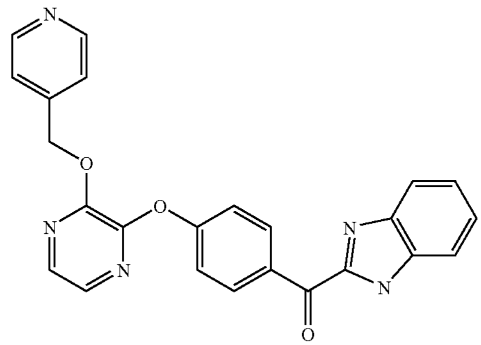 | +++ | (1H-benzo[d]imidazol-2-yl)(4-(3-(pyridin-4-ylmethoxy)pyrazin-2-yloxy)phenyl)methanone | 424 |
| 177 | 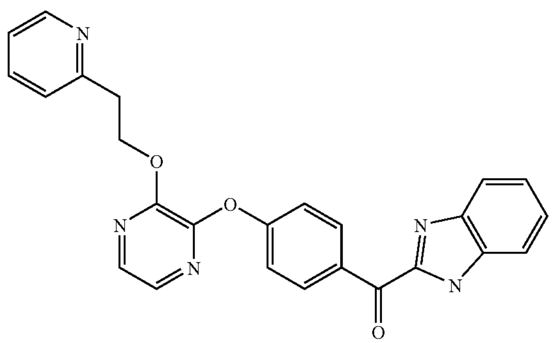 | ++++ | (1H-benzo[d]imidazol-2-yl)(4-(3-(2-(pyridin-2-yl)ethoxy)pyrazin-2-yloxy)phenyl)methanone | 438 |
| 178 | 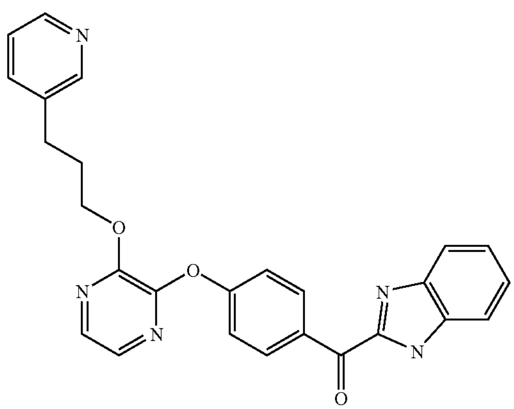 | ++++ | (1H-benzo[d]imidazol-2-yl)(4-(3-(3-(pyridin-3-yl)propoxy)pyrazin-2-yloxy)phenyl)methanone | 452 |
| 179 | 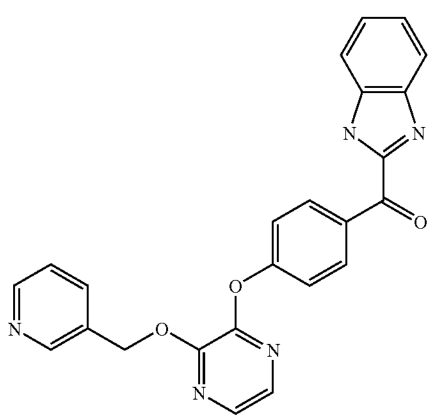 | +++ | (1H-benzo[d]imidazol-2-yl)(4-(3-(pyridin-3-ylmethoxy)pyrazin-2-yloxy)phenyl)methanone | 424 |

TABLE (VA)-continued

EXAMPLES 160 TO 180 ARE TABULATED BELOW:

| Ex # | Structure | IC50 (uM) | IUPAC names | MS (M + 1) |
|---|---|---|---|---|
| 180 | 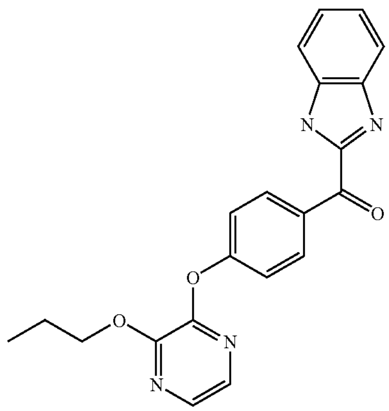 | + | (1H-benzo[d]imidazol-2-yl)(4-(3-propoxypyrazin-2-yloxy)phenyl)methanone | 375 |

TABLE (VB)

PREPARATION OF EXAMPLES 160 TO 180 ARE TABULATED BELOW:

| Ex# | Synthetic Scheme | How Different from Main Route | Reagent Difference |
|---|---|---|---|
| 160 | 10 | Same | ethanol |
| 161 | 10 | Same | isopropanol |
| 162 | 10 | Same | isobutanol |
| 163 | 10 | Same | cyclopropylmethanol |
| 164 | 10 | Same | 2,2,2-trifluoroethanol |
| 165 | 10 | Same | 2-methoxyethanol |
| 166 | 10 | Same | pyridin-2-ylmethanol |
| 167 | 10 | Same | phenol |
| 168 | 10 | Same | pyridin-3-ol |
| 169 | 10 | Same | but-2-yn-1-ol |
| 170 | 10 | Same | 2-(4-methylthiazol-5-yl)ethanol |
| 171 | 10 | Same | (tetrahydrofuran-3-yl)methanol |
| 172 | 10 | Same | 2-morpholinoethanol |

TABLE (VB)-continued

PREPARATION OF EXAMPLES 160 TO 180 ARE TABULATED BELOW:

| Ex# | Synthetic Scheme | How Different from Main Route | Reagent Difference |
|-----|------------------|------------------------------|--------------------|
| 173 | 10 | Same | pyrrolidin-1-yl-ethanol |
| 174 | 10 | Same | 2-(dimethylamino)ethanol |
| 175 | 10 | Same | 2-(1-methylpyrrolidin-2-yl)ethanol |
| 176 | 10 | Same | pyridin-4-yl-methanol |
| 177 | 10 | Same | 2-(pyridin-2-yl)ethanol |
| 178 | 10 | Same | 3-(pyridin-3-yl)propan-1-ol |
| 179 | 10 | Same | pyridin-3-yl-methanol |
| 180 | 10 | Same | propan-1-ol |

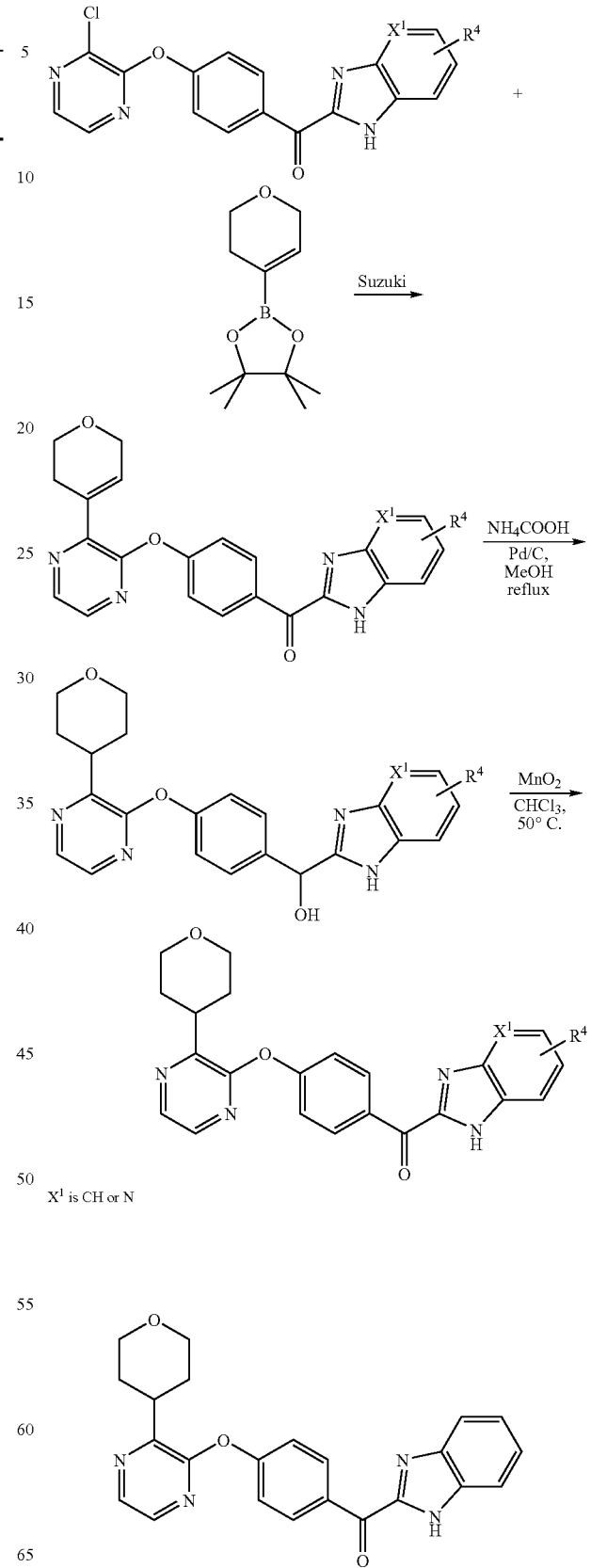

SCHEME 11

$X^1$ is CH or N

EXAMPLE 181

(1H-BENZO[D]IMIDAZOL-2-YL)(4-(3-(TETRAHYDRO-2H-PYRAN-4-YL)PYRAZIN-2-YLOXY)PHENYL)METHANONE

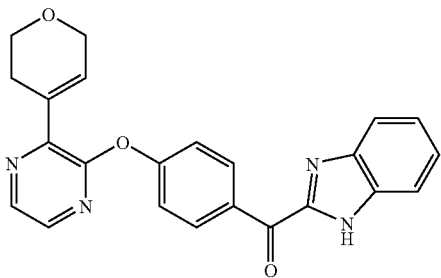

STEP 1. (1H-BENZO[D]IMIDAZOL-2-YL)(4-(3-(3,6-DIHYDRO-2H-PYRAN-4-YL)PYRAZIN-2-YLOXY)PHENYL)METHANONE

A clear 150 ml pressure tube was charged with (1H-benzo[d]imidazol-2-yl)(4-(3-chloropyrazin-2-yloxy)phenyl)methanone (1.00 g, 2.85 mmol),2-(3,6-dihydro-2H-pyran-4-yl)-4,4,5,5-tetramethyl-1,3,2-dioxaborolane (2.396 g, 11.40 mmol), Bis-[4-(di-tert-butylphosphino)-N,N-dimethylbenzenamine]palladium dichloride (0.101 g, 0.143 mmol), potassium acetate (0.616 g, 6.27 mmol), dioxane (9 mL) and water (1.000 mL). The reaction flask was flushed with nitrogen and capped. The reaction was heated to 100° C. for 16 hours. The reaction was then cooled down to RT and partitioned with ethyl acetate (50 ml) and water (50 ml). The organic layer was washed (2×) with an aqueous saturated solution of sodium bicarbonate, then with water and then brine. The organic layer was then dried with sodium sulfate and then filtered. The volatile were reduced to a smaller volume and the solid that precipitated out was filtered off. The cake obtained was suspended in hot MeOH, filtered and dried to give (1H-benzo[d]imidazol-2-yl)(4-(3-(3,6-dihydro-2H-pyran-4-yl)pyrazin-2-yloxy)phenyl)methanone as a yellow solid.

[M+1] 398.9

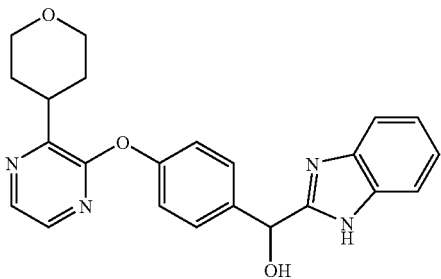

STEP 2. (1H-BENZO[D]IMIDAZOL-2-YL)(4-(3-(TETRAHYDRO-2H-PYRAN-4-YL)PYRAZIN-2-YLOXY)PHENYL)METHANOL

A 1 L heavy wall vessel equipped with a magnetic stir bar flask was charged with (1H-benzo[d]imidazol-2-yl)(4-(3-(3,6-dihydro-2H-pyran-4-yl)pyrazin-2-yloxy)phenyl)methanone (1.00 g, 2.26 mmol), ammonium formate (3.16 g, 50 mmol), THF (125 mL) and MeOH (125 mL). Nitrogen was bubbled into the mixture for 15 mins. The mixture was kept under nitrogen and treated with Pd/C (0.267 g, 0.251 mmol). The vessel was capped and the reaction was stirred at 75° C. After 5 hours, the reaction was cooled down to RT. An aliquot was analyzed via LC-MS showed the reaction was incomplete. The reaction was filtered through celite and the filtrate was transferred back to the reaction vessel. An additional 4.15 g of ammonium formate and 0.350 of 10% Pd/C was added to the reaction under nitrogen. The vessel capped again and heated to 75° C. overnight. The reaction was cooled down and filtered through a pad of celite. The filtrate was reduced under vacuum. The residue obtained was portioned with DCM and water. The organic layer was washed (2×) with an aqueous saturated solution of sodium bicarbonate, then with water and then brine. The organic layer was then dried with sodium sulfate reduced. The volatiles were removed under vacuum. The residue obtained was triturated with hot MeOH, filtered and dried in a vacuum oven to give (1H-benzo[d]imidazol-2-yl)(4-(3-(tetrahydro-2H-pyran-4-yl)pyrazin-2-yloxy)phenyl)methanol as a white solid. [M+1] 402.9.

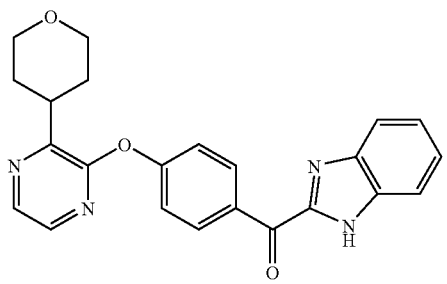

STEP 3. (1H-BENZO[D]IMIDAZOL-2-YL)(4-(3-(TETRAHYDRO-2H-PYRAN-4-YL)PYRAZIN-2-YLOXY)PHENYL)METHANONE

A mixture of (1H-benzo[d]imidazol-2-yl)(4-(3-(tetrahydro-2H-pyran-4-yl)pyrazin-2-yloxy)phenyl)methanol (0.50 g, 1.24 mmol) in chloroform (7.5 mL) and acetone (4.00 mL) under nitrogen was treated with was treated with manganese dioxide (0.504 g, 6.21 mmol) in one portion. The reaction was heated to 50° C. After 40 minutes, the reaction was filtered through a pad of Celite™. The filtrate was washed (2×) with an aqueous saturated solution of sodium bicarbonate, with water and then brine. The organic layer was then dried with sodium sulfate and purified by column chromatography on silica gel using a gradient of 30 to 80% ethyl acetate in hexanes. The pure fractions were reduced under vacuum and the solid obtained was slurried in 1:1 EtOAc:ether, filtered and dried under vacuum to give (1H-benzo[d]imidazol-2-yl)(4-(3-(tetrahydro-2H-pyran-4-yl)pyrazin-2-yloxy)phenyl)methanone as a white solid. MS (ESI, pos. ion) m/z: 400.9 (M+1). IC50 (uM) +++++.

TABLE (VIA)

EXAMPLES 182 TO 185 ARE TABULATED BELOW:

| Ex# | Structure | IC50 (uM) | IUPAC names | MS |
|---|---|---|---|---|
| 182 | 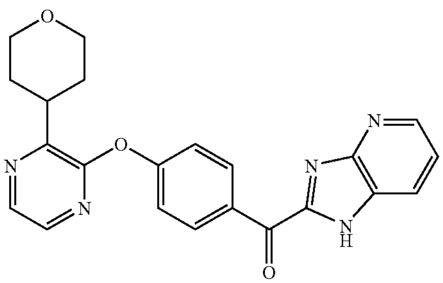 | +++++ | (1H-imidazo[4,5-b]pyridin-2-yl)(4-(3-(tetrahydro-2H-pyran-4-yl)pyrazin-2-yloxy)phenyl)methanone | 401.9 |
| 183 | 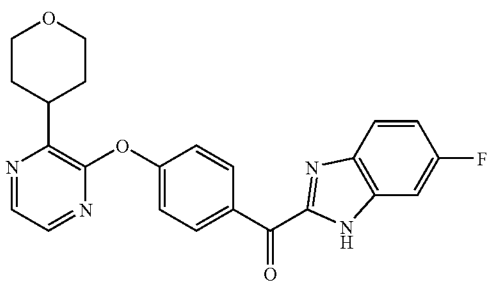 | +++++ | (6-fluoro-1H-benzo[d]imidazol-2-yl)(4-(3-(tetrahydro-2H-pyran-4-yl)pyrazin-2-yloxy)phenyl)methanone | 419 |
| 184 | 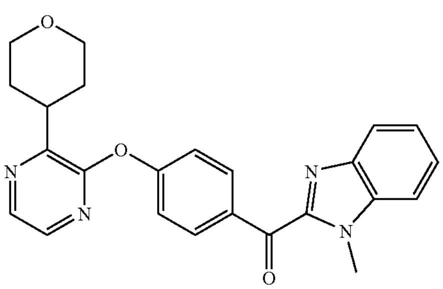 | +++++ | (1-methyl-1H-benzo[d]imidazol-2-yl)(4-(3-(tetrahydro-2H-pyran-4-yl)pyrazin-2-yloxy)phenyl)methanone | 415 |
| 185 | | +++++ | (6-fluoro-1-methyl-1H-benzo[d]imidazol-2-yl)(4-(3-(tetrahydro-2H-pyran-4-yl)pyrazin-2-yloxy)phenyl)methanone and (5-fluoro-1-methyl-1H-benzo[d]imidazol-2-yl)(4-(3-(tetrahydro-2H-pyran-4-yl)pyrazin-2-yloxy)phenyl)methanone | 433 |

TABLE (VIB)
PREPARATION OF EXAMPLES 182 TO 185 ARE TABULATED BELOW:
| Ex# | Synthetic Scheme | How Different from Main Route | Reagent Difference |
|---|---|---|---|
| 182 | 11 | Same | 2,3-diaminopyridine |
| 183 | 11 | Same | 4-fluoro-1,2-diaminobenzene |
| 184 | 4 | Same | (3-(tetrahydro-2H-pyran-4-yl)pyrazin-2-yloxy)phenyl)(1H-benzimidazol-2-yl)methanone |
| 185 | 4 | Same | (3-(tetrahydro-2H-pyran-4-yl)pyrazin-2-yloxy)phenyl)(6-fluoro-1H-benzimidazol-2-yl)methanone |
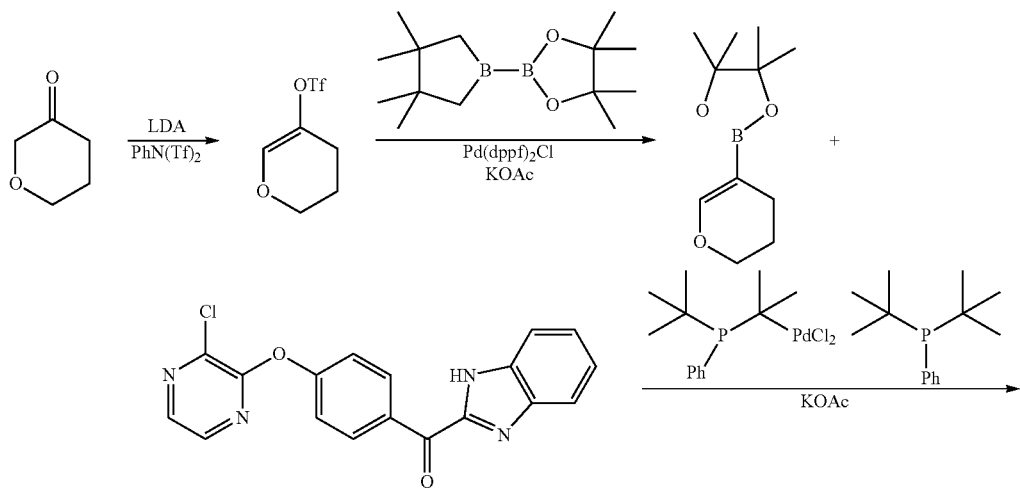
SCHEME 12

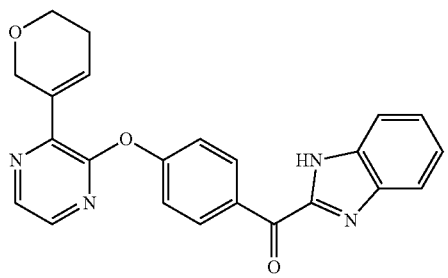

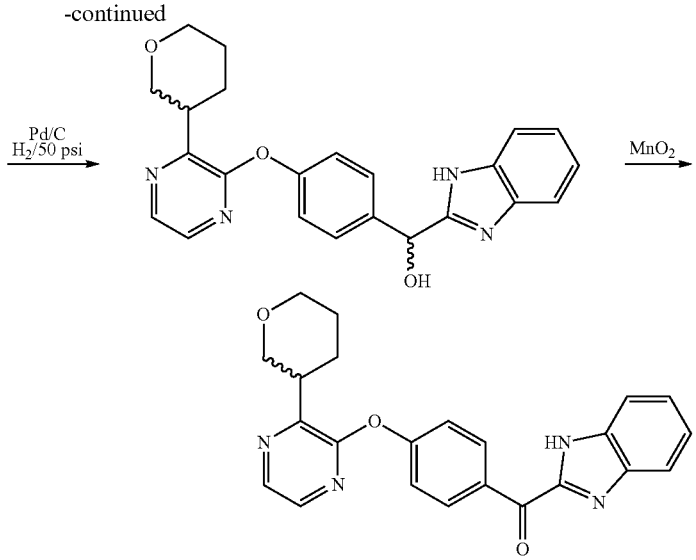

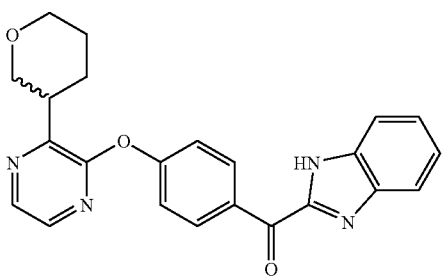

EXAMPLE 186

1H-BENZIMIDAZOL-2-YL(4-4-((3-(TETRAHYDRO-2H-PYRAN-3-YL)-2-PYRAZINYL)OXY)PHENYL)METHANONE

STEP 1: 3,4-DIHYDRO-2H-PYRAN-5-YL TRIFLUOROMETHANESULFONATE.

Diisopropylamine (1.7 mL, 12.0 mmol) was taken up in 30 mL of THF and chilled to −78° C. N-butyllithium (4.8 mL, 2.5 M in hexanes) was added to the mixture. After 5 minutes, dihydro-2H-pyran-3(4H)-one (1.0 g, 10.0 mmol) was added slowly in 8 mL of THF. After 10 minutes, N-phenyltriflimide (3.9 g, 11 mmol) was added slowly in 8 mL of THF. After 15 minutes, the mixture was warmed to rt. The mixture was stirred for 1.5 hours and quenched with 30 mL of aq NaHCO₃. The mixture was then extracted twice with 35 mL of ether and the combined organic extracts were washed with 25 mL of brine and dried over MgSO₄. Filtration and concentration under reduced pressure, followed by flash chromatography on silica gel (2.5% to 20% EtOAc/hexanes) afforded 3,4-dihydro-2H-pyran-5-yl trifluoromethanesulfonate.

STEP 2: 5-(4,4,5,5-TETRAMETHYL-1,3,2-DIOXABOROLAN-2-YL)-3,4-DIHYDRO-2H-PYRAN.

3,4-Dihydro-2H-pyran-5-yl trifluoromethanesulfonate (0.66 g, 2.8 mmol), bis(pinacolato)diboron (0.79 g, 3.1 mmol), potassium acetate (0.84 g, 8.5 mmol), and 1,1'-bis(diphenylphosphino)ferrocene-palladium (ii) dichloride dichloromethane complex (0.070 g, 0.085 mmol) were taken up in 10 mL of dioxane in a sealable tube. The mixture was purged with nitrogen and the tube was sealed. The tube was then heated to 80° C. After 12 hours, the mixture was cooled to rt. The mixture was diluted with 40 mL of EtOAc and washed with 10 mL of water and 10 mL of brine, then dried over MgSO₄. Filtration and concentration under reduced pressure, followed by flash chromatography on silica gel (1% to 10% EtOAc/hexanes) afforded 5-(4,4,5,5-tetramethyl-1,3,2-dioxaborolan-2-yl)-3,4-dihydro-2H-pyran.

STEP 3: 1H-BENZIMIDAZOL-2-YL(4-((3-(5,6-DIHYDRO-2H-PYRAN-3-YL)-2-PYRAZINYL)OXY)PHENYL)METHANONE.

H-benzimidazol-2-yl (44(3-chloro-2-pyrazinyl)oxy)phenyl)methanone (0.46 g, 1.3 mmol), 5-(4,4,5,5-tetramethyl-1,3,2-dioxaborolan-2-yl)-3,4-dihydro-2H-pyran (0.39 g, 1.9 mmol), potassium acetate (0.99 g, 10.0 mmol), and bis[di-tert-butyl(phenyl)phosphane]dichloropalladium (0.062 g, 0.099 mmol) were taken up in 16 mL of 3:1 MeCN:water. The mixture as purged with nitrogen and the reaction was heated to 100° C. After 48 hours, the mixture was diluted with 20 mL of water and extracted three times with 20 mL of 9:1 chloroform/isopropanol. The combined organic extracts were dried over MgSO₄. Filtration and concentration under reduced pressure, followed by flash chromatography on silica gel (0 to 2% MeOH/dichloromethane) afforded 1H-benzimidazol-2-yl(4-(3-(5,6-dihydro-2H-pyran-3-yl)-2-pyrazinyl)oxy)phenyl)methanone.

STEP 4: 1H-BENZIMIDAZOL-2-YL(4-((3-(TETRAHYDRO-2H-PYRAN-3-YL)-2-PYRAZINYL)OXY)PHENYL)METHANOL.

1H-Benzimidazol-2-yl(4-((3-(5,6-dihydro-2H-pyran-3-yl)-2-pyrazinyl)oxy)phenyl)methanone (0.20 g, 0.50 mmol) was suspended in 15 mL of EtOAc in a pressure tube. Palladium on carbon, 10% (0.20 g) was added. The mixture was hydrogenated at 50 psi. After 24 hours, the mixture was filtered through celite and eluted with 50 mL of 9:1 chloroform:isopropanol. The product was taken up in 10 mL of dichloromethane. Manganese dioxide (0.58 g, 6.7 mmol) was added. After 1 h, the mixture was filtered through celite and concentrated under reduced pressure. The residue was purified by flash chromatography on silica gel (0 to 2% MeOH/dichloromethane) affording 1H-benzimidazol-2-yl(4-((3-(tetrahydro-2H-pyran-3-yl)-2-pyrazinyl)oxy)phenyl)methanone. MS (ESI, pos. ion) m/z: 401 (M+1). IC50 (uM) +++++.

SCHEME 13

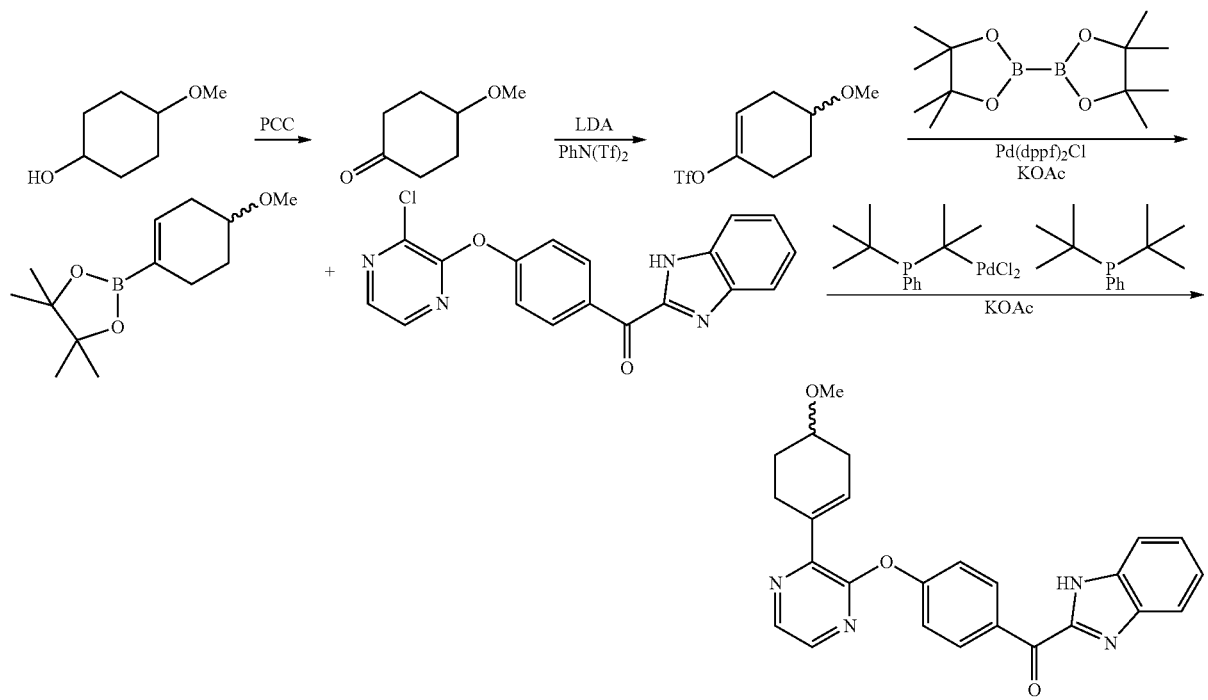

EXAMPLE 187

1H-BENZIMIDAZOL-2-YL(4-((3-(4-METHOXY-1-CYCLOHEXEN-1-YL)-2-PYRAZINYL) OXY) PHENYL)METHANONE

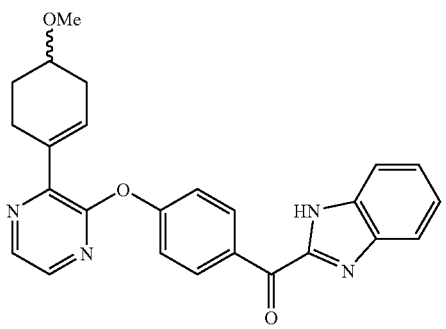

STEP 1. 4-METHOXYCYCLOHEXANONE

4-Methoxycyclohexanol (2.0 g, 15.0 mmol) was taken up in 150 mL of DCM. Pyridinium chlorochromate (5.0 g, 23.0 mmol) was added. After 60 hours, the mixture was filtered through a plug of Florisil and concentrated under reduced pressure. The residue was taken up in 50 mL of ether and filtered through a plug of silica gel. The solvent was removed under reduced pressure, affording 4-methoxycyclohexanone as a light yellow oil.

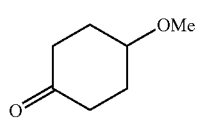

STEP 2. 4-METHOXY-1-CYCLOHEXEN-1-YL TRIFLUOROMETHANESULFONATE

Diisopropylamine (1.5 mL, 10.0 mmol) was taken up in 25 mL of THF and chilled to −78° C. Butyllithium, 2.5 M in hexanes (4.1 mL, 10.0 mmol) was added slowly. After 5 minutes, 4-methoxycyclohexanone (1.1 g, 8.6 mmol) was added slowly in 7 mL of THF. After 10 minutes, n-phenyltriflimide (3.4 g, 9.4 mmol) was added slowly in 7 mL of THF. After 15 minutes, the mixture was warmed to room temperature. The mixture was stirred for 90 minutes, then quenched with 25 mL of aq $NH_4Cl$. The mixture was then diluted with 20 mL of water and extracted twice with 30 mL of ether. The combined organic extracts were dried over $MgSO_4$. Filtration and concentration under reduced pressure, followed by flash chromatography on silica gel (1% to 10% EtOAc/hexanes) afforded 4-methoxy-1-cyclohexen-1-yl trifluoromethanesulfonate as a clear oil.

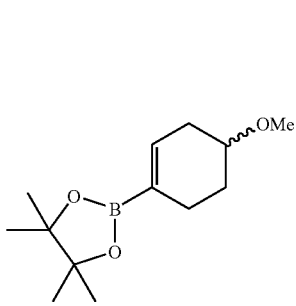

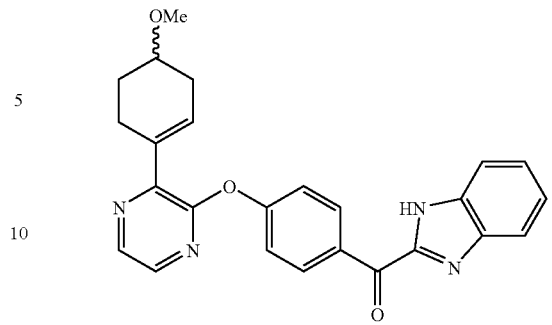

STEP 3. 2-(4-METHOXY-1-CYCLOHEXEN-1-YL)-4,4,5,5-TETRAMETHYL-1,3,2-DIOXABOROLANE 4-methoxy-1-cyclohexen-1-yl trifluoromethanesulfonate (1.3 g, 5.0 mmol), bis(pinacolato)diboron (1.5 g, 6.0 mmol), potassium acetate (1.5 g, 15.0 mmol), and 1,1'-bis(diphenylphosphino)ferrocene-palladium (ii) dichloride dichloromethane complex (0.12 g, 0.15 mmol) were taken up in 25 mL of dioxane. The mixture was purged with nitrogen and heated to 80° C. After 12 hours, the mixture was cooled to room temperature and diluted with 50 mL of EtOAc. The mixture was washed with 10 mL of water and 10 mL of brine, then dried over MgSO$_4$. Filtration and concentration under reduced pressure, followed by flash chromatography on silica gel (1.5 to 10% EtOAc/hexanes) afforded 2-(4-methoxy-1-cyclohexen-1-yl)-4,4,5,5-tetramethyl-1,3,2-dioxaborolane as a clear oil.

STEP 4. 1H-BENZIMIDAZOL-2-YL(4-((3-(4-METHOXY-1-CYCLOHEXEN-1-YL)-2-PYRAZINYL)OXY)PHENYL)METHANONE (1H-Benzo[d]imidazol-2-yl)(4-(3-chloropyrazin-2-yloxy)phenyl)methanone (1.0 g, 2.8 mmol), potassium acetate (2.1 g, 21.0 mmol), 2-(4-methoxy-1-cyclohexen-1-yl)-4,4,5,5-tetramethyl-1,3,2-dioxaborolane (0.88 g, 3.7 mmol), and bis[di-tert-butyl(phenyl)phosphane]dichloropalladium (0.13 g, 0.213 mmol) were taken up in 40 mL of 3:1 MeCN:water. The mixture was purged with nitrogen and heated to 100° C. After 12 hours, the mixture was cooled to room temperature and diluted with 40 mL of water. The mixture was extracted twice with 30 mL of 9:1 chloroform:IPA. The combined organic extracts were dried over MgSO$_4$. Filtration and concentration under reduced pressure, followed by flash chromatography on silica gel (0.5 to 5% MeOH/DCM) afforded 1H-Benzimidazol-2-yl(4-((3-(4-methoxy-1-cyclohexen-1-yl)-2-pyrazinyl)oxy)phenyl) methanone as a yellow solid. MS (ESI, pos. ion) m/z: 427.1 (M+1). IC50 (uM) +++++.

SCHEME 14

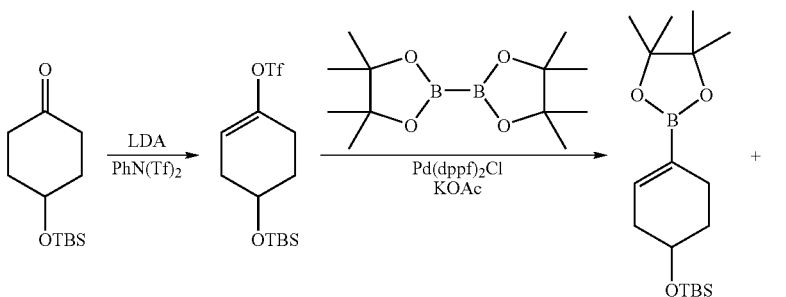

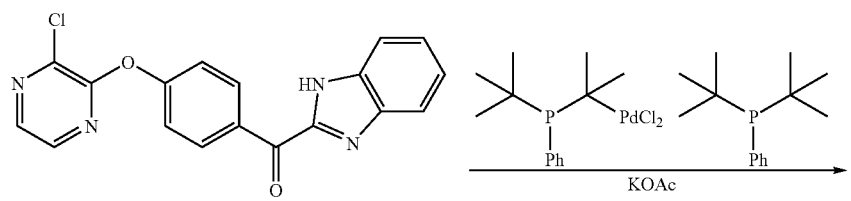

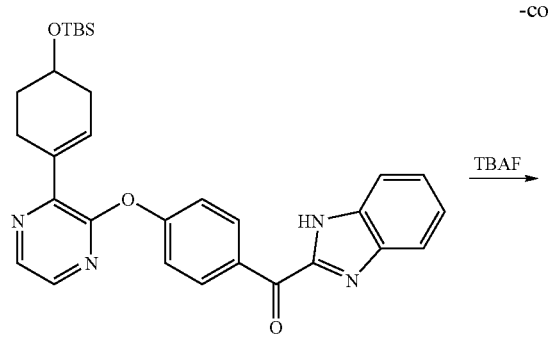
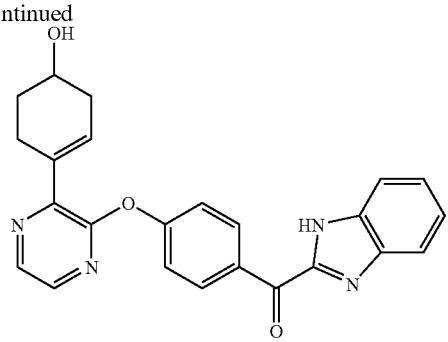
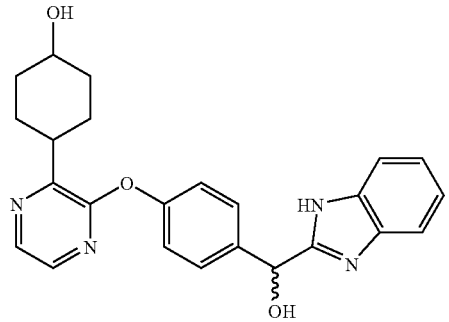
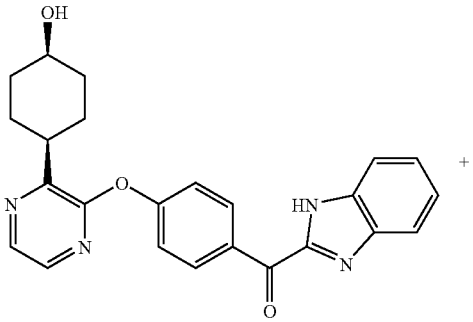
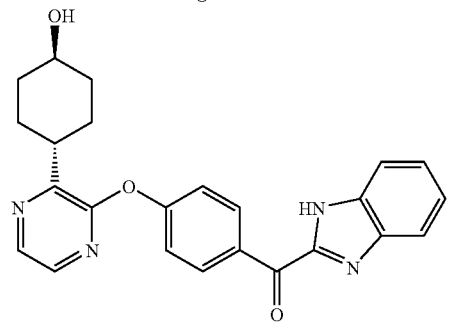
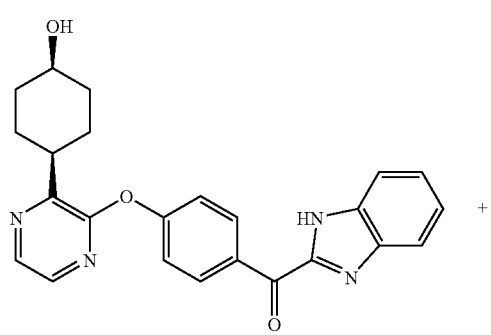
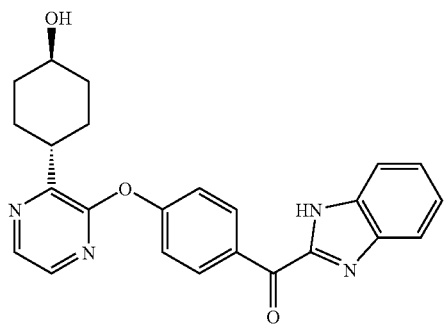

EXAMPLE 188

1H-BENZIMIDAZOL-2-YL(4-((3-(CIS-4-HYDROXYCYCLOHEXYL)-2-PYRAZINYL)OXY)PHENYL)METHANONE AND 1H-BENZIMIDAZOL-2-YL(4-((3-(TRANS-4-HYDROXYCYCLOHEXYL)-2-PYRAZINYL)OXY)PHENYL)METHANONE

STEP 1. 4-((TERT-BUTYL(DIMETHYL)SILYL)OXY)-1-CYCLOHEXEN-1-YL TRIFLUOROMETHANESULFONATE.

Diisopropylamine (1.7 mL, 12.0 mmol) was taken up in 30 mL of THF and chilled to −78° C. N-butyllithium, (4.8 mL, 2.5 M in hexanes) was added. After 5 minutes, 4-((tert-butyl(dimethyl)silyl)oxy)cyclohexanone (2.3 g, 10.0 mmol) was added dropwise in 8 mL of THF. After 10 minutes, n-phenyltriflimide (4.0 g, 11.0 mmol) was added dropwise in 8 mL of THF. After 10 minutes, the mixture was warmed to rt and stirred for 12 hours. The mixture was quenched with 40 mL of aq NH$_4$Cl and extracted twice with 40 mL of EtOAc. The combined organic extracts were washed with 40 mL of brine and dried over MgSO$_4$. Filtration and concentration under reduced pressure, followed by flash chromatography on silica gel (0 to 5% EtOAc/hexanes) afforded 4-((tert-butyl(dimethyl)silyl)oxy)-1-cyclohexen-1-yl trifluoromethanesulfonate.

STEP 2. ((4-(4,4,5,5-TETRAMETHYL-1,3,2-DIOX-ABOROLAN-2-YL)-3-CYCLOHEXEN-1-YL)OXY)SI-LANE.

4-((tert-butyl(dimethyl)silyl)oxy)-1-cyclohexen-1-yl trifluoromethanesulfonate (2.6 g, 7.2 mmol), bis(pinacolato)diboron (2.2 g, 8.7 mmol), potassium acetate (5.3 g, 54.0 mmol), and 1,1'-bis(diphenylphosphino)ferrocene-palladium (ii) dichloride dichloromethane complex (0.18 g, 0.22 mmol) were taken up in 35 mL of dioxane. The mixture was purged with nitrogen and heated to 80° C. After 12 hours, the mixture was diluted with 75 mL of EtOAc and 75 mL of water. The mixture was partitioned and the aqueous portion was extracted with 75 mL of EtOAc. The combined organic extracts were washed with 75 mL of brine and dried over MgSO$_4$. Filtration and concentration under reduced pressure, followed by flash chromatography on silica gel (0.5% to 2.5 EtOAc/hexanes) afforded ((4-(4,4,5,5-tetramethyl-1,3,2-dioxaborolan-2-yl)-3-cyclohexen-1-yl)oxy)silane.

STEP 3. 1H-BENZIMIDAZOL-2-YL(4-((3-(4-((TERT-BUTYL(DIMETHYL)SILYL)OXY)-1-CYCLOHEXEN-1-YL)-2-PYRAZINYL)OXY)PHENYL)METHANONE.

1H-benzimidazol-2-yl(4-((3-chloro-2-pyrazinyl)oxy)phenyl)methanone (0.50 g,
1.4 mmol), ((4-(4,4,5,5-tetramethyl-1,3,2-dioxaborolan-2-yl)-3-cyclohexen-1-yl)oxy)silane (0.68 g, 2.0 mmol), potassium acetate (1.0 g, 11.0 mmol), and bis[di-tert-butyl (phenyl)phosphane]dichloropalladium (0.066 g, 0.11 mmol) were taken up in 24 mL of 3:1 MeCN:water. The mixture was purged with nitrogen and heated to 100° C. After 18 hours, the mixture was diluted with 30 mL of water and extracted three times with 25 mL of 9:1 chloroform:isopropanol. The combined organic extracts were dried over MgSO$_4$. Filtration and concentration under reduced pressure, followed by flash chromatography on silica gel (5% to 25% EtOAc/hexanes) afforded 1H-benzimidazol-2-yl(4-((3-(4-((tert-butyl(dimethyl)silyl)oxy)-1-cyclohexen-1-yl)-2-pyrazinyl)oxy)phenyl)methanone.

STEP 4. 1H-BENZIMIDAZOL-2-YL(4-((3-(4-HYDROXY-1-CYCLOHEXEN-1-YL)-2-PYRAZINYL)OXY)PHENYL)METHANONE.

H-benzimidazol-2-yl(4-((3-(4-((tert-butyl(dimethyl)silyl)oxy)-1-cyclohexen-1-yl)-2-pyrazinyl)oxy)phenyl)methanone (0.15 g, 0.28 mmol) was taken up in 5 mL of THF. Tetrabutylammonium fluoride (0.34 mL, 1.0 M in THF) was added to the mixture. The mixture was stirred for 60 hours. The mixture was diluted with 10 mL of aq NH$_4$Cl. The mixture was extracted twice with 10 mL of EtOAc and the combined organic extracts were dried over MgSO$_4$. Filtration and concentration under reduced pressure, followed by flash chromatography on silica gel (0 to 3% MeOH/dichloromethane) afforded 1H-benzimidazol-2-yl(4-((3-(4-hydroxy-1-cyclohexen-1-yl)-2-pyrazinyl)oxy)phenyl)methanone.

STEP 5. 1H-BENZIMIDAZOL-2-YL(4-((3-(CIS-4-HYDROXYCYCLOHEXYL)-2-PYRAZINYL)OXY)PHENYL)METHANONE AND 1H-BENZIMIDAZOL-2-YL(4-((3-(TRANS-4-HYDROXYCYCLOHEXYL)-2-PYRAZINYL)OXY)PHENYL)METHANONE.

1H-benzimidazol-2-yl(4-((3-(4-hydroxy-1-cyclohexen-1-yl)-2-pyrazinyl)oxy)-phenyl)methanone (0.27 g, 0.66 mmol) was suspended in 20 mL of EtOAc in a pressure tube. Palladium on carbon, 10% (0.20 g) was added. The mixture was hydrogenated at 50 psi. After 60 hours the mixture was filtered through a plug of celite and eluted with 50 mL of 9:1 chloroform:isopropanol. The solvent was removed under reduced pressure. The residue was taken up in 50 mL of dichloromethane. The mixture was sonicated for 5 minutes to dissolve the starting material. Manganese dioxide (0.84 g, 9.7 mmol) was added. After 2 hours, the mixture was filtered through celite, eluted with 50 mL of 9:1 chloroform/isopropanol, and concentrated under reduced pressure. The residue was purified by flash chromatography on silica gel (0 to 2.5% MeOH/dichloromethane). Two products of identical mass that co-eluted were isolated. The mixture was further purified by preparatory HPLC (Phenomenex Gemini column [C18, 10 micro, 150×30 mm] 15% to 100% MeCN/water over 20 min at 35 mL/min) affording 1H-benzimidazol-2-yl(4-((3-(cis-4-hydroxycyclohexyl)-2-pyrazinyl)oxy)phenyl)methanone (MS m/z: 401(M+1) and 1H-benzimidazol-2-yl(4-((3-(trans-4-hydroxycyclohexyl)-2-pyrazinyl)oxy)-phenyl)methanone. MS (ESI, pos. ion) m/z: 401 (M+1). IC50 (uM) +++++.

SCHEME 15A

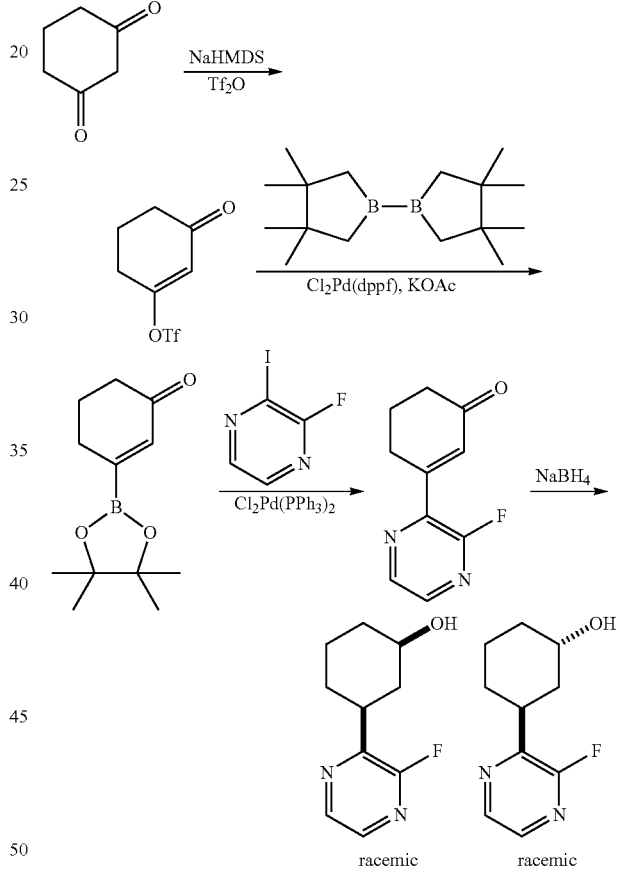

STEP 1: 3-OXOCYCLOHEX-1-ENYL TRIFLUOROMETHANESULFONATE

A 1.0M solution of sodium bis(trimethylsilyl)amide in tetrahydrofuran (102 mL, 102 mmol) was added dropwise to a solution of cyclohexane-1,3-dione (11.4 g, 102 mmol) in THF (200 ml) at −50° C. The mixture was stirred at −50° C.

for 15 min and trifluoromethanesulfonic anhydride (30.1 g, 107 mmol) was added through an addition funnel. After completion of the addition the reaction mixture was allowed to slowly warm to RT. The reaction mixture was then cooled to −30° C., and 200 mL of saturated aqueous sodium bicarbonate was added slowly. The solvent was removed under reduced pressure and the remaining aqueous layer was extracted with EtOAc (2×400 ml). The combined organic layers were washed with brine and dried over sodium sulfate. Filtration and concentration under reduced pressure, followed by flash chromatography on silica gel (0% to 10% EtOAc in hexanes) afforded 3-oxocyclohex-1-enyl trifluoromethanesulfonate as a yellow oil. MS (ESI, pos. ion) m/z: 245.0 (M+1).

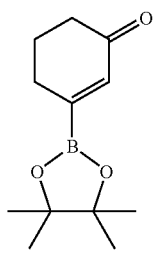

STEP 2. 3-(4,4,5,5-TETRAMETHYL-1,3,2-DIOXABOROLAN-2-YL)CYCLOHEX-2-ENONE

3-Oxocyclohex-1-enyl trifluoromethanesulfonate (9 g, 36.9 mmol), 4,4,4',4',5,5,5',5'-octamethyl-2,2'-bi(1,3,2-dioxaborolane) (10.30 g, 40.5 mmol), and potassium acetate (7.23 g, 73.7 mmol) were suspended in 100 ml dioxane. Argon was bubbled through the reaction mixture for 5 minutes, and dichloro 1,1'-bis(diphenylphosphino)ferrocene palladium (ii) (2.107 g, 2.58 mmol) was added. The mixture was stirred at 80° C. for 3 h, cooled to RT, and concentrated under reduced pressure. Water (300 ml) was added and the mixture was extracted with EtOAc (3×200 ml). The combined organic layer were washed by brine and dried over sodium sulfate. Filtration and concentration under reduced pressure, followed by flash chromatography on silica gel (0% to 20% EtOAc in hexanes) afforded 3-(4,4,5,5-tetramethyl-1,3,2-dioxaborolan-2-yl)cyclohex-2-enone as colorless crystals.

STEP 3. 3-(3-FLUOROPYRAZIN-2-YL)CYCLOHEX-2-ENONE

2-Fluoro-3-iodopyrazine (2.5 g, 11.16 mmol), 3-(4,4,5,5-tetramethyl-1,3,2-dioxaborolan-2-yl)cyclohex-2-enone (3.10 g, 13.95 mmol), and sodium carbonate (3.55 g, 33.5 mmol) were suspended in DME (20 ml) and distilled water (5 ml). Argon was bubbled through the resulting mixture for 3 minutes, and dichlorobis(triphenylphosphino)palladium (ii) (0.431 g, 0.614 mmol) was added. The resulting mixture was stirred at 80° C. for 16 hours, the reaction was cooled to RT, and water (200 ml) was added. The resulting mixture was concentrated under reduced pressure and was extracted with EtOAc (3×200 ml). The combined organic layers were washed with brine and dried over sodium sulfate. Filtration and concentration under reduced pressure, followed by flash chromatography on silica gel (0% to 20% EtOAc in hexanes) afforded 3-(3-fluoropyrazin-2-yl)cyclohex-2-enone as a light yellow solid. MS (ESI, pos. ion) m/z: 193.1 (M+1).

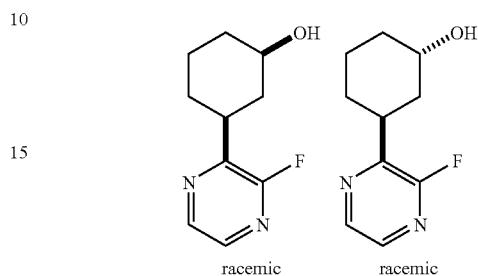

STEP 4. (RAC)-CIS-3-(3-FLUOROPYRAZIN-2-YL)CYCLOHEXANOL AND (RAC)-TRANS-3-(3-FLUOROPYRAZIN-2-YL)CYCLOHEXANOL

Sodium borohydride (295 mg, 7.80 mmol) was added was added portion wise to a solution of 3-(3-fluoropyrazin-2-yl)cyclohex-2-enone (500 mg, 2.60 mmol) in MeOH (15 ml) at RT. After completion of the addition the reaction mixture was stirred at RT for 30 minutes. It was then cooled in an ice-water bath, saturated aqueous ammonium chloride (25 ml) was added dropwise, and the resulting mixture was extracted with EtOAc (2×100 ml). The combined organic layers were washed with brine and dried over sodium sulfate. Filtration and concentration under reduced pressure, followed by flash chromatography on silica gel (0% to 20% EtOAc in hexanes) afforded (rac)-cis-3-(3-fluoropyrazin-2-yl)cyclohexanol and (rac)-trans-3-(3-fluoropyrazin-2-yl)cyclohexanol as colorless oils. MS (ESI, pos. ion) m/z: 197.0 (M+1) and MS (ESI, pos. ion) m/z: 197.0 (M+1), respectively. IC50 (uM) +++++.

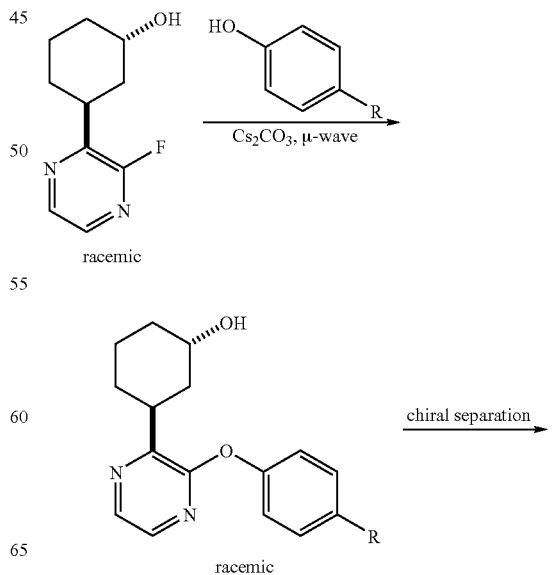

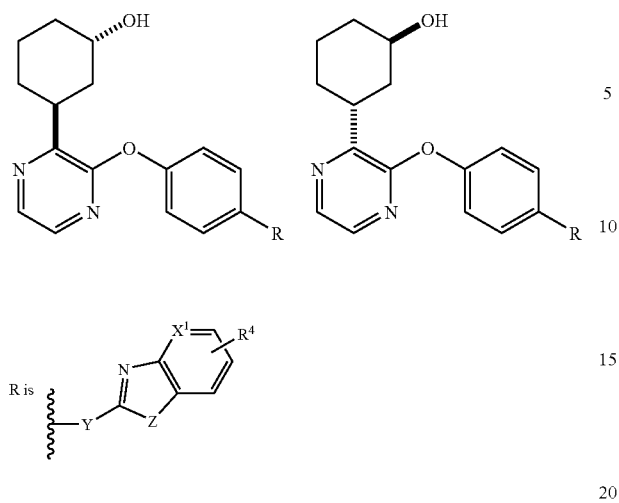

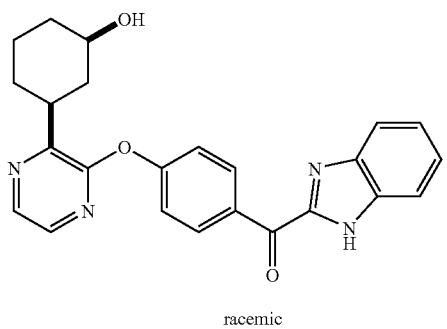

racemic

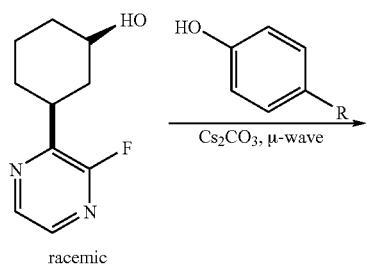

SCHEME 15C

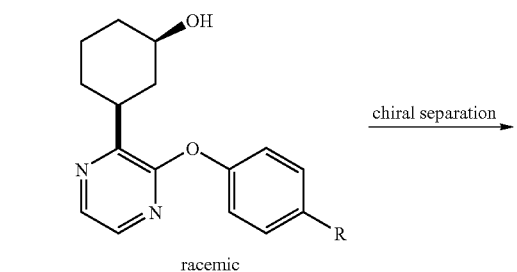

racemic chiral separation

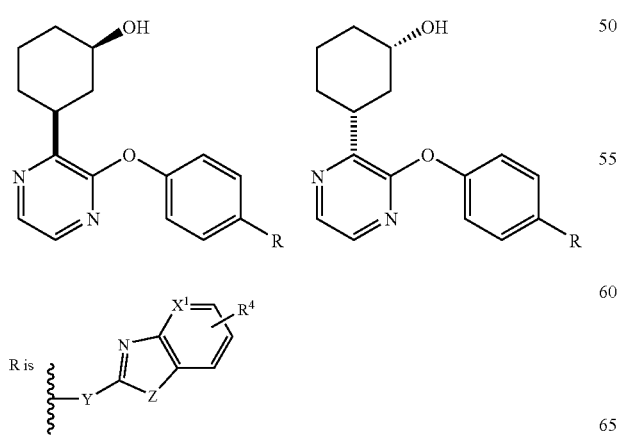

EXAMPLE 189

(RAC)-CIS-(1H-BENZO[D]IMIDAZOL-2-YL)(4-(3-(3-HYDROXYCYCLOHEXYL)PYRAZIN-2-YLOXY)PHENYL)METHANONE

A mixture of (rac)-cis-3-(3-fluoropyrazin-2-yl)cyclohexanol (140 mg, 0.713 mmol), (1H-benzo[d]imidazol-2-yl)(4-hydroxyphenyl)methanone (340 mg, 1.427 mmol), and cesium carbonate (465 mg, 1.427 mmol) in NMP (1.8 ml) was heated in a Biotage™ microwave reactor at 180° C. for 45 min. The mixture was partitioned between $H_2O$ (10 ml) and $CH_2Cl_2$ (20 ml), the layers were separated, and the aqueous layer was extracted with $CH_2Cl_2$ (3×20 ml). The combined organic layers were dried ($MgSO_4$), concentrated under reduced pressure, and the resulting brown oil was purified by reversed phase HPLC (Gilson Gemini-NX 10u C18 110A, 100×50.0 mm, 10% to 95% $H_2O$/MeCN, 0.1% TFA). The product containing fractions were combined, neutralized by the addition of solid $Na_2CO_3$, and extracted with $CH_2Cl_2$ (3×20 mL). The combined organic layers were dried ($MgSO_4$) and concentrated under reduced pressure to deliver (rac)-cis-(1H-benzo[d]imidazol-2-yl)(4-(3-(3-hydroxycyclohexyl)pyrazin-2-yloxy)phenyl)methanone as a brown foam. MS (ESI, pos. ion) m/z: 415.0 (M+1). IC50 (uM) +++++.

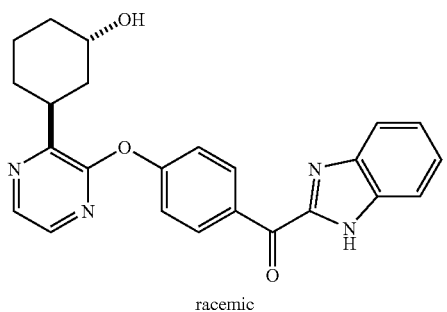

racemic

EXAMPLE 190

(RAC)-TRANS-(1H-BENZO[D]IMIDAZOL-2-YL)(4-(3-(3-HYDROXYCYCLOHEXYL)PYRAZIN-2-YLOXY)PHENYL)METHANONE

A mixture of (rac)-trans-3-(3-fluoropyrazin-2-yl)cyclohexanol (106 mg, 0.540 mmol), (1H-benzo[d]imidazol-2-yl)(4-hydroxyphenyl)methanone (257 mg, 1.080 mmol), and cesium carbonate (352 mg, 1.080 mmol) was heated in a Biotage™ microwave reactor at 150° C. for 30 min. The mixture was partitioned between $H_2O$ (10 ml) and $CH_2Cl_2$ (20 ml), the layers were separated, and the aqueous layer was extracted with $CH_2Cl_2$ (3×20 ml). The combined organic layers were dried ($MgSO_4$), concentrated under reduced pressure, and the resulting brown oil was purified by reversed phase HPLC (Gilson Gemini-NX 10u C18 110A, 100×50.0 mm, 10% to 95% $H_2O$/MeCN, 0.1% TFA). The product containing fractions were combined, neutralized by the addition of solid $Na_2CO_3$, and extracted with $CH_2Cl_2$ (3×20 mL). The combined organic layers were dried ($MgSO_4$) and concentrated under reduced pressure to deliver (rac)-trans-(1H-benzo[d]imidazol-2-yl)(4-(3-(3-hydroxycyclohexyl)pyrazin-2-yloxy)phenyl)methanone as a light yellow solid. MS (ESI, pos. ion) m/z: 415.1 (M+1). IC50 (uM) +++++.

TABLE (VIIA)

EXAMPLES 191 TO 192 ARE TABULATED BELOW:

| Ex# | Structure | IC50 (uM) | IUPAC names | MS |
|---|---|---|---|---|
| 191 | 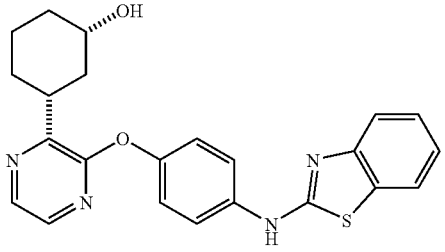 | +++++ | (rac)-cis-3-(3-(4-(benzo[d]thiazol-2-ylamino)phenoxy)pyrazin-2-yl)cyclohexanol | 419 |
| 192 | 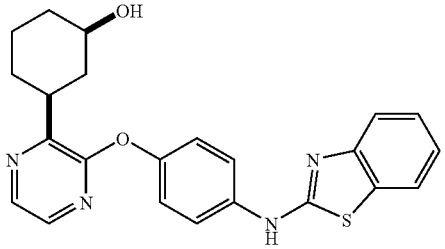 | +++++ | (rac)-trans-3-(3-(4-(benzo[d]thiazol-2-ylamino)phenoxy)pyrazin-2-yl)cyclohexanol | 419 |

TABLE (VIIB)

PREPARATION OF EXAMPLES 191 TO 192 ARE TABULATED BELOW:

| Ex# | Synthetic Scheme | How Different from Main Route | Reagent Difference |
|---|---|---|---|
| 191 | 3 | Same | 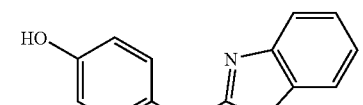 |
| 192 | 4 | Same | 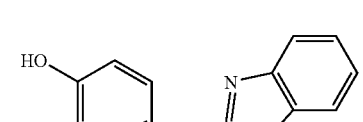 |

SCHEME 16

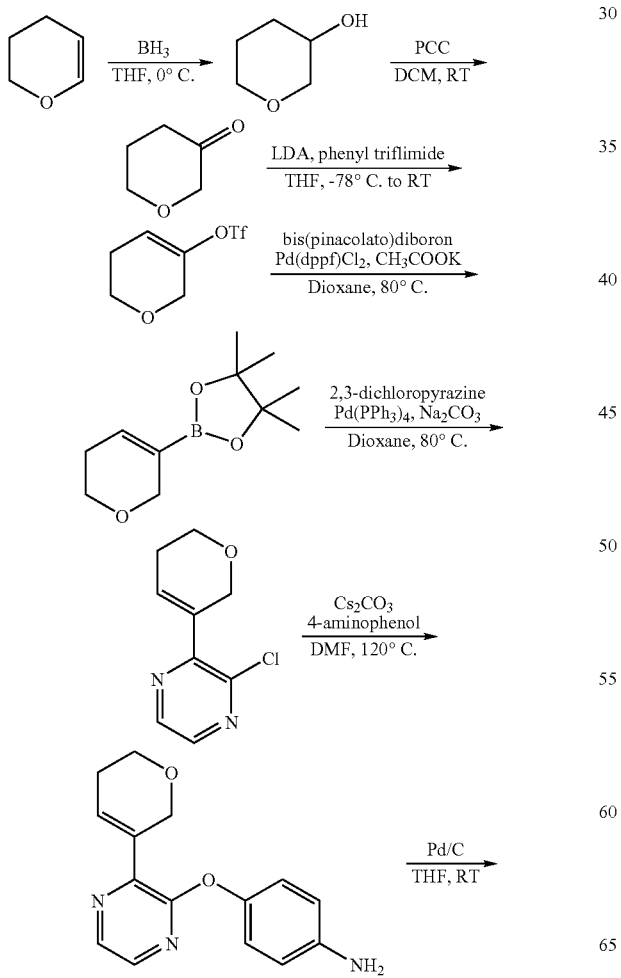

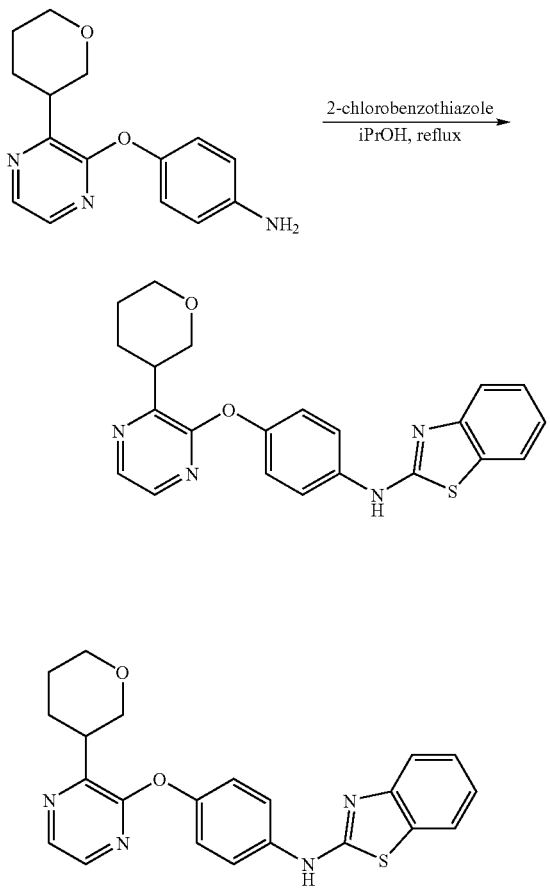

EXAMPLE 193

N-(4-(3-(TETRAHYDRO-2H-PYRAN-3-YL)PYRAZIN-2-YLOXY)PHENYL)BENZO[D]THIAZOL-2-AMINE

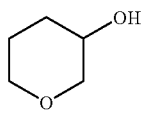

STEP 1. TETRAHYDRO-2H-PYRAN-3-OL

To a stirred solution of 3,4-dihydro-2H-pyran (5.42 mL, 59.4 mmol) in THF (100 mL) at 0° C. under a nitrogen atmosphere was added borane tetrahydrofuran complex, (29.7 mL, 29.7 mmol, 1.0 M in THF) via syringe. The reaction mixture was stirred at 0° C. for 3 h before a mixture of 5 M aqueous sodium hydroxide (40 mL) and 30% aqueous hydrogen peroxide (20 mL) was added. The reaction mixture was warmed to room temperature and stirred for 3 h. Sat. aqueous sodium bicarbonate was added, and the mixture was extracted with EtOAc (2×). The combined organic layers were washed with sat. aqueous sodium chloride, dried over magnesium sulfate, filtered, and concentrated in vacuo to give tetrahydro-2H-pyran-3-ol.

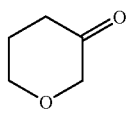

STEP 2. DIHYDRO-2H-PYRAN-3(4H)-ONE

To a stirred mixture of pyridinium chlorochromate (11.02 g, 51.1 mmol) and 3 Å molecular sieves (10.00 g) in DCM (100 mL) was added a solution of tetrahydro-2H-pyran-3-ol (3.48 g, 34.1 mmol) in DCM (100 mL). The reaction mixture was refluxed for 3 h before being cooled to room temperature and partially concentrated in vacuo. The mixture was then diluted with EtOAc and filtered through Celite. The filtrate was concentrated in vacuo and purified by silica gel chromatography to give dihydro-2H-pyran-3(4H)-one.

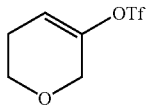

STEP 3. 5,6-DIHYDRO-2H-PYRAN-3-YL TRIFLUOROMETHANESULFONATE

To a stirred solution of diisopropylamine (3.06 mL, 21.81 mmol) in THF (50 mL) at −78° C. under an argon atmosphere was added butyllithium (8.73 mL, 21.81 mmol, 2.5 M in hexanes). The mixture was stirred for 5 min before dihydro-2H-pyran-3(4H)-one (1.82 g, 18.18 mmol) in THF (15 mL) was added slowly via syringe. The mixture was stirred for an additional 15 min before n-phenyltrifluoromethanesulfonimide (7.14 g, 20.00 mmol) in THF (15 mL) was added slowly via syringe. The reaction mixture was then stirred at −78° C. for an additional 15 min before being allowed to warm to room temperature and stir for 1 h. Sat. aqueous sodium bicarbonate was added, and the mixture was extracted with EtOAc (2×). The combined organic layers were washed with sat. sodium chloride, dried over magnesium sulfate, filtered, and concentrated in vacuo. The resulting crude oil was purified by silica gel chromatography to give 5,6-dihydro-2H-pyran-3-yl trifluoromethanesulfonate.

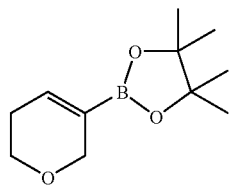

STEP 4. 2-(5,6-DIHYDRO-2H-PYRAN-3-YL)-4,4,5,5-TETRAMETHYL-1,3,2-DIOXABOROLANE 5,6-Dihydro-2H-pyran-3-yl trifluoromethanesulfonate (1.83 g, 7.88 mmol), 4,4,4',4',5,5,5',5'-octamethyl-2,2'-bi(1,3,2-dioxaborolane) (2.20 g, 8.67 mmol), [1,1'-bis(diphenylphosphino)ferrocene]dichloride palladium(ii)complex with dichloromethane (0.193 g, 0.236 mmol), and potassium acetate (1.48 mL, 23.65 mmol) were mixed in dioxane (30 mL) under an argon atmosphere. The reaction mixture was stirred at 80° C. for 17 h. The reaction mixture was cooled to room temperature, diluted with water, and extracted with EtOAc. The organic layer was separated, washed with sat. aqueous sodium chloride, dried over magnesium sulfate, filtered, and concentrated in vacuo. The resulting crude product was purified by silica gel chromatography to give 2-(5,6-dihydro-2H-pyran-3-yl)-4,4,5,5-tetramethyl-1,3,2-dioxaborolane.

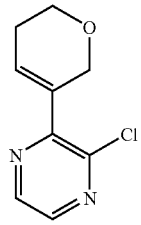

STEP 5. 2-CHLORO-3-(5,6-DIHYDRO-2H-PYRAN-3-YL)PYRAZINE

Sodium carbonate (6.48 mL, 12.95 mmol, 2.0 M in water) was added to a stirred mixture of 2,3-dichloropyrazine (1.28 mL, 8.63 mmol), 2-(5,6-dihydro-2H-pyran-3-yl)-4,4,5,5-tetramethyl-1,3,2-dioxaborolane (0.91 g, 4.32 mmol), and tetrakis(triphenylphosphine)palladium (0.50 g, 0.43 mmol) in dioxane (16 mL) under an argon atmosphere. The reaction mixture was stirred at 80° C. for 16 h before being cooled to room temperature and diluted with EtOAc. The mixture was washed with water, washed with sat. sodium chloride, dried over magnesium sulfate, filtered, and concentrated in vacuo. The resulting crude product was purified by silica gel chromatography to give 2-chloro-3-(5,6-dihydro-2H-pyran-3-yl)pyrazine. [M+1]=197.0.

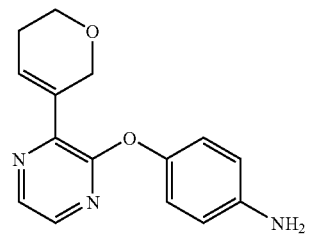

STEP 6. 4-(3-(5,6-DIHYDRO-2H-PYRAN-3-YL)PYRAZIN-2-YLOXY)ANILINE

2-Chloro-3-(5,6-dihydro-2H-pyran-3-yl)pyrazine (0.13 g, 0.68 mmol), 4-aminophenol (0.15 g, 1.35 mmol), and cesium carbonate (0.44 g, 1.35 mmol) were mixed in DMF (2 mL) in a microwave tube. The tube was sealed and placed under a nitrogen atmosphere. The reaction mixture was stirred at 120° C. for 2.5 h. The reaction mixture was cooled to room temperature and diluted with water. The resulting precipitate was filtered and washed with water to give 4-(3-(5,6-dihydro-2H-pyran-3-yl)pyrazin-2-yloxy)aniline. [M+1]=270.1.

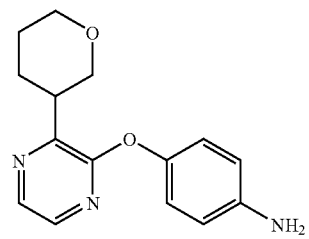

STEP 7. 4-(3-(TETRAHYDRO-2H-PYRAN-3-YL)PYRAZIN-2-YLOXY)ANILINE

Palladium (10 mg, 0.0094 mmol, 10% wt. on activated carbon) was added to a stirred solution of 4-(3-(5,6-dihydro-2H-pyran-3-yl)pyrazin-2-yloxy)aniline (0.16 g, 0.59 mmol) in THF (3 mL). The reaction mixture was placed under a hydrogen atmosphere (balloon) and stirred at room temperature for 23 h. The reaction mixture was filtered through Celite, and the filtrate was concentrated in vacuo to give 4-(3-(tetrahydro-2H-pyran-3-yl)pyrazin-2-yloxy)aniline. [M+1]= 272.1.

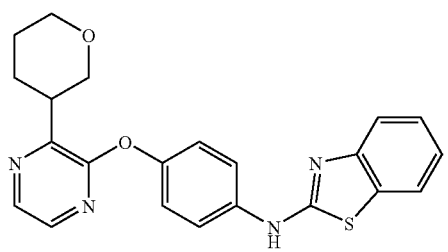

STEP 8. N-(4-(3-(TETRAHYDRO-2H-PYRAN-3-YL)PYRAZIN-2-YLOXY)PHENYL)BENZO[D]THIAZOL-2-AMINE 4-(3-(Tetrahydro-2H-pyran-3-yl)pyrazin-2-yloxy)aniline (0.082 g, 0.30 mmol) and 2-chlorobenzothiazole (0.039 mL, 0.30 mmol) were mixed in isopropyl alcohol (0.50 mL) in a microwave tube. The tube was sealed, and the reaction mixture was refluxed for 2.5 h. The reaction mixture was cooled to room temperature, diluted with sat. sodium bicarbonate, and extracted with EtOAc (2×). The combined organic layers were washed with sat. sodium chloride, dried over magnesium sulfate, filtered, and concentrated in vacuo. The resulting crude product was purified by silica gel chromatography to give N-(4-(3-(tetrahydro-2H-pyran-3-yl)pyrazin-2-yloxy)phenyl)benzo[d]thiazol-2-amine. MS (ESI, pos. ion) m/z: 405.1 (M+1). IC50 (uM) +++++.

SCHEME 17

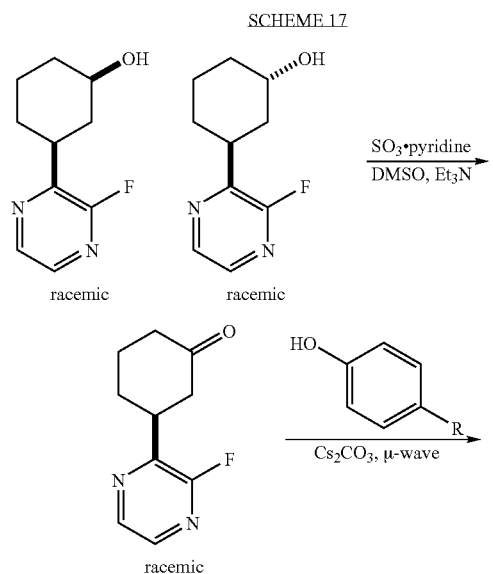

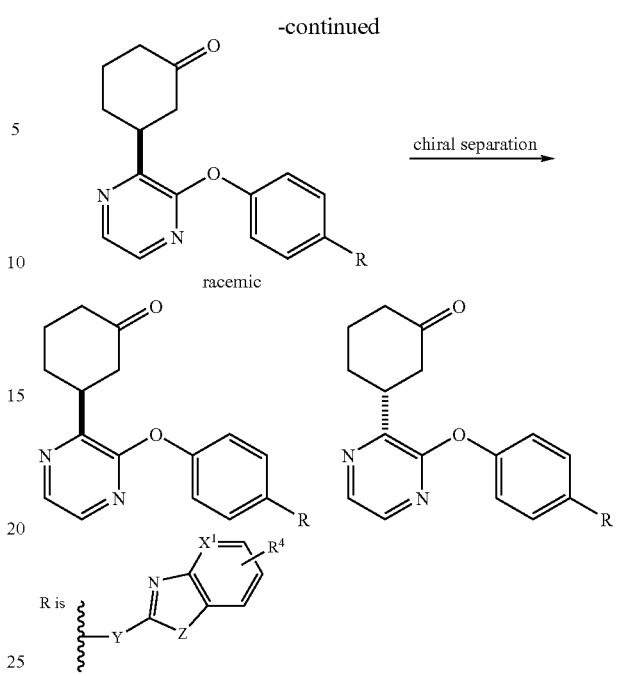

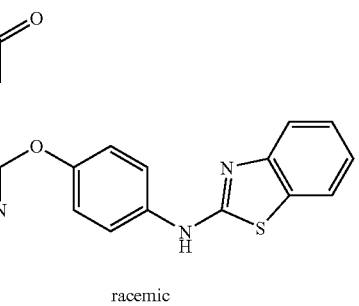

EXAMPLE 194

(RAC)-3-(3-(4-(BENZO[D]THIAZOL-2-YLAMINO)PHENOXY)PYRAZIN-2-YL)CYCLOHEXANONE

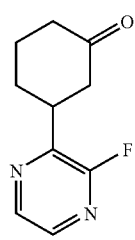

STEP 1: (RAC)-3-(3-FLUOROPYRAZIN-2-YL)CYCLOHEXANONE.

Pyridine sulfur trioxide (1022 mg, 6.42 mmol) was added to a mixture of (rac)-3-(3-fluoropyrazin-2-yl)cyclohexanone (535 mg, 2.75 mmol) and triethylamine (975 mg, 9.63 mmol) in DCM (10 ml) and DMSO (20 ml) at 0° C. After 30 min water (100 ml) was added and the resulting mixture was extracted with DCM (3×50 ml). The organic layer was washed with water and brine and dried over sodium sulfate. Filtration and concentration under reduced pressure afforded (rac)-3-(3-fluoropyrazin-2-yl)cyclohexanone as a white solid. MS (ESI, pos. ion) m/z: 195.1 (M+1).

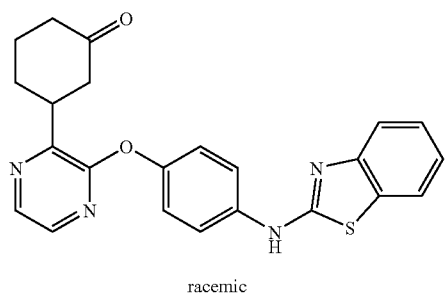

racemic

STEP 1: (RAC)-3-(3-(4-(BENZO[D]THIAZOL-2-YLAMINO)PHENOXY)PYRAZIN-2-YL)CYCLOHEX-ANONE

Argon was bubbled through a mixture of (rac)3-(3-fluoropyrazin-2-yl)cyclohexanone (250 mg, 1.287 mmol), cesium carbonate (1258 mg, 3.86 mmol) and 4-(benzo[d]thiazol-2-ylamino)phenol (468 mg, 1.931 mmol) in NMP (3 ml) for 5 min. The mixture was heated to 125° C. for 3 hrs and was then cooled to RT. Distilled water (100 ml) was added and the resulting mixture was extracted with EtOAc (3×50 ml). The organic layer was washed with water and brine and dried over sodium sulfate. Filtration and concentration under reduced pressure, followed by flash chromatography on silica gel (20% to 50% EtOAc in hexanes) afforded (rac)-3-(3-(4-(benzo[d]thiazol-2-ylamino)phenoxy)pyrazin-2-yl)cyclohexanone as a white solid. MS (ESI, pos. ion) m/z: 417.0 (M+1). IC50 (uM) +++++.

SCHEME 18

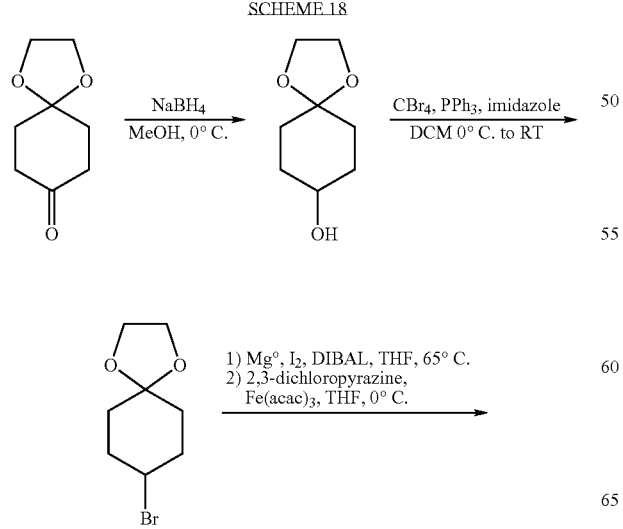

-continued

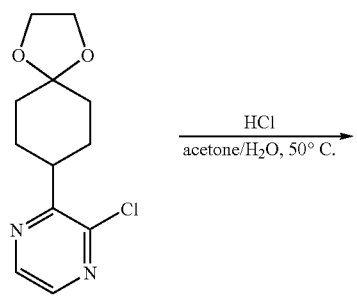

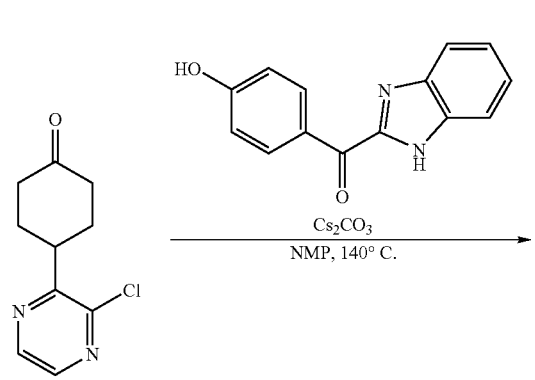

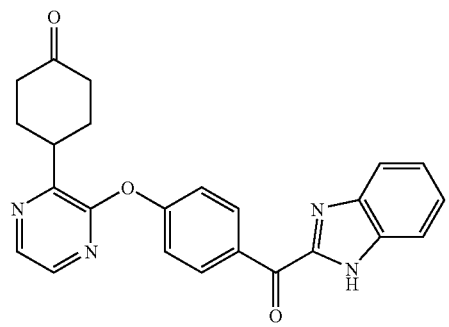

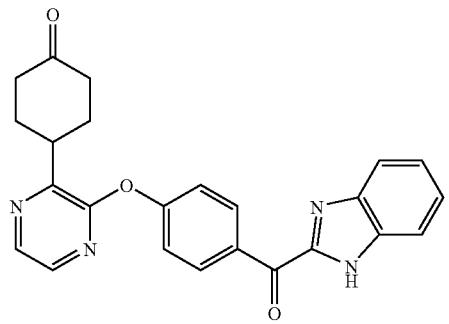

EXAMPLE 195

4-(2-(4-(1H-BENZO[D]IMIDAZOLE-2-CARBONYL)PHENOXY)PYRIDIN-3-YL)CYCLOHEXANONE

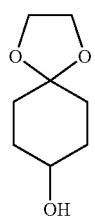

STEP 1. 1,4-DIOXASPIRO[4.5]DECAN-8-OL

Sodium borohydride (4.84 g, 128 mmol) was added in 1 g portions over 30 min to a solution of 1,4-dioxaspiro[4.5]decan-8-one (20.0 g, 128 mmol) in MeOH (400 mL) at 0° C. The ice bath was removed and the mixture was stirred for another 30 min while keeping the temperature of the mixture around room room temperature. The solvent was then removed in vacuo and then the resulting solid was suspended in 1:1 Et$_2$O/EtOAc (400 mL). The boron salts were dissolved by the addition of sat. aqueous ammonium chloride, and the resulting layers were separated. The organic layer was washed with saturated aqueous ammonium chloride (2×), brine (1×), dried over magnesium sulfate, filtered, and concentrated in vacuo to give 1,4-dioxaspiro[4.5]decan-8-ol.

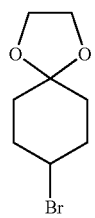

STEP 2. 8-BROMO-1,4-DIOXASPIRO[4.5]DECANE

Carbon tetrabromide (11.0 g, 33.2 mmol) was added to a solution of triphenylphosphine (8.70 g, 33.2 mmol), imidazole (2.47 g, 36.3 mmol), and 1,4-dioxaspiro[4.5]decan-8-ol (5.0 g, 31.6 mmol) in DCM (150 mL) under argon at 0° C. The ice bath was removed and the mixture was stirred for 24 h at RT. The solvent was removed in vacuo to give an oil that was purified by silica gel chromatography to give 8-Bromo-1,4-dioxaspiro[4.5]decane.

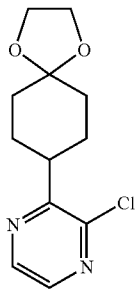

STEP 3. 2-CHLORO-3-(1,4-DIOXASPIRO[4.5]DECAN-8-YL)PYRAZINE

Diisobutylaluminum hydride (0.34 mL, 0.34 mmol, 1.0 M in toluene) and iodine (0.011 g, 0.045 mmol) were added to a mixture of magnesium turnings (0.34 g, 14.13 mmol) and THF (18 mL) under argon. This mixture was heated to 65° C. for 45 min, then cooled to RT. 8-Bromo-1,4-dioxaspiro[4.5]decane (2.50 g, 11.31 mmol) was added via syringe and the mixture was then heated to reflux for 1 h to give 1,4-dioxaspiro[4.5]decan-8-ylmagnesium bromide.

This solution was added to a mixture of Iron (III) acetylacetonate (0.061 g, 0.17 mmol) and 2,3-dichloropyrazine (514 mg, 3.45 mmol) in THF (10 mL) and NMP (1.5 mL) at 0° C. The reaction mixture was stirred at 0° C. for 1 h, quenched with satd. Aqueous ammonium chloride, and extracted with EtOAc (3×). The combined organic extracts were dried over magnesium sulfate, filtered, and concentrated in vacuo. The resulting oil was purified by silica gel chromatography to give 2-chloro-3-(1,4-dioxaspiro[4.5]decan-8-yl)pyrazine. [M+1]= 255.1.

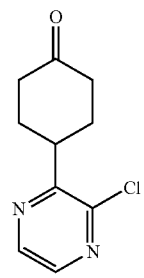

STEP 4. 4-(3-CHLOROPYRAZIN-2-YL)CYCLOHEXANONE

2-Chloro-3-(1,4-dioxaspiro[4.5]decan-8-yl)pyrazine (0.29 g, 1.14 mmol) was dissolved in acetone (8 mL) and 1M aqueous hydrochloric acid (1.0 mL, 1.0 mmol) was heated to 50° C. for 4 h, then cooled to RT. The acetone was removed under vacuum and the solution was then diluted with EtOAc. This mixture was transferred to a reparatory funnel and washed with sat. aqueous sodium bicarbonate (1×), brine (1×), dried over magnesium sulfate, filtered, and concentrated in vacuo. The resulting oil was purified by silica gel chromatography to give 4-(3-chloropyrazin-2-yl)cyclohexanone.

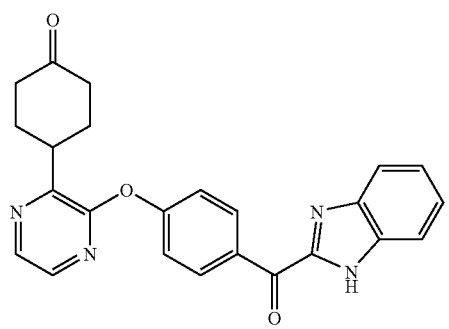

STEP 5. 4-(2-(4-(1H-BENZO[D]IMIDAZOLE-2-CARBONYL)PHENOXY)PYRIDIN-3-YL)CYCLOHEXANONE 4-(3-Chloropyrazin-2-yl)cyclohexanone (0.10 g, 0.48 mmol), (1H-benzo[d]imidazol-2-yl)(4-hydroxyphenyl)methanone (0.34 g, 1.42 mmol), and cesium carbonate (0.46 mL, 1.42 mmol) were mixed in NMP (1.5 mL). The reaction mixture was placed under a nitrogen atmosphere and stirred at 140° C. for 16 h. The reaction mixture was cooled to room temperature, diluted with water, and extracted with EtOAc. The organic layer was washed with 1 M aqueous sodium hydroxide, washed with sat. sodium chloride, dried over magnesium sulfate, and concentrated in vacuo. The resulting crude product was purified by silica gel chromatography to give 4-(2-(4-(1H-benzo[d]imidazole-2-carbonyl)phenoxy)pyridin-3-yl)cycloexanone. MS (ESI, pos. ion) m/z: 413.1 (M+1). IC50 (uM) +++++.

SCHEME 19

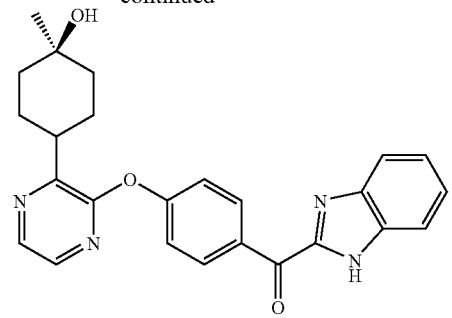

-continued

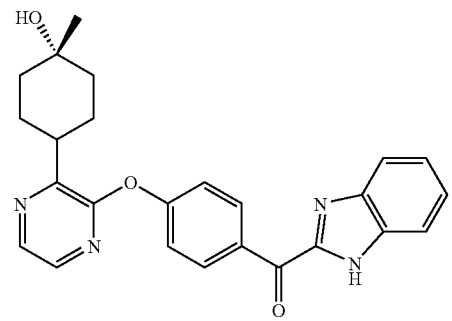

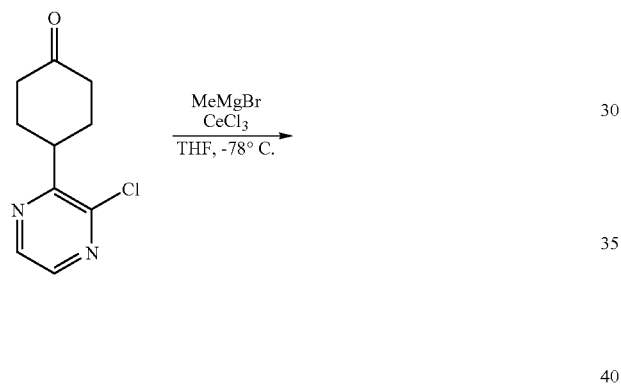

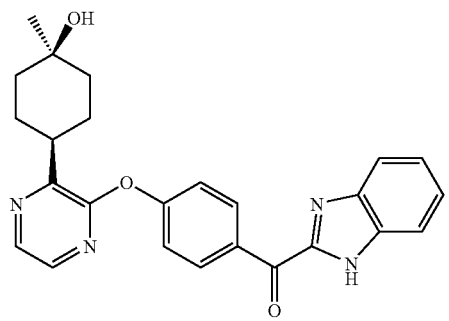

EXAMPLE 196

(1H-BENZO[D]IMIDAZOL-2-YL)(4-(3-((1S,4S)-4-HYDROXY-4-METHYLCYCLOHEXYL)PYRIDIN-2-YLOXY)PHENYL)METHANONE

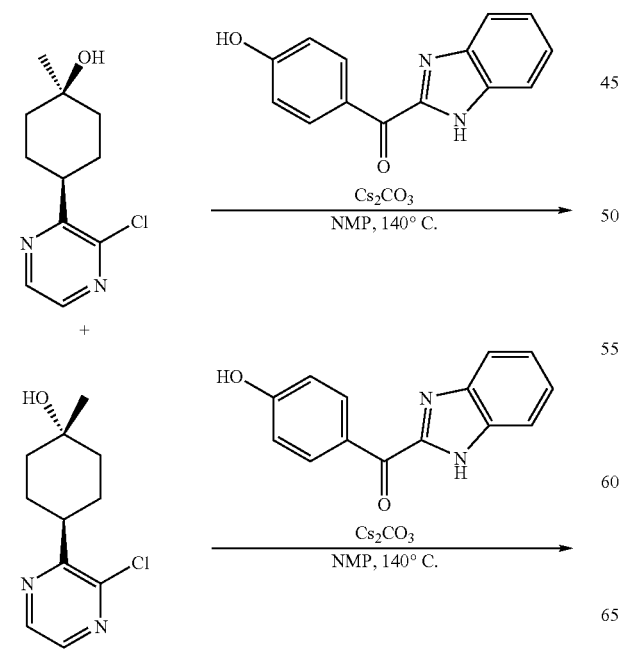

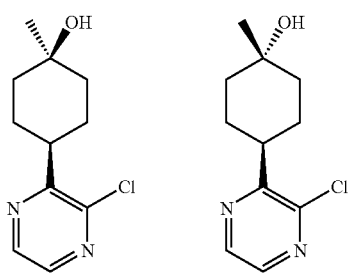

STEP 1. (1S,4S)-4-(3-CHLOROPYRAZIN-2-YL)-1-METHYLCYCLOHEXANOL AND (1R,4R)-4-(3-CHLOROPYRAZIN-2-YL)-1-METHYLCYCLOHEXANOL

A suspension of dry cerium(III) chloride (0.20 g, 0.80 mmol) in THF (2 mL) was stirred at 40° C. for 2 h under an argon atmosphere. The suspension was cooled to −78° C., and methylmagnesium bromide (0.27 mL, 0.80 mmol, 3.0 M solution in diethyl ether) was added dropwise via syringe. The reaction mixture was stirred for 30 min before 4-(3-chloropyrazin-2-yl)cyclohexanone (0.14 g, 0.665 mmol) in THF (0.5 mL) was added dropwise via syringe. The reaction mixture was stirred at −78° C. for an additional 1.5 h before being quenched with sat. ammonium chloride and extracted with EtOAc. The organic layer was separated, washed with sat. sodium chloride, dried over magnesium sulfate, filtered, and concentrated in vacuo. The resulting crude product was purified by silica gel chromatography to give (1s,4s)-4-(3-chloropyrazin-2-yl)-1-methylcyclohexanol and (1r,4r)-4-(3-chloropyrazin-2-yl)-1-methylcyclohexanol. [M+1]=227.1 for both isomers.

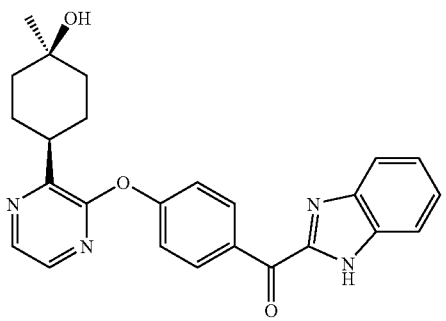

STEP 2. (1H-BENZO[D]IMIDAZOL-2-YL)(4-(3-((1S,4S)-4-HYDROXY-4-METHYLCYCLOHEXYL)PYRIDIN-2-YLOXY)PHENYL)METHANONE (1s,4s)-4-(3-Chloropyrazin-2-yl)-1-methylcyclohexanol (0.060 g, 0.27 mmol), (1H-benzo[d]imidazol-2-yl)(4-hydroxyphenyl)methanone (019 g, 0.80 mmol), and cesium carbonate (0.26 mL, 0.79 mmol) were mixed in NMP (0.7 mL) under a nitrogen atmosphere. The reaction mixture was stirred at 140° C. for 18 h. The reaction mixture was cooled to room temperature, diluted with water, and extracted with EtOAc (3×). The combined organic layers were washed with 1 M aqueous sodium hydroxide, washed with sat. sodium chloride, dried over magnesium sulfate, and concentrated in vacuo. The resulting crude product was purified by silica gel chromatography (EtOAc/hexanes) to give (1H-benzo[d]imidazol-2-yl)(4-(3-((1s,4s)-4-hydroxy-4-methylcyclohexyl)pyridin-2-yloxy)phenyl)methanone. MS (ESI, pos. ion) m/z: 429.2 (M+1). IC50 (uM) +++++.

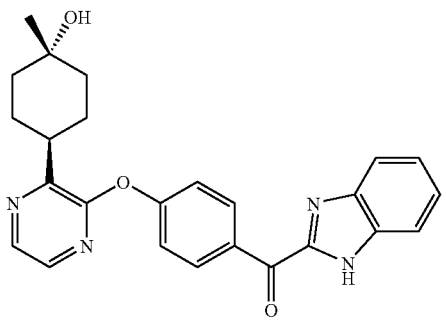

EXAMPLE 197

(1H-BENZO[D]IMIDAZOL-2-YL)(4-(3-((1R,4R)-4-HYDROXY-4-METHYLCYCLOHEXYL)PYRIDIN-2-YLOXY)PHENYL)METHANONE (1r,4r)-4-(3-Chloropyrazin-2-yl)-1-methylcyclohexanol (0.05 g, 0.22 mmol), (1H-benzo[d]imidazol-2-yl)(4-hydroxyphenyl)methanone (0.16 g, 0.66 mmol), and cesium carbonate (0.22 g, 0.66 mmol) were mixed in NMP (0.6 mL) under a nitrogen atmosphere. The reaction mixture was stirred at 140° C. for 18 h. The reaction mixture was cooled to room temperature, diluted with water, and extracted with EtOAc (3×). The combined organic layers were washed with 1 M aqueous sodium hydroxide, washed with sat. sodium chloride, dried over magnesium sulfate, and concentrated in vacuo. The resulting crude product was purified by silica gel chromatography to give (1H-benzo[d]imidazol-2-yl)(4-(3-((1r,4r-4-hydroxy-4-methylcyclohexyl)pyridin-2-yloxy)phenyl)methanone. MS (ESI, pos. ion) m/z: 429.2 (M+1). IC50 (uM) +++++.

SCHEME 20

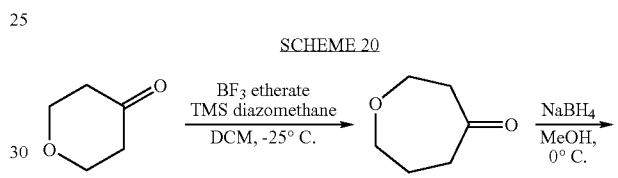

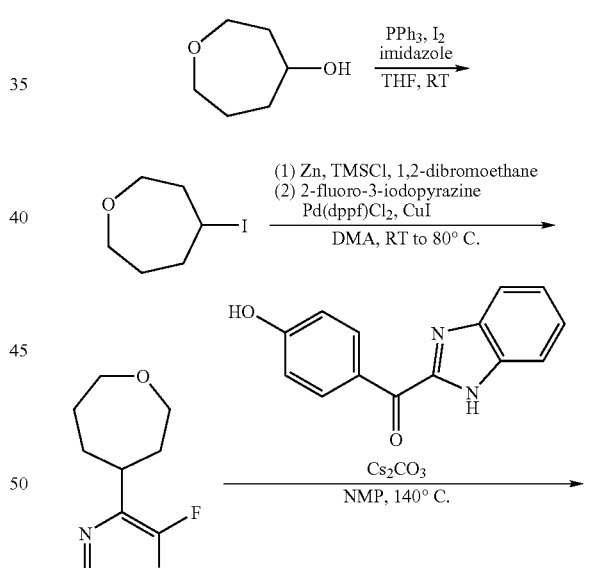

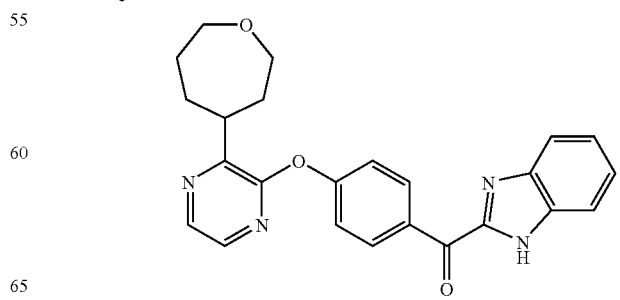

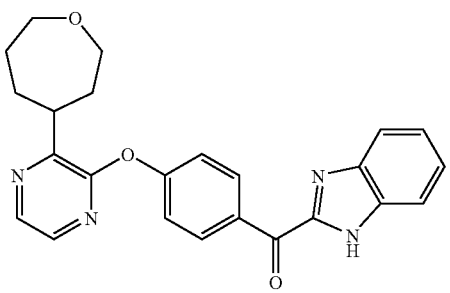

EXAMPLE 198

(1H-BENZO[D]IMIDAZOL-2-YL)(4-(3-(OXEPAN-4-YL)PYRAZIN-2-YLOXY)PHENYL)METHA-NOE

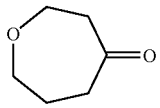

STEP 1. OXEPAN-4-ONE

To a stirred solution of dihydro-2H-pyran-4(3H)-one (9.23 mL, 100 mmol) and boron trifluoride diethyl etherate (13.80 mL, 110 mmol) in DCM (400 mL) at −25° C. was added (trimethylsilyl)diazomethane (54.9 mL, 110 mmol, 2.0 m in hexanes) slowly via syringe. The reaction mixture was stirred at −25° C. for 2.5 h. The reaction mixture was diluted with water and extracted with DCM. The organic layer was separated, washed with 10:1 sat. ammonium chloride:ammonium hydroxide, washed with sat. sodium chloride, dried over magnesium sulfate, filtered, and concentrated in vacuo. The resulting crude product was purified by silica gel chromatography to give oxepan-4-one.

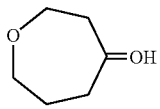

STEP 2. OXEPAN-4-OL

To a stirred solution of oxepan-4-one (3.40 g, 29.8 mmol) in MeOH (100 mL) at 0° C. was added sodium borohydride (1.05 mL, 29.8 mmol). The reaction mixture was stirred at 0° C. for 30 min. The reaction mixture was concentrated in vacuo and then partitioned between 1:1 EtOAc/diethyl ether and sat. ammonium chloride. The organic layer was separated, and the aqueous layer was extracted once more with 1:1 EtOAc/diethyl ether. The combined organic layers were washed with sat. sodium chloride, dried over magnesium sulfate, filtered, and concentrated in vacuo to give oxepan-4-ol

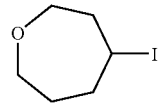

STEP 3. 4-IODOOXEPANE

Imidazole (1.58 g, 23.14 mmol), triphenylphosphine (6.07 g, 23.14 mmol), and oxepan-4-ol (2.24 g, 19.28 mmol) were mixed in THF (12 mL) at 0° C. A solution of iodine (5.87 g, 23.14 mmol) in THF (12 mL) was added dropwise via syringe. The reaction mixture was allowed to warm to room temperature and stir for 16 h. The reaction mixture was diluted with EtOAc and washed with 2 M aqueous sodium bisulfite. The aqueous layer was separated and extracted once more with EtOAc. The combined organic layers were washed with sat. sodium chloride, dried over magnesium sulfate, filtered, and concentrated in vacuo. The resulting crude product was purified by silica gel chromatography to give 4-iodooxepne.

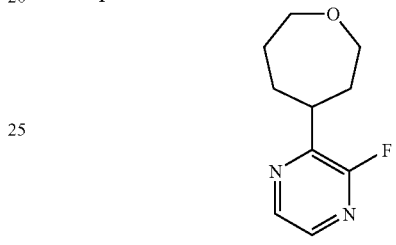

STEP 4. 2-FLUORO-3-(OXEPAN-4-YL)PYRAZINE

A mixture of chlorotrimethylsilane (0.11 mL, 0.87 mmol) and 1,2 dibromoethane (0.075 mL, 0.87 mmol) was added slowly to a stirred mixture of zinc dust (0.71 g, 10.9 mmol) in DMA (2 mL) at room temperature under a nitrogen atmosphere. The mixture was stirred for 15 min before a solution of 4-iodooxepane (1.97 g, 8.71 mmol) in DMA (5 mL) was added dropwise via syringe. The reaction mixture was stirred at room temperature for an additional 30 min before being warmed to 60° C. for 15 min. The reaction mixture was cooled to room temperature and added directly via syringe to a stirred mixture of 2-fluoro-3-iodopyrazine (1.39 g, 6.23 mmol), copper(i) iodide (0.12 g, 0.62 mmol), and dichloro(1,1-bis(diphenylphosphinoferrocene))palladium(ii) (0.25 g, 0.31 mmol) in DMA (8 mL) under an argon atmosphere. The reaction mixture was stirred at 80° C. for 3 h. The reaction mixture was cooled to room temperature, quenched with sat. ammonium chloride, and extracted with EtOAc. The organic layer was separated, washed with sat. sodium chloride, dried over magnesium sulfate, filtered, and concentrated in vacuo. The resulting crude product was purified by silica gel chromatography to give 2-fluoro-3-(oxepan-4-yl)pyrazine. [M+1]= 197.1.

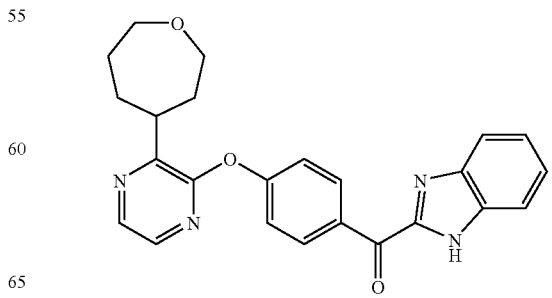

STEP 5. (1H-BENZO[D]IMIDAZOL-2-YL)(4-(3-(OX-EPAN-4-YL)PYRAZIN-2-YLOXY)PHENYL)METHA-NONE

2-Fluoro-3-(oxepan-4-yl)pyrazine (0.08 g, 0.40 mmol), (1H-benzo[c]imidazol-2-yl)(4-hydroxyphenyl)methanone (028 g, 1.19 mmol), and cesium carbonate (0.39 mL, 1.19 mmol) were mixed in NMP (1 mL) under a nitrogen atmosphere. The reaction mixture was stirred at 140° C. for 6 h. The reaction mixture was cooled to room temperature, diluted with water, and extracted with EtOAc (2×). The combined organic layers were washed with 1 M aqueous sodium hydroxide, washed with sat. sodium chloride, dried over magnesium sulfate, and concentrated in vacuo. The resulting crude product was purified by silica gel chromatography to give (1H-benzo[c]imidazol-2-yl)(4-(3-(oxepan-4-yl)pyrazin-2-yloxy)phenyl)methanone. MS (ESI, pos. ion) m/z: 415.1 (M+1). IC50 (uM) +++++.

SCHEME 21

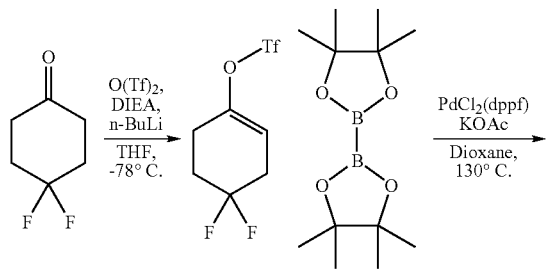

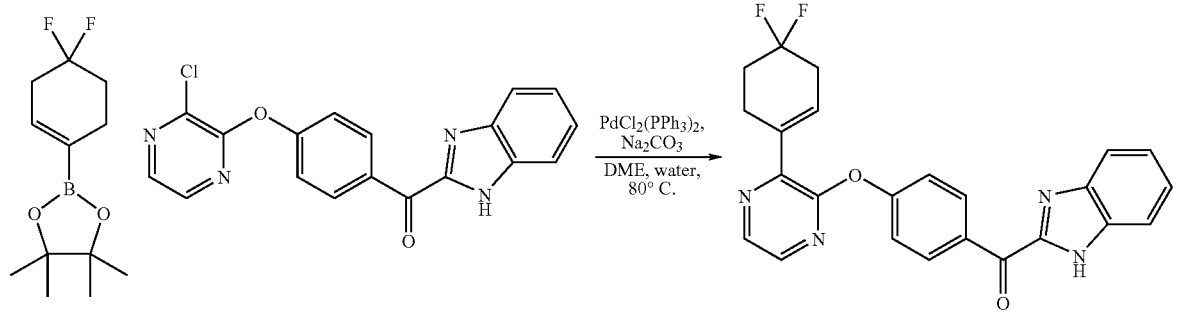

EXAMPLE 199

(1H-BENZO[D]IMIDAZOL-2-YL)(4-(3-(4,4-DIF-LUOROCYCLOHEX-1-ENYL)PYRAZIN-2-YLOXY)PHENYL)METHANONE

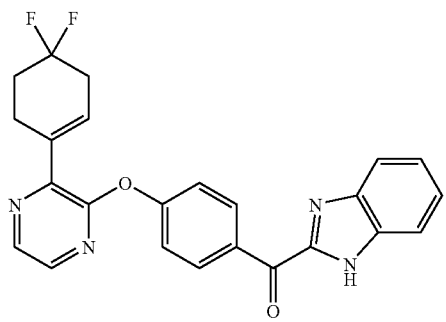

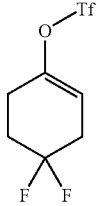

STEP 1. 4,4-DIFLUOROCYCLOHEX-1-ENYL TRIFLU-OROMETHANESULFONATE.

To a round bottomed flask was added diisopropylamine (3.76 mL, 26.8 mmol) in THF. The temperature was brought to −78° C. and n-butyllithium (10.74 mL, 26.8 mmol) (2.5M in hexanes) was added dropwise. The temperature was brought to 0° C. and was allowed to stir for 10 minutes. The temperature was brought back to −78° C. and 4,4-difluoro-cyclohexanone (3.0000 g, 22.37 mmol) was added and allowed to stir. After 30 minutes, triflate anhydride (5.63 mL, 33.6 mmol) was added and the temperature was allowed to slowly warm to room temperature. The reaction mixture was diluted with 50% sodium chloride solution and extracted with DCM. The organic extract was washed with water, brine, dried with magnesium sulfate, filtered, and concentrated to provide 4,4-difluorocyclohex-1-enyl trifluoromethane-sulfonate.

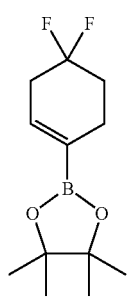

STEP 2. 2-(4,4-DIFLUOROCYCLOHEX-1-ENYL)-4,4,5,5-TETRAMETHYL-1,3,2-DIOXABOROLANE.

To a sealed tube was added 4,4-difluorocyclohex-1-enyl trifluoromethanesulfonate (5.950 g, 22.35 mmol), bis(pinacolato)diboron (6.81 g, 26.8 mmol), potassium acetate (3.77 mL, 60.4 mmol), and dppf (0.867 g, 1.565 mmol) in dioxane (75 mL) to stir at 130° C. overnight. Reaction was worked up via reparatory funnel. The crude product was adsorbed onto a plug of silica gel and chromatographed through a Redi-Sep® pre-packed silica gel column (40 g), eluting with isocratic DCM, to provide 2-(4,4-difluorocyclohex-1-enyl)-4,4,5,5-tetramethyl-1,3,2-dioxaborolane.

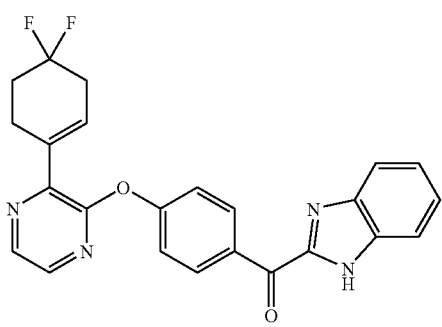

STEP 3. (1H-BENZO[D]IMIDAZOL-2-YL)(4-(3-(4,4-DIFLUOROCYCLOHEX-1-ENYL)PYRAZIN-2-YLOXY) PHENYL)METHANONE.

To a round bottomed flask was added (1H-benzo[d]imidazol-2-yl)(4-(3-chloropyrazin-2-yloxy)phenyl)methanone (0.5018 g, 1.431 mmol), 2-(4,4-difluorocyclohex-1-enyl)-4,4,5,5-tetramethyl-1,3,2-dioxaborolane (0.698 g, 2.86 mmol), trans-dichlorobis(triphenylphosphine) palladium (II) (0.080 g, 0.114 mmol), and sodium carbonate (0.455 g, 4.29 mmol) in DME (3.58 mL) and water (1.192 mL) at 80° C. to stir overnight. Upon completion, solvent was removed. The crude product was purified by reverse-phase preparative HPLC using a Phenomenex Synergi column, 4 micron, MAX-RP, 80 Å, 150×30 MM, 0.1% TFA in CH$_3$CN/H$_2$O, gradient 10% to 100% over 15 min to provide (1H-benzo[d]imidazol-2-yl)(4-(3-(4,4-difluorocyclohex-1-enyl)pyrazin-2-yloxy)phenyl) methanone. MS (ESI, pos. ion) m/z: 433.0 (M+1). IC50 (uM) +++++.

SCHEME 22

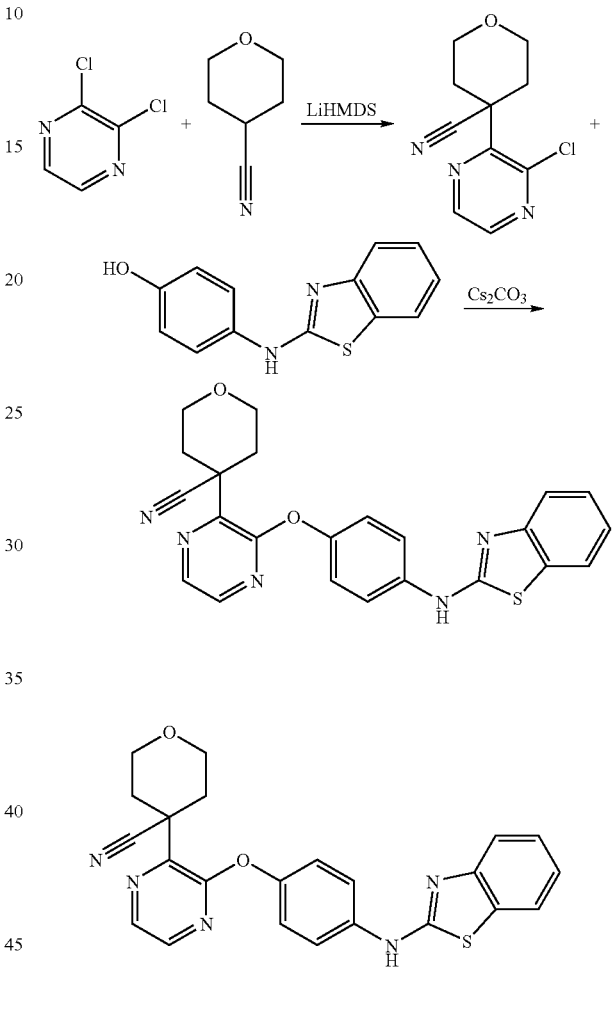

EXAMPLE 200

4-(3-(4-(BENZO[D]THIAZOL-2-YLAMINO)PHENOXY)PYRAZIN-2-YL)TETRAHYDRO-2H-PYRAN-4-CARBONITRILE

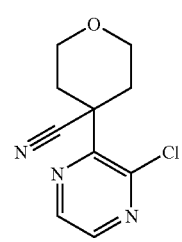

245

STEP 1: 4-(3-CHLOROPYRAZIN-2-YL)TETRAHYDRO-2H-PYRAN-4-CARBONITRILE

To a solution of 2,3-dichloropyrazine (1.219 g, 8.18 mmol) and tetrahydro-2H-pyran-4-carbonitrile (1 g, 9.00 mmol) in Toluene (16.36 mL) at room temperature was added LiHMDS (18.00 mL, 18.00 mmol) dropwise. The reaction mixture was stirred overnight at room temperature. Reaction was quenched with saturated NH$_4$Cl and extracted with EtOAc. Two purifications with Biotage (0-10% MeOH/DCM & 0-100% EtOAc/Hexane) were conducted to isolate product.

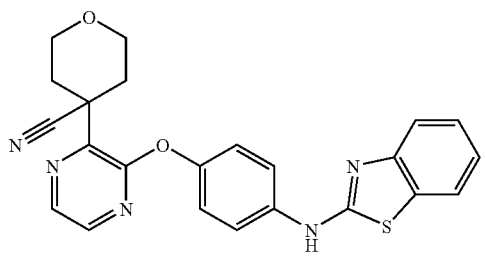

STEP 2: 4-(3-(4-(BENZO[D]THIAZOL-2-YLAMINO)PHENOXY)PYRAZIN-2-YL)TETRAHYDRO-2H-PYRAN-4-CARBONITRILE

To a solution of 4-(benzo[d]thiazol-2-ylamino)phenol (0.097 g, 0.402 mmol) and 4-(3-chloropyrazin-2-yl)tetrahydro-2H-pyran-4-carbonitrile (0.09 g, 0.402 mmol) in DMSO (1 mL) was added cesium carbonate (0.262 g, 0.805 mmol). The resulting mixture was heated to 60° C. overnight. Purification by Biotage (0-100% EtOAc/hexane) provided product. MS (ESI, pos. ion) m/z: 430.0 (M+1). IC50 (uM) +++++.

SCHEME 23

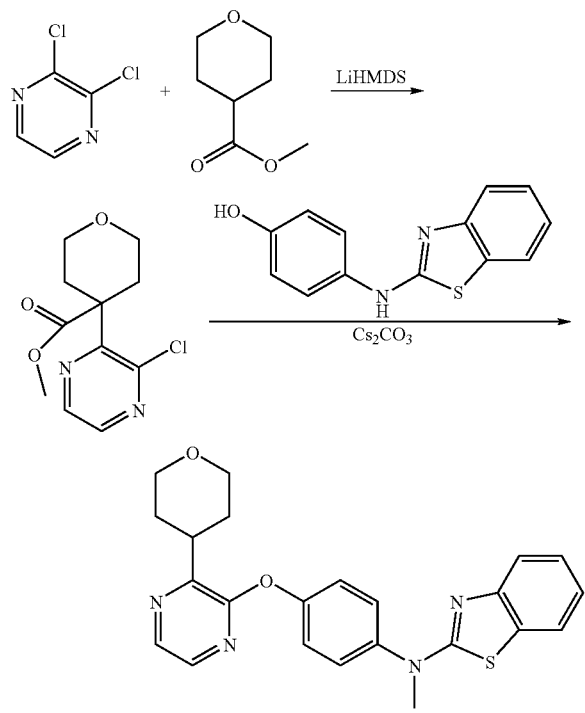

246

EXAMPLE 201

N-METHYL-N-(4-(3-(TETRAHYDRO-2H-PYRAN-4-YL)PYRAZIN-2-YLOXY)PHENYL)BENZO[D]THIAZOL-2-AMINE

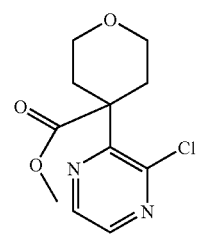

STEP 1: METHYL 4-(3-CHLOROPYRAZIN-2-YL)TETRAHYDRO-2H-PYRAN-4-CARBOXYLATE

To a solution of 2,3-dichloropyrazine (1.45 g, 9.73 mmol) and methyl tetrahydro-2H-pyran-4-carboxylate (2.60 mL, 19.47 mmol) in Toluene (19.47 mL) at room temperature was added LiHMDS (19.47 mL, 19.47 mmol, 1M solution) dropwise. After overnight room temperature stirring, reaction was quenched with saturated NH$_4$Cl solution and extracted with EtOAc. Purification by Biotage (0-10% MeOH/DCM) produced product.

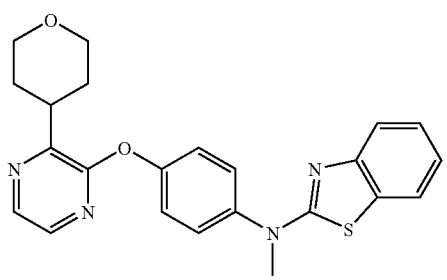

STEP 2: N-METHYL-N-(4-(3-(TETRAHYDRO-2H-PYRAN-4-YL)PYRAZIN-2-YLOXY)PHENYL)BENZO[D]THIAZOL-2-AMINE

To a solution of 4-(benzo[d]thiazol-2-ylamino)phenol (0.094 g, 0.390 mmol) and methyl 4-(3-chloropyrazin-2-yl)tetrahydro-2H-pyran-4-carboxylate (0.1 g, 0.390 mmol) in DMSO (1 mL) was added cesium carbonate (0.254 g, 0.779 mmol). The resulting mixture was heated to 163° C. for ~20 minutes. Reaction mixture was cooled back to 100 C and stirred overnight. Aqueous work up with multiple water and brine washes to remove DMSO and extraction with DCM. Purification by Shimadzu (phenomenex Gemini C18 5 um 100×30 mm; 254 UV; solvent A=0.1% TFA in water, solvent B=0.1% TFA in ACN; gradient run: 35% B to 80% B in 9 min; 1 min@ 80% B; flow rate=30 ml/min; 2 peaks contained mass 418: R1 =3.91 to 4.26 min; R2=5.83 to 6.36 min) to afford the product. MS (ESI, pos. ion) m/z: 419.0 (M+1). IC50 (uM) +++++.

SCHEME 24

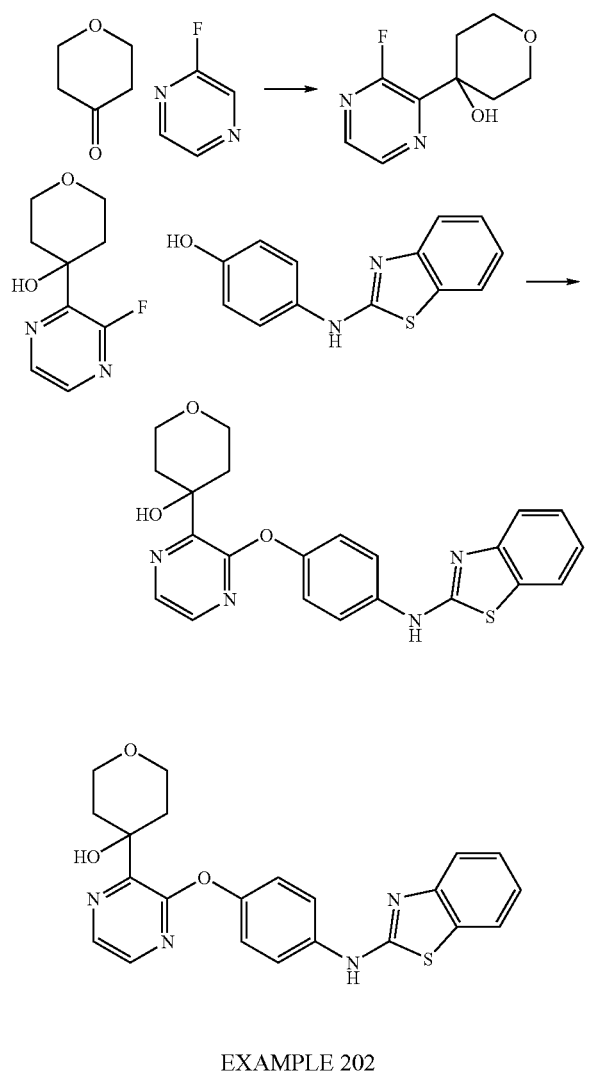

EXAMPLE 202

4-(3-(4-(BENZO[D]THIAZOL-2-YLAMINO)PHE-NOXY)PYRAZIN-2-YL)TETRAHYDRO-2H-PY-RAN-4-OL

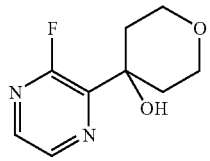

STEP 1: 4-(3-FLUOROPYRAZIN-2-YL)TETRAHYDRO-2H-PYRAN-4-OL

A 2.5M solution of nbuli (4.49 mL, 11.22 mmol)/hexane in THF (3 mL) was first cooled to −78° C. To the cooled solution was added dropwise, 2,2,6,6-tetramethylpiperidine (2.065 mL, 12.24 mmol). The dry ice bath was then switched to a 0° C. bath. The reaction mixture was stirred for 10 min at 0° C. and then the dry ice bath was switched back to recool the reaction mixture to −78° C. To the cooled solution was added 2-fluoropyrazine (1 g, 10.20 mmol), dropwise. After 5 min of stirring at −78° C., a solution of dihydro-2H-pyran-4(3H)-one (0.937 mL, 10.20 mmol) in 0.6 mL of THF was added dropwise. The resulting mixture was allowed to gradually warm to room temperature overnight. Reaction was quenched with saturated NH₄Cl and extracted with EtOAc. Purification by Biotage (0-100% EtOAc/hexane) produced product.

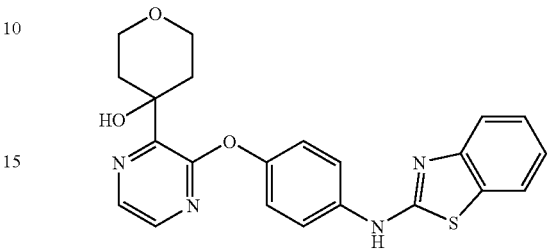

STEP 2: 4-(3-(4-(BENZO[D]THIAZOL-2-YLAMINO)PHENOXY)PYRAZIN-2-YL)TETRAHYDRO-2H-PYRAN-4-OL

To a solution of 4-(3-fluoropyrazin-2-yl)tetrahydro-2H-pyran-4-ol (0.1 g, 0.505 mmol) in DMSO (1 mL) was added 4-(benzo[d]thiazol-2-ylamino)phenol (0.183 g, 0.757 mmol) and cesium carbonate (0.329 g, 1.009 mmol). The resulting mixture was heated to 80° C. overnight. Reaction mixture was diluted with DCM and washed with alternating washes of water and brine to remove DMSO. Purification by Biotage (0-10% MeOH/DCM) produced product. MS (ESI, pos. ion) m/z: 421.1 (M+1). IC50 (uM) +++++.

SCHEME 25

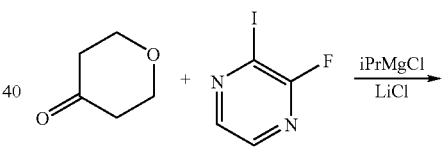

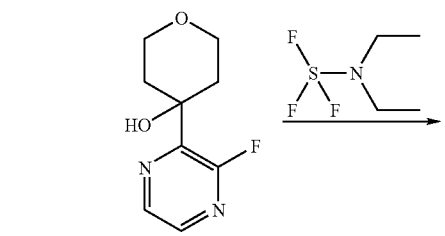

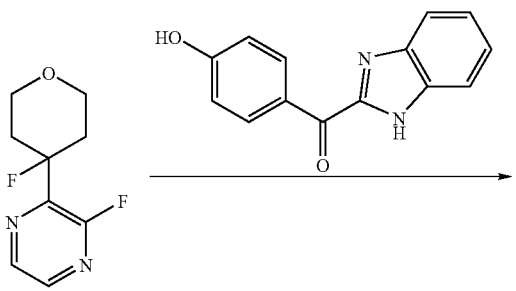

-continued

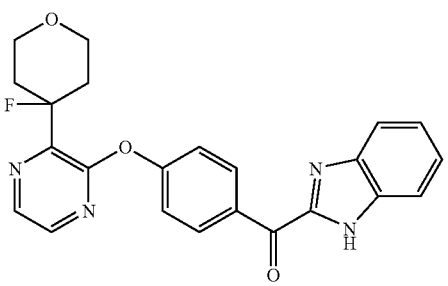

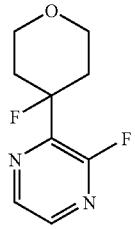

STEP 2: 2-FLUORO-3-(4-FLUOROTETRAHYDRO-2H-PYRAN-4-YL)PYRAZINE

A solution of 4-(3-fluoropyrazin-2-yl)tetrahydro-2H-pyran-4-ol (0.4 g, 2.018 mmol) in CH$_2$Cl$_2$ (6.73 mL) was cooled to 0° C. DAST (0.533 mL, 4.04 mmol) was added to the reaction mixture dropwise and the resulting mixture was allowed to stir at 0° C. for 2 hr. A solution of saturated sodium carbonate was added dropwise to the reaction mixture at 0° C. to quench the reaction. The heterogeneous mixture was stirred vigorously for 1 hr to ensure complete quenching. Mixture was transferred to a separatory funnel and the layers were separated after addition of more DCM and saturated bicarbonate solution. The organic layer was dried over magnesium sulfate and rotovapped to remove the volatile solvent.

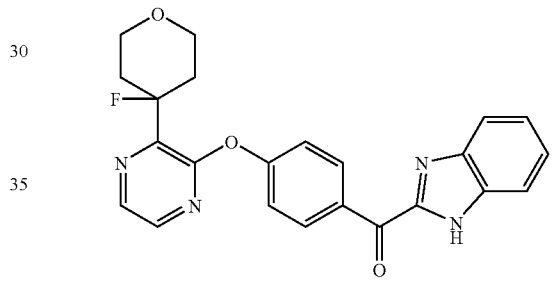

EXAMPLE 203

(1H-BENZO[D]IMIDAZOL-2-YL)(4-(3-(4-FLUOROTETRAHYDRO-2H-PYRAN-4-YL)PYRAZIN-2-YLOXY)PHENYL)METHANONE

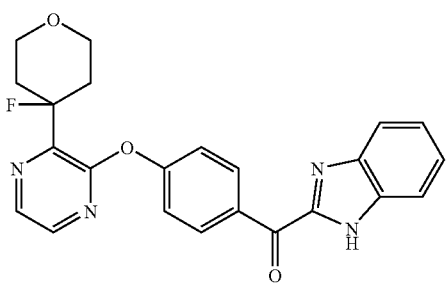

STEP 3: (1H-BENZO[D]IMIDAZOL-2-YL)(4-(3-(4-FLUOROTETRAHYDRO-2H-PYRAN-4-YL)PYRAZIN-2-YLOXY)PHENYL)METHANONE

A solution of (1H-benzo[d]imidazol-2-yl)(4-hydroxyphenyl)methanone (0.543 g, 2.278 mmol), 2-fluoro-3-(4-fluorotetrahydro-2H-pyran-4-yl)pyrazine (0.304 g, 1.519 mmol), cesium carbonate (0.990 g, 3.04 mmol), and N-Methyl-2-pyrrolidinone (3.04 mL) in a sealed tube was heated to 100° C. overnight. Aqueous work up with DCM and washing with alternating water and brine washes. The organic layer was rotovapped and loaded onto a Biotage samplet. Purification by Biotage (0-100% EtOAc/hexane, slow gradient, over 12 CV). The product containing fractions were concentrated by rotovap. The residue was further purified by trituration with EtOH at room temperature overnight to produce product. MS (ESI, pos. ion) m/z: 419.1 (M+1). IC50 (uM) +++++.

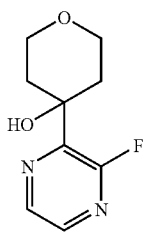

STEP 1: 4-(3-FLUOROPYRAZIN-2-YL)TETRAHYDRO-2H-PYRAN-4-OL

To a solution of 2-fluoro-3-iodopyrazine (1 g, 4.46 mmol) in THF (4.46 mL) at 0° C. was added isopropylmagnesium chloride lithium chloride complex, 1.0M solution in THF (4.87 mL, 4.46 mmol). The resulting mixture was stirred for 5 min before addition of dihydro-2H-pyran-4(3H)-one (0.410 mL, 4.46 mmol). Reaction mixture was allowed to warm to room temperature and stirred overnight. Purification by Biotage (0-100% EtOAc/hexane) produced the product.

SCHEME 26

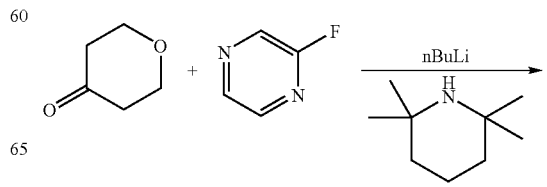

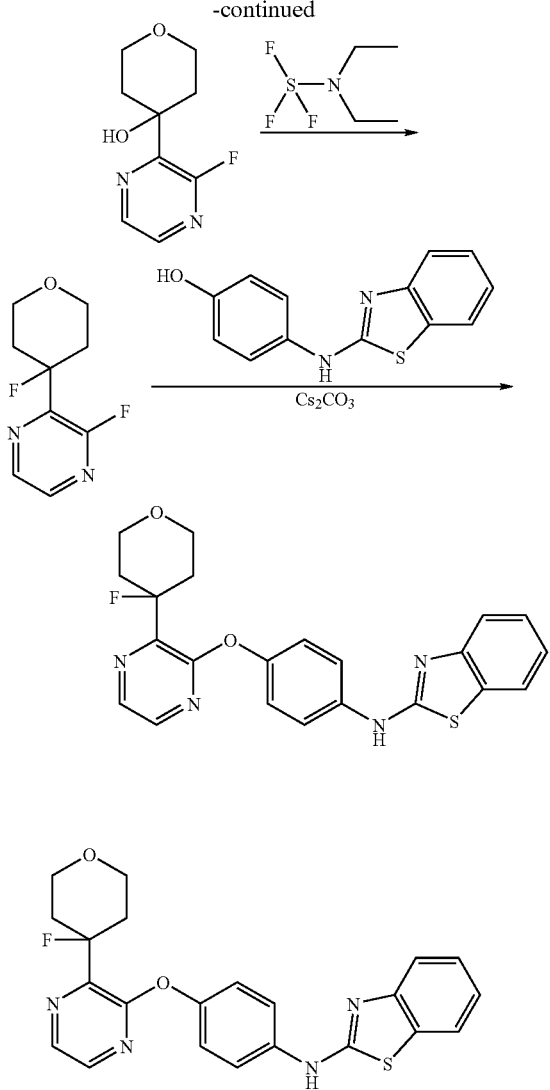

EXAMPLE 204

N-(4-(3-(4-FLUOROTETRAHYDRO-2H-PYRAN-4-YL)PYRAZIN-2-YLOXY)PHENYL)BENZO[D]THIAZOL-2-AMINE

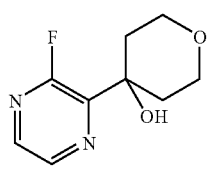

STEP 1: 4-(3-FLUOROPYRAZIN-2-YL)TETRAHYDRO-2H-PYRAN-4-OL

A 2.5M solution of nBuLi (4.49 mL, 11.22 mmol)/hexane in THF (3 mL) was first cooled to −78° C. To the cooled solution was added dropwise, 2,2,6,6-tetramethylpiperidine (2.065 mL, 12.24 mmol). The dry ice bath was then switched to a 0° C. bath. The reaction mixture was stirred for 10 min at 0° C. and then the dry ice bath was switched back to recool the reaction mixture to −78° C. To the cooled solution was added 2-fluoropyrazine (1 g, 10.20 mmol), dropwise. After 5 min of stirring at −78° C., a solution of dihydro-2H-pyran-4(3H)-one (0.937 mL, 10.20 mmol) in 0.6 mL of THF was added dropwise. The resulting mixture was allowed to gradually warm to room temperature overnight. Reaction was quenched with saturated NH₄Cl and extracted with EtOAc. Purification by Biotage (0-100% EtOAc/hexane) produced product.

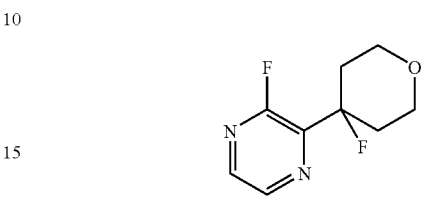

STEP 2: 2-FLUORO-3-(4-FLUOROTETRAHYDRO-2H-PYRAN-4-YL)PYRAZINE

To a solution of 4-(3-fluoropyrazin-2-yl)tetrahydro-2H-pyran-4-ol (0.123 g, 0.621 mmol) in DCM (2 mL) cooled to 0° C. was added dropwise dast (0.164 mL, 1.241 mmol). The resulting mixture was stirred for 2 hr. Reaction was quenched with dropwise addition of saturated NaHCO₃ solution and back extracted with DCM to produce product.

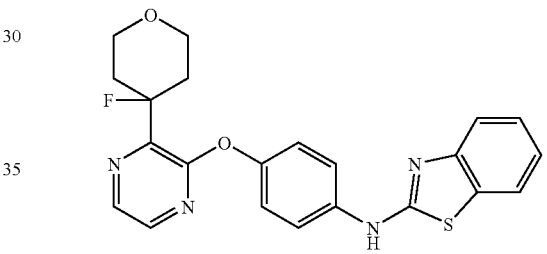

STEP 3: N-(4-(3-(4-FLUOROTETRAHYDRO-2H-PYRAN-4-YL)PYRAZIN-2-YLOXY)PHENYL)BENZO[D]THIAZOL-2-AMINE

To a solution of 2-fluoro-3-(4-fluorotetrahydro-2H-pyran-4-yl)pyrazine (0.055 g, 0.275 mmol) and 4-(benzo[d]thiazol-2-ylamino)phenol (0.100 g, 0.412 mmol) in DMSO (0.9 mL) was added cesium carbonate (0.179 g, 0.549 mmol). The resulting mixture was heated to 80° C. overnight. The reaction mixture was partitioned between water, brine and DCM. The aqueous layer was back extracted with DCM and the combined organic layer was dried (Na₂SO₄) and concentrated. Purification by prep-plate TLC (5% MeOH/DCM) produced product. MS (ESI, pos. ion) m/z: 423.0 (M+1). IC50 (uM) +++++.

SCHEME 27

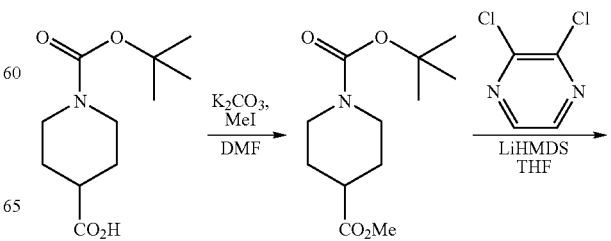

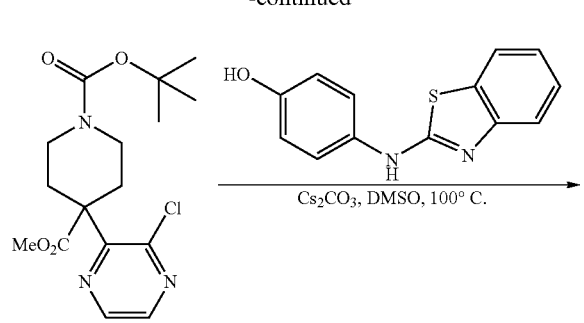

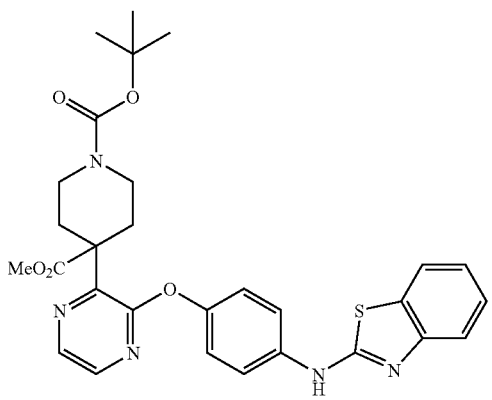

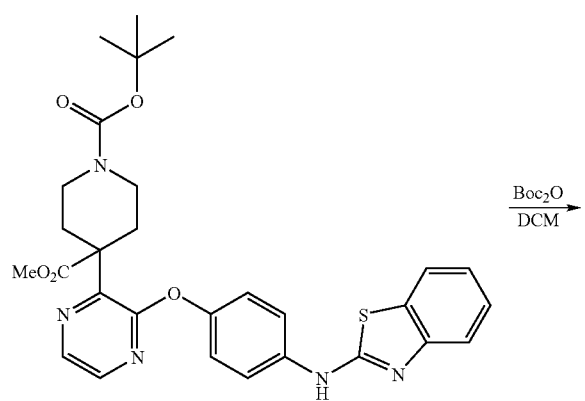

EXAMPLE 205

1-TERT-BUTYL 4-METHYL 4-(3-(4-(BENZO[D]THIAZOL-2-YLAMINO)PHENOXY)PYRAZIN-2-YL)PIPERIDINE-1,4-DICARBOXYLATE

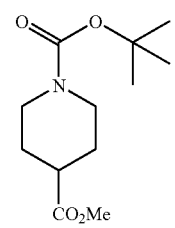

STEP 1. 1-TERT-BUTYL 4-METHYL PIPERIDINE-1,4-DICARBOXYLATE

To a solution of 1-(tert-butoxycarbonyl)piperidine-4-carboxylic acid (10.50 g, 45.8 mmol) in DMF (200 mL) was added potassium carbonate (6.33 g, 45.8 mmol) followed by iodomethane (3.42 mL, 55.0 mmol). The reaction was stirred under $N_2$ at RT 3 h. The reaction was poured into 10% aqueous $K_2CO_3$ (500 mL) and extracted with EtOAc (3×150 mL). The combined organic layers were washed with saturated NaCl (2×150 mL), dried ($MgSO_4$) and concentrated to give 1-tert-butyl 4-methyl piperidine-1,4-dicarboxylate (11.8 g, 48.5 mmol, 106% yield) as a light yellow oil.

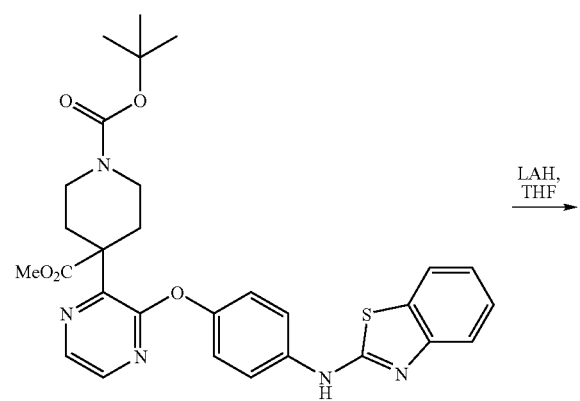

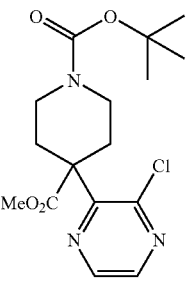

STEP 2. 1-TERT-BUTYL 4-METHYL 4-(3-CHLOROPYRAZIN-2-YL)PIPERIDINE-1,4-DICARBOXYLATE

To a vial containing 1-tert-butyl 4-methyl piperidine-1,4-dicarboxylate (408 mg, 1.678 mmol) and 2,3-dichloropyrazine (250 mg, 1.678 mmol) in THF (2.5 mL) at rt under $N_2$ is

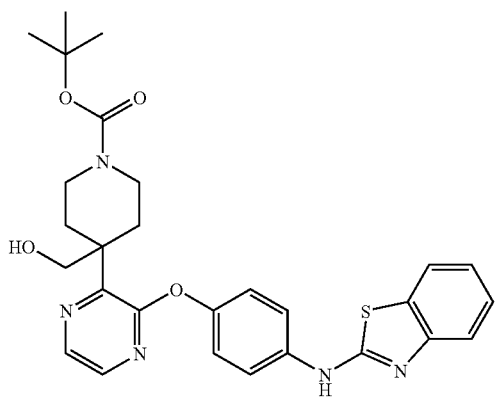

added dropwise LiHMDS (1.678 mL, 1.678 mmol). The reaction was stirred at rt 16 h. The reaction mixture was poured into H₂O (10 mL) and extracted with EtOAc (3×20 mL). The combined organic layers were washed with saturated NaCl (10 mL), dried (MgSO₄), and concentrated. Purification by ISCO (40 g SiO₂, 0-75% EtOAc/Hexane) gives 1-tert-butyl 4-methyl 4-(3-chloropyrazin-2-yl)piperidine-1,4-dicarboxylate (565 mg, 1.588 mmol, 95% yield) as a clear, colorless oil. [M+Na]=378.0

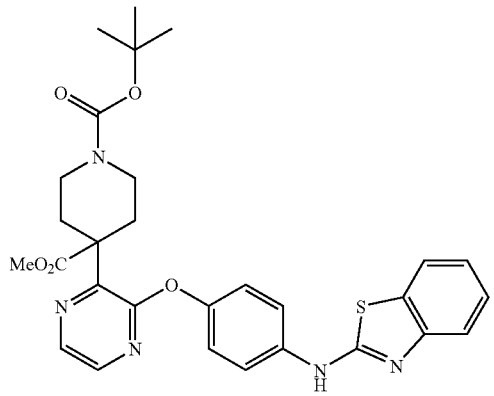

STEP 3. 1-TERT-BUTYL 4-METHYL 4-(3-(4-(BENZO[D]THIAZOL-2-YLAMINO)PHENOXY)PYRAZIN-2-YL)PIPERIDINE-1,4-DICARBOXYLATE

To a vial with 1-tert-butyl 4-methyl 4-(3-chloropyrazin-2-yl)piperidine-1,4-dicarboxylate (58 mg, 0.163 mmol), 4-(benzo[d]thiazol-2-ylamino)phenol (39.5 mg, 0.163 mmol), and cesium carbonate (106 mg, 0.326 mmol) under N₂ is added DMSO (1.0 mL). The reaction is heated to 100° C. in an oil bath 3 h. The reaction was cooled to rt, added to H₂O (5 mL) and extracted with EtOAc (3×5 mL). The combined organic layers were dried (MgSO₄) and concentrated. The residue was purified by RPHPLC to give 1-tert-butyl 4-methyl 4-(3-(4-(benzo[d]thiazol-2-ylamino)phenoxy)pyrazin-2-yl)piperidine-1,4-dicarboxylate (36 mg, 0.064 mmol, 39.3% yield) as a white solid. [M+1]=562.1. IC50 (uM) +++++.

EXAMPLE 206

TERT-BUTYL 4-(3-(4-(BENZO[D]THIAZOL-2-YLAMINO)PHENOXY)PYRAZIN-2-YL)-4-(HYDROXYMETHYL)PIPERIDINE-1-CARBOXYLATE

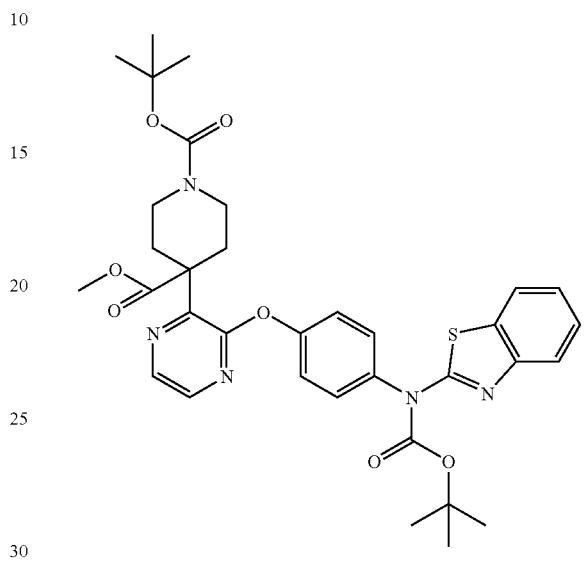

STEP 1. 1-TERT-BUTYL 4-METHYL 4-(3-(4-(BENZO[D]THIAZOL-2-YL(TERT-BUTOXYCARBONYL)AMINO)PHENOXY)PYRAZIN-2-YL)PIPERIDINE-1,4-DICARBOXYLATE

To a solution of 1-tert-butyl 4-methyl 4-(3-(4-(benzo[d]thiazol-2-ylamino)phenoxy)pyrazin-2-yl)piperidine-1,4-dicarboxylate (266 mg, 0.474 mmol) in DCM (10 mL) was added (Boc)₂O, 1M in THF (0.5 mL, 0.500 mmol). After 24 hours, the crude reaction was adsorbed onto a plug of silica gel and chromatographed through a Redi-Sep® pre-packed silica gel column (12 g), eluting with 0% to 50% EtOAc in hexane, to provide 1-tert-butyl 4-methyl 4-(3-(4-(benzo[d]thiazol-2-yl(tert-butoxycarbonyl)amino)phenoxy)pyrazin-2-yl)piperidine-1,4-dicarboxylate (122 mg, 0.184 mmol) as a colorless oil.

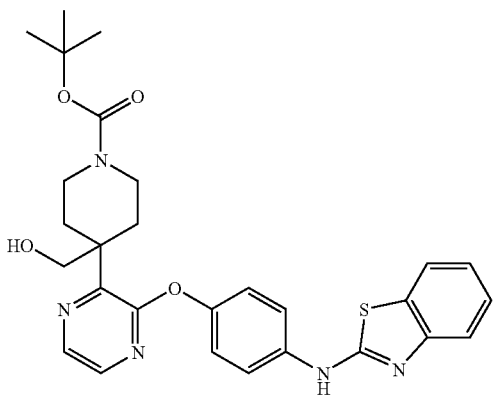

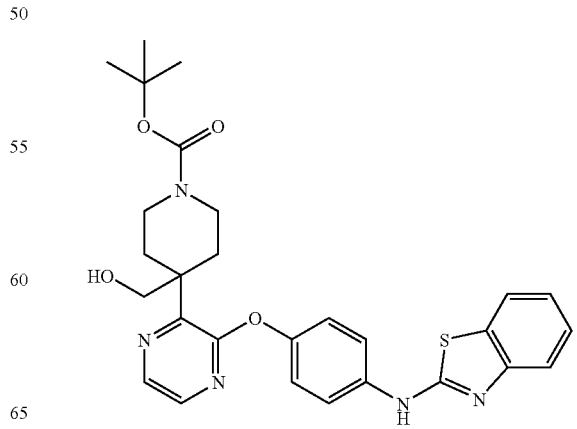

STEP 2. TERT-BUTYL 4-(3-(4-(BENZO[D]THIAZOL-2-YLAMINO)PHENOXY)PYRAZIN-2-YL)-4-(HYDROXYMETHYL)PIPERIDINE-1-CARBOXYLATE

To an ice cooled solution of 1-tert-butyl 4-methyl 4-(3-(4-(benzo[d]thiazol-2-yl(tert-butoxycarbonyl)amino)phenoxy)pyrazin-2-yl)piperidine-1,4-dicarboxylate (122 mg, 0.184 mmol) in dry THF (5 mL) was added LAH, 2M in THF (0.08 mL, 0.160 mmol). After stirring for 16 hours, LC-MS indicates a mixture of product, starting material, desBoc starting material and desBoc product. The reaction was treated with more LAH, 2M in THF (0.09 mL). After 4 hours, LC-MS shows one main peak that is consistent with desired product minus Boc (m/z 534 MH+). The reaction was quenched with sat'd rochelle's salt and diluted with EtOAc (10 mL). The aqueous layer was extracted with EtOAc (10 mL) and the combined EtOAc layers were concentrated in vacuo. The brown residue was purified by reverse-phase preparative HPLC (Shimadzu) on a Phenomenex Gemini column (5 micron, C18, 110 Å, Axia, 100×50 mm) eluting at 90 mL/min with an linear gradient of 10% to 80% MeCN (0.1% TFA) in water (0.1% TFA) over 20 minutes to give tert-butyl 4-(3-(4-(benzo[d]thiazol-2-ylamino)phenoxy)pyrazin-2-yl)-4-(hydroxymethyl)piperidine-1-carboxylate (8.2 mg) as a TFA salt and white solid after lypholization. MS (ESI, pos. ion) m/z: 534.0 (M+1). IC50 (uM) ++++.

EXAMPLE 207

N-(4-(3-(TETRAHYDRO-2H-PYRAN-4-YL)PYRAZIN-2-YLOXY)PHENYL)-1H-BENZO[D]IMIDAZOL-2-AMINE

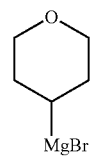

STEP 1. (TETRAHYDRO-2H-PYRAN-4-YL)MAGNESIUM BROMIDE

To a solution of Reike's magnesium in THF at 0° C. was added 4-bromotetrahydro-2H-pyran (1.000 g, 6.06 mmol) to stir for 1 hr to provide (tetrahydro-2H-pyran-4-yl)magnesium bromide.

SCHEME 28

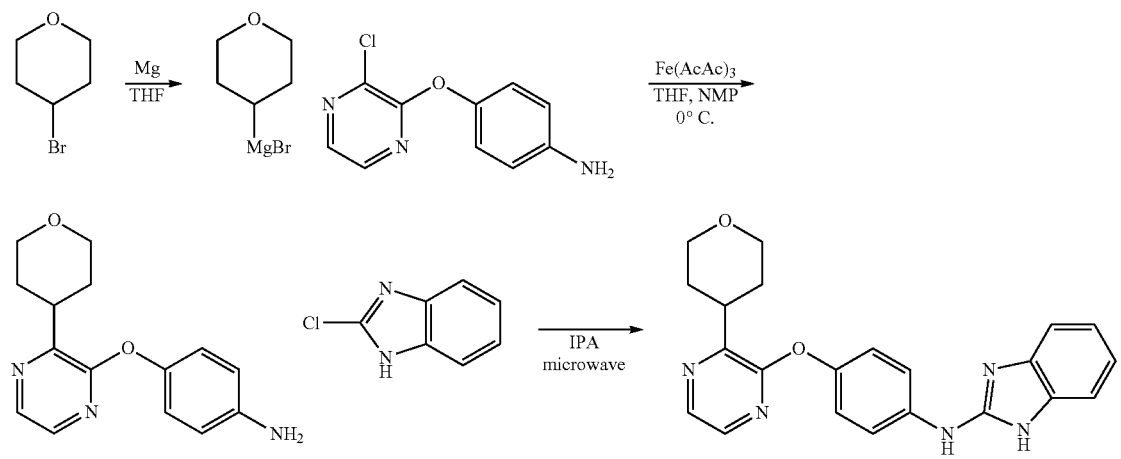

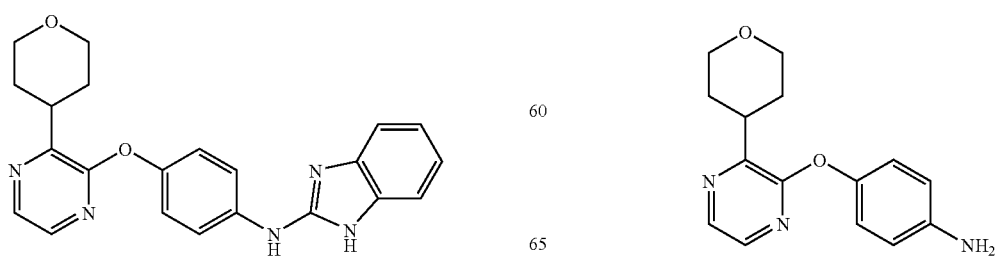

STEP 2. 4-(3-(TETRAHYDRO-2H-PYRAN-4-YL)PYRAZIN-2-YLOXY)ANILINE.

To a round bottomed flask was added 4-(3-chloropyrazin-2-yloxy)aniline (1.2276 g, 5.54 mmol) dissolved in a mixture of THF (8.86 mL) and NMP (2.215 mL). Iron(iii) acetylacetonate (0.098 g, 0.277 mmol) was added and the temperature was brought to 0° C. (Tetrahydro-2H-pyran-4-yl)magnesium chloride (8.31 mL, 6.65 mmol) was added dropwise to the reaction mixture. Upon completion, the reaction was quenched with saturated ammonia chloride solution. The reaction mixture was diluted with water and extracted with EtOAc. The organic extract was washed with water, brine, dried with magnesium sulfate, filtered, and concentrated. The crude product was adsorbed onto a plug of silica gel and chromatographed through a Redi-Sep® pre-packed silica gel column (120 g), eluting with a gradient of 10% to 100% EtOAc in hexane, to provide 4-(3-(tetrahydro-2H-pyran-4-yl)pyrazin-2-yloxy)aniline.

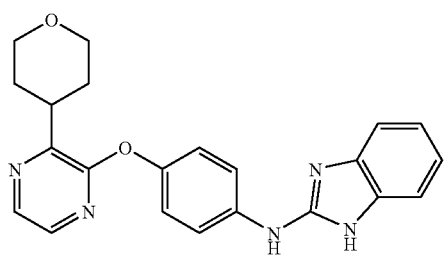

STEP 3. N-(4-(3-(TETRAHYDRO-2H-PYRAN-4-YL)PYRAZIN-2-YLOXY)PHENYL)-1H-BENZO[D]IMIDAZOL-2-AMINE.

A glass microwave reaction vessel was charged with 4-(3-(tetrahydro-2H-pyran-4-yl)pyrazin-2-yloxy)aniline (0.1536 g, 0.566 mmol) and 2-chlorobenzimidazole (0.095 g, 0.623 mmol) in IPA. The reaction mixture was stirred and heated in a Biotage Initiator microwave reactor at 170° C. for 30 min. The crude product was adsorbed onto a plug of silica gel and chromatographed through a Biotage pre-packed silica gel column (40S), eluting with a gradient of 1% to 5% MeOH in DCM, to provide N-(4-(3-(tetrahydro-2H-pyran-4-yl)pyrazin-2-yloxy)phenyl)-1H-benzo[d]imidazol-2-amine. MS (ESI, pos. ion) m/z: 388.0 (M+1). IC50 (uM) +++++.

SCHEME 29

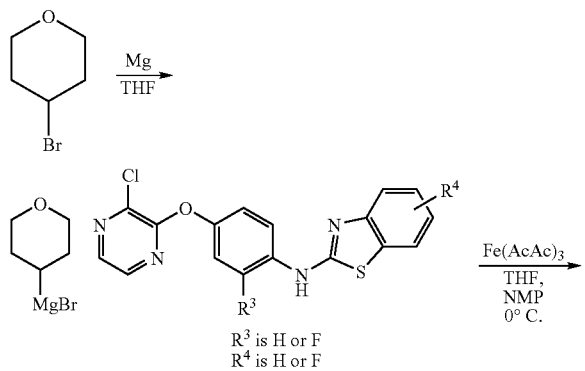

R³ is H or F
R⁴ is H or F

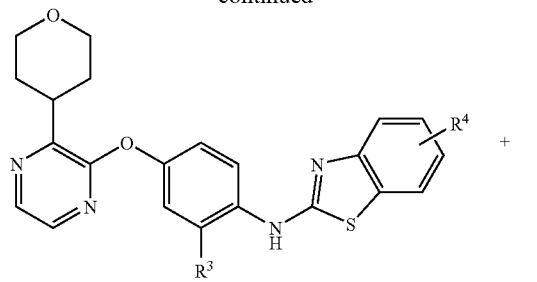

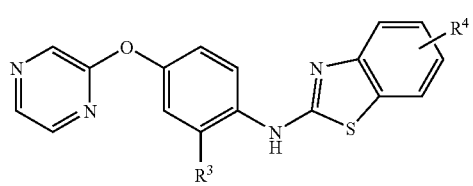

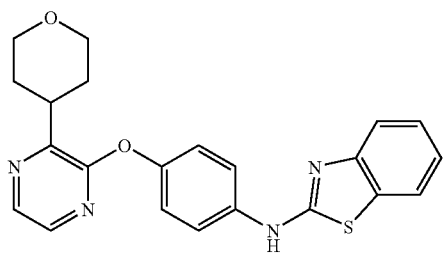

EXAMPLE 208

N-(4-(3-(TETRAHYDRO-2H-PYRAN-4-YL)PYRAZIN-2-YLOXY)PHENYL)BENZO[D]THIAZOL-2-AMINE

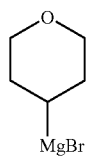

STEP 1. (TETRAHYDRO-2H-PYRAN-4-YL)MAGNESIUM BROMIDE

To a solution of Reike's magnesium in THF at 0° C. was added 4-bromotetrahydro-2H-pyran (1.000 g, 6.06 mmol) to stir for 1 hr to provide (tetrahydro-2H-pyran-4-yl)magnesium bromide.

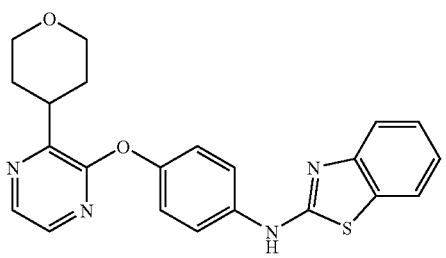

The organic extract was washed with water, brine, dried with magnesium sulfate, filtered, and concentrated. LC showed formation of N-(4-(3-(tetrahydro-2H-pyran-4-yl)pyrazin-2-yloxy)phenyl)benzo[d]thiazol-2-amine and N-(4-(pyrazin-2-yloxy)phenyl)benzo[d]thiazol-2-amine. The crude product was adsorbed onto a plug of silica gel and chromatographed through a Biotage pre-packed silica gel column (40S), eluting with a gradient of 1% to 5% MeOH in DCM, to provide N-(4-(3-(tetrahydro-2H-pyran-4-yl)pyrazin-2-yloxy)phenyl)benzo[d]thiazol-2-amine. MS (ESI, pos. ion) m/z: 405.0 (M+1). IC50 (uM) +++++.

SCHEME 30

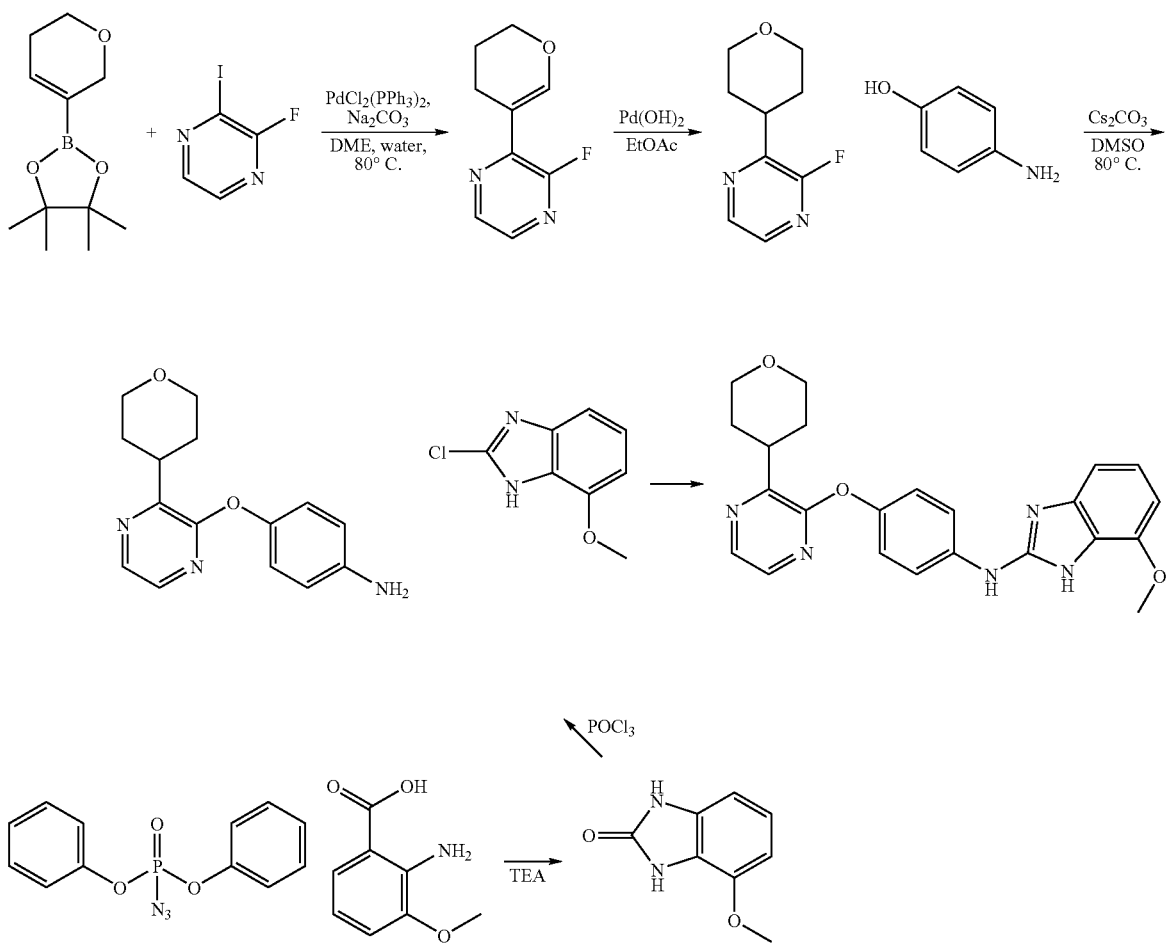

STEP 2. N-(4-(3-(TETRAHYDRO-2H-PYRAN-4-YL)PYRAZIN-2-YLOXY)PHENYL)BENZO[D]THIAZOL-2-AMINE.

To a round bottomed flask was added N-(4-(3-chloropyrazin-2-yloxy)phenyl)benzo[d]thiazol-2-amine (0.3000 g, 0.846 mmol) dissolved in a mixture of THF (1.353 mL) and NMP (0.338 mL). Iron(III)acetylacetonate (0.015 g, 0.042 mmol) was added and the temperature was brought to 0° C. (Tetrahydro-2H-pyran-4-yl)magnesium bromide (3.70 mL, 2.96 mmol) was added dropwise to the reaction. The reaction was quenched with sat. ammonium chloride. The reaction mixture was diluted with water and extracted with EtOAc.

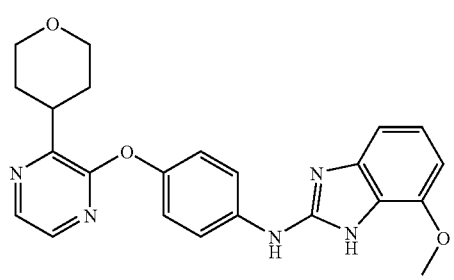

EXAMPLE 209

7-METHOXY-N-(4-(3-(TETRAHYDRO-2H-PY-RAN-4-YL)PYRAZIN-2-YLOXY)PHENYL)-1H-BENZO[D]IMIDAZOL-2-AMINE

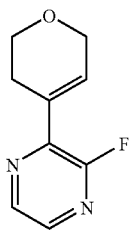

STEP 1. 2-(3,6-DIHYDRO-2H-PYRAN-4-YL)-3-FLUOROPYRAZINE.

To a glass microwave vial was added 2-fluoro-3-iodopyrazine (1.6485 g, 7.36 mmol), 2-(3,6-dihydro-2H-pyran-4-yl)-4,4,5,5-tetramethyl-1,3,2-dioxaborolane (2.319 g, 11.04 mmol), trans-dichlorobis(triphenylphosphine) palladium (II) (0.413 g, 0.589 mmol), and sodium carbonate (3.90 g, 36.8 mmol) in DME (19.63 mL) and water (4.91 mL) to stir at 80° C. overnight. Reaction was allowed to cool to room temperature. The reaction mixture was diluted with water and extracted with DCM. The organic extract was washed with water, brine, dried with magnesium sulfate, filtered, and concentrated. The crude product was adsorbed onto a plug of silica gel and chromatographed through a Biotage pre-packed silica gel column (40S), eluting with a gradient of 10% to 100% EtOAc in hexane, to provide 2-(3,6-dihydro-2H-pyran-4-yl)-3-fluoropyrazine. [M+H]=181.1.

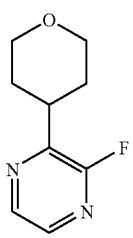

STEP 2. 2-FLUORO-3-(TETRAHYDRO-2H-PYRAN-4-YL)PYRAZINE.

To a round bottomed flask was added 2-(3,6-dihydro-2H-pyran-4-yl)-3-fluoropyrazine (1.1754 g, 6.52 mmol) and palladium hydroxide on carbon (0.458 g, 0.652 mmol) in EtOAc (21.75 mL). The round bottomed flask was flushed with argon and then placed under vacuum three times. A hydrogen balloon was then attached to the reaction. After stirring overnight, the reaction was filtered through celite to provide 2-fluoro-3-(Tetrahydro-2H-pyran-4-yl)pyrazine. [M+H]= 183.1.

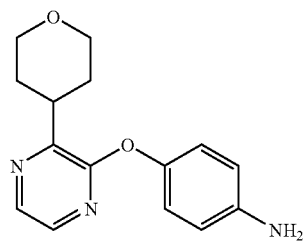

STEP 3. 4-(3-(TETRAHYDRO-2H-PYRAN-4-YL)PYRAZIN-2-YLOXY)ANILINE.

To a round bottomed flask was added 2-fluoro-3-(tetrahydro-2H-pyran-4-yl)pyrazine (1.1147 g, 6.12 mmol), 4-aminophenol (0.801 g, 7.34 mmol), and cesium carbonate (5.98 g, 18.35 mmol) in DMSO (20.39 mL) in DMSO at 110° C. to stir overnight. The reaction was allowed to cool to room temperature. The reaction mixture was diluted with water and extracted with DCM. The organic extract was washed with 50% sodium chloride solution, dried with magnesium sulfate, filtered, and concentrated. The crude product was adsorbed onto a plug of silica gel and chromatographed through a Biotage pre-packed silica gel column (40M), eluting with a gradient of 1% to 5% MeOH in DCM, to provide 4-(3-(tetrahydro-2H-pyran-4-yl)pyrazin-2-yloxy)aniline. [M+H]= 272.1.

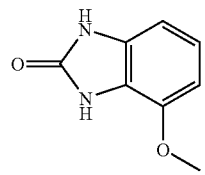

STEP 4. 4-METHOXY-1H-BENZO[D]IMIDAZOL-2(3H)-ONE.

To a round bottomed flask was added 2-amino-3-methoxybenzoic acid (2.2705 g, 13.58 mmol), diphenyl phosphorazidate (3.51 mL, 16.30 mmol), and triethylamine (3.79 mL, 27.2 mmol) in THF to stir at 80° C. Upon completion the reaction was allowed to cool to room temperature. Solvent was evaporated. The residue was taken up in DCM. The reaction mixture was diluted with water and extracted with DCM. A white precipitate was noted to form during extraction The solid was filtered to provide 4-methoxy-1H-benzo[d]imidazol-2(3H)-one. [M+H]=165.0.

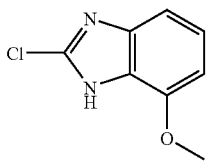

STEP 5. 2-CHLORO-7-METHOXY-1H-BENZO[D]IMIDAZOLE.

To a round bottomed flask was added 4-methoxy-1H-benzo[d]imidazol-2(3H)-one (1.8163 g, 11.06 mmol). POCl$_3$ (1.031 mL, 11.06 mmol) was added and the reaction was brought to reflux. Upon completion, POCL$_3$ was evaporated off. The residue was taken up in DCM. The reaction mixture was diluted with water and saturated sodium bicarbonate and extracted with DCM. The organic extract was washed with sat. sodium bicarbonate solution, water, brine, dried with, magnesium sulfate, filtered, and concentrated to provide 2-Chloro-7-methoxy-1H-benzo[d]imidazole. [M+H]=182.9.

STEP 6. 7-METHOXY-N-(4-(3-(TETRAHYDRO-2H-PYRAN-4-YL)PYRAZIN-2-YLOXY)PHENYL)-1H-BENZO[D]IMIDAZOL-2-AMINE.

A glass microwave reaction vessel was charged with 4-(3-(tetrahydro-2H-pyran-4-yl)pyridin-2-yloxy)aniline (0.2573 g, 0.952 mmol) and 2-chloro-1-(4-methoxybenzyl)-1H-benzo[d]imidazole (0.312 g, 1.142 mmol) in IPA. The reaction mixture was stirred and heated in a Biotage Initiator microwave reactor at 170° C. for 30 min. The crude product was adsorbed onto a plug of silica gel and chromatographed through a Biotage pre-packed silica gel column (40S), eluting with a gradient of 10% to 80% EtOAc in hexane, to provide 1-(4-methoxybenzyl)-N-(4-(3-(tetrahydro-2H-pyran-4-yl)pyridin-2-yloxy)phenyl)-1H-benzo[d]imidazol-2-amine. MS (ESI, pos. ion) m/z: 507.1 (M+1). IC50 (uM) +++++.

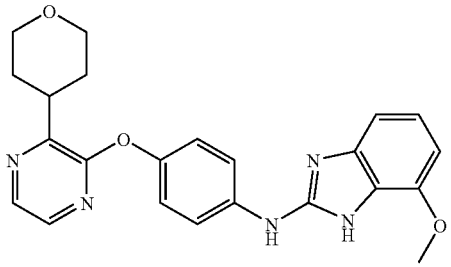

TABLE (VIIIA)

EXAMPLES 210 TO 219 ARE TABULATED BELOW:

| Ex# | Structure | IC50 (uM) | IUPAC names | MS (M + 1) |
|---|---|---|---|---|
| 210 | racemic | +++++ | (rac)-3-(3-(4-(1H-benzo[d]imidazole-2-carbonyl)phenoxy)pyrazin-2-yl)cyclohexanone | 413 |
| 211 | 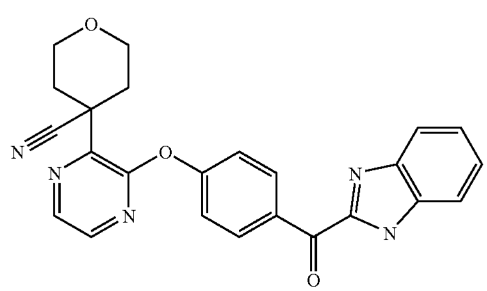 | +++++ | 4-(3-(4-(1H-benzo[d]imidazole-2-carbonyl)phenoxy)pyrazin-2-yl)tetrahydro-2H-pyran-4-carbonitrile | 426 |
| 212 | 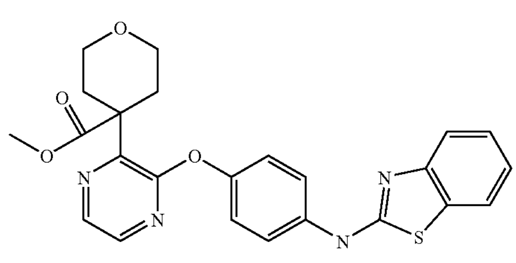 | +++++ | methyl 4-(3-(4-(benzo[d]thiazol-2-ylamino)phenoxy)pyrazin-2-yl)tetrahydro-2H-pyran-4-carboxylate | 463 |

TABLE (VIIIA)-continued

EXAMPLES 210 TO 219 ARE TABULATED BELOW:

| Ex# | Structure | IC50 (uM) | IUPAC names | MS (M + 1) |
|---|---|---|---|---|
| 213 | 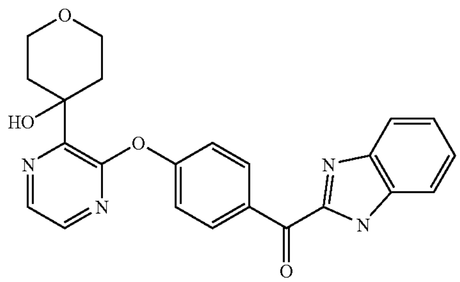 | +++++ | (1H-benzo[d]imidazol-2-yl)(4-(3-(4-hydroxytetrahydro-2H-pyran-4-yl)pyrazin-2-yloxy)phenyl)methanone | 417 |
| 214 | 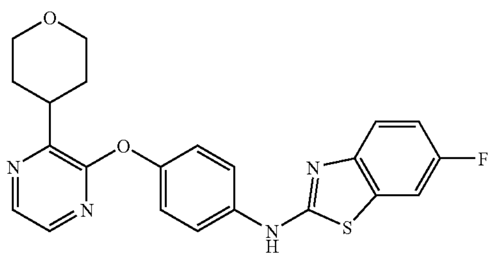 | +++++ | 6-fluoro-N-(4-(3-(tetrahydro-2H-pyran-4-yl)pyrazin-2-yloxy)phenyl)benzo[d]thiazol-2-amine | 423 |
| 215 | 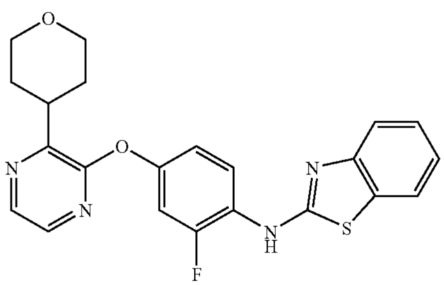 | +++++ | N-(2-fluoro-4-(3-(tetrahydro-2H-pyran-4-yl)pyrazin-2-yloxy)phenyl)benzo[d]thiazol-2-amine | 423 |
| 216 | 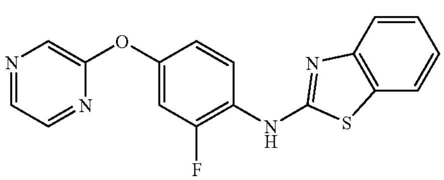 | + | N-(2-fluoro-4-(pyrazin-2-yloxy)phenyl)benzo[d]thiazol-2-amine | 339 |
| 217 | 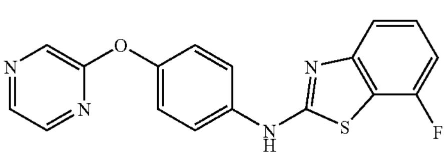 | + | 7-fluoro-N-(4-(pyrazin-2-yloxy)phenyl)benzo[d]thiazol-2-amine 339 | |
| 218 | 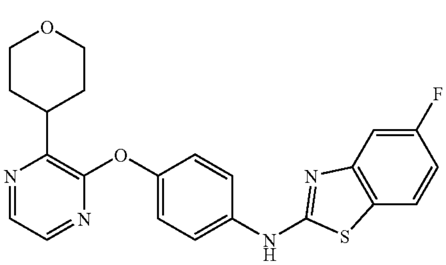 | +++++ | 5-fluoro-N-(4-(3-(tetrahydro-2H-pyran-4-yl)pyrazin-2-yloxy)phenyl)benzo[d]thiazol-2-amine | 423 |

TABLE (VIIIA)-continued

EXAMPLES 210 TO 219 ARE TABULATED BELOW:

| Ex# | Structure | IC50 (uM) | IUPAC names | MS (M + 1) |
|---|---|---|---|---|
| 219 | 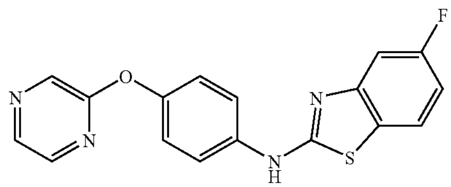 | + | 5-fluoro-N-(4-(pyrazin-2-yloxy)phenyl)benzo[d]thiazol-2-amine | 339 |

TABLE (VIIIB)

PREPARATION OF EXAMPLES 210 TO 219 ARE TABULATED BELOW:

| Ex# | Synthetic Scheme | How Different from Main Route | Reagent Difference |
|---|---|---|---|
| 210 | 18 | Reaction performed at 140° C. | |
| 211 | 23 | lower heating temperature to 60° C. | |
| 212 | 24 | lower heating temperature to 60° C. | Same |
| 213 | 25 | Same | |
| 214 | 30 | Same | |
| 215 | 30 | Same | |

TABLE (VIIIB)-continued
PREPARATION OF EXAMPLES 210 TO 219 ARE TABULATED BELOW:
| Ex# | Synthetic Scheme | How Different from Main Route | Reagent Difference |
|---|---|---|---|
| 216 | 30 | Same | |
| 217 | 30 | Same | |
| 218 | 30 | Same | |
| 219 | 30 | Same | |
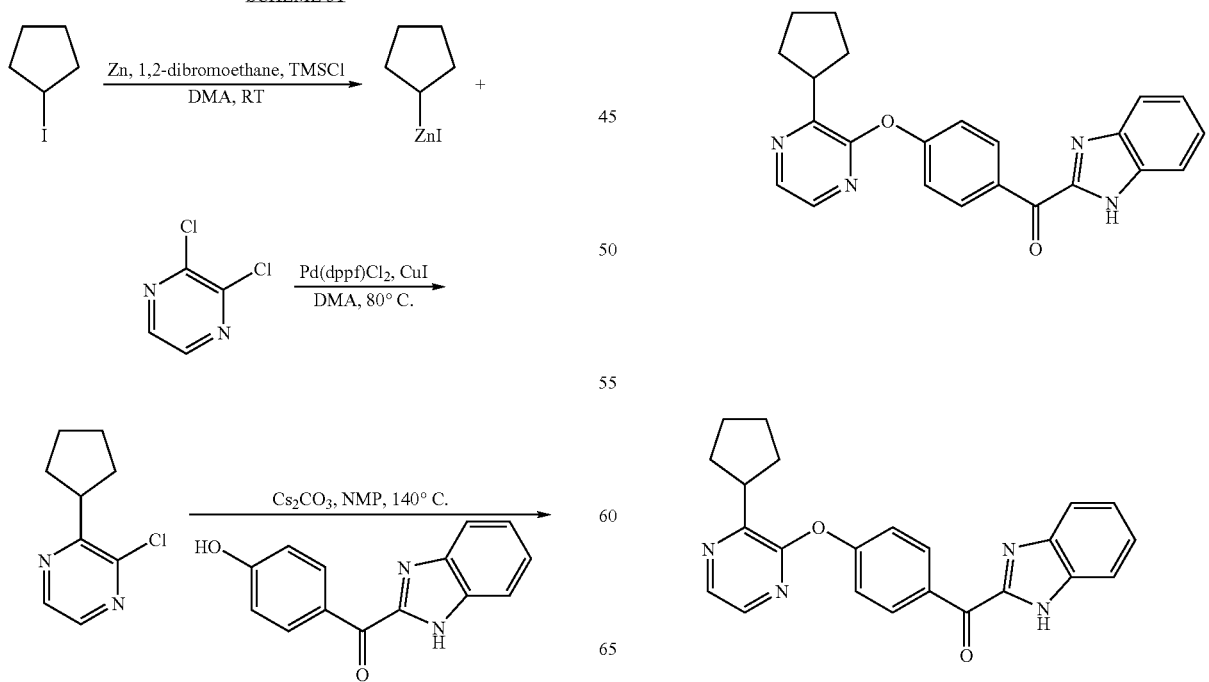

EXAMPLE 220

(1H-BENZO[D]IMIDAZOL-2-YL)(4-(3-CYCLOPENTYLPYRAZIN-2-YLOXY)PHENYL)METHANONE

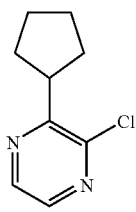

STEP 1. 2-CHLORO-3-CYCLOPENTYLPYRAZINE

To a suspension of zinc dust (2.00 g, 30.6 mmol) in N,N-dimethylacetamide (20 mL) was added a mixture of trimethylsilyl chloride and 1,2-dibromoethane (7:5, v/v, 0.95 mL total volume) dropwise over 5 minutes. The mixture was stirred for 15 min before cyclopentyl iodide (5.00 g, 25.5 mmol) was added dropwise over 15 min. This mixture was stirred for an additional 15 min and then was added via syringe over 5 min to a mixture of copper(I) iodide (0.30 g, 1.60 mmol), dichloro(1,1-bis(diphenylphosphinoferrocene)) palladium(II) (0.65 g, 0.80 mmol), and 2,3-dichloropyrazine (1.66 mL, 16.0 mmol) in N,N-dimethylacetamide (30 mL) under argon atmosphere. The mixture was heated to 80° C. for 7 h, cooled to room temperature and partitioned between ethyl acetate and saturated aqueous ammonium chloride. The resulting layers were separated and the aqueous layer was extracted with ethyl acetate (1×). The combined extracts were washed with water (2×), saturated aqueous sodium chloride (1×), dried over anhydrous magnesium sulfate, filtered, and concentrated in vacuo. The residue was purified by silica gel chromatography to give 2-chloro-3-cyclopentylpyrazine.

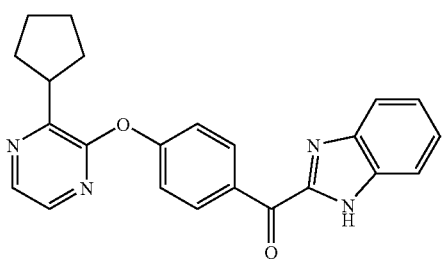

STEP 2. (1H-BENZO[D]IMIDAZOL-2-YL)(4-(3-CYCLOPENTYLPYRAZIN-2-YLOXY)PHENYL)METHANONE

A mixture of (1H-benzo[d]imidazol-2-yl)(4-hydroxyphenyl)methanone (0.98 g, 4.11 mmol), cesium carbonate (1.34 g, 4.11 mmol), and 2-chloro-3-cyclopentylpyrazine (0.38 g, 2.05 mmol) in 1-methyl-2-pyrrolidinone (2 mL) under argon was heated to 140° C. for 24 h. The mixture was cooled to room temperature and then partitioned between ethyl acetate and water. The resulting layers were separated and the organic layer was washed with 1N aqueous sodium hydroxide (2×), saturated aqueous sodium chloride (1×), dried over anhydrous magnesium sulfate, filtered, and concentrated in vacuo. The resulting oil was purified by silica gel chromatography to give (1H-benzo[d]imidazol-2-yl)(4-(3-cyclopentylpyrazin-2-yloxy)phenyl)methanone. MS (ESI, pos. ion) m/z: 385.2 (M+1). IC50 (uM) ++++.

SCHEME 32

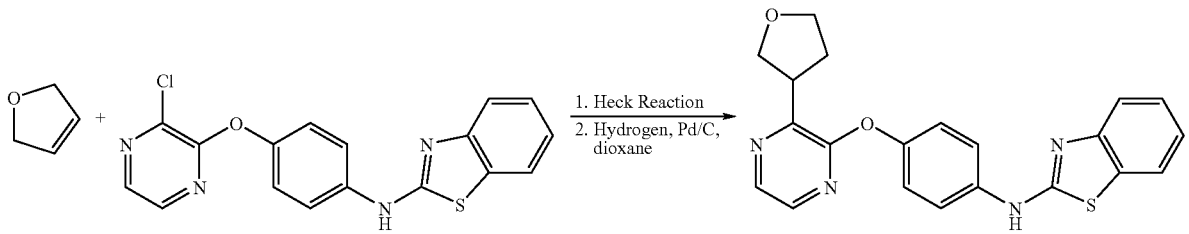

EXAMPLE 221

N-(4-(3-(TETRAHYDROFURAN-3-YL)PYRAZIN-2-YLOXY)PHENYL)BENZO[D]THIAZOL-2-AMINE

A mixture of N-(4-(3-chloropyrazin-2-yloxy)phenyl)benzo[d]thiazol-2-amine (0.600 g, 1.691 mmol), 2,5-dihydrofuran (1.25 mL, 16.53 mmol, Aldrich), bis(tri-tert-butylphosphine)palladium (0) (0.092 g, 0.180 mmol, Strem) and N-methyldicyclohexylamine (0.700 mL, 3.30 mmol, Aldrich) in DMF (5 mL) was sealed under argon in a 20 mL microwave reaction vessel and heated at 80° C. thermally overnight. The solvent was removed in vacuo and the residue was dissolved in dioxane. To the solution was added 10% palladium on carbon, wet (0.178 g, 0.167 mmol) and the mixture was evacuated and purged with hydrogen (1 atm) and the reaction was stirred at rt. Upon complete conversion the mixture was diluted with MeOH, evaporated onto silica gel and purified by flash chromatography (Isco, (80 gram)) eluting with 2M $NH_3$ in MeOH:$CH_2Cl_2$ (0:1→3:97) to give impure material. The fractions containing product were concentrated and purified by reverse-phase HPLC (Gilson; Gemini-NX 10μ C18 110A AXIA, 100×50 mm column) eluting with 0.1% TFA-$H_2O$:0.1% TFA $CH_3CN$ (9:1→1:9). The fractions containing the desired product were combined and concentrated in vacuo to give a solid. The residue was dissolved in MeOH and loaded onto an SCX II cartridge eluting with MeOH then 2M $NH_3$ in MeOH to give a yellow crystalline solid. MS (ESI, pos. ion) m/z: 391.0 (M+1). IC50 (uM) +++++.

SCHEME 33
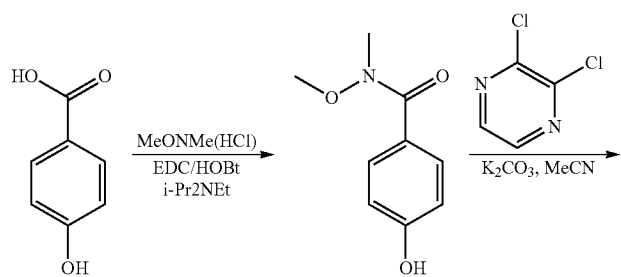
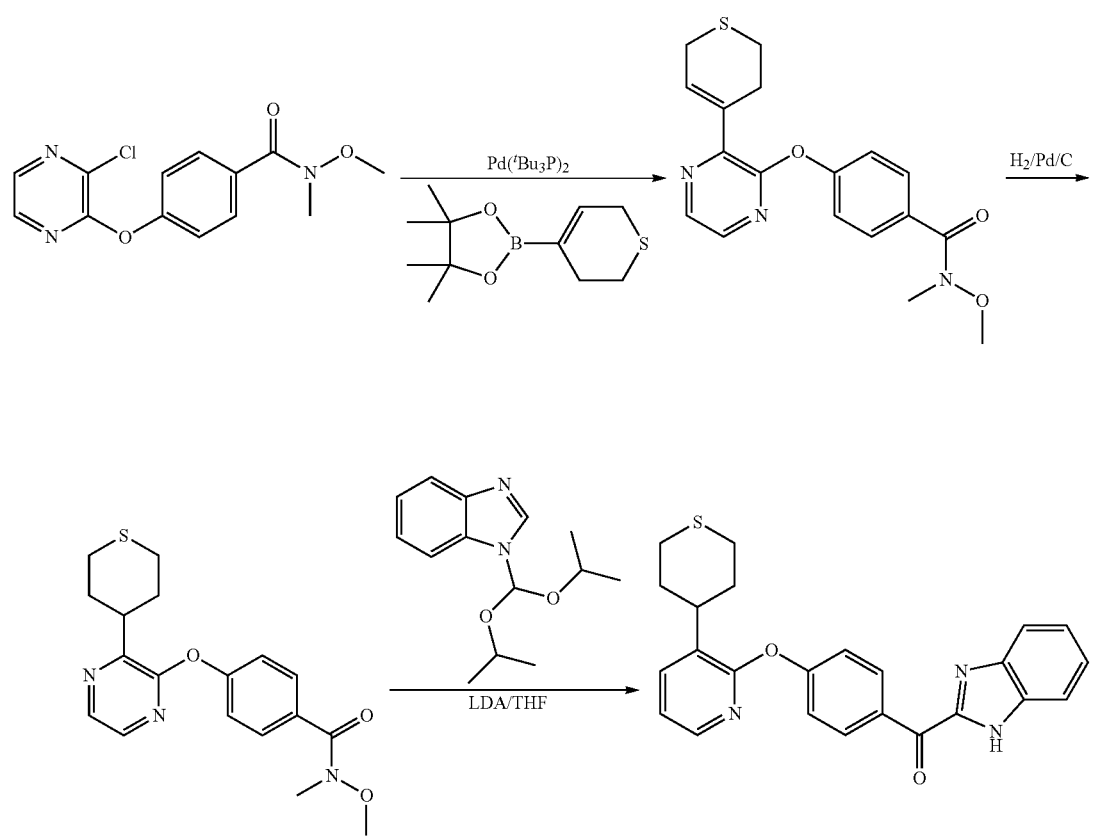
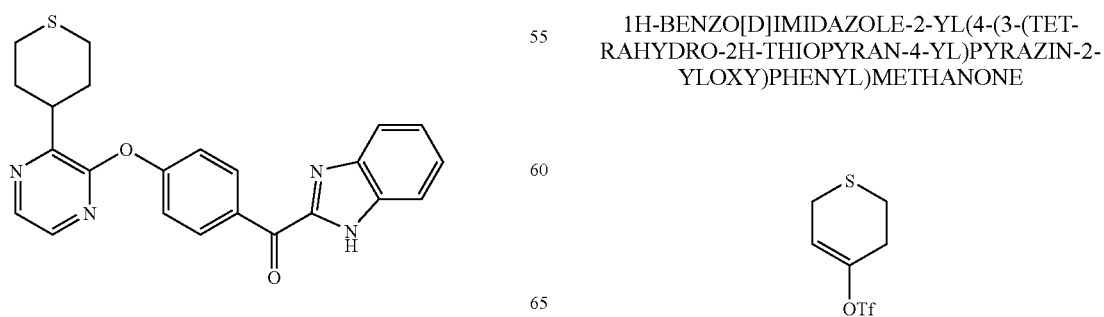
EXAMPLE 222
1H-BENZO[D]IMIDAZOLE-2-YL(4-(3-(TETRAHYDRO-2H-THIOPYRAN-4-YL)PYRAZIN-2-YLOXY)PHENYL)METHANONE

STEP 1: 3,6-DIHYDRO-2H-THIOPYRAN-4-YL-TRIF-LUOROMETHANESULFONATE

To a stirred solution of dihydro-2H-thiopyran-4(3H)-one (5.0 g, 43.0 mmol) in THF (30 mL) at −78° C. was added LDA (25.8 mL, 51.6 mmol) dropwise. After stirring for 1 h, a solution of 2-(n,n-bis(trifluoromethylsulfonyl)amino)-5-chloropyridine (17.74 g, 45.2 mmol) in THF (50 mL) was added. The reaction mixture was then warmed to RT and stirred overnight, quenched by saturated NH$_4$Cl, extracted with ether (3×), dried over MgSO$_4$, concentrated and purified by ISCO (0-10% EtOAc/Hexanes) to give the yellow oil. MS [M+1]: 249.2.

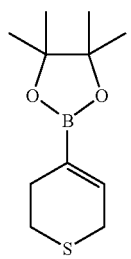

STEP 2: 2-(3,6-DIHYDRO-2H-THIOPYRAN-4-YL)-4,4,5,5-TETRAMETHYL-1,3,2-DIOXABOROLANE

A mixture of 3,6-dihydro-2H-thiopyran-4-yltrifluoromethanesulfonate (4.5 g, 18.13 mmol), 4,4,4',4',5,5,5',5'-octamethyl-2,2'-bi(1,3,2-dioxaborolane) (6.90 g, 27.2 mmol), potassium acetate (5.34 g, 54.4 mmol), and PdCl$_2$(dppf)$_2$ (1.480 g, 1.813 mmol) in p-dioxane/H$_2$O (10:1, 22 ml) was heated at 100° C. in 24 h, cooled, diluted with EtOAc, washed with H$_2$O, dried over MgSO$_4$, concentrated and purified by ISCO (0-10% EtOAc/Hexanes) to give the yellow oil. MS [M+1]: 227.1.

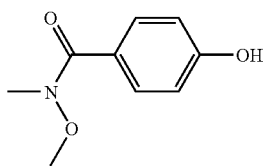

STEP 3: 4-HYDROXY-N-METHOXY-N-METHYLBENZAMIDE

A mixture of 4-hydroxybenzoic acid (20.29 g, 147 mmol), N,O-dimethylhydroxylamine hydrochloride (21.49 g, 220 mmol), N-ethyl-N-isopropylpropan-2-amine (77 mL, 441 mmol), hobt (22.50 g, 147 mmol), and EDC (33.8 g, 176 mmol) in DMF (100 mL) was stirred at RT in 24 h. H$_2$O was added, extracted with ether (3×), dried over MgSO$_4$, concentrated, and purified by ISCO (40% EtOAc/Hexanes) to give the titled compound. MS [M+1]: 182.1.

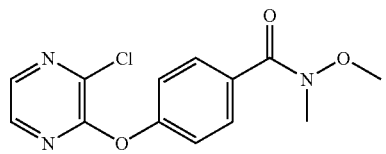

STEP 4: 4-(3-CHLOROPYRAZIN-2-YLOXY)-N-METHOXY-N-METHYLBENZAMIDE

A mixture of 4-hydroxy-N-methoxy-N-methylbenzamide (6.50 g, 35.9 mmol), 2,3-dichloropyrazine (6.95 g, 46.6 mmol), and potassium carbonate (12.40 g, 90 mmol) in acetonitrile (70 mL) was heated at reflux in 18 h. The reaction mixture was cooled, concentrated, taken up in H$_2$O, extracted with EtOAc, dried over MgSO$_4$, concentrated and purified by ISCO (50% EtOAc/Hexanes) to give the titled compound. MS [M+1]: 294.1.

STEP 5: 4-(3-(3,6-DIHYDRO-2H-THIOPYRAN-4-YL)PYRAZIN-2-YLOXY)-N-METHOXY-N-METHYLBENZAMIDE

A mixture of 4-(3-chloropyrazin-2-yloxy)-N-methoxy-N-methylbenzamide (1.4 g, 4.77 mmol), 2-(3,6-dihydro-2H-thiopyran-4-yl)-4,4,5,5-tetramethyl-1,3,2-dioxaborolane (1.132 g, 5.01 mmol), potassium carbonate (1.976 g, 14.30 mmol), and bis(tri-tert-butylphosphine)palladium(0) (0.244 g, 0.477 mmol) in p-dioxane/H$_2$O (10:1, 11 ml) was heated to 120° C. in 4 h, cooled, taken up in H$_2$O, extracted with EtOAc (3×), dried over MgSO$_4$, concentrated and purified by ISCO (50% EtOAc/hexanes) to give the titled compound. MS [M+1]: 358.1.

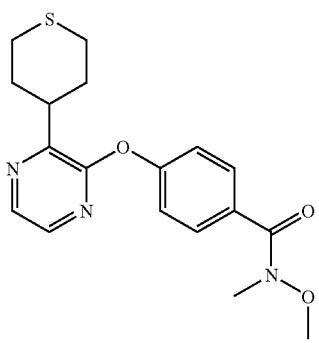

STEP 7: 1H-BENZO[D]IMIDAZOLE-2-YL(4-(3-(TETRAHYDRO-2H-THIOPYRAN-4-YL)PYRAZIN-2-YLOXY)PHENYL)METHANONE

A mixture of 1H-benzo[d]imidazole (0.039 g, 0.334 mmol), triisopropoxymethane (0.529 g, 2.78 mmol), benzenesulfonic acid (2.200 mg, 0.014 mmol) in toluene (5 mL) was heated at reflux for 3 h. The mixture was cooled, neutralized with diisopropylamine (0.1 ml), concentrated to dryness and diluted with 1 ml THF. The above solution was added to a stirred mixture of N-methoxy-N-methyl-4-(3-(tetrahydro-2H-thiopyran-4-yl)pyrazin-2-yloxy)benzamide (0.100 g, 0.278 mmol) in THF (3 mL). The resulting mixture was cooled to 0° C. and LDA (0.167 mL, 0.334 mmol) was added dropwise. The reaction mixture was stirred at RT overnight, quenched with saturated $NH_4Cl$, extracted with EtOAc (3×), dried over $MgSO_4$, concentrated and purified by ISCO (0-5% MeOH/DCM) to give the title compound as a white solid. MS (ESI, pos. ion) m/z: 416.1 (M+1). IC50 (uM) +++++.

TABLE (IXA)

EXAMPLE 223 IS TABULATED BELOW:

| Ex# | Structure | IC50 (uM) | IUPAC names | MS |
|---|---|---|---|---|
| 223 | 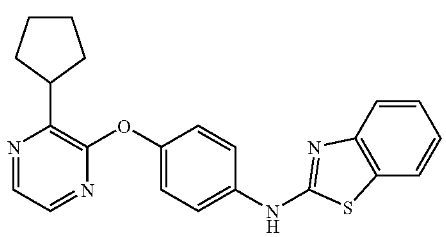 | +++++ | N-(4-(3-cyclopentylpyrazin-2-yloxy)phenyl)benzo[d]thiazol-2-amine | 389 |

STEP 6: N-METHOXY-N-METHYL-4-(3-(TETRAHYDRO-2H-THIOPYRAN-4-YL)PYRAZIN-2-YLOXY)BENZAMIDE

A solution of 4-(3-(3,6-dihydro-2H-thiopyran-4-yl)pyrazin-2-yloxy)-N-methoxy-N-methylbenzamide (0.500 g, 1.399 mmol) in MeOH (10 ml) was hydrogenated at RT in 10% Pd/C (0.200 mg) in 72 h. The solid was filtered off, and the filtrate was concentrated and purified by ISCO (3% MeOH/DCM) to give the title compound. MS [M+1]: 360.1.

TABLE (IXB)

PREPARATION OF EXAMPLE 223 IS TABULATED BELOW:

| Ex# | Synthetic Scheme | how different from main route | reagent difference |
|---|---|---|---|
| 223 | 30 | 120° C. | |

SCHEME 34
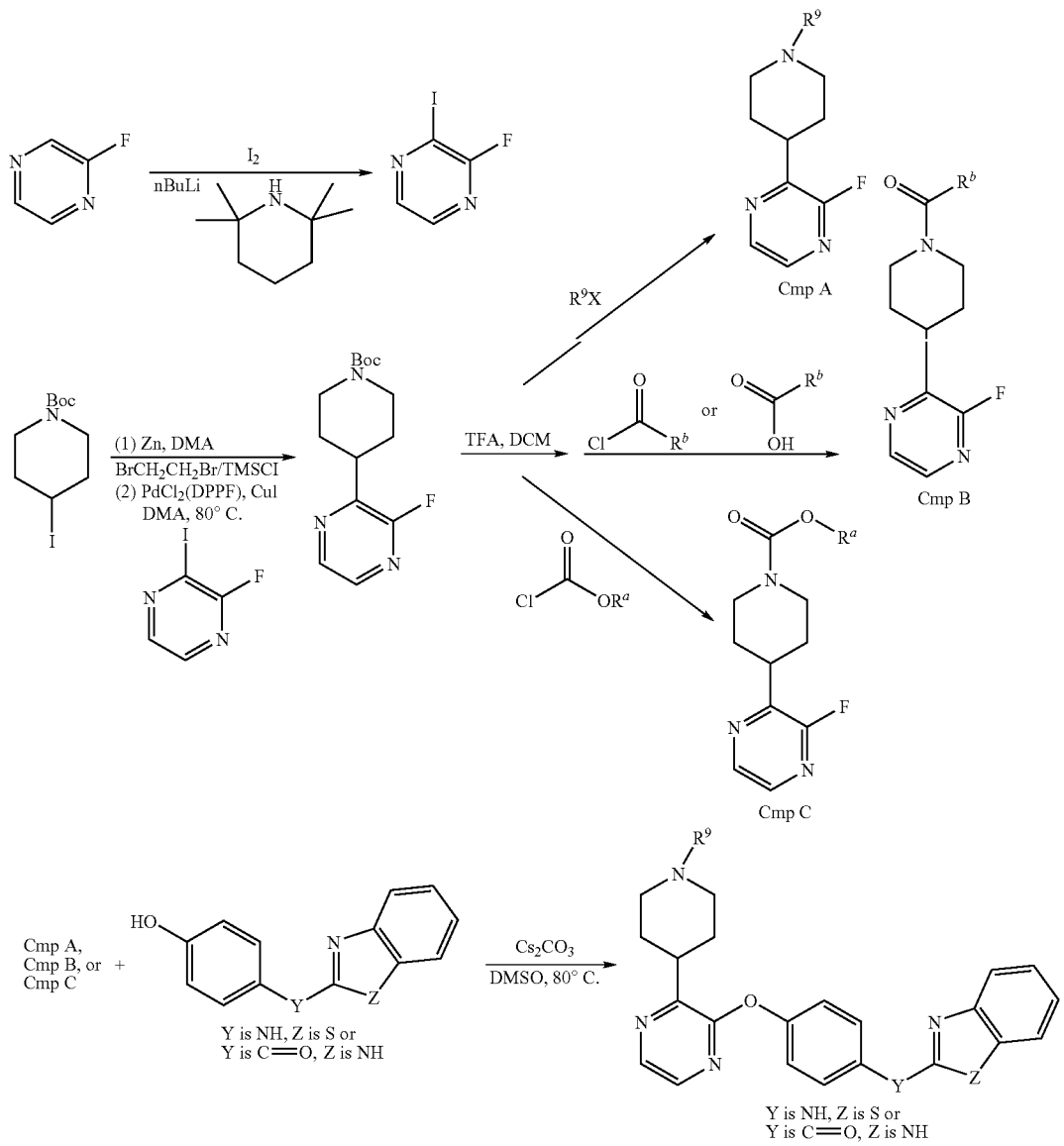
EXAMPLE 224
1-(4-(3-(4-(1H-BENZO[D]IMIDAZOLE-2-CAR-
BONYL)PHENOXY)PYRAZIN-2-YL)PIPERIDIN-
1-YL)ETHANONE
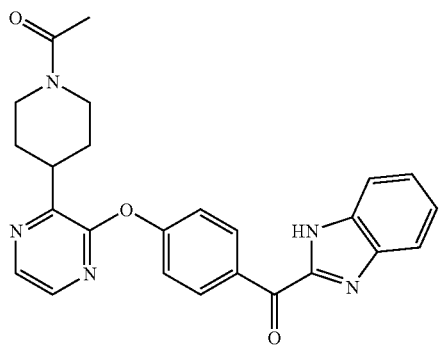
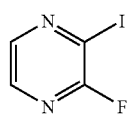
STEP 1. 2-FLUORO-3-IODOPYRAZINE
Butyl lithium solution (2.5 M in hexane, 881 mL, 2.01 mol) and 1.5 L of dry THF were charged into a flame-dried 5.0 L round bottomed flask. The flask was cooled to −50° C. and 2,2,6,6-tetramethylpiperidine (312.0 mL, 2.20 mol) was added dropwise. The reaction mixture was warmed to 0° C. without taking the cold bath away and kept at that temperature for 20 min. The reaction was then cooled to −78° C., and 2-fluoropyrazine (180 g, 1.84 mol) in 150 mL of THF was added dropwise. The mixture was kept at −78° C. for 5 min. Iodine (464 g, 1.84 mol) in 500 mL of THF was added dropwise and the reaction mixture was kept at −78° C. for 1 h. The reaction was quenched with the addition of 250 mL of concentrated HCl, 250 mL MeOH and 250 mL THF at −78° C. The cold bath was then removed, and aqueous sodium bisulfite was added to get rid of traces of unreacted iodine. The solvent was evaporated and the residue was diluted with water and adjusted to pH 8. The mixture was extracted with ethyl acetate (3×1.5 L). Combined ethyl acetate layer was dried over sodium sulfate and concentrated. The crude product was purified by column chromatography (Silica: 100-200 mess, solvent: 10% Teac/hexanes) to give the title compound as a white solid.

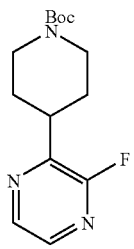

STEP 2: TERT-BUTYL 4-(3-FLUOROPYRAZIN-2-Yl)PIPERIDINE-1-CARBOXYLATE.

In an oven-dried 25 mL round bottomed flask was charged dry DMA (1 mL), zinc dust (0.430 g, 6.58 mmol). The mixture was stirred at RT while the mixture of chlorotrimethylsilane (0.07 mL, 0.553 mmol) and 1,2-dibromoethane (0.05 mL, 0.580 mmol) was added slowly. The resulting slurry was aged for 15 min. A solution of n-boc-4-iodo-piperidine (1.65 g, 5.30 mmol) in DMA (2.6 mL) was added slowly to the above mixture. Zinc slurry reacted exothermically with the gradual addition of the iodide. After stirring for 30 min, the resulting milky solution was cooled to RT and used directly in the next step.

In an oven-dried flask were charged 2-fluoro-3-iodopyrazine (0.829 g, 3.70 mmol), 1,1'-bis(diphenylphosphino)ferrocene]dichloride palladium(ii) complex with dichloramethane (0.091 g, 0.111 mmol), copper(i) iodide (0.042 g, 0.222 mmol), and DMA (3 mL). The resulting mixture was degassed with alternating vacuum/nitrogen purges. The (1-(tert-butoxycarbonyl)piperidin-4-yl)zinc(II) iodide (1.951 g, 5.18 mmol) solution from previous step was filtered into the mixture. It was degassed one more time and then heated to 80° C. with stirring for 16 h. After cooling to RT, the reaction mixture was treated with methyl bert-butylether (13 ml) and 1 N NH₄Cl (13 ml). The organic layer was partitioned between Teac and 1 N NH₄Cl and the aqueous layer was back extracted with Teac (2×). The combined organic layer was washed with water, brine, dried (Na₂SO₄) and concentrated. The crude material was chromatography through a Redi-Sep pre-packed silica gel column (40 g), eluting with a gradient of 0% to 20% Teac in hexane, to provide tert-butyl 4-(3-fluoropyrazin-2-yl)piperidine-1-carboxylate as orange oil. MS (ESI, pos. ion) m/z: 226.0 (M-56).

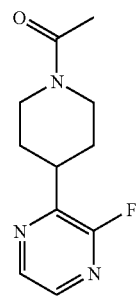

STEP 3. 1-(4-(3-FLUOROPYRAZIN-2-YL)PIPERIDIN-1-YL)ETHANONE.

To tert-butyl 4-(3-fluoropyrazin-2-yl)piperidine-1-carboxylate (0.658 g, 2.34 mmol) dissolved in DCM (5 mL) was added trifluoroacetic acid, 99% (1.39 mL, 18.7 mmol) dropwise. The reaction mixture was stirred at RT for 1 h. The solvent was evaporated and to the residue was added DCM and then evaporated. The process was repeated twice. The residue was redissolved in DCM and treated with solid NaHCO₃. The mixture was stirred for 1 h, filtered and concentrated. The orange oil was used directly in the following step.

To 2-fluoro-3-(piperidin-4-yl)pyrazine (0.311 g, 1.716 mmol) dissolved in DCM (5 mL) was added triethylamine (0.286 mL, 2.06 mmol), then acetyl chloride, reagent grade (0.134 mL, 1.89 mmol). The reaction mixture was stirred at RT for 1 h then partitioned between DCM and water. The aqueous layer was extracted with DCM (3×) and the combined organic layer was washed with brine, dried (Na₂SO₄) and concentrated to give 1-(4-(3-fluoropyrazin-2-yl)piperidin-1-yl)ethanone as a yellow oil. MS (ESI, pos. ion) m/z: 224.0 (M-56).

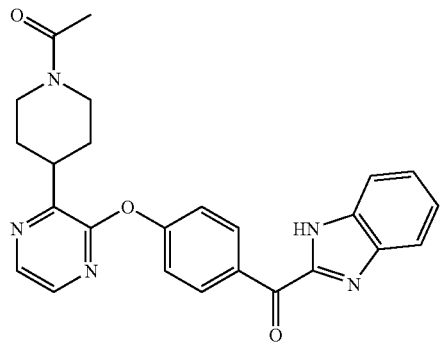

STEP 4. 1-(4-(3-(4-(1H-BENZO[D]IMIDAZOLE-2-CARBONYL)PHENOXY)PYRAZIN-2-Yl)PIPERIDIN-1-YL) ETHANONE.

The mixture of (1H-benzo[d]imidazol-2-yl)(4-hydroxyphenyl)methanone (0.16 g, 0.67 mmol), 1-(4-(3-fluoropyrazin-2-yl)piperidin-1-yl)ethanone (0.1 g, 0.45 mmol), and cesium carbonate (0.22 g, 0.67 mmol) in DMSO (1.5 mL) was heated at 80° C. for 20 h. After cooling to RT, the reaction mixture was partitioned between Teac and brine. The aqueous layer was back extracted with Teac (2×) and the combined organic layer was dried (Na₂SO₄) and concentrated. The crude material was purified by chromatography through a Redi-Sep pre-packed silica gel column (40 g), eluting with a gradient of 0% to 100% Teac in hexane, then 5% MeOH in Teac, to provide 1-(4-(3-(4-(1H-benzo[d]imidazole-2-carbonyl)phenoxy)pyrazin-2-yl)piperidin-1-yl)ethanone as off-white solid. MS (ESI, pos. ion) m/z: 442.1 (M+1). IC50 (uM) +++++.

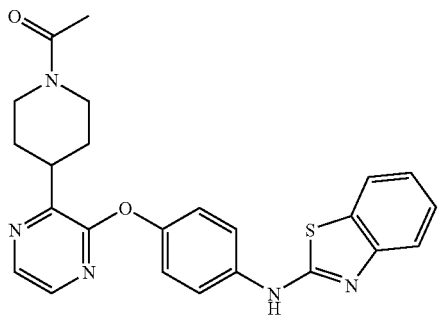

Example 225

1-(4-(3-(4-(BENZO[D]THIAZOL-2-YLAMINO) PHENOXY)PYRAZIN-2-YL)PIPERIDIN-1-YL) ETHANONE

The mixture of 4-(benzo[d]thiazol-2-ylamino)phenol (91 mg, 0.38 mmol), 1-(4-(3-fluoropyrazin-2-yl)piperidin-1-yl) ethanone (56 mg, 0.25 mmol), and cesium carbonate (123 mg, 0.38 mmol) in DMSO (0.85 mL) was heated at 80° C. for 16 h. After cooling to RT, the reaction mixture was partitioned between Teac and brine. The aqueous layer was back extracted with Teac (2×) and the combined organic layer was dried (Na$_2$SO$_4$) and concentrated. The crude material was purified by chromatography through a Redi-Sep pre-packed silica gel column (40 g), eluting with a gradient of 0% to 100% Teac in hexane, then 3% MeOH in Teac, followed by reverse-phase preparative HPLC using a Germini C18 5 uM column, 0.1% TFA in CH$_3$CN/H$_2$O, gradient 10% to 100% over 15 min, then neutralize with Si carbonate resin, to provide 1-(4-(3-(4-(benzo[d]thiazol-2-ylamino)phenoxy) pyrazin-2-yl)piperidin-1-yl) as a white solid. MS (ESI, pos. ion) m/z: 445.9 (M+1). IC50 (uM) +++++.

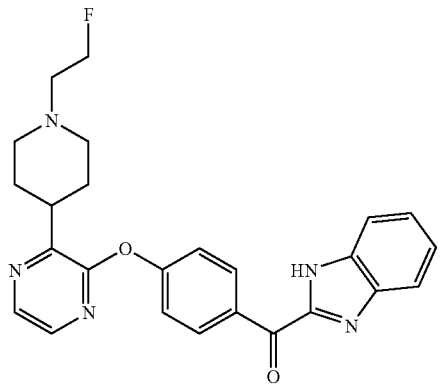

Example 226

(1H-BENZO[D]IMIDAZOL-2-YL)(4-(3-(1-(2-FLUOROETHYL)PIPERIDIN-4-YL)PYRAZIN-2-YLOXY)PHENYL)METHANONE

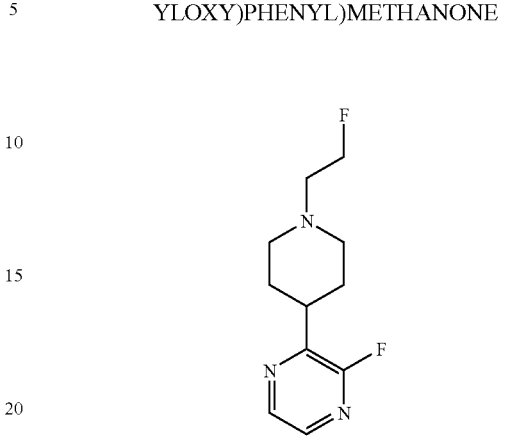

STEP 1. 2-FLUORO-3-(1-(2-FLUOROETHYL)PIPERIDIN-4-YL)PYRAZINE.

In a glass microwave vial containing 2-fluoro-3-(piperidin-4-yl)pyrazine 2,2,2-trifluoroacetate (0.2 g, 0.68 mmol), cesium carbonate (0.12 mL, 1.5 mmol) was added 2-fluoroethyl tosylate (0.22 mL, 1.0 mmol) and Acetonitrile (2.5 mL). The reaction mixture was stirred and heated in a Discover® model microwave reactor (CEM, Matthews, N C) at 120° C. for 10 min (300 watts, Powermax feature on), then at the same temperature for another 10 min. LCMS showed desired product formation 104960-15-1.

The reaction mixture was partitioned between Teac and water. The aqueous layer was back extracted with Teac (3×) and the combined organic layer was washed with brine, dried (Na2SO4) and concentrated and used directly in the following step.

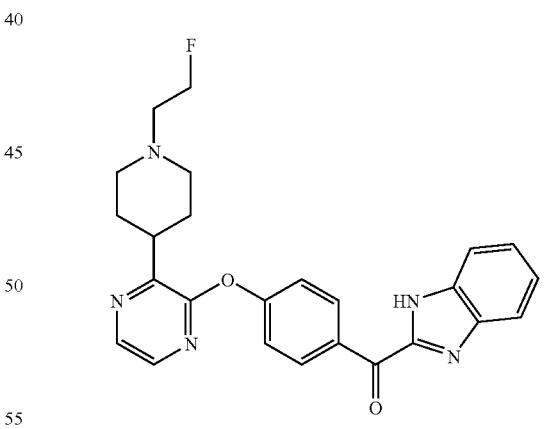

STEP 2. (1H-BENZO[D]IMIDAZOL-2-YL)(4-(3-(1-(2-FLUOROETHYL)PIPERIDIN-4-YL)PYRAZIN-2-YLOXY)PHENYL)METHANONE.

The mixture of (1H-benzo[d]imidazol-2-yl)(4-hydroxyphenyl)methanone (78 mg, 0.326 mmol), 2-fluoro-3-(1-(2-fluoroethyl)piperidin-4-yl)pyrazine (37 mg, 0.163 mmol), and cesium carbonate (106 mg, 0.326 mmol) in DMSO (0.5 mL) was heated at 80° C. for 20 h. The reaction mixture was partitioned between Teac and brine. The aqueous layer was back extracted with Teac (3×) and the combined organic layer was dried (Na$_2$SO$_4$) and concentrated. The crude material was purified by chromatography through a Redi-Sep pre-packed silica gel column (40 g), eluting with a gradient of 0% to 100% Teac in hexane, followed by reverse-phase preparative HPLC using a Phenomenex Gemini column, 10 micron, C18, 110 Å, 150×30 mm, 0.1% TFA in CH$_3$CN/H$_2$O, gradient 5% to 95% over 15 min then neutralization to provide (1H-benzo[d]imidazol-2-yl)(4-(3-(1-(2-fluoroethyl)piperidin-4-yl)pyrazin-2-yloxy)phenyl) as white solid. MS (ESI, pos. ion) m/z: 446.1 (M+1). IC50 (uM) +++++.

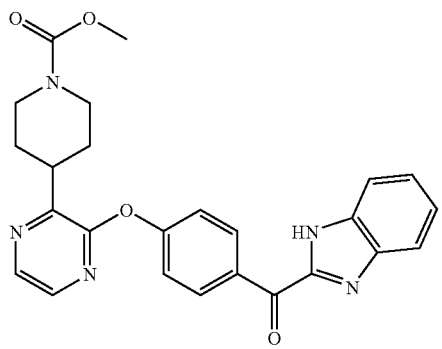

Example 227

METHYL 4-(3-(4-(1H-BENZO[D]IMIDAZOLE-2-CARBONYL)PHENOXY)PYRAZIN-2-YL)PIPERIDINE-1-CARBOXYLATE

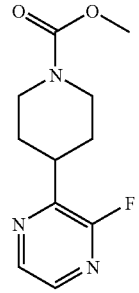

STEP 1. METHYL 4-(3-FLUOROPYRAZIN-2-YL)PIPERIDINE-1-CARBOXYLATE.

To 2-fluoro-3-(piperidin-4-yl)pyrazine 2,2,2-trifluoroacetate (0.2 g, 0.68 mmol) dissolved in DCM (2.5 mL) was added triethylamine (0.24 mL, 1.7 mmol) and methyl chloroformate (63 uL, 0.81 mmol). The reaction mixture was stirred at RT under N2 for 2 h.

The reaction mixture was partitioned between saturated NaHCO$_3$ and DCM. The aqueous layer was back extracted with DCM (3×) and the combined DCM layer was washed with brine, dried (Na$_2$SO$_4$) and concentrated to give methyl 4-(3-fluoropyrazin-2-yl)piperidine-1-carboxylate as orange oil. MS (ESI, pos. ion) m/z: 240.1 (M+1).

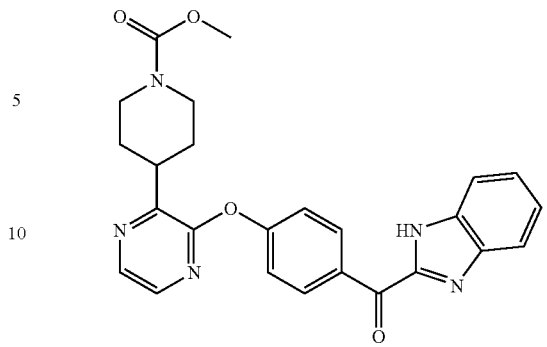

STEP 2. METHYL 4-(3-(4-(1H-BENZO[D]IMIDAZOLE-2-CARBONYL)PHENOXY)PYRAZIN-2-YL)PIPERIDINE-1-CARBOXYLATE.

The mixture of (1H-benzo[d]imidazol-2-yl)(4-hydroxyphenyl)methanone (112 mg, 0.468 mmol), methyl 4-(3-fluoropyrazin-2-yl)piperidine-1-carboxylate (56 mg, 0.23 mmol), and cesium carbonate (153 mg, 0.468 mmol) in DMSO (0.8 mL) was heated at 80° C. for 20 h. The reaction mixture was partitioned between Teac and brine. The aqueous layer was back extracted with Teac (3×) and the combined organic layer was dried (Na$_2$SO$_4$) and concentrated. The crude material was purified by chromatography through a Redi-Sep pre-packed silica gel column (12 g), eluting with a gradient of 0% to 100% Teac in hexane, to provide methyl 4-(3-(4-(1H-benzo[d]imidazole-2-carbonyl)phenoxy)pyrazin-2-yl)piperidine-1-carboxylate as white solid. MS (ESI, pos. ion) m/z: 458.1 (M+1). IC50 (uM) +++++.

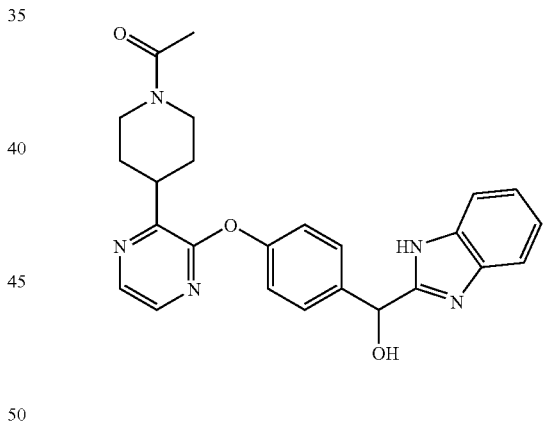

Example 228

1-(4-(3-(4-((1H-BENZO[D]IMIDAZOL-2-YL)(HYDROXY)METHYL)PHENOXY)PYRAZIN-2-YL)PIPERIDIN-1-YL)ETHANONE

To the solution of 1-(4-(3-(4-(1H-benzo[d]imidazole-2-carbonyl)phenoxy)pyrazin-2-yl)piperidin-1-yl)ethanone (100 mg, 0.23 mmol) in THF (4.5 mL) was added palladium hydroxide, 20 wt % pd (dry basis) on carbon, wet, degussa type e101 ne/w (31.8 mg, 0.045 mmol). The reaction mixture was stirred at RT under 1 atm of H$_2$ for 40 h. The reaction mixture was filtered through a pad of celite and washed with THF. The filtrate was washed with a mixture 1 N NaOH and brine. The aqueous layer was extracted with Teac and MeOH (3×) and the combined organics were dried and concentrated. The crude material was purified by reverse-phase preparative HPLC using a Phenomenex Gemini column, 10 micron, C18, 110 Å, 150×30 mm, 0.1% TFA in CH₃CN/H₂O, gradient 5% to 95% over 15 min then neutralization to provide 1-(4-(3-(4-((1H-benzo[d]imidazol-2-yl)(hydroxy)methyl)phenoxy)pyrazin-2-yl)piperidin-1-yl)ethanone as white solid. MS (ESI, pos. ion) m/z: 444.0 (M+1). IC50 (uM) +++++.

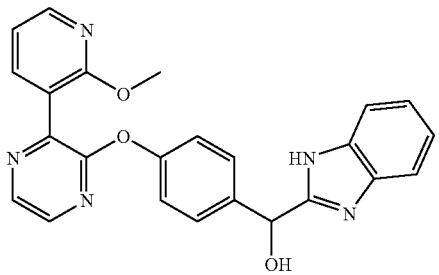

Example 229

(1H-BENZO[D]IMIDAZOL-2-YL)(4-(3-(2-METH-OXYPYRIDIN-3-YL)PYRAZIN-2-YLOXY)PHE-NYL)METHANOL

Same as the previous example to provide the compound. MS (ESI, pos. ion) m/z: 426.0 (M+1). IC50 (uM) +++++.

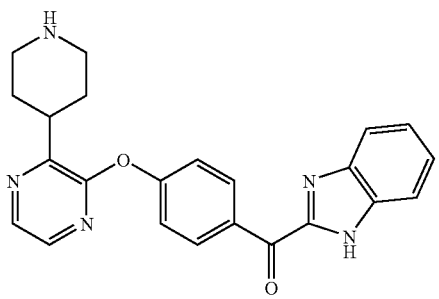

Example 230

(1H-BENZO[D]IMIDAZOL-2-YL)(4-(3-(PIPERI-DIN-4-YL)PYRAZIN-2-YLOXY)PHENYL)METHANONE

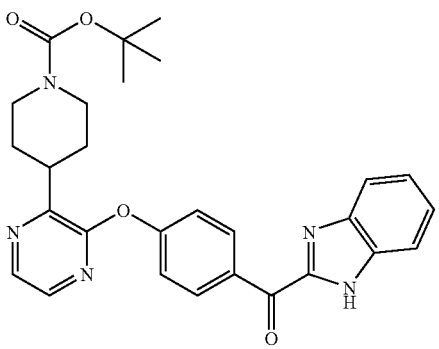

STEP 1. TERT-BUTYL 4-(3-(4-(1H-BENZO[D]IMIDA-ZOLE-2-CARBONYL)PHENOXY)PYRAZIN-2-YL)PIP-ERIDINE-1-CARBOXYLATE

To a 350 mL pressure vial is added tert-butyl 4-(3-fluoro-pyrazin-2-yl)piperidine-1-carboxylate (200 mg, 0.711 mmol), Cs₂CO₃ (417 mg, 1.280 mmol), and (1H-benzo[d]imidazol-2-yl)(4-hydroxyphenyl)methanone (305 mg, 1.280 mmol) and N-methylpyrrolidinone (1.3 mL). The reaction was heated in the microwave at 150° C. 1 h. The reaction was added to a flask containing H₂O (20 mL) with rapid stirring. The resulting slurry was filtered and the solid filter cake washed with H₂O (3×5 mL). The solid was purified by ISCO (40 g SiO₂, 0-20% MeOH/CH₂Cl₂) to give tert-butyl 4-(3-(4-(1H-benzo[d]imidazole-2-carbonyl)phenoxy)pyrazin-2-yl)piperidine-1-carboxylate as a brown solid.

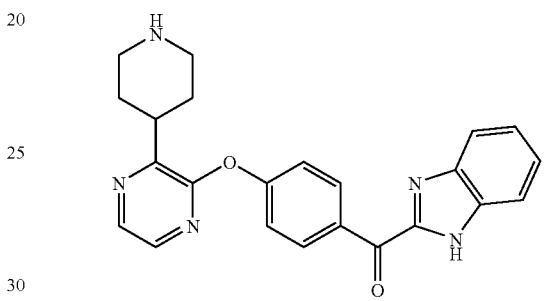

STEP 2. (1H-BENZO[D]IMIDAZOL-2-YL)(4-(3-(PIPERI-DIN-4-YL)PYRAZIN-2-YLOXY)PHENYL)METHA-NONE

To a flask containing tert-butyl 4-(3-(4-(1H-benzo[d]imidazole-2-carbonyl)phenoxy)pyrazin-2-yl)piperidine-1-carboxylate (230 mg, 0.460 mmol) is added chloroform (5 mL) and 2,2,2-trifluoroacetic acid (0.709 mL, 9.21 mmol). The reaction was stirred at rt 18 h. The solution was concentrated, followed by azeotropic removal of residual trifluoroacetic acid by concentration from toluene (5 mL×2). The crude salt was freebased by dissolving in MeOH and application to a 5 g Bondesil-SCX ion exchange column. Elution of the product with NH₃ in MeOH (2.0 M) and concentration of the product containing fractions gives (1H-benzo[d]imidazol-2-yl)(4-(3-(piperidin-4-yl)pyrazin-2-yloxy)phenyl)methanone as a brown solid. MS (ESI, pos. ion) m/z: 400.0 (M+1). IC50 (uM) +++++.

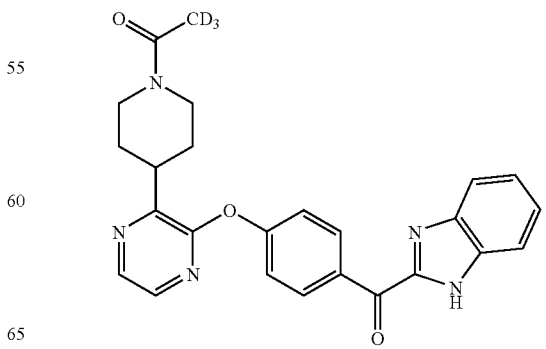

Example 231

1-(4-(3-(4-(1H-BENZO[D]IMIDAZOLE-2-CARBONYL)PHENOXY)PYRAZIN-2-YL)PIPERIDIN-1-YL)PERDEUTEROETHANONE

To a flask containing (1H-benzo[d]imidazol-2-yl)(4-(3-(piperidin-4-yl)pyrazin-2-yloxy)phenyl)methanone (60 mg, 0.150 mmol) is added dichloromethane (2 mL), triethylamine (0.021 mL, 0.150 mmol), Reactant 3 (10.16 μL, 0.180 mmol) and .HATU (57.1 mg, 0.150 mmol). After stirring for 16 hours, the reaction was concentrated and taken up in a minimum of MeOH. The solution was purified by reverse-phase preparative HPLC to give 1-(4-(3-(4-(1H-benzo[d]imidazole-2-carbonyl)phenoxy)pyrazin-2-yl)piperidin-1-yl)perdeuteroethanone as a white solid. MS (ESI, pos. ion) m/z: 445.1 (M+1). IC50 (uM) +++++.

TABLE (XA)

EXAMPLES 232 TO 248 ARE TABULATED BELOW:

| Ex# | Structure | IC50 (uM) | IUPAC names | MS |
|---|---|---|---|---|
| 232 | 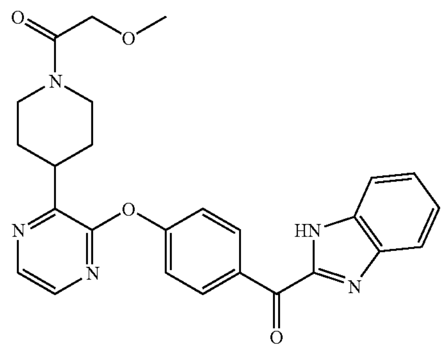 | +++++ | 1-(4-(3-(4-(1H-benzo[d]imidazole-2-carbonyl)phenoxy)pyrazin-2-yl)piperidin-1-yl)-2-methoxyethanone | 472 |
| 233 | 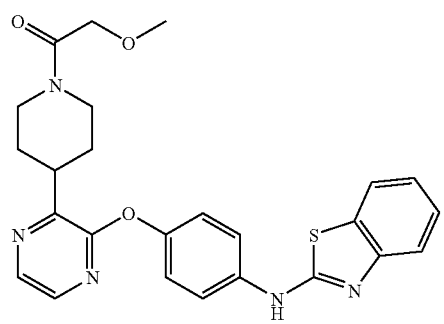 | +++++ | 1-(4-(3-(4-(benzo[d]thiazol-2-ylamino)phenoxy)pyrazin-2-yl)piperidin-methoxyethanone | 476 |
| 234 | 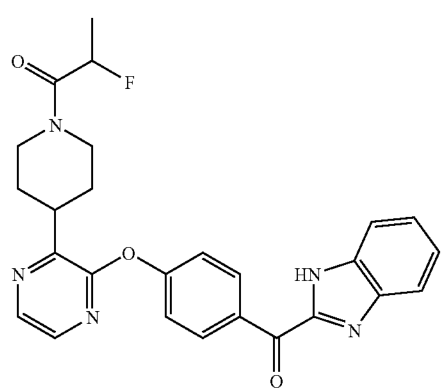 | +++++ | 1-(4-(3-(4-(1H-benzo[d]imidazole-2-carbonyl)phenoxy)pyrazin-2-yl)piperidin-1-yl)-2-fluoropropan-1-one | 474 |

TABLE (XA)-continued

EXAMPLES 232 TO 248 ARE TABULATED BELOW:

| Ex# | Structure | IC50 (uM) | IUPAC names | MS |
|---|---|---|---|---|
| 235 | 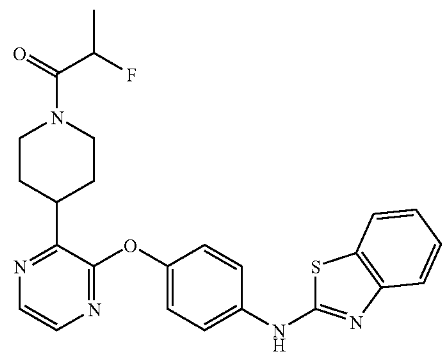 | +++++ | 1-(4-(3-(4-(benzo[d]thiazol-2-ylamino)phenoxy)pyrazin-2-yl)piperidin-fluoropropan-1-one | 478.1 |
| 236 | 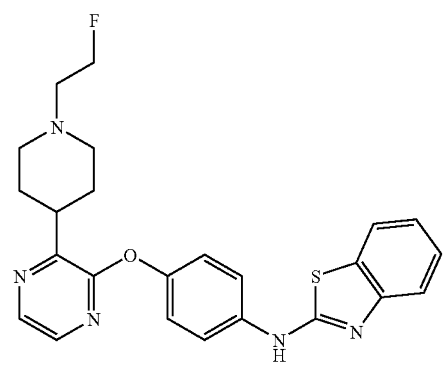 | +++++ | N-(4-(3-(1-(2-fluoroethyl)piperidin-4-yl)pyrazin-2-yloxy)phenyl)benzo[d]thiazol-2-amine | 450.0 |
| 237 | 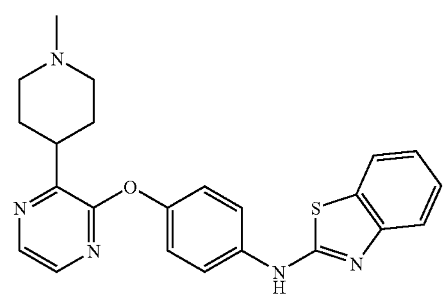 | +++++ | N-(4-(3-(1-methylpiperidin-4-yl)pyrazin-2-yloxy)phenyl)benzo[d]thiazol-2-amine | 418.1 |
| 238 | 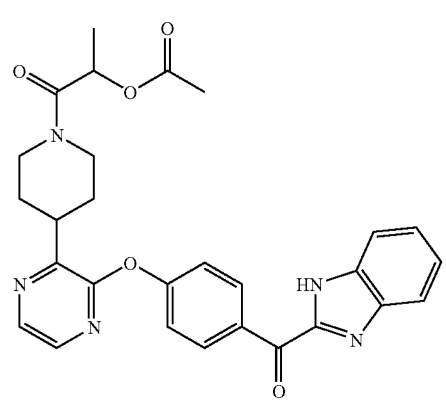 | +++++ | 1-(4-(3-(4-(1H-benzo[d]imidazole-2-carbonyl)phenoxy)pyrazin-2-yl)piperidin-1-yl)-1-oxopropan-2-yl acetate | 514.1 |

TABLE (XA)-continued

EXAMPLES 232 TO 248 ARE TABULATED BELOW:

| Ex# | Structure | IC50 (uM) | IUPAC names | MS |
|---|---|---|---|---|
| 239 | 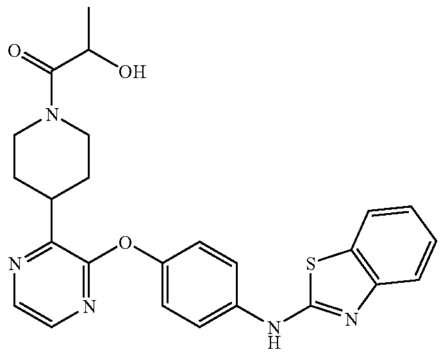 | +++++ | 1-(4-(3-(4-(benzo[d]thiazol-2-ylamino)phenoxy)pyrazin-2-yl)piperidin-1-yl)-2-hydroxypropan-1-one | 476.1 |
| 240 | 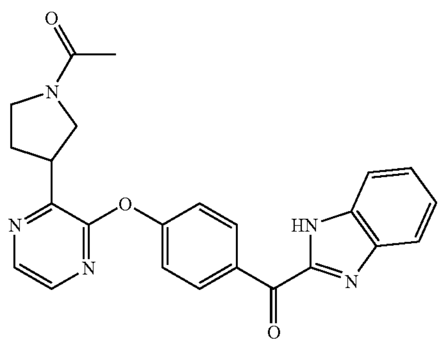 | +++++ | 1-(3-(3-(4-(1H-benzo[d]imidazole-2-carbonyl)phenoxy)pyrazin-2-yl)pyrrolidin-1-yl)ethanone | 428.1 |
| 241 | 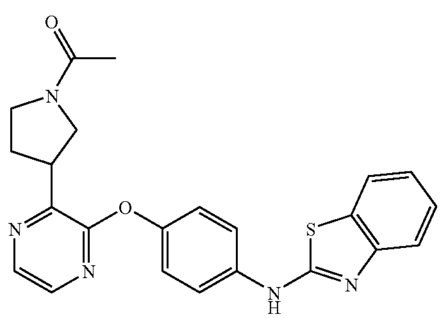 | +++++ | 1-(3-(3-(4-(benzo[d]thiazol-2-ylamino)phenoxy)pyrazin-2-yl)pyrrolidin-1-yl)ethanone | 432.0 |
| 242 | 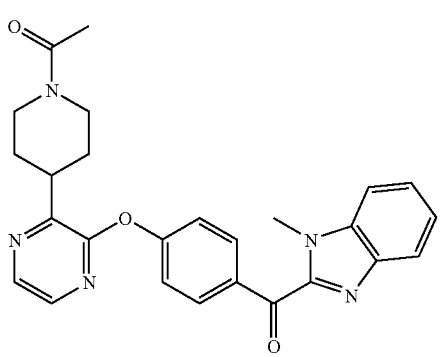 | +++++ | 1-(4-(3-(4-(1-methyl-1H-benzo[d]imidazole-2-carbonyl)phenoxy)pyrazin-2-yl)piperidin-1-yl)ethanone | 456.0 |

TABLE (XA)-continued

EXAMPLES 232 TO 248 ARE TABULATED BELOW:

| Ex# | Structure | IC50 (uM) | IUPAC names | MS |
|---|---|---|---|---|
| 243 | 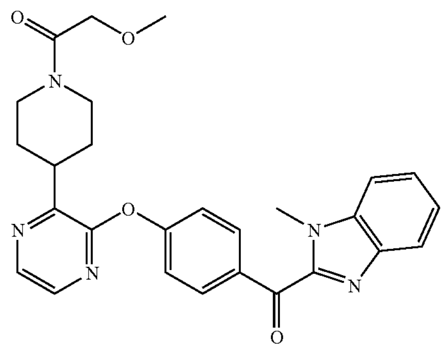 | +++++ | 2-methoxy-1-(4-(3-(4-(1-methyl-1H-benzo[d]imidazole-2-carbonyl)phenoxy)pyrazin-2-yl)piperidin-1-yl)ethanone | 486.0 |
| 244 | 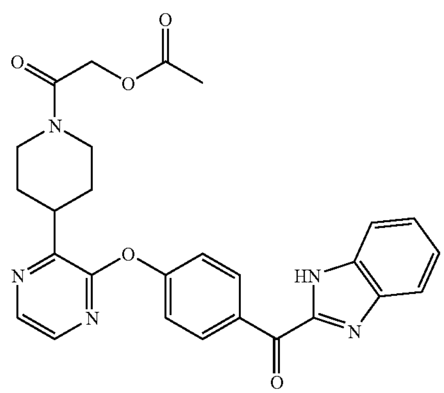 | +++++ | 2-(4-(3-(4-(1H-benzo[d]imidazole-2-carbonyl)phenoxy)pyrazin-2-yl)piperidin-1-yl)-2-oxoethyl acetate | 500.1 |
| 245 | 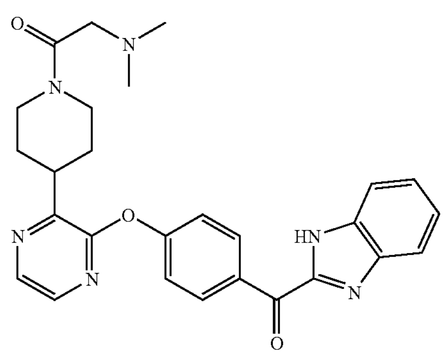 | +++++ | 1-(4-(3-(4-(1H-benzo[d]imidazole-2-carbonyl)phenoxy)pyrazin-2-yl)piperidin-1-yl)-2-(dimethylamino)ethanone | 485.1 |
| 246 | 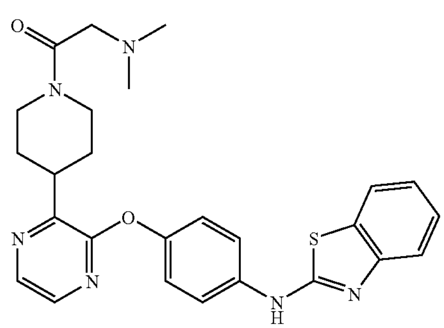 | +++++ | 1-(4-(3-(4-(benzo[d]thiazol-2-ylamino)phenoxy)pyrazin-2-yl)piperidin-1-yl)-2-(dimethylamino)ethanone | 489.0 |

TABLE (XA)-continued

EXAMPLES 232 TO 248 ARE TABULATED BELOW:

| Ex# | Structure | IC50 (uM) | IUPAC names | MS |
|---|---|---|---|---|
| 247 | 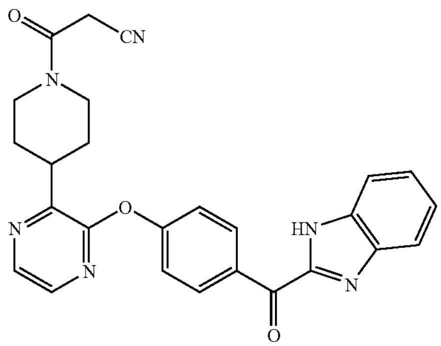 | +++++ | 3-(4-(3-(4-(1H-benzo[d]imidazole-2-carbonyl)phenoxy)pyrazin-2-yl)piperidin-1-yl)-3-oxopropanenitrile | 467.1 |
| 248 | 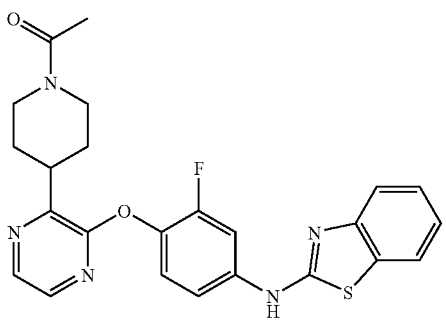 | +++++ | 1-(4-(3-(4-(benzo[d]thiazol-2-ylamino)-2-fluorophenoxy)pyrazin-2-yl)piperidin-1-yl)ethanone | 464.4 |

TABLE (XB)

PREPARATION OF EXAMPLES 232 TO 248 ARE TABULATED BELOW:

| Ex# | Synthetic Scheme | How Different from Main Route | Reagent Difference |
|---|---|---|---|
| 232 and 233 | 33 | Same | |
| 234 and 235 | 33 | O-(-7-azabenzotriazol-1-yl)-n,'n,'n,'n'-tetramethyluronium-hexafluorophosphate Et$_3$N | |
| 236 | 33 | Cs$_2$CO$_3$, CH$_3$CN Microwave, 120° C. | |
| 237 | 33 | AcOH, NaBH(OAc)$_3$ | HCHO |
| 238 and 239 | 33 | O-(-7-azabenzotriazol-1-yl)-n,'n,'n,'n'-tetramethyluronium-hexafluorophosphate Et$_3$N | |
| 240 and 241 | 33 | Same | |

TABLE (XB)-continued
PREPARATION OF EXAMPLES 232 TO 248 ARE TABULATED BELOW:
| Ex# | Synthetic Scheme | How Different from Main Route | Reagent Difference |
|---|---|---|---|
| 242 | 4 | Same | 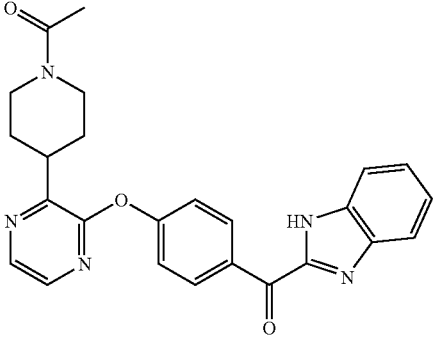 |
| 243 | 4 | Same | 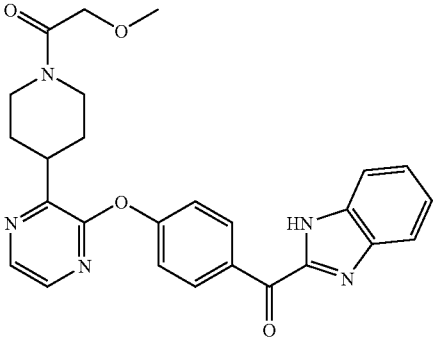 |
| 244 | 33 | Same | 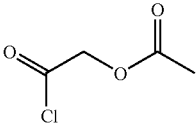 |
| 245 and 246 | 33 | Same | 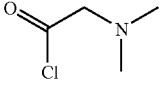 |
| 247 | 33 | O-(-7-azabenzotriazol-1-yl)-n,'n,'n,'n'-tetramethyluronium-hexafluorophosphate Et$_3$N | 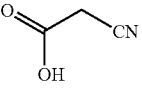 |
| 248 | 5, 33 | Heated reaction to 150° C. (scheme 5). Heated reaction to 140° C. (scheme 32). | 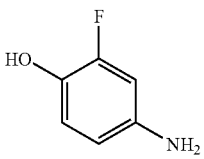 |

SCHEME 35

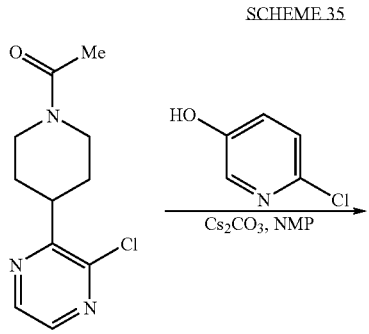

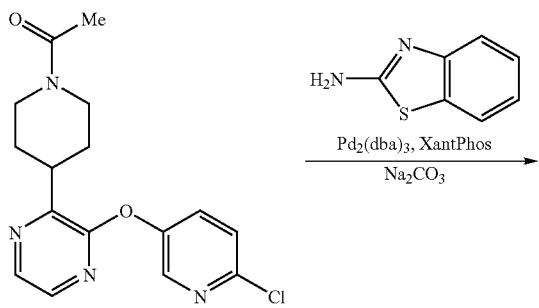

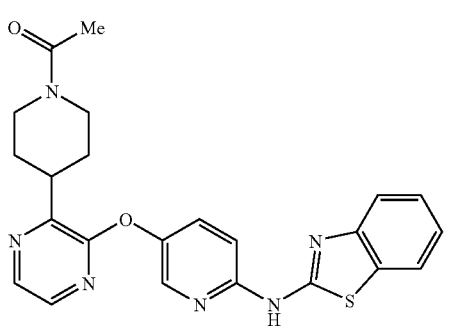

Example 249

1-(4-(3-(6-(BENZO[D]THIAZOL-2-YLAMINO)PYRIDIN-3-YLOXY)PYRAZIN-2-YL)PIPERIDIN-1-YL)ETHANONE

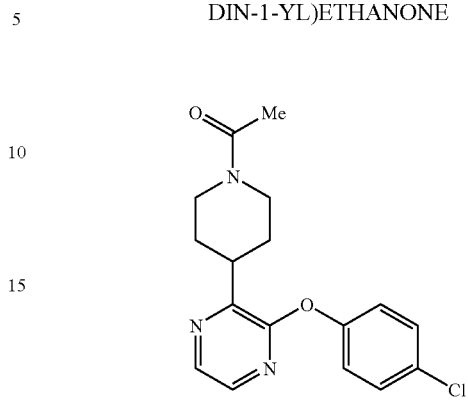

STEP 1. 1-(4-(3-(6-CHLOROPYRIDIN-3-YLOXY)PYRAZIN-2-YL)PIPERIDIN-1-YL)ETHANONE

To a mixture of cesium carbonate (0.505 g, 1.55 mmol), 1-(4-(3-chloropyrazin-2-yl)piperidin-1-yl)ethanone (0.129 g, 0.538 mmol), and 6-chloropyridin-3-ol (0.140 g, 1.08 mmol) was added NMP (2 mL). The reaction mixture was degassed and heated to 130° C. for 2 h. The reaction mixture was diluted with Teac. The organic phase was washed with water (1×), brine (1×), dried over MgSO$_4$, filtered, and concentrated. Purification by flash column chromatography on silica gel (50% to 100% Teac (10% MeOH) in hexanes) gave 1(4-(3-(6-chloropyridin-3-yloxy)pyrazin-2-yl)piperidin-1-yl)ethanone as a colorless oil that was used in the next step without further purification. MS (ESI, pos. ion) m/z: 333.2 (M+1).

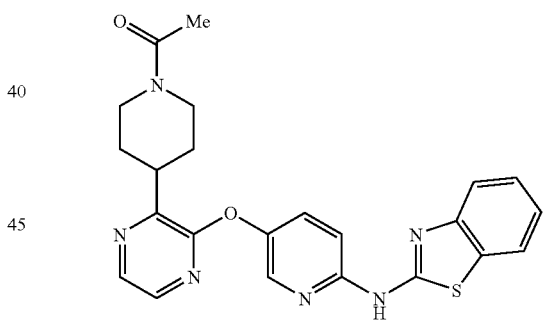

STEP 2. 1-(4-(3-(6-(BENZO[D]THIAZOL-2-YLAMINO)PYRIDIN-3-YLOXY)PYRAZIN-2-YL)PIPERIDIN-1-YL)ETHANONE

To a mixture of tris(dibenzylideneacetone)dipalladium(0) (0.021 g, 0.023 mmol), Na$_2$CO$_3$ (0.081 g, 0.76 mmol), 9,9-dimethyl-9H-xanthene-4,5-diyl)bis(diphenylphosphine (0.040 g, 0.069 mmol), benzo[d]thiazol-2-amine (0.110 g, 0.732 mmol), and 1-(4-(3-(6-chloropyridin-3-yloxy)pyrazin-2-yl)piperidin-1-yl)ethanone (0.182 g, 0.547 mmol) was added PhMe (3 mL). The reaction mixture was degassed and heated to 100° C. for 40 h. The reaction mixture was diluted with Teac and the organic phase was washed with water (1×), brine (1×), dried over MgSO$_4$, filtered, and concentrated. Purification by flash column chromatography on silica gel (10% to 80% Teac (10% MeOH) in hexanes) gave 1-(4-(3-(6-(benzo[d]thiazol-2-ylamino)pyridin-3-yloxy)pyrazin-2-yl)piperidin-1-yl)ethanone as a white solid. MS (ESI, pos. ion) m/z: 447.2 (M+1). IC50 (uM) ++.

SCHEME 36

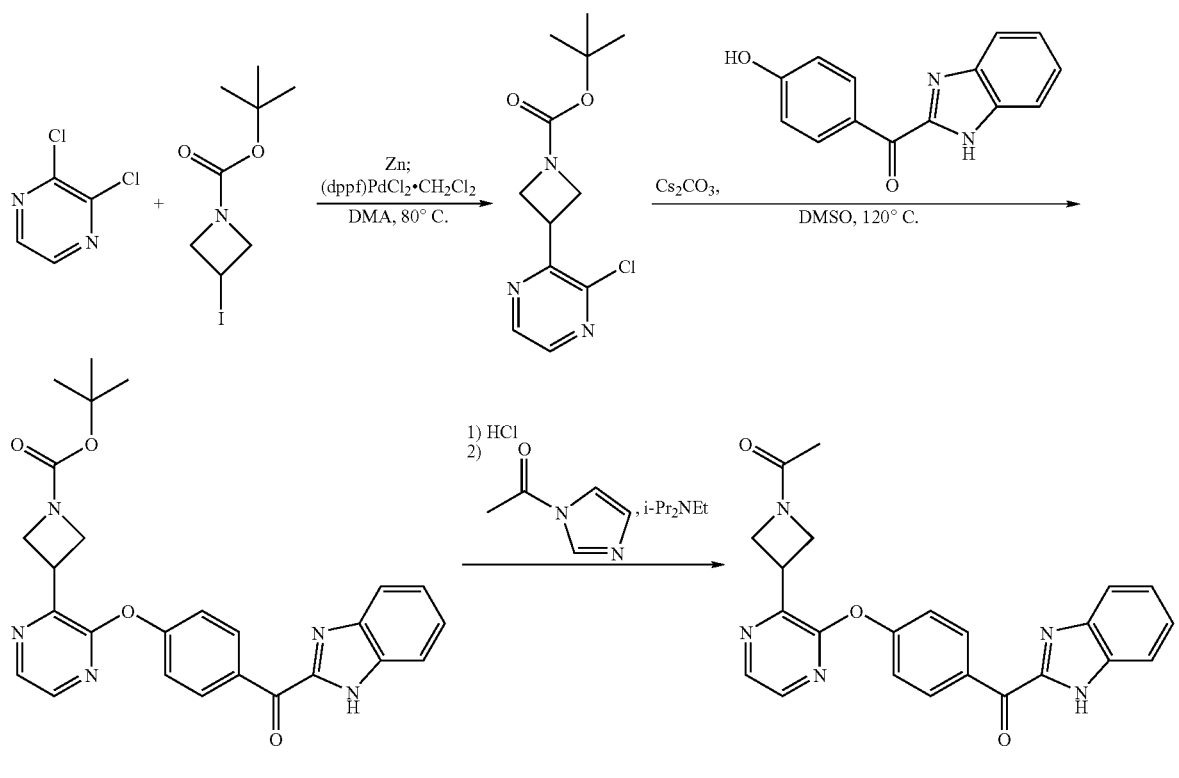

Example 250

1-(3-(3-(4-(1H-BENZO[D]IMIDAZOLE-2-CAR-BONYL)PHENOXY)PYRAZIN-2-YL)AZETIDIN-1-YL)ETHANONE

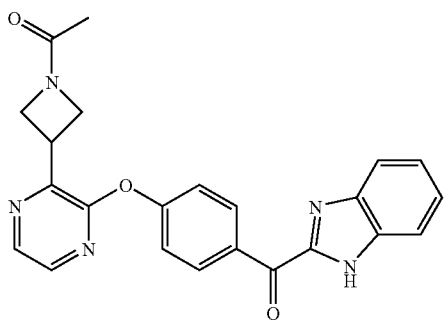

STEP 1. TERT-BUTYL 3-(3-CHLOROPYRAZIN-2-YL) AZETIDINE-1-CARBOXYLATE

To a flame dried 25 mL flask with zinc dust (217 mg, 3.31 mmol) and N,N-dimethylacetamide (2 mL) was added chlorotrimethylsilane (33.5 μL, 0.265 mmol) and 1,2-dibromoethane (22.83 μL, 0.265 mmol). The resulting slurry was stirred 15 min, then tert-butyl 3-iodoazetidine-1-carboxylate (753 mg, 2.66 mmol) was added to the above mixture (mild exotherm). The suspension was stirred at rt 30 min.

The zinc solution was added via syringe to a solution of 2,3-dichloropyrazine (277 mg, 1.862 mmol), (dppf)PdCl$_2$·CH$_2$Cl$_2$ (65.2 mg, 0.080 mmol), and copper(I) iodide (30.4 mg, 0.160 mmol) in N,N-dimethylacetamide (1.0 mL) that was degassed with N$_2$ (3×). The solution was heated to 80° C. and stirred 1 h. The reaction was quenched with NH$_4$Cl (10 mL) and extracted with Teac (3×10 mL). The combined organic fractions were dried (MgSO$_4$), concentrated, and purified by ISCO (40 g SiO$_2$, 10-100% Teac/Hexane) to give tert-butyl 3-(3-chloropyrazin-2-yl)azetidine-1-carboxylate (262 mg, 0.971 mmol, 36.5% yield) as a clear, colorless oil.

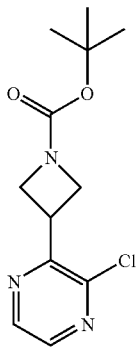

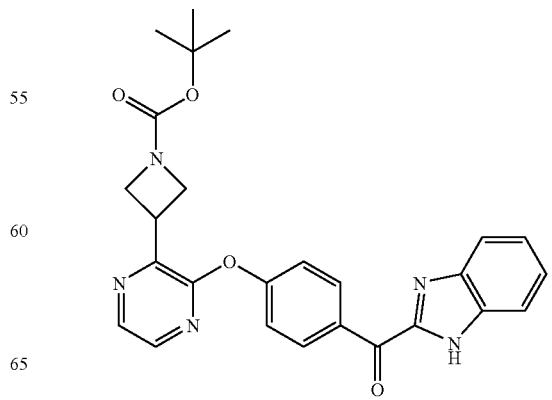

STEP 2. TERT-BUTYL 3-(3-(4-(1H-BENZO[D]IMIDAZOLE-2-CARBONYL)PHENOXY)PYRAZIN-2-YL)AZETIDINE-1-CARBOXYLATE

To a vial with tert-butyl 3-(3-chloropyrazin-2-yl)azetidine-1-carboxylate (100 mg, 0.371 mmol), (1H-benzo[d]imidazol-2-yl)(4-hydroxyphenyl)methanone (265 mg, 1.112 mmol) and cesium carbonate (362 mg, 1.112 mmol) under $N_2$ is added DMSO (1.0 mL). The reaction is heated to 120° C. in an oil bath 1 h. The reaction was cooled to rt, added to $H_2O$ (5 mL), and extracted with Teac (3×5 mL). The combined organic layers were dried ($MgSO_4$) and concentrated to give tert-butyl 3-(3-(4-(1H-benzo[d]imidazole-2-carbonyl)phenoxy)pyrazin-2-yl)azetidine-1-carboxylate (175 mg) as a yellow oil which was carried on to the next step without purification.

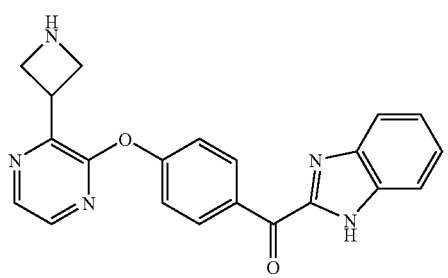

STEP 3. (4-(3-(AZETIDIN-3-YL)PYRAZIN-2-YLOXY)PHENYL)(1H-BENZO[D]IMIDAZOL-2-YL)METHANONE

To a solution of tert-butyl 3-(3-(4-(1H-benzo[d]imidazole-2-carbonyl)phenoxy)pyrazin-2-yl)azetidine-1-carboxylate (175 mg, 0.371 mmol) in $CH_2Cl_2$ (1 mL) is added 2,2,2-trifluoroacetic acid (1.0 mL). The reaction was stirred at rt 1 h. The solution was concentrated and $CH_2Cl_2$ (5 mL) and saturated $NaHCO_3$ (0.5 mL) was added. $MgSO_4$ was added to remove water and the solution filtered and concentrated to give the crude amine as a dark green oil which was carried on to the next step without purification. (Note: An insoluble solid crashed out during the extraction, which later was identified as the desired crude amine product, which is sparingly soluble in $CH_2Cl_2$, but soluble in THF. The insoluble solid from the extraction was dissolved in THF, dried ($MgSO_4$), concentrated, and combined with the material from aqueous extraction and carried on into the next step.

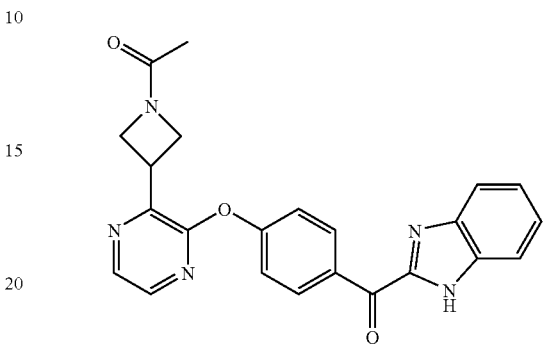

STEP 4. 1-(3-(3-(4-(1H-BENZO[D]IMIDAZOLE-2-CARBONYL)PHENOXY)PYRAZIN-2-YL)AZETIDIN-1-YL)ETHANONE

To a solution of (4-(3-(azetidin-3-yl)pyrazin-2-yloxy)phenyl)(1H-benzo[d]imidazol-2-yl)methanone in DMF (1.0 mL) is added triethylamine (104 μL, 0.743 mmol) and 1-(1H-imidazol-1-yl)ethanone (60.0 mg, 0.545 mmol). The reaction was stirred at rt 7 h. The reaction mixture was added to saturated $NaHCO_3$ (5 mL) and extracted with Teac (3×5 mL). The combined organic layers were washed with water (5 mL), saturated NaCl (5 mL), dried ($MgSO_4$) and concentrated. Purification by RPHPLC gives 1-(3-(3-(4-(1H-benzo[d]imidazole-2-carbonyl)phenoxy)pyrazin-2-yl)azetidin-1-yl)ethanone (55.4 mg, 36.0% over 3 steps) as a white solid. MS (ESI, pos. ion) m/z: 414.0 (M+1). IC50 (uM) +++++.

SCHEME 37

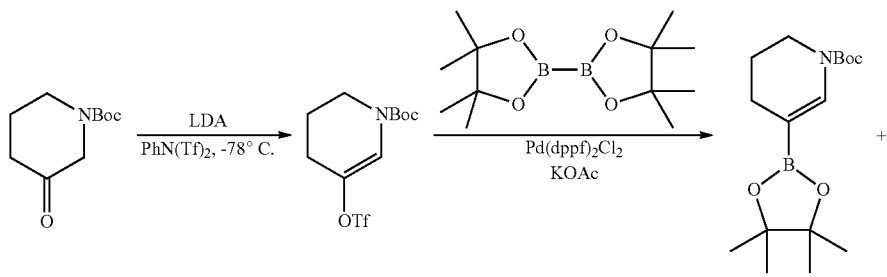

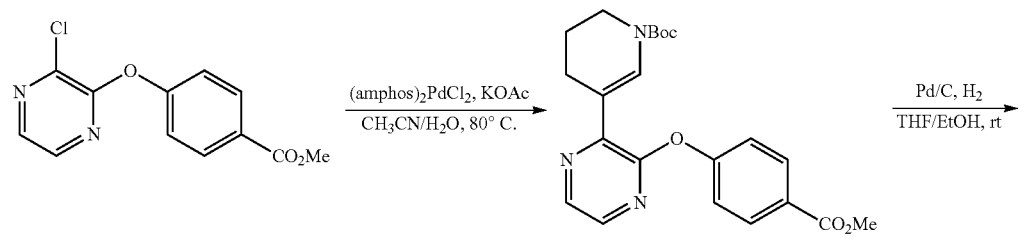

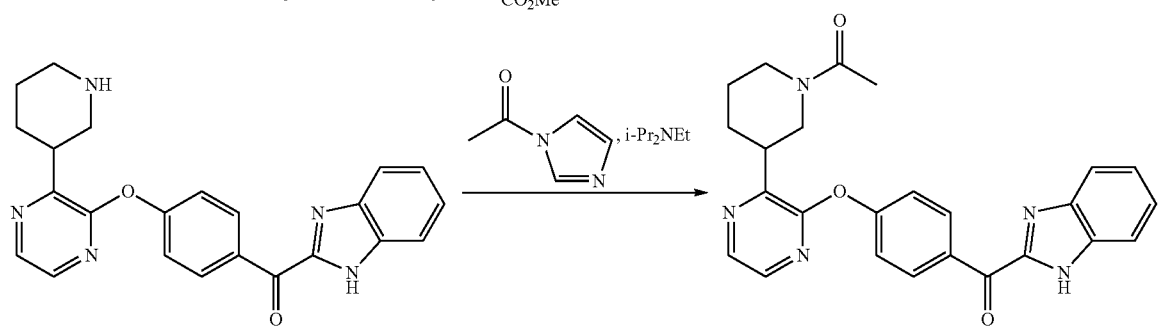

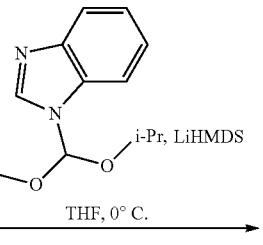

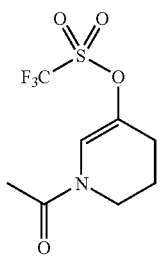

Example 251

1-(3-(3-(4-(1H-BENZO[D]IMIDAZOLE-2-CAR-BONYL)PHENOXY)PYRAZIN-2-YL)PIPERIDIN-1-YL)ETHANONE

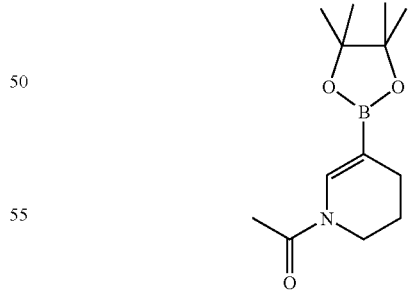

STEP 1. 1-ACETYL-1,4,5,6-TETRAHYDROPYRIDIN-3-YL TRIFLUOROMETHANESULFONATE

To a −78° C. solution of diisopropylamine (3.60 mL, 25.5 mmol) in THF (30 mL) was added butyllithium (9.35 mL, 23.38 mmol) dropwise. After the addition was complete the reaction was allowed to stir at −78° C. for 15 minutes, then a solution of 1-acetylpiperidin-3-one (3.0 g, 21.25 mmol) in THF (5 mL) was added dropwise. After a further 20 minutes, a solution of 1,1,1-trifluoro-N-phenyl-N-(trifluoromethyl-sulfonyl)methanesulfonamide (8.35 g, 23.38 mmol) in THF (15 mL) was added dropwise to the reaction. The solution was allowed to slowly warm to room temperature. After 16 hours, the reaction was quenched with sat'd $NH_4Cl$ and the diluted with water (20 mL). The aqueous solution was basified and extracted with Teac (4×30 mL). The combined organics were washed with brine and concentrated in vacuo. The crude product was adsorbed onto a plug of silica gel and chromatographed through a Redi-Sep® pre-packed silica gel column (40 g), eluting with 0% to 70% Teac in hexane, to provide 1-acetyl-1,4,5,6-tetrahydropyridin-3-yl trifluoromethane-sulfonate as a golden oil. [M+1]=274.0.

STEP 2. 1-(5-(4,4,5,5-TETRAMETHYL-1,3,2-DIOX-ABOROLAN-2-YL)-3,4-DIHYDROPYRIDIN-1(2H)-YL) ETHANONE.

To a solution of 1-acetyl-1,4,5,6-tetrahydropyridin-3-yl trifluoromethanesulfonate (2.5 g, 9.15 mmol), bis(pinacola-to)diboron (2.88 g, 11.34 mmol), potassium acetate (1.91 g, 19.46 mmol), and dioxane (60 mL) was added 1,1'-bis(diphe-nylphosphino)ferrocenedichloro palladium(ii) dichloromethane complex (400 mg, 0.547 mmol). The mixture was purged with nitrogen and then was heated to 80° C. After 16 hours, the reaction was cooled to room temperature. The mixture was diluted with 150 mL of Teac and washed with 50 mL of water and 50 mL of brine, dried over MgSO₄, and concentrated in vacuo. The crude product was adsorbed onto a plug of silica gel and chromatographed through a Redi-Sep® pre-packed silica gel column (40 g), eluting with 0% to 40% Teac in hexane, to provide 1-(5-(4,4,5,5-tetramethyl-1,3,2-dioxaborolan-2-yl)-3,4-dihydropyridin-1(2H)-yl)ethanone as an orange oil. [M+1]=252.1.

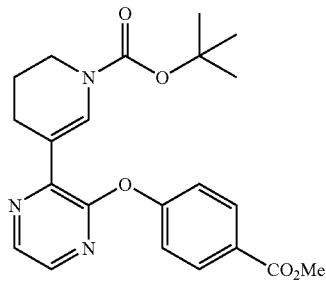

STEP 3. TERT-BUTYL 5-(3-(4-(METHOXYCARBONYL) PHENOXY)PYRAZIN-2-YL)-3,4-DIHYDROPYRIDINE-1(2H)-CARBOXYLATE

To a mixture of (amphos)₂PdCl₂ (0.145 g, 0.205 mmol), potassium acetate (1.045 g, 10.65 mmol), methyl 4-(3-chloropyrazin-2-yloxy)benzoate (1.084 g, 4.10 mmol), and tert-butyl 5-(4,4,5,5-tetramethyl-1,3,2-dioxaborolan-2-yl)-3,4-dihydropyridine-1(2H)-carboxylate (1.900 g, 6.14 mmol) under N₂ was added MeCN (7.0 mL) and Ar degassed water (0.70 mL). The reaction mixture was degassed with Ar (10 min) then heated to 80° C. for 20 h. The reaction mixture was diluted with H₂O (20 mL) and extracted with Teac (2×10 mL). The combined organic extracts were washed with brine (10 mL), dried (MgSO₄), and concentrated. Purification by ISCO (120 g SiO₂, 10-100% Teac/hexanes) gave tert-butyl 5-(3-(4-(methoxycarbonyl)phenoxy)pyrazin-2-yl)-3,4-dihydropyridine-1(2H)-carboxylate as a yellow oil.

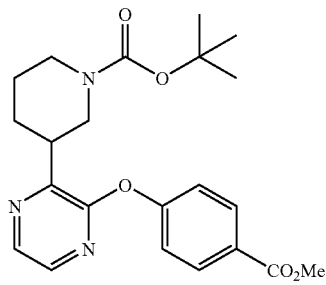

STEP 4. TERT-BUTYL 3-(3-(4-(METHOXYCARBONYL) PHENOXY)PYRAZIN-2-YL)PIPERIDINE-1-CARBOXYLATE

To a rb flask containing tert-butyl 5-(3-(4-(methoxycarbonyl)phenoxy)pyrazin-2-yl)-3,4-dihydropyridine-1(2H)-carboxylate (900 mg, 2.187 mmol) and palladium on carbon (233 mg, 0.219 mmol) (10 wt %) under N₂ is added THF (5.5 mL) and EtOH (5.5 mL). The flask is purged with H₂ (3×), then stirred under H₂ at rt 3 h. The reaction was filtered through celite and the filter cake washed with Teac (2×10 mL). The combined filtrates were concentrated and the residue purified by ISCO (12 g SiO₂, 0-50% Teac/Hexane) to give tert-butyl 3-(3-(4-(methoxycarbonyl)phenoxy)pyrazin-2-yl) piperidine-1-carboxylate as a brown solid.

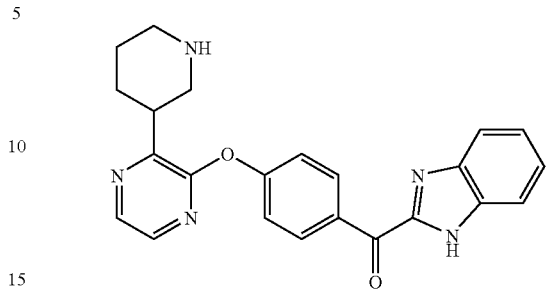

STEP 5. (1H-BENZO[D]IMIDAZOL-2-YL)(4-(3-(PIPERIDIN-3-YL)PYRAZIN-2-YLOXY)PHENYL)METHANONE

To a solution of 1-(diisopropoxymethyl)-1H-benzo[d]imidazole (306 mg, 1.233 mmol) in THF (5 mL) at 0° C. is added LiHMDS (1.233 mL, 1.233 mmol) over 1 min. The reaction was stirred 5 min., then 1 mL of the 6.5 mL solution (0.5 theoretical equivalent of the lithium benzoimidazole) was added to a solution of tert-butyl 3-(3-(4-(methoxycarbonyl) phenoxy)pyrazin-2-yl)piperidine-1-carboxylate (170 mg, 0.411 mmol) in THF (2 mL) at 0° C. The reaction was stirred at 0° C. 30 min. LCMS showed 59% conversion. An additional 1 mL of lithium benzoimidazole solution (0.5 equivalents) was added and the reaction stirred 5 min. at 0° C. The reaction was quenched with HCl (2 mL, 4 M in 1,4-dioxane), MeOH was added, and the reaction warmed to rt and stirred 2 h, the reaction was concentrated to give the crude amine hydrochloride, which was taken on to the next step without purification.

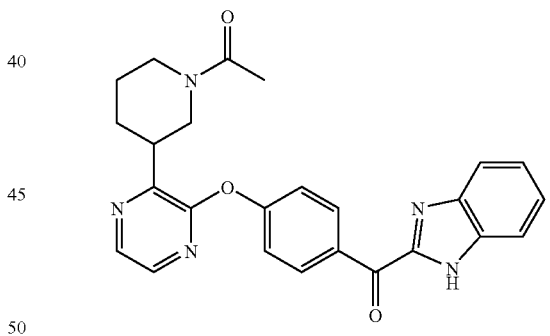

STEP 6. 1-(3-(3-(4-(1H-BENZO[D]IMIDAZOLE-2-CARBONYL)PHENOXY)PYRAZIN-2-YL)PIPERIDIN-1-YL) ETHANONE 2,2,2-TRIFLUOROACETATE

To the crude amine in DMF (1.0 mL) is added N-ethyl-N-isopropylpropan-2-amine (0.280 mL, 1.643 mmol) and 1-(1H-imidazol-1-yl)ethanone (56.5 mg, 0.513 mmol). The reaction was stirred at rt 5 h. The reaction mixture was added to saturated NaHCO₃ (5 mL) and extracted with Teac (3×5 mL). The combined organic layers were washed with water (5 mL), saturated NaCl (5 mL), dried (MgSO₄) and concentrated to give the crude product. Purification by RPHPLC gives 1-(3-(3-(4-(1H-benzo[d]imidazole-2-carbonyl)phenoxy)pyrazin-2-yl)piperidin-1-yl)ethanone 2,2,2-trifluoroacetate (9 mg, 0.016 mmol, 3.95% yield) as a racemic mixture of enantiomers. MS (ESI, pos. ion) m/z: 442.1 (M+1). IC50 (uM) +++++.

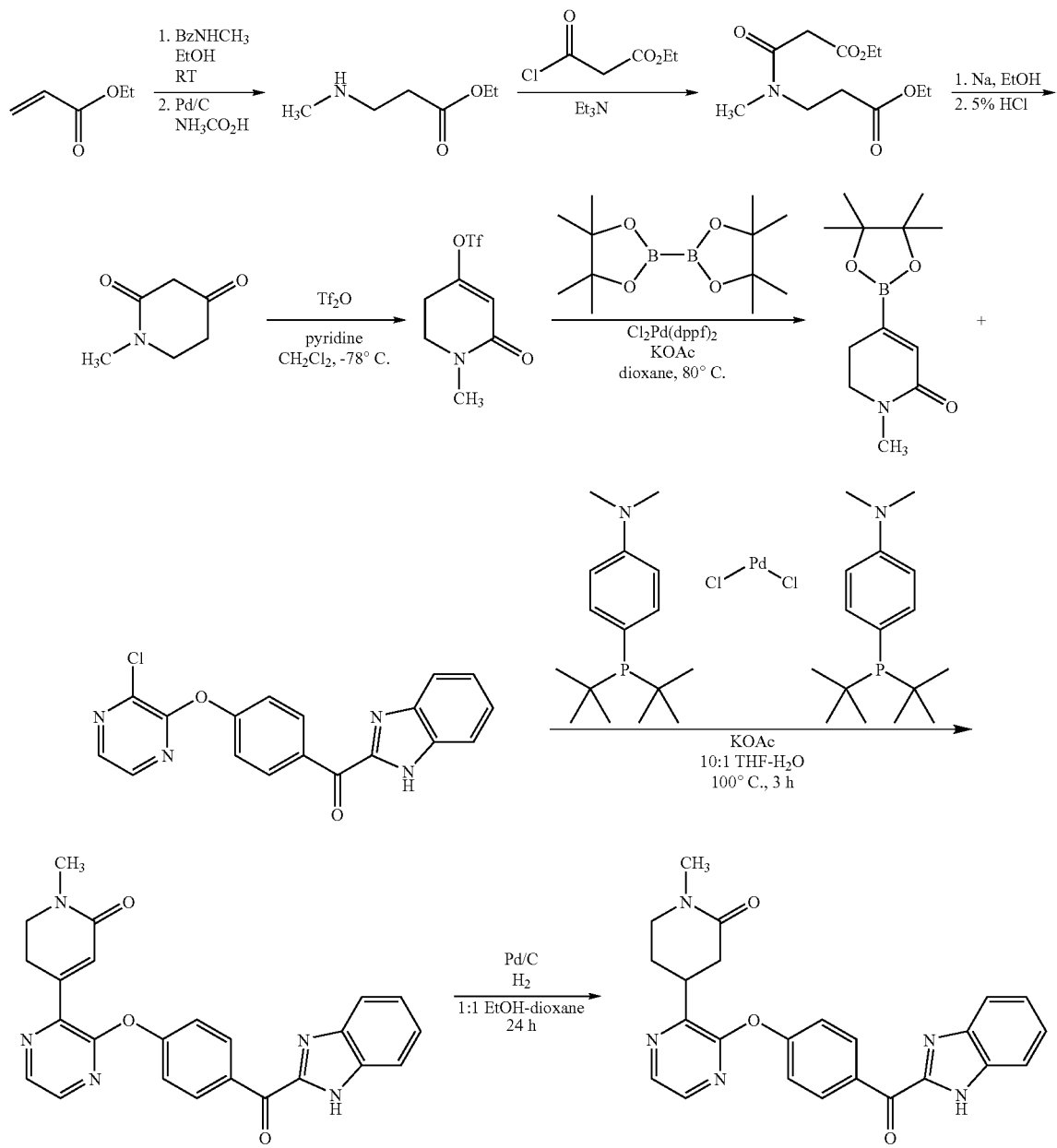
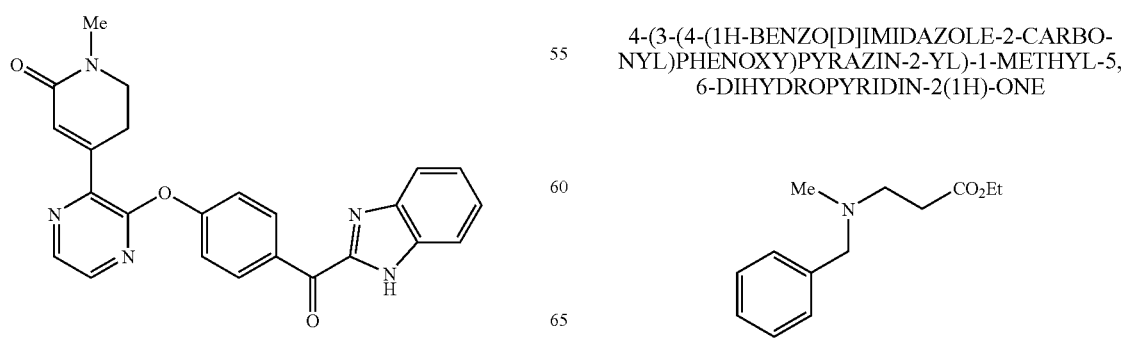
Example 252
4-(3-(4-(1H-BENZO[D]IMIDAZOLE-2-CARBO-NYL)PHENOXY)PYRAZIN-2-YL)-1-METHYL-5,6-DIHYDROPYRIDIN-2(1H)-ONE

STEP 1. ETHYL 3-(BENZYL(METHYL)AMINO)PROPANOATE

A solution of ethyl acrylate (6.51 mL, 59.9 mmol) and N-benzylmethylamine (8.48 mL, 65.9 mmol) in ethanol (33.3 mL) was stirred at room temperature for 18 h. The reaction was diluted with Teac and washed with aqueous saturated NaHCO$_3$ solution. The organic layer was dried (MgSO$_4$), filtered, and concentrated in vacuo. Flash column chromatography (10% to 50% Teac/Hexanes) provided ethyl 3-(benzyl(methyl)amino)propanoate as a colorless oil. [M+1]=222.1.

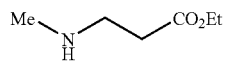

STEP 2. ETHYL 3-(METHYLAMINO)PROPANOATE

A solution of ethyl 3-(benzyl(methyl)amino)propanoate (3 g, 13.56 mmol) in ethanol (67.8 mL) was added palladium, 10 wt. % on carbon (0.3 g, 0.282 mmol) and hydrogenated (double-walled balloon pressure) at room temperature for 3 h. The reaction mixture was filtered via a pad of Celite, and the filtrate was concentrated in vacuo to give ethyl 3-(methylamino)propanoate (1.12 g, 63.0% yield) as a light golden yellow oil.

STEP 3. ETHYL 3-((3-ETHOXY-3-OXOPROPYL)(METHYL)AMINO)-3-OXOPROPANOATE

A solution of ethyl 3-(methylamino)propanoate (1.12 g, 8.54 mmol) and triethylamine (1.425 mL, 10.25 mmol) in dichloromethane (42.7 mL) under argon was cooled to 0° C. and added ethyl malonoyl chloride (1.182 mL, 9.39 mmol). The resulting yellow solution was allowed to warm to room temperature and stirred for 1 h. The reaction was diluted with CH$_2$Cl$_2$ and washed with aqueous saturated NaHCO$_3$ solution; the aqueous layer was back-extracted with CH$_2$Cl$_2$ (1×). The combined organic extracts were dried (MgSO$_4$), filtered, and concentrated in vacuo. Flash column chromatography (10% to 50% Teac/Hexanes) afforded ethyl 3-((3-ethoxy-3-oxopropyl)(methyl)amino)-3-oxopropanoate as a clear golden oil. [M+1]=246.2.

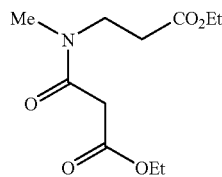

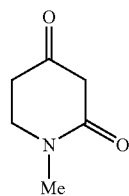

STEP 4. 1-METHYLPIPERIDINE-2,4-DIONE

Into a 50-mL round bottomed flask was added ethanol (4 mL) under argon, followed by sodium (0.121 g, 5.25 mmol). The mixture was stirred at room temperature for 15 min, during which a solution of ethyl 3-((3-ethoxy-3-oxopropyl)(methyl)amino)-3-oxopropanoate (1.17 g, 4.77 mmol) in ethanol (5 mL) was added. The resulting clear, colorless mixture was heated at 80° C. for 1 h, during which LC-MS indicated completion of reaction and a clean conversion to the desired ethyl 1-methyl-2,4-dioxopiperidine-3-carboxylate intermediate. Upon cooling to room temperature, the reaction was diluted with Et$_2$O, resulting in the formation of a white precipitate (desired product). The white precipitate was collected via filtration, taken up in 5% aqueous HCl solution (8 mL), and refluxed for 1 h. The cooled mixture was extracted with CH$_2$Cl$_2$ (5×) and the combined organic extracts were dried (MgSO$_4$), filtered, and concentrated in vacuo. Flash column chromatography (20% Teac/Hexanes to 100% Teac) afforded 1-methylpiperidine-2,4-dione as a viscous milky oil. [M+1]=128.1.

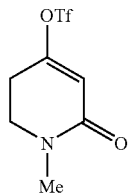

STEP 5. 1-METHYL-6-OXO-1,2,3,6-TETRAHYDROPYRIDIN-4-YL TRIFLUOROMETHANESULFONATE

A solution of 1-methylpiperidine-2,4-dione (0.295 g, 2.320 mmol) and pyridine (0.378 mL) in dichloromethane (14.50 mL) under argon was cooled to −78° C. and added trifluoromethanesulfonic anhydride (0.468 mL, 2.78 mmol). After stirring at −78° C. for 10 min, the reaction was warmed to 0° C. and stirred for 1 h. The mixture was quenched with aqueous saturated NH$_4$Cl solution and extracted with CH$_2$Cl$_2$; the aqueous layer was back-extracted with CH$_2$Cl$_2$ (2×). The combined organic extracts were dried (MgSO$_4$), filtered, and concentrated in vacuo. Flash column chromatography on basic alumina (10% to 50% Teac/Hexanes) gave 1-methyl-6-oxo-1,2,3,6-tetrahydropyridin-4-yl trifluoromethanesulfonate as a colorless oil. [M+1]=260.0.

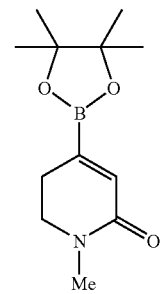

STEP 6. 1-METHYL-4-(4,4,5,5-TETRAMETHYL-1,3,2-DIOXABOROLAN-2-YL)-5,6-DIHYDROPYRIDIN-2 (1H)-ONE

1-Methyl-6-oxo-1,2,3,6-tetrahydropyridin-4-yl trifluoromethanesulfonate (0.56 g, 2.160 mmol), bis(pinacolato)diboron (0.658 g, 2.59 mmol), 1,1'-bis(diphenylphosphino)ferrocene-palladium dichloride (0.141 g, 0.173 mmol), potassium acetate (0.424 g, 4.32 mmol) and 1,4-dioxane (7.2 mL) were combined in a sealed tube and heated at 80° C. for 18 h. The cooled reaction was diluted with CH$_2$Cl$_2$ and washed with aqueous saturated NaHCO$_3$ solution; the aqueous layer was back-extracted with CH$_2$Cl$_2$ (1×). The combined organic extracts were dried (MgSO$_4$), filtered, and concentrated in vacuo. Flash column chromatography (1% to 10% MeOH/CH$_2$Cl$_2$) provided 1-methyl-4-(4,4,5,5-tetramethyl-1,3,2-dioxaborolan-2-yl)-5,6-dihydropyridin-2(1H)-one as a brown solid. [M+1]=156.1 (for boronic acid).

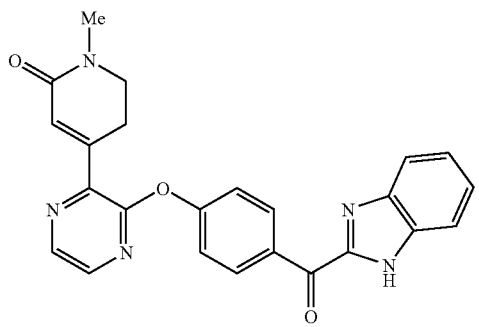

STEP 7. 4-(3-(4-(1H-BENZO[D]IMIDAZOLE-2-CARBONYL)PHENOXY)PYRAZIN-2-YL)-1-METHYL-5,6-DIHYDROPYRIDIN-2(1H)-ONE

1-Methyl-4-(4,4,5,5-tetramethyl-1,3,2-dioxaborolan-2-yl)-5,6-dihydropyridin-2(1H)-one (0.365 g, 1.539 mmol), (1H-benzo[d]imidazol-2-yl)(4-(3-chloropyrazin-2-yloxy) phenyl)methanone (0.540 g, 1.539 mmol), bis(di-tert-butyl (4-dimethylaminophenyl)phosphine)dichloropalladium(II) (0.076 g, 0.108 mmol), potassium acetate (0.453 g, 4.62 mmol), and 9:1 dioxane-H$_2$O (7.5 mL) were combined in a sealed tube and heated at 100° C. for 3 h. The cooled reaction was diluted with CH$_2$Cl$_2$ and washed with water; the aqueous layer was back-extracted with CH$_2$Cl$_2$ (1×). The organic extracts were combined, dried (MgSO$_4$), filtered, and concentrated in vacuo. Flash column chromatography (1% to 5% MeOH/CH$_2$Cl$_2$) provided a crude crop of the desired product. Further trituration with MeOH afforded 4-(3-(4-(1H-benzo [d]imidazole-2-carbonyl)phenoxy)pyrazin-2-yl)-1-methyl-5,6-dihydropyridin-2(1H)-one as a yellow amorphous solid. [M+1]=426.8. IC50 (uM) +++++.

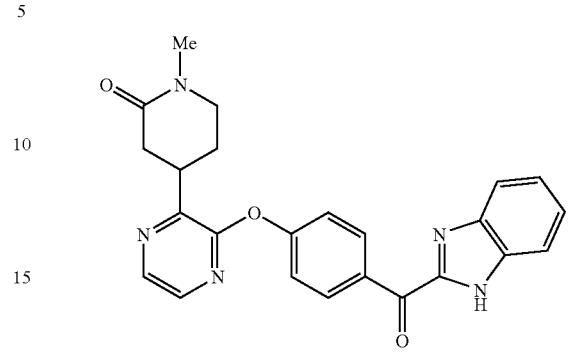

Example 253

4-(3-(4-(1H-BENZO[D]IMIDAZOLE-2-CARBONYL)PHENOXY)PYRAZIN-2-YL)-1-METHYLPIPERIDIN-2-ONE

A solution of 4-(3-(4-(1H-benzo[d]imidazole-2-carbonyl) phenoxy)pyrazin-2-yl)-1-methyl-5,6-dihydropyridin-2(1H)-one (0.0687 g, 0.161 mmol) (Step 7, Example 252) in 1:1 EtOH-dioxane (8 mL) was added palladium, 10% wt. on activated carbon (0.007 g, 6.58 μmol) and hydrogenated (double-walled balloon pressure) at room temperature for 24 h. The reaction mixture was filtered via a pad of Celite, and the filtrate was concentrated in vacuo and purified via flash column chromatography (20% to 80% Teac (10% MeOH)/ Hexanes) to give 4-(3-(4-(1H-benzo[d]imidazole-2-carbonyl)phenoxy)pyrazin-2-yl)-1-methylpiperidin-2-one (0.0262 g, 38.0% yield) as a light yellow amorphous solid. MS (ESI, pos. ion) m/z: 428.9 (M+1). IC50 (uM) +++++.

SCHEME 39

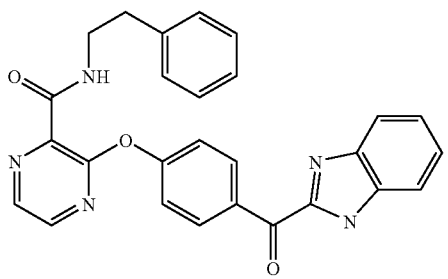

Example 254

3-(4-(1H-BENZO[D]IMIDAZOLE-2-CARBONYL)
PHENOXY)-N-PHENETHYLPYRAZINE-2-CARBOXAMIDE

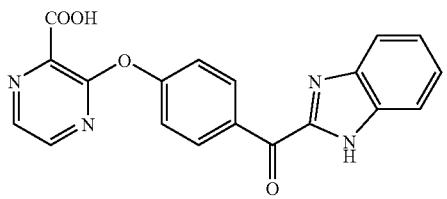

STEP 2. 3-(4-(1H-BENZO[D]IMIDAZOLE-2-CARBONYL)PHENOXY)PYRAZINE-2-CARBOXYLIC ACID

To the solution of ethyl 3-(4-(1H-benzo[d]imidazole-2 carbonyl)phenoxy)pyrazine-2-carboxylate (30 g, 77 mmol) in methanol (250 mL) was added aqueous NaOH solution (4.62 g, 115 mmol) in 50 mL of water. The reaction mixture was heated to reflux for 1 h. The reaction mixture was concentrated then diluted with water. The aqueous layer was washed with ethyl acetate and then acidified by addition of 2N HCl to pH 6. The precipitate was collected by filtration, dried to give the title compound as a light brown solid. MS [M+H]=351.2.

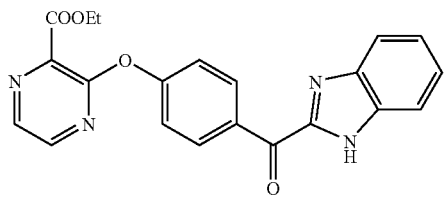

STEP 1. ETHYL 3-(4-(1H-BENZO[D]IMIDAZOLE-2 CARBONYL)PHENOXY)PYRAZINE-2-CARBOXYLATE

In a 2 L autoclave was added a solution (1H-benzo[d]imidazol-2-yl)(4-(3-chloropyrazin-2-yloxy)phenyl)methanone (5.0 g, 14.2 mmol) in ethanol (150 mL), followed by dppf (0.273 g, 0.42 mmol), palladium acetate (25 mg, 0.11 mmol) and sodium acetate (4.65 g, 56.8 mmol). The autoclave was applied CO(g) 15 kg/cm2 pressure. Then the reaction mixture was heated to 135° C. and maintained at that temperature for 1 h. After cooling to RT, the reaction mixture was concentrated and diluted with water, then extracted by ethyl acetate (3×200 mL). The combined organic extracts were dried over sodium sulfate and concentrate under vacuum to give a dark brown solid which was used directly in the following step. MS [M+H]=389.1.

STEP 3. 3-(4-(1H-BENZO[D]IMIDAZOLE-2-CARBONYL)PHENOXY)-N-PHENETHYLPYRAZINE-2-CARBOXAMIDE

HATU (123 mg, 0.324 mmol) was added to a mixture of 3-(4-(1H-benzo[d]imidazole-2-carbonyl)phenoxy)pyrazine-2-carboxylic acid (106 mg, 0.294 mmol) and diisopropylethylamine (102 µL, 0.588 mmol) in DMF (1 mL) and the mixture was stirred at RT for 10 min. 2-Phenylethylamine (55.8 µL, 0.441 mmol) was added and the mixture was stirred at RT for 1 h. The mixture was purified by chromatography on silica gel to deliver 3-(4-(1H-benzo[d]imidazole-2-carbonyl)phenoxy)-N-phenethylpyrazine-2-carboxamide as a white solid. MS (ESI, pos. ion) m/z: 464.0 (M+1). IC50 (uM) +++++.

TABLE (XIA)

EXAMPLES 255 TO 260 ARE TABULATED BELOW:

| Ex# | Structure | IC50 (uM) | IUPAC names | MS |
|---|---|---|---|---|
| 255 | 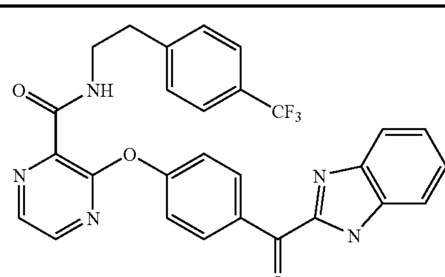 | +++++ | 3-(4-(1H-benzo[d]imidazole-2-carbonyl)phenoxy)-N-(4-(trifluoromethyl)phenethyl)pyrazine-2-carboxamide | 532 |

TABLE (XIA)-continued

EXAMPLES 255 TO 260 ARE TABULATED BELOW:

| Ex# | Structure | IC50 (uM) | IUPAC names | MS |
|---|---|---|---|---|
| 256 | 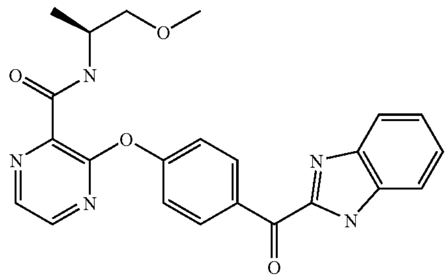 | +++++ | (S)-3-(4-(1H-benzo[d]imidazole-2-carbonyl)phenoxy)-N-(1-methoxypropan-2-yl)pyrazine-2-carboxamide | 432 |
| 257 | 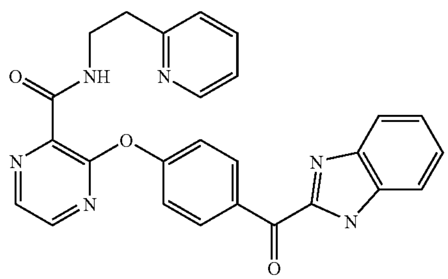 | +++++ | 3-(4-(1H-benzo[d]imidazole-2-carbonyl)phenoxy)-N-(2-(pyridin-2-yl)ethyl)pyrazine-2-carboxamide | 465 |
| 258 | 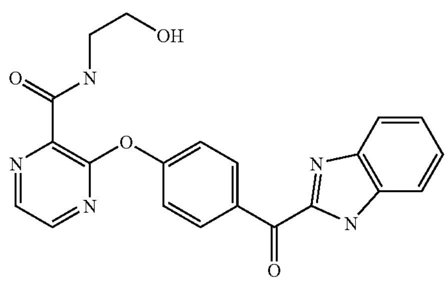 | +++++ | 3-(4-(1H-benzo[d]imidazole-2-carbonyl)phenoxy)-N-(2-hydroxyethyl)pyrazine-2-carboxamide | 404 |
| 259 | 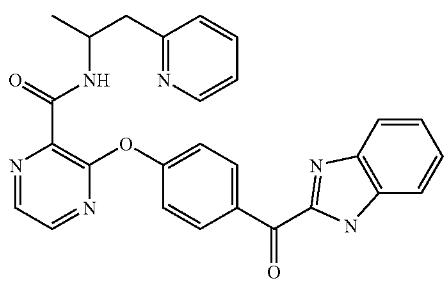 | +++++ | (rac)-3-(4-(1H-benzo[d]imidazole-2-carbonyl)phenoxy)-N-(1-(pyridin-2-yl)propan-2-yl)pyrazine-2-carboxamide | 479 |
| 260 | 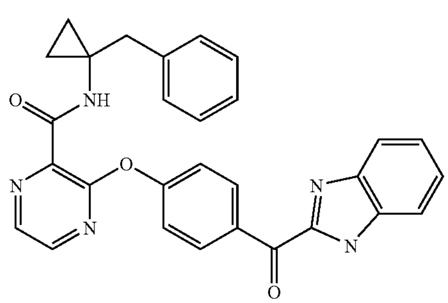 | +++++ | 3-(4-(1H-benzo[d]imidazole-2-carbonyl)phenoxy)-N-(1-benzylcyclopropyl)pyrazine-2-carboxamide | 490 |

TABLE (XIB)

PREPARATION OF EXAMPLES 255 TO 260 ARE TABULATED BELOW:

| Ex# | Synthetic Scheme | How Different from Main Route | Reagent Difference |
|---|---|---|---|
| 255 | 40 | Same | 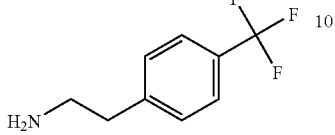 |
| 256 | 40 | Same | 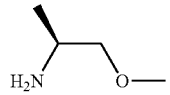 |
| 257 | 40 | Same | 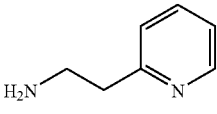 |
| 258 | 40 | Same |  |
| 259 | 40 | Same | 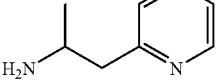 |
| 260 | 40 | Same | 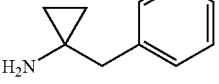 HCl |

The racemic mixtures were/can be separated by chiral HPLC to give the following chiral compounds by known methods. Prep* means preparative experiment was performed according to the tabulated previous examples.

TABLE (XIIA)

EXAMPLES 261 TO 280 ARE TABULATED BELOW.

| Ex. No | Structure | IC50 (uM) | Prep* | IUPAC names | MS |
|---|---|---|---|---|---|
| 261 | 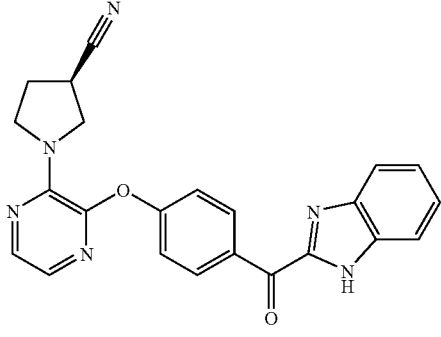 | +++++ | See ex. 40 | (R)-1-(3-(4-(1H-benzo[d]imidazole-2-carbonyl)phenoxy)pyrazin-2-yl)pyrrolidine-3-carbonitrile | 411 |
| 262 | 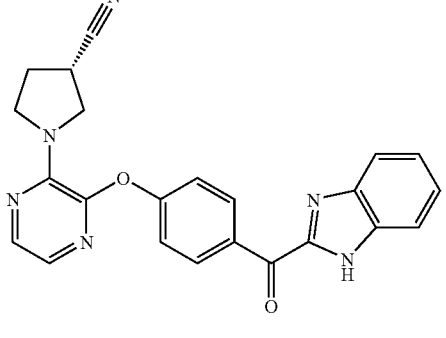 | +++++ | See ex. 40 | (S)-1-(3-(4-(1H-benzo[d]imidazole-2-carbonyl)phenoxy)pyrazin-2-yl)pyrrolidine-3-carbonitrile | 411 |

TABLE (XIIA)-continued

EXAMPLES 261 TO 280 ARE TABULATED BELOW.

| Ex. No | Structure | IC50 (uM) | Prep* | IUPAC names | MS |
|---|---|---|---|---|---|
| 263 | 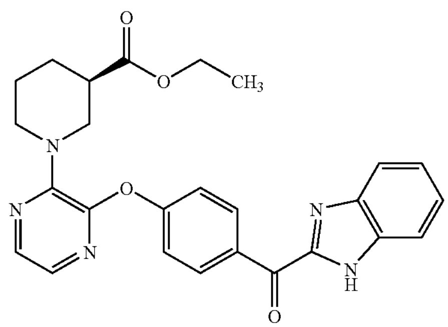 | +++++ | See ex. 43 | (R)-ethyl 1-(3-(4-(1H-benzo[d]imidazole-2-carbonyl)phenoxy)pyrazin-2-yl)piperidine-3-carboxylate | 472 |
| 264 | 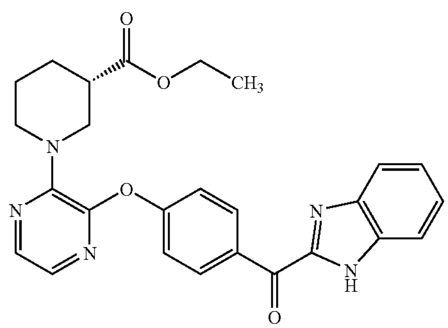 | +++++ | See ex. 43 | (S)-ethyl 1-(3-(4-(1H-benzo[d]imidazole-2-carbonyl)phenoxy)pyrazin-2-yl)piperidine-3-carboxylate | 472 |
| 265 | 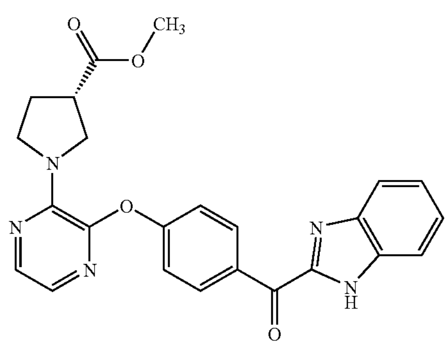 | +++++ | See ex. 42 | (S)-methyl 1-(3-(4-(1H-benzo[d]imidazole-2-carbonyl)phenoxy)pyrazin-2-yl)pyrrolidine-3-carboxylate | 444 |
| 266 | 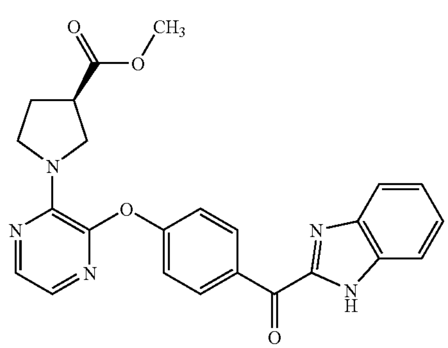 | +++++ | See ex. 42 | (R)-methyl 1-(3-(4-(1H-benzo[d]imidazole-2-carbonyl)phenoxy)pyrazin-2-yl)pyrrolidine-3-carboxylate | 444 |

TABLE (XIIA)-continued

EXAMPLES 261 TO 280 ARE TABULATED BELOW.

| Ex. No | Structure | IC50 (uM) | Prep* | IUPAC names | MS |
|---|---|---|---|---|---|
| 267 | 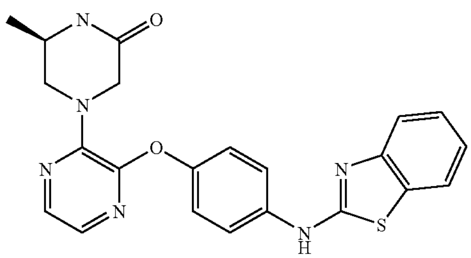 | +++++ | See ex. 94 | (R)-4-(3-(4-(benzo[d]thiazol-2-ylamino)phenoxy)pyrazin-2-yl)-6-methylpiperazin-2-one | 433 |
| 268 | 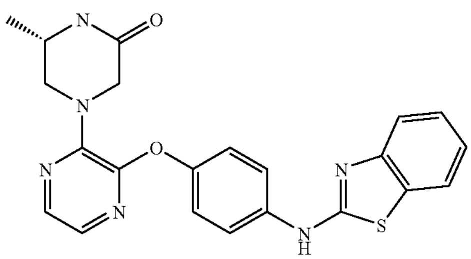 | +++++ | See ex. 94 | (R)-4-(3-(4-(benzo[d]thiazol-2-ylamino)phenoxy)pyrazin-2-yl)-6-methylpiperazin-2-one | 433 |
| 269 | 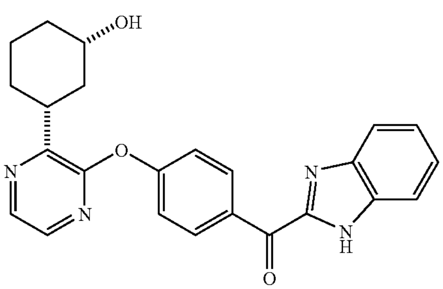 | +++++ | See ex. 189 | (1H-benzo[d]imidazol-2-yl)(4-(3-((1R,3S)-3-hydroxycyclohexyl)pyrazin-2-yloxy)phenyl)methanone | 415 |
| 270 | 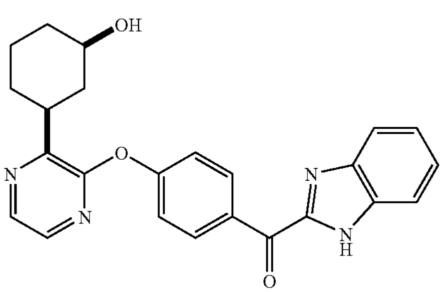 | +++++ | See ex. 189 | (1H-benzo[d]imidazol-2-yl)(4-(3-((1S,3R)-3-hydroxycyclohexyl)pyrazin-2-yloxy)phenyl)methanone | 415 |
| 271 | 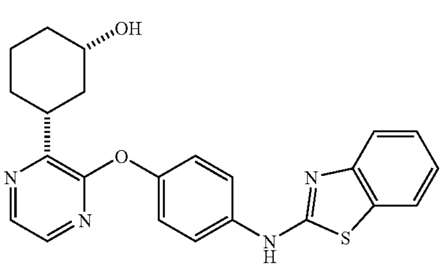 | +++++ | See ex. 191 | (1S,3R)-3-(3-(4-(benzo[d]thiazol-2-ylamino)phenoxy)pyrazin-2-yl)cyclohexanol | 419 |

TABLE (XIIA)-continued

EXAMPLES 261 TO 280 ARE TABULATED BELOW.

| Ex. No | Structure | IC50 (uM) | Prep* | IUPAC names | MS |
|---|---|---|---|---|---|
| 272 | 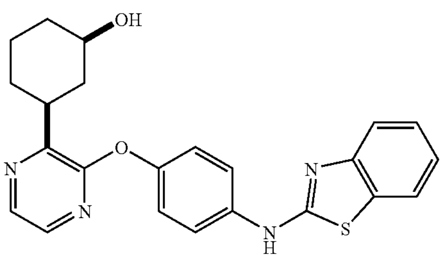 | +++++ | See ex. 191 | (1R,3S)-3-(3-(4-(benzo[d]thiazol-2-ylamino)phenoxy)pyrazin-2-yl)cyclohexanol | 419 |
| 273 | 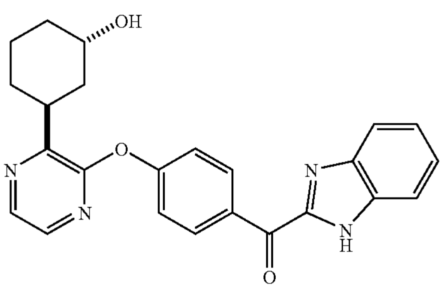 | +++++ | See ex. 190 | (1H-benzo[d]imidazol-2-yl)(4-(3-((1S,3S)-3-hydroxycyclohexyl)pyrazin-2-yloxy)phenyl)methanone | 415 |
| 274 | 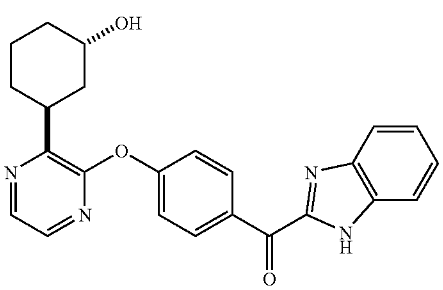 | +++++ | See ex. 190 | (1H-benzo[d]imidazol-2-yl)(4-(3-((1R,3R)-3-hydroxycyclohexyl)pyrazin-2-yloxy)phenyl)methanone | 415 |
| 275 | 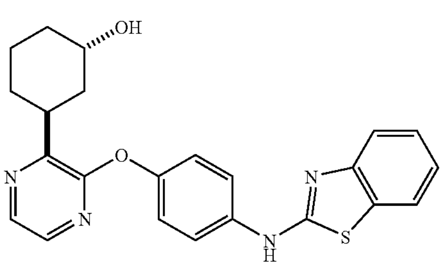 | +++++ | See ex. 192 | (1S,3S)-3-(3-(4-(benzo[d]thiazol-2-ylamino)phenoxy)pyrazin-2-yl)cyclohexanol | 419 |
| 276 | 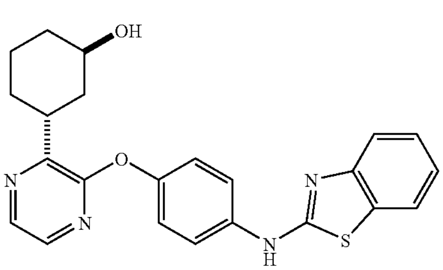 | +++++ | See ex. 192 | (1R,3R)-3-(3-(4-(benzo[d]thiazol-2-ylamino)phenoxy)pyrazin-2-yl)cyclohexanol | 419 |

TABLE (XIIA)-continued

EXAMPLES 261 TO 280 ARE TABULATED BELOW.

| Ex. No | Structure | IC50 (uM) | Prep* | IUPAC names | MS |
|---|---|---|---|---|---|
| 277 | 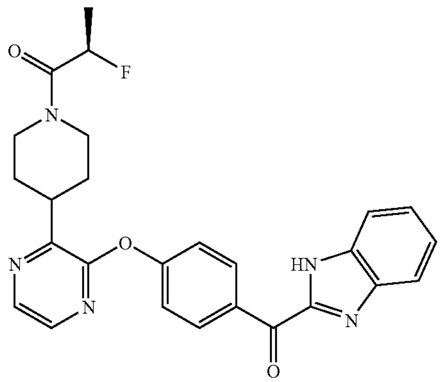 | +++++ | See ex. 234 | (R)-1-(4-(3-(4-(1H-benzo[d]imidazole-2-carbonyl)phenoxy)pyrazin-2-yl)piperidin-1-yl)-2-fluoropropan-1-one | 474 |
| 278 | 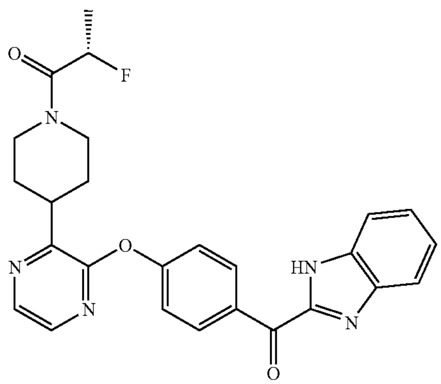 | +++++ | See ex. 234 | (S)-1-(4-(3-(4-(1H-benzo[d]imidazole-2-carbonyl)phenoxy)pyrazin-2-yl)piperidin-1-yl)-2-fluoropropan-1-one | 474 |
| 279 | 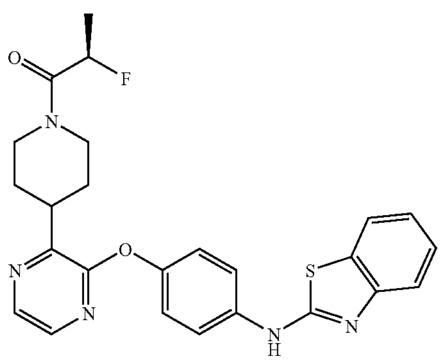 | +++++ | See ex. 235 | (R)-1-(4-(3-(4-(benzo[d]thiazol-2-ylamino)phenoxy)pyrazin-2-yl)piperidin-1-yl)-2-fluoropropan-1-one | 478 |
| 280 | 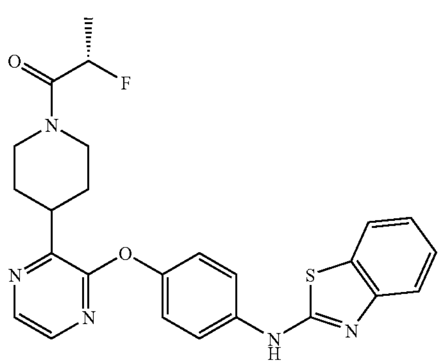 | +++++ | See ex. 235 | (S)-1-(4-(3-(4-(benzo[d]thiazol-2-ylamino)phenoxy)pyrazin-2-yl)piperidin-1-yl)-2-fluoropropan-1-one | 478 |

TABLE (XIIA)-continued

EXAMPLES 261 TO 280 ARE TABULATED BELOW.

| Ex. No | Structure | IC50 (uM) | Prep* | IUPAC names | MS |
|---|---|---|---|---|---|
| 281 | 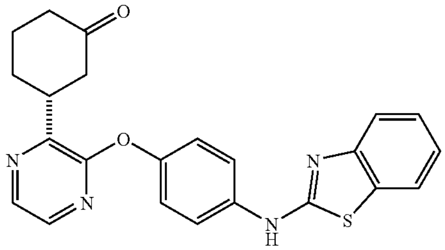 | +++++ | See ex. 194 | (R)-3-(3-(4-(benzo[d]thiazol-2-ylamino)phenoxy)pyrazin-2-yl)cyclohexanone | 417 |
| 282 | 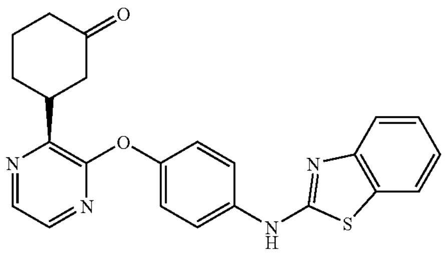 | +++++ | See ex. 194 | (S)-3-(3-(4-(benzo[d]thiazol-2-ylamino)phenoxy)pyrazin-2-yl)cyclohexanone | 417 |

BIOLOGICAL EXAMPLES

Example 1

MPDE10A7 ENZYME ACTIVITY AND INHIBITION

Enzyme Activity. An IMAP TR-FRET assay was used to analyze the enzyme activity (Molecular Devices Corp., Sunnyvale Calif.). 5 μL of serial diluted PDE10A (BPS Bioscience, San Diego, Calif.) or tissue homogenate was incubated with equal volumes of diluted fluorescein labeled cAMP or cGMP for 60 min in 384-well polystyrene assay plates (Corning, Corning, N.Y.) at room temperature. After incubation, the reaction was stopped by adding 60 μL, of diluted binding reagents and was incubated for 3 hours to overnight at room temperature. The plates were read on an Envision (Perkin Elmer, Waltham, Mass.) for time resolved fluorescence resonance energy transfer. The data were analyzed with GraphPad Prism (La Jolla, Calif.).

Enzyme Inhibition. To check the inhibition profile, 5 μL, of serial diluted compounds were incubated with 5 μL, of diluted PDE10 enzyme (BPS Bioscience, San Diego, Calif.) or tissue homogenate in a 384-well polystyrene assay plate (Corning, Corning, N.Y.) for 30 min at room temperature. After incubation, 10 μL, of diluted fluorescein labeled cAMP or cGMP substrate were added and incubated for 60 min at room temperature. The reaction was stopped by adding 60 μL, of diluted binding reagents and plates were read on an Envision (Perkin Elmer, Waltham, Mass.) for time resolved fluorescence resonance energy transfer. The data were analyzed with GraphPad Prism (La Jolla, Calif.).

Exemplary compounds of the invention having useful activity as measured by IC50 are shown in Table XIII below. The tabulated IC50 data represent an average IC50 data for each compound.

TABLE XIII

AVERAGE IC50 OF REPRESENTATIVE COMPOUNDS OF THE INVENTION.

| Structure | MS | Average IC50 (μM) |
|---|---|---|
| 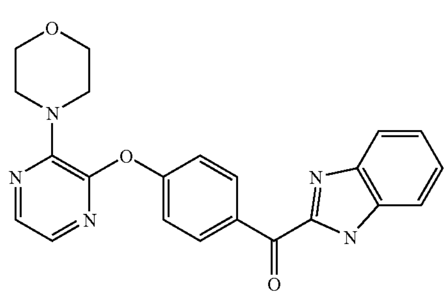 | 401.424 | 0.0156 |

TABLE XIII-continued

AVERAGE IC50 OF REPRESENTATIVE COMPOUNDS OF THE INVENTION.

| Structure | MS | Average IC50 (μM) |
|---|---|---|
| (structure) | 350.764 | 0.287 |
| (structure) | 415.451 | 0.00873 |
| (structure) | 429.478 | 0.0158 |
| (structure) | 419.507 | 0.00817 |
| (structure) | 419.463 | 0.00216 |

TABLE XIII-continued

AVERAGE IC50 OF REPRESENTATIVE COMPOUNDS OF THE INVENTION.

| Structure | MS | Average IC50 (μM) |
|---|---|---|
| 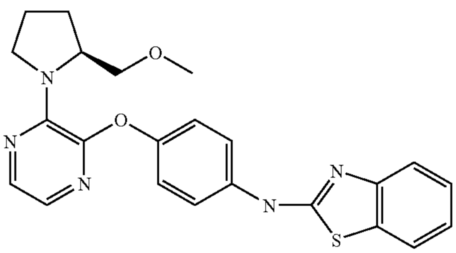 | 433.534 | 0.00944 |
| 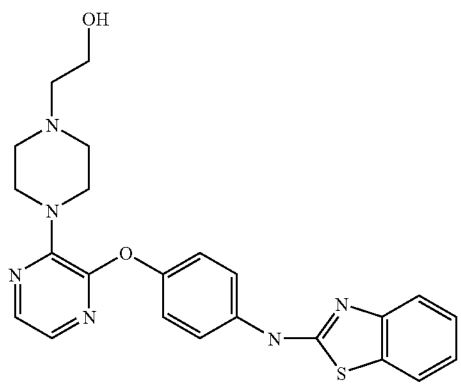 | 448.549 | 0.00844 |
| 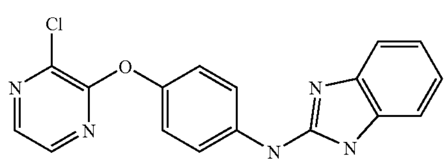 | 354.82 | 0.603 |
| 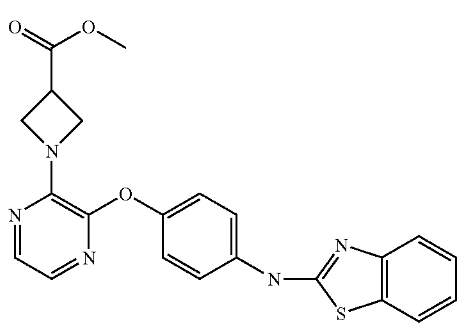 | 433.49 | 0.0084 |

TABLE XIII-continued
AVERAGE IC50 OF REPRESENTATIVE COMPOUNDS OF THE INVENTION.
| Structure | MS | Average IC50 (μM) |
|---|---|---|
| 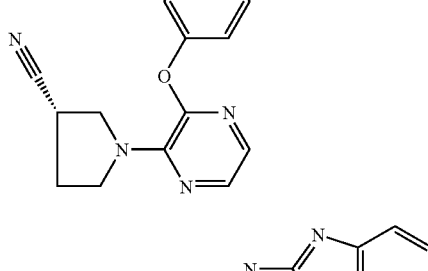 | 414.491 | 0.0033 |
| 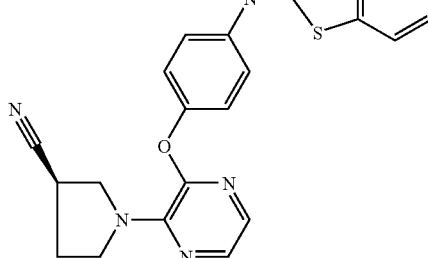 | | |
| 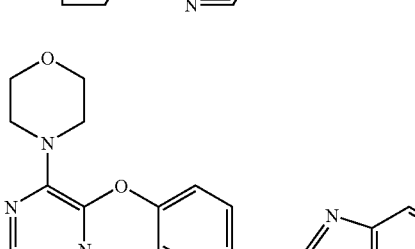 | 418.475 | 0.502 |
| 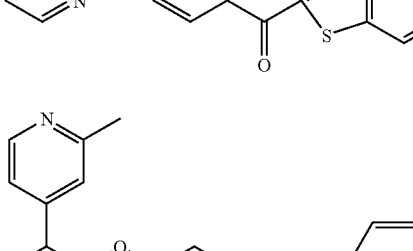 | 407.431 | 0.00567 |
| 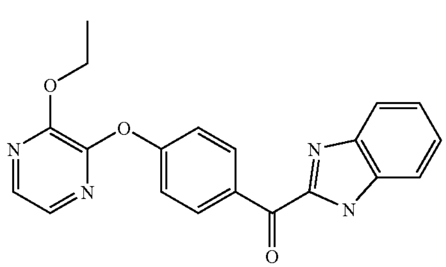 | 360.371 | 0.046 |

TABLE XIII-continued

AVERAGE IC50 OF REPRESENTATIVE COMPOUNDS OF THE INVENTION.

| Structure | MS | Average IC50 (μM) |
|---|---|---|
| 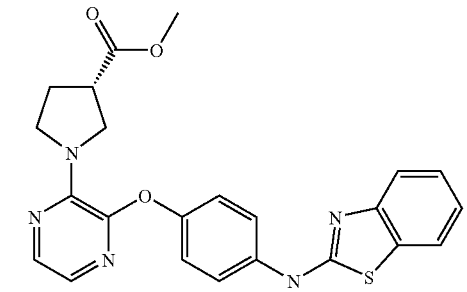 | 447.517 | 0.023 |
| | | |
| 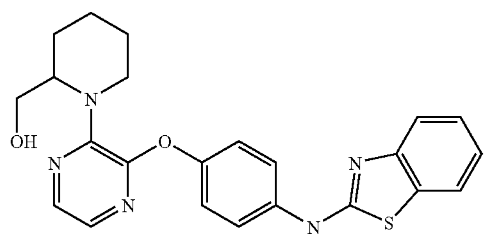 | 433.534 | 0.0217 |
| 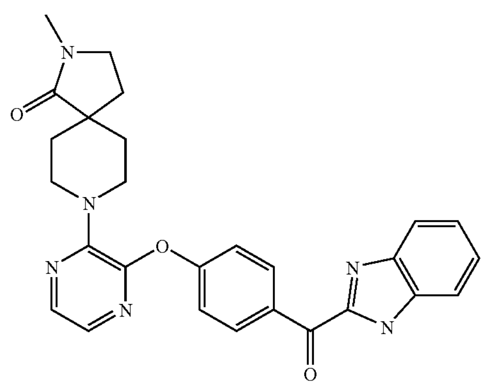 | 482.541 | 0.0128 |
| 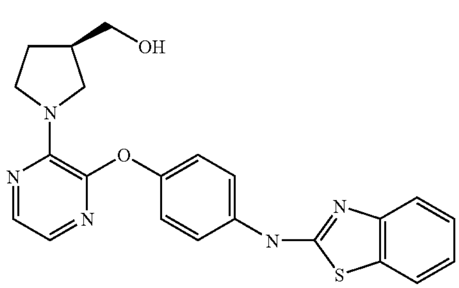 | 419.507 | 0.00289 |

TABLE XIII-continued

AVERAGE IC50 OF REPRESENTATIVE COMPOUNDS OF THE INVENTION.

| Structure | MS | Average IC50 (μM) |
|---|---|---|
| 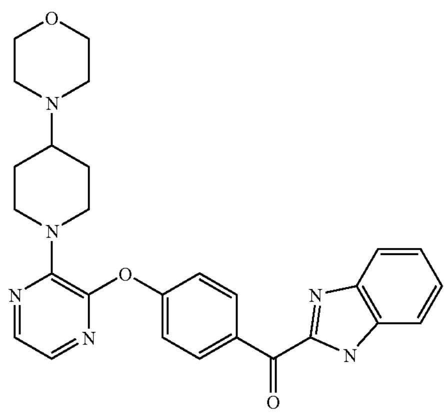 | 484.557 | 0.027 |
| 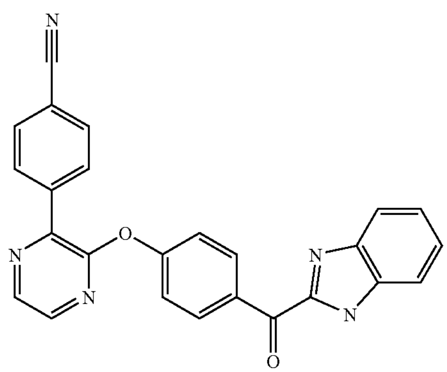 | 417.427 | 0.0175 |
| | 447.561 | 0.00955 |
| | 447.561 | 0.0185 |

TABLE XIII-continued

AVERAGE IC50 OF REPRESENTATIVE COMPOUNDS OF THE INVENTION.

| Structure | MS | Average IC50 (μM) |
|---|---|---|
| | 447.561 | 0.06 |
| 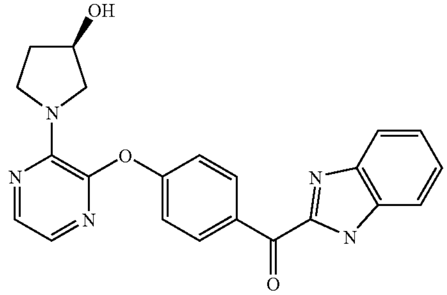 | 401.424 | 0.0076 |
| | | |
| 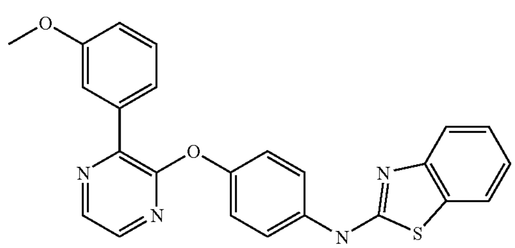 | 426.498 | 0.0961 |
| | 447.561 | 0.0395 |

TABLE XIII-continued
AVERAGE IC50 OF REPRESENTATIVE COMPOUNDS OF THE INVENTION.
| Structure | MS | Average IC50 (μM) |
|---|---|---|
| 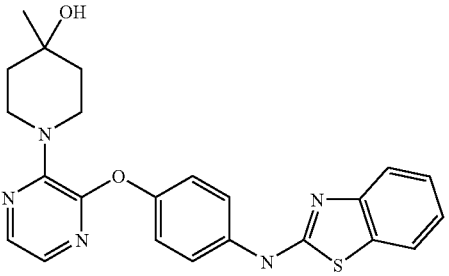 | 433.534 | 0.00808 |
| 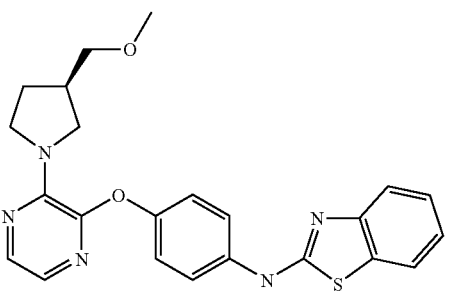 | 433.534 | 0.0226 |
| 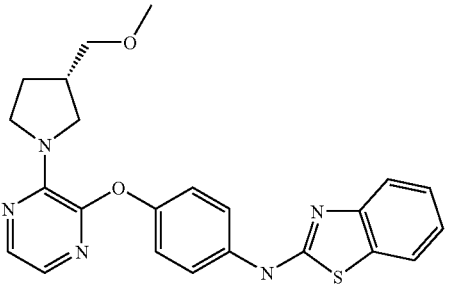 | | |
| 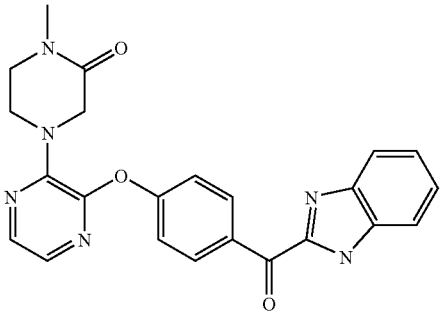 | 428.45 | 0.00216 |
| 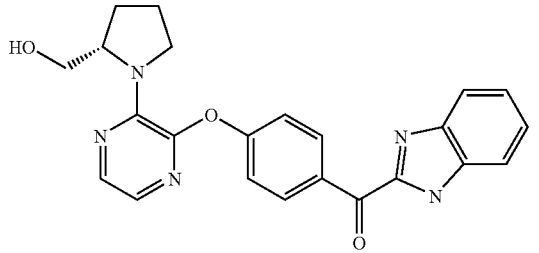 | 415.451 | 0.00112 |

TABLE XIII-continued

AVERAGE IC50 OF REPRESENTATIVE COMPOUNDS OF THE INVENTION.

| Structure | MS | Average IC50 (μM) |
|---|---|---|
| 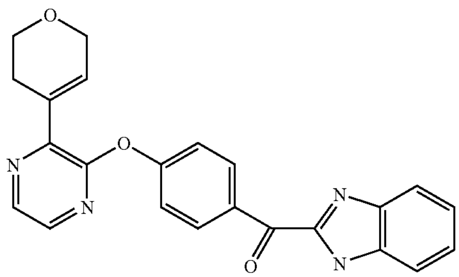 | 398.42 | 0.00336 |
| 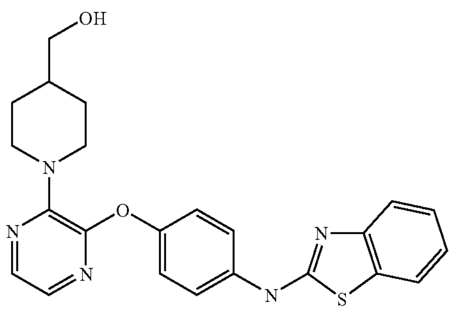 | 433.534 | 0.000117 |
| 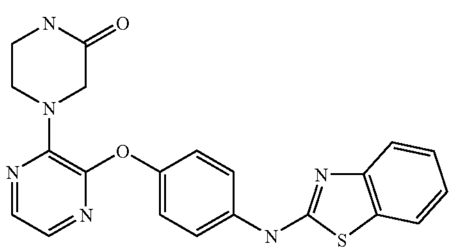 | 418.479 | 0.00641 |
| 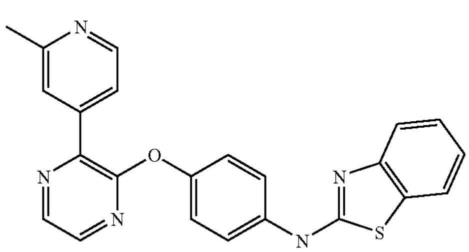 | 411.487 | 0.0175 |
| 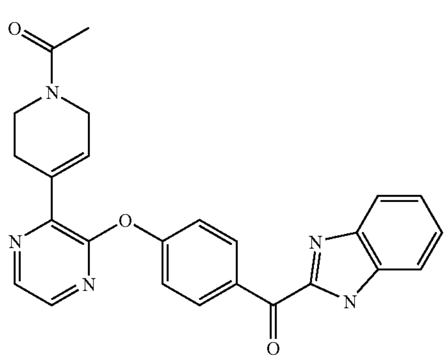 | 439.473 | 0.00116 |

TABLE XIII-continued
AVERAGE IC50 OF REPRESENTATIVE COMPOUNDS OF THE INVENTION.
| Structure | MS | Average IC50 (µM) |
|---|---|---|
| 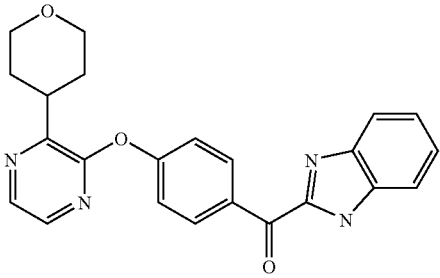 | 400.436 | 0.000486 |
| 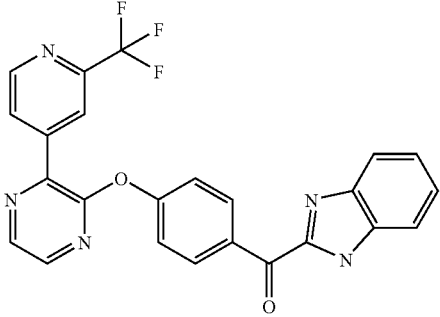 | 461.402 | 0.242 |
| 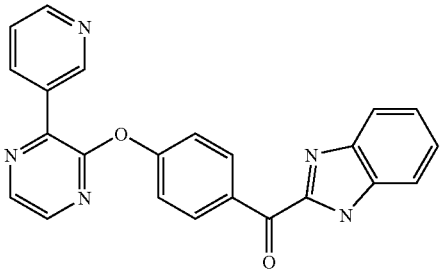 | 393.405 | 0.00805 |
| 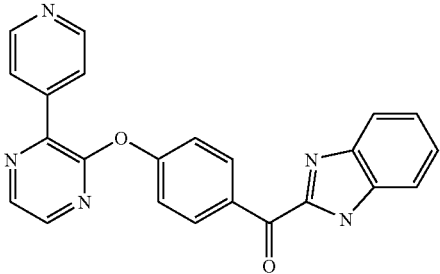 | 393.405 | 0.0075 |
| 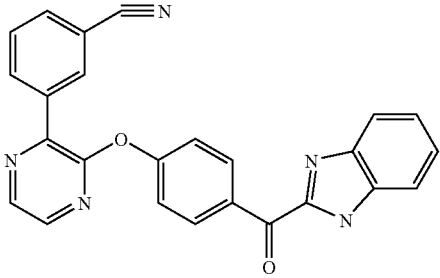 | 417.427 | 0.042 |

TABLE XIII-continued

AVERAGE IC50 OF REPRESENTATIVE COMPOUNDS OF THE INVENTION.

| Structure | MS | Average IC50 (μM) |
|---|---|---|
| 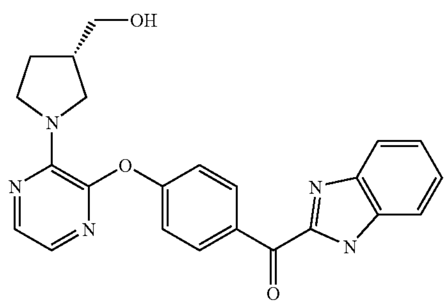 | 415.451 | 0.00254 |
| 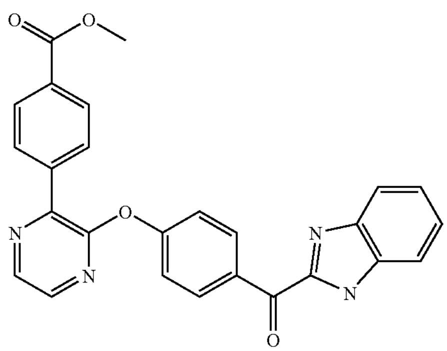 | 450.452 | 0.033 |
| 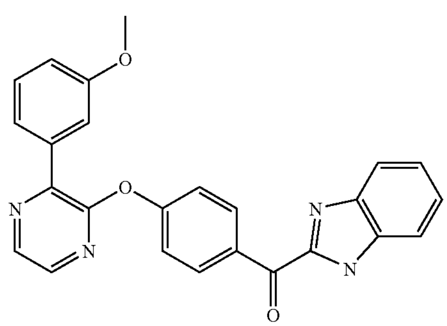 | 422.442 | 0.036 |
| 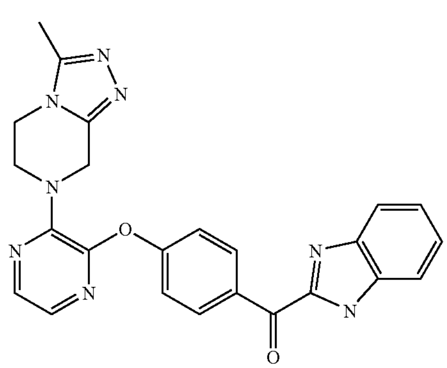 | 452.476 | 0.00603 |

TABLE XIII-continued

AVERAGE IC50 OF REPRESENTATIVE COMPOUNDS OF THE INVENTION.

| Structure | MS | Average IC50 (μM) |
|---|---|---|
| 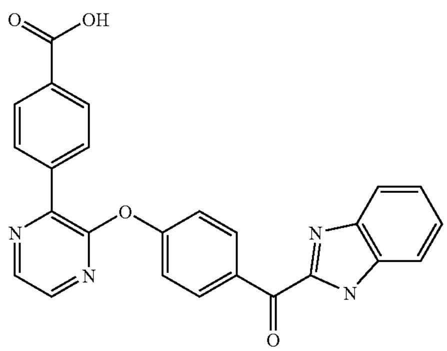 | 436.425 | 0.00206 |
| 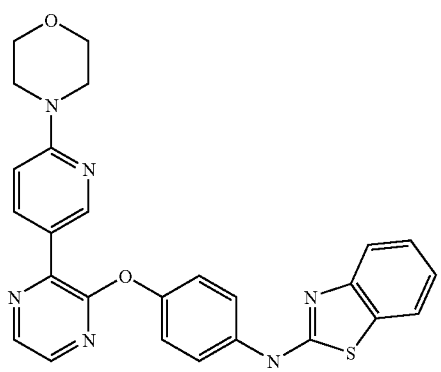 | 482.566 | 0.078 |
| 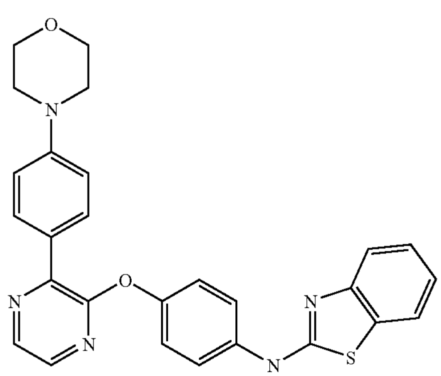 | 481.578 | 1.07 |
| 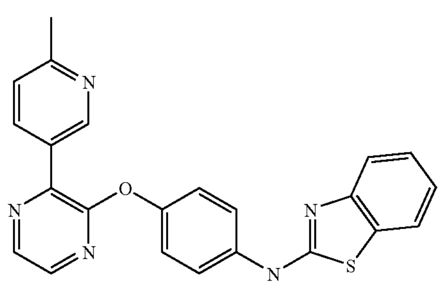 | 411.487 | 0.0113 |

TABLE XIII-continued

AVERAGE IC50 OF REPRESENTATIVE COMPOUNDS OF THE INVENTION.

| Structure | MS | Average IC50 (μM) |
|---|---|---|
| 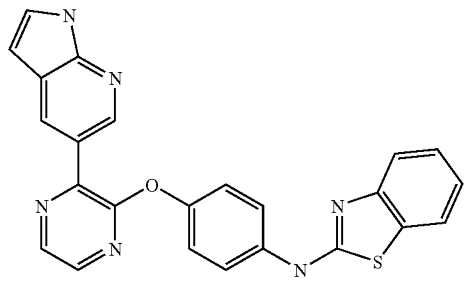 | 436.497 | 0.076 |
| 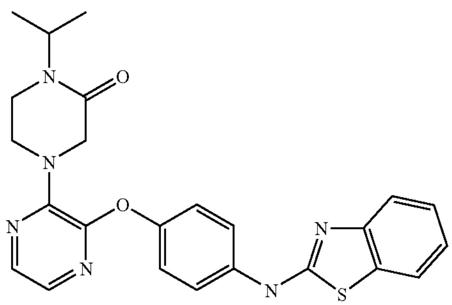 | 460.56 | 0.0127 |
| 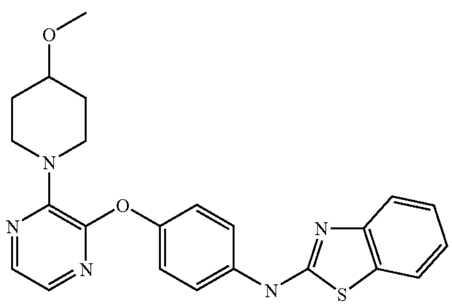 | 433.534 | 0.037 |
| 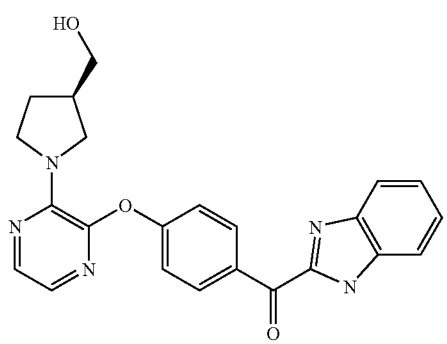 | 415.451 | 0.00205 |
| 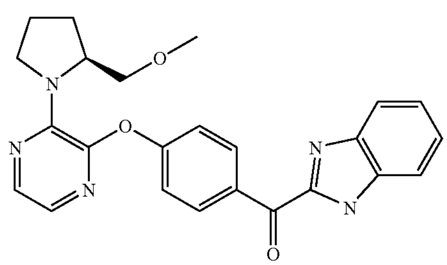 | 429.478 | 0.00137 |

TABLE XIII-continued

AVERAGE IC50 OF REPRESENTATIVE COMPOUNDS OF THE INVENTION.

| Structure | MS | Average IC50 (μM) |
|---|---|---|
| 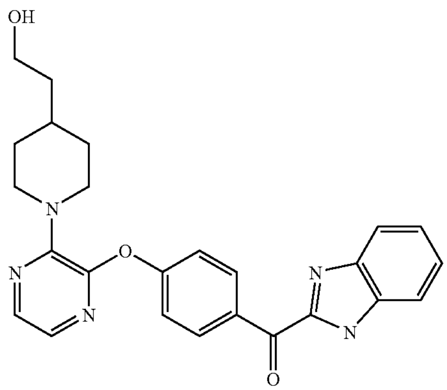 | 443.505 | 0.004 |
| 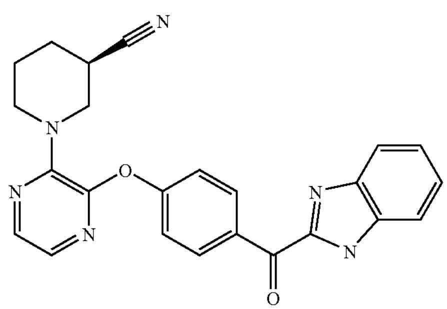 | 424.462 | 0.00679 |
| | | |
| 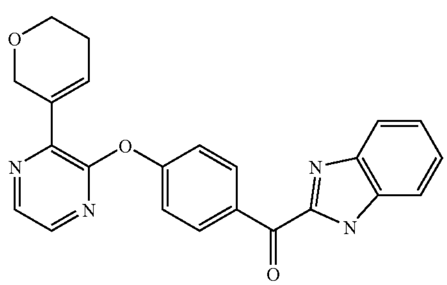 | 398.42 | 0.0161 |

TABLE XIII-continued

AVERAGE IC50 OF REPRESENTATIVE COMPOUNDS OF THE INVENTION.

| Structure | MS | Average IC50 (μM) |
|---|---|---|
| 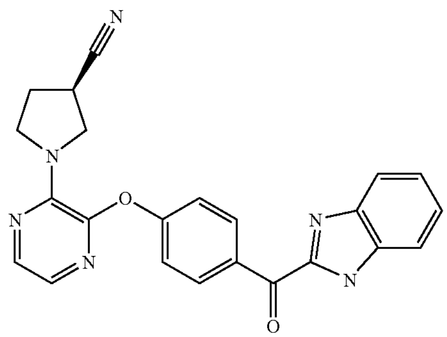 | 410.435 | 0.00132 |
| 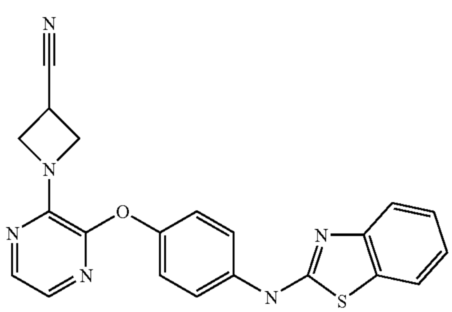 | 400.464 | 0.00675 |
| 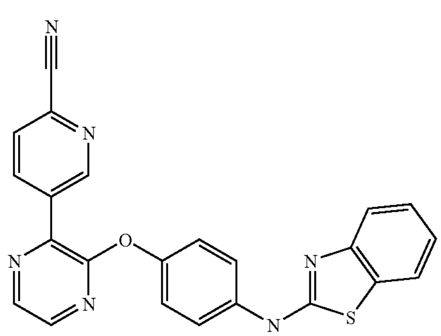 | 422.471 | 0.0638 |

TABLE XIII-continued

AVERAGE IC50 OF REPRESENTATIVE COMPOUNDS OF THE INVENTION.

| Structure | MS | Average IC50 (μM) |
|---|---|---|
| 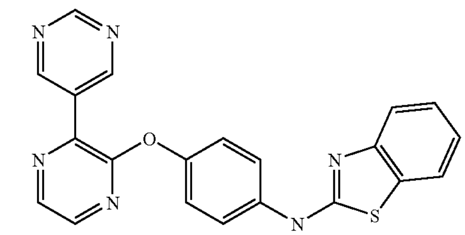 | 398.449 | 0.0129 |
| 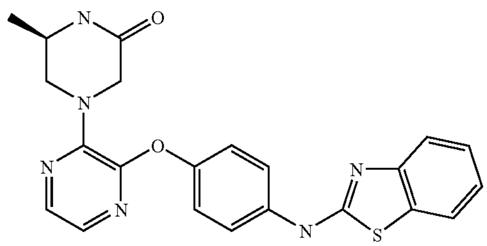 | 432.506 | 0.00464 |
| | | |
| 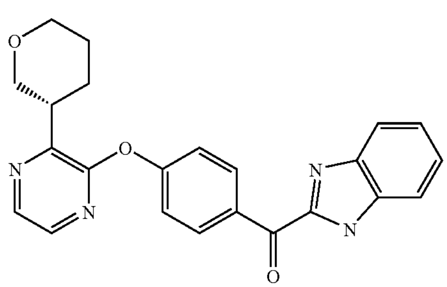 | 400.436 | 0.00259 |
| | | |

TABLE XIII-continued

AVERAGE IC50 OF REPRESENTATIVE COMPOUNDS OF THE INVENTION.

| Structure | MS | Average IC50 (µM) |
|---|---|---|
| 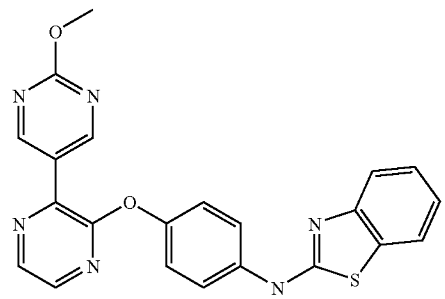 | 428.474 | 0.0232 |
| 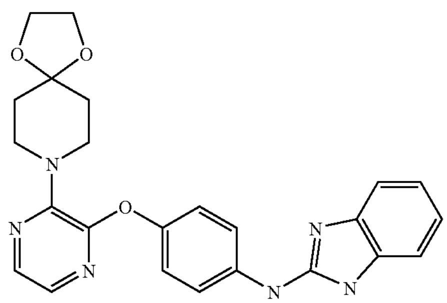 | 461.544 | 0.0678 |
| 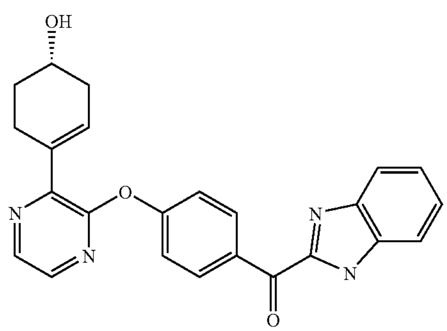 | 412.447 | 0.00169 |
| | | |

TABLE XIII-continued

AVERAGE IC50 OF REPRESENTATIVE COMPOUNDS OF THE INVENTION.

| Structure | MS | Average IC50 (μM) |
|---|---|---|
| 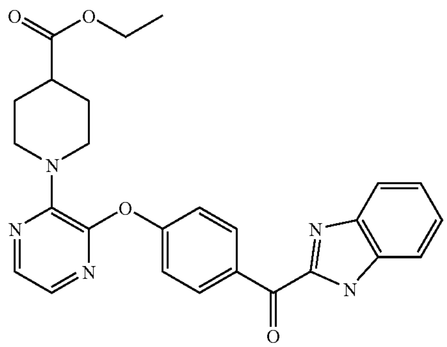 | 471.515 | 0.00519 |
| 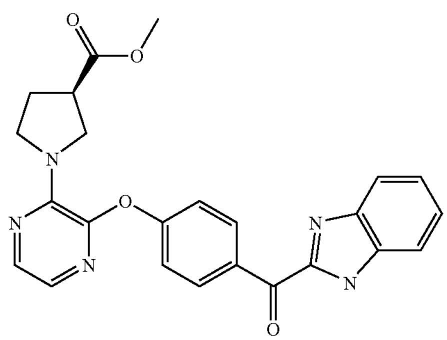 | 443.461 | 0.00343 |

TABLE XIII-continued

AVERAGE IC50 OF REPRESENTATIVE COMPOUNDS OF THE INVENTION.

| Structure | MS | Average IC50 (μM) |
|---|---|---|
| 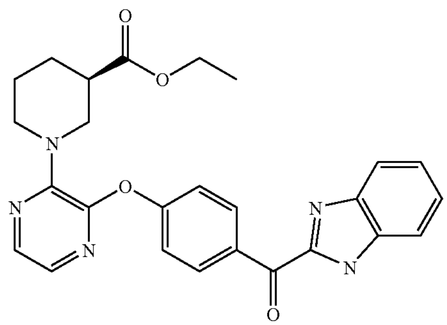 | 471.515 | 0.000773 |
| | | |
| 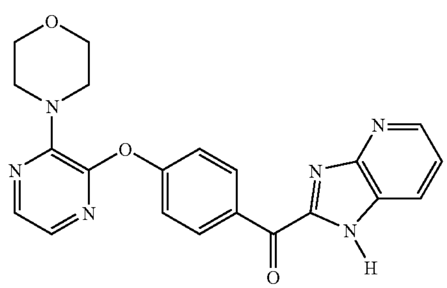 | 402.412 | 0.0116 |
| 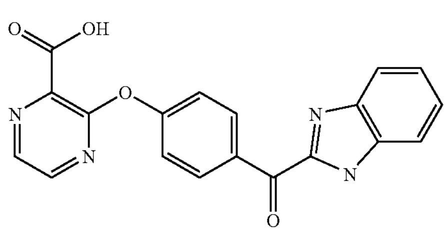 | 360.328 | 0.556 |
| 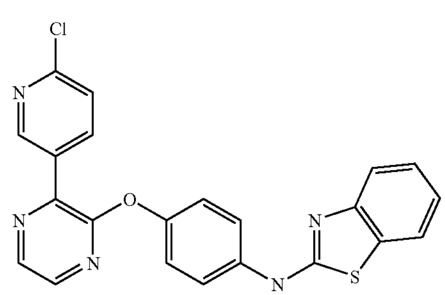 | 431.906 | 0.0146 |

TABLE XIII-continued
AVERAGE IC50 OF REPRESENTATIVE COMPOUNDS OF THE INVENTION.
| Structure | MS | Average IC50 (μM) |
|---|---|---|
| 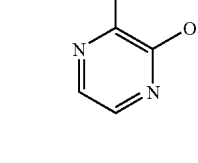 | 464.483 | 0.00808 |
| 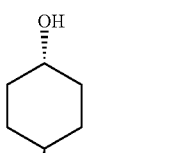 | 414.463 | 0.000426 |
| 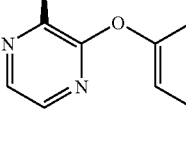 | 414.463 | 0.00104 |
| 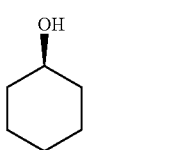 | | |
| 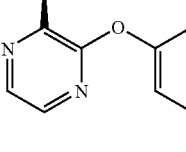 | 443.464 | 0.00359 |

TABLE XIII-continued

AVERAGE IC50 OF REPRESENTATIVE COMPOUNDS OF THE INVENTION.

| Structure | MS | Average IC50 (μM) |
|---|---|---|
| 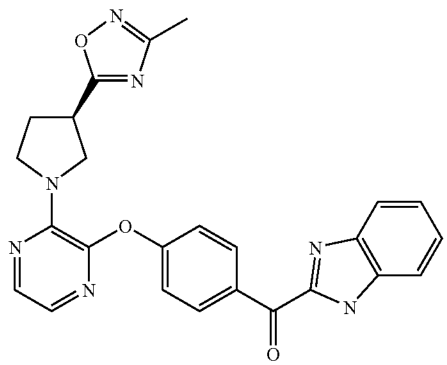 | 467.487 | 0.00373 |
|  | | |
| 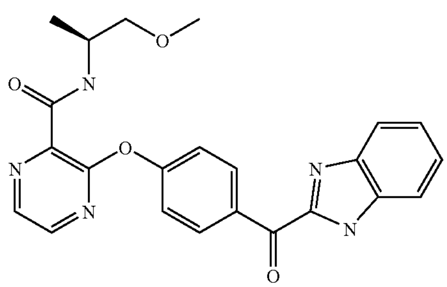 | 431.45 | 0.0454 |
| 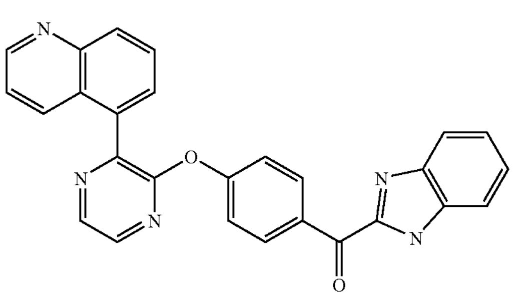 | 443.464 | 0.00318 |

TABLE XIII-continued

AVERAGE IC50 OF REPRESENTATIVE COMPOUNDS OF THE INVENTION.

| Structure | MS | Average IC50 (μM) |
|---|---|---|
| 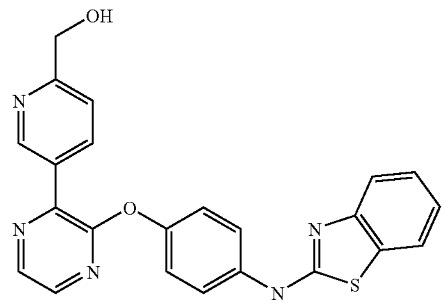 | 427.486 | 0.00412 |
| 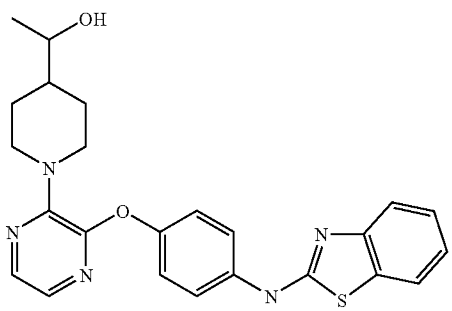 | 447.561 | 0.00461 |
| 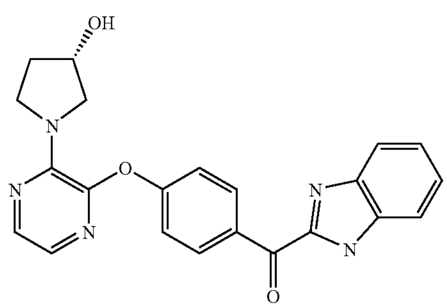 | 401.424 | 0.00512 |
| 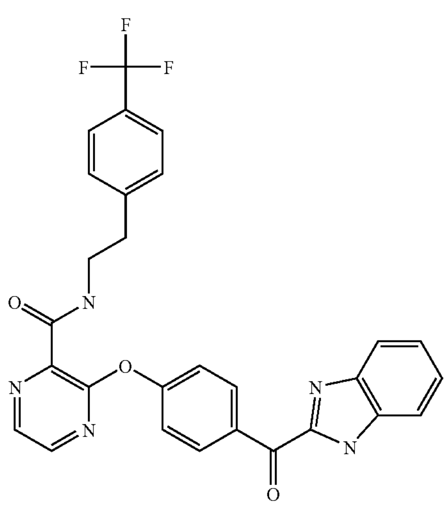 | 531.492 | 0.0246 |

TABLE XIII-continued
AVERAGE IC50 OF REPRESENTATIVE COMPOUNDS OF THE INVENTION.
| Structure | MS | Average IC50 (μM) |
|---|---|---|
| 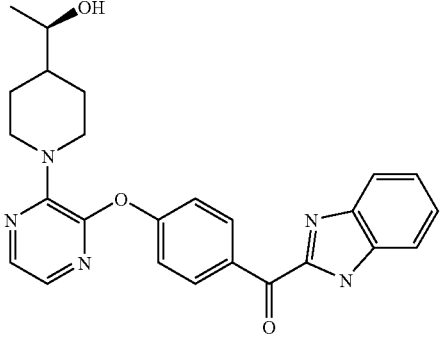 | 443.505 | 0.000749 |
| 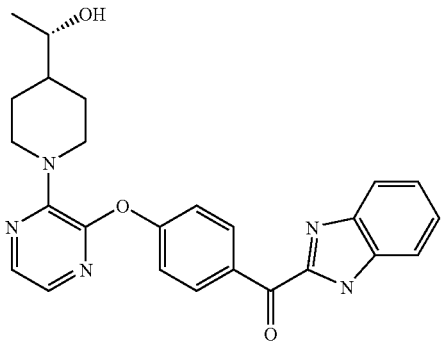 | | |
| 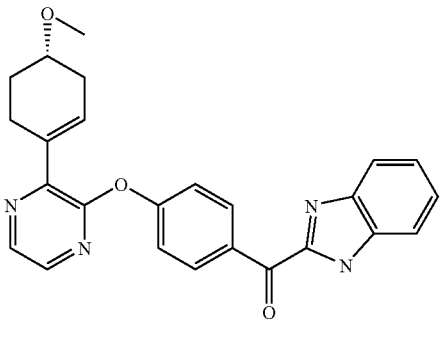 | 426.474 | 0.004 |
| 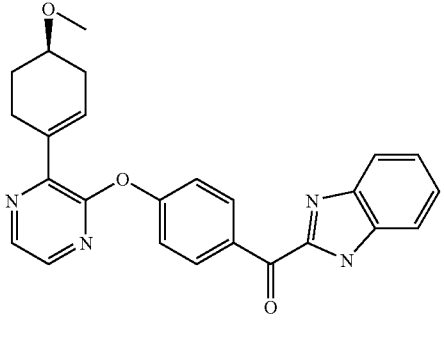 | | |

TABLE XIII-continued

AVERAGE IC50 OF REPRESENTATIVE COMPOUNDS OF THE INVENTION.

| Structure | MS | Average IC50 (μM) |
|---|---|---|
| (structure) | 443.461 | 0.00118 |
| (structure) | 368.754 | 1.58 |
| (structure) | 351.752 | 0.171 |
| (structure) | 443.505 | 0.00186 |
| (structure) | | |

TABLE XIII-continued

AVERAGE IC50 OF REPRESENTATIVE COMPOUNDS OF THE INVENTION.

| Structure | MS | Average IC50 (μM) |
|---|---|---|
| 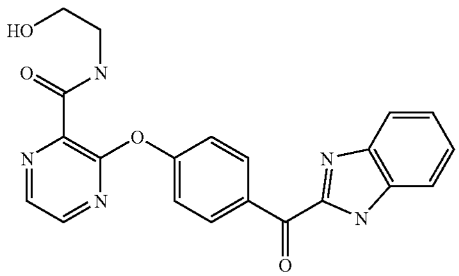 | 403.396 | 0.0655 |
| | 478.51 | 0.00472 |
| | 478.51 | |
| 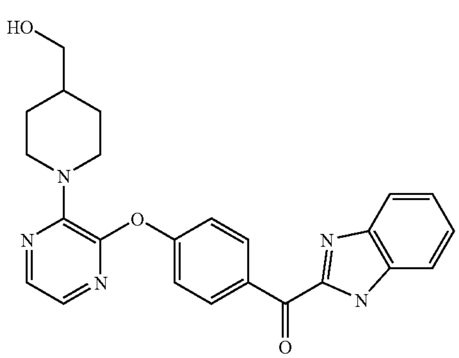 | 429.478 | 0.00032 |

TABLE XIII-continued
AVERAGE IC50 OF REPRESENTATIVE COMPOUNDS OF THE INVENTION.
| Structure | MS | Average IC50 (μM) |
|---|---|---|
| 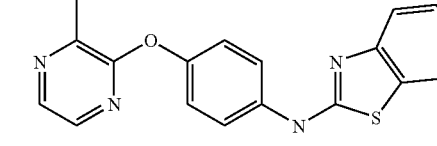 | 447.52 | 0.0144 |
| 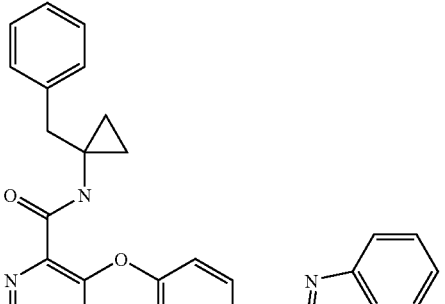 | 489.533 | 0.000575 |
| 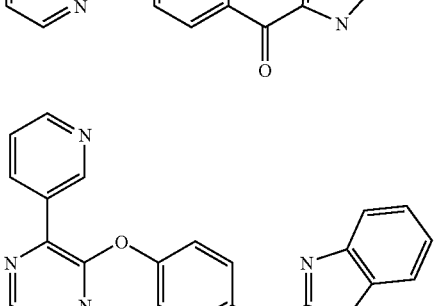 | 397.461 | 0.0104 |
| 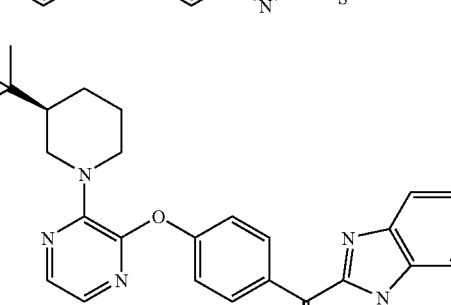 | 457.531 | 0.029 |
| 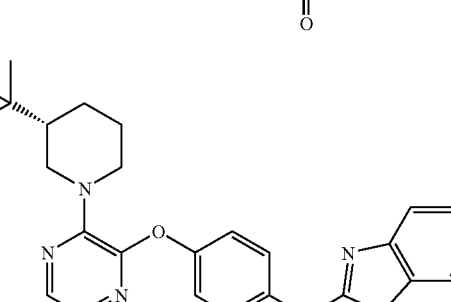 | | |

TABLE XIII-continued
AVERAGE IC50 OF REPRESENTATIVE COMPOUNDS OF THE INVENTION.
| Structure | MS | Average IC50 (µM) |
|---|---|---|
| 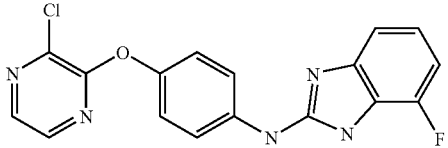 | 372.81 | 0.751 |
| 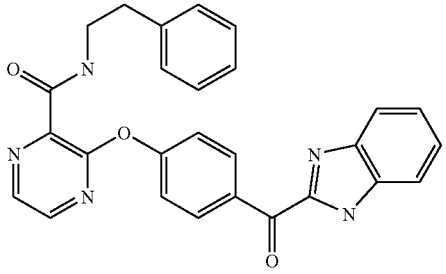 | 463.495 | 0.00447 |
| 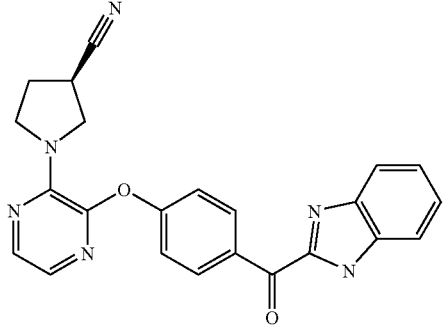 | 410.435 | 0.00176 |
| 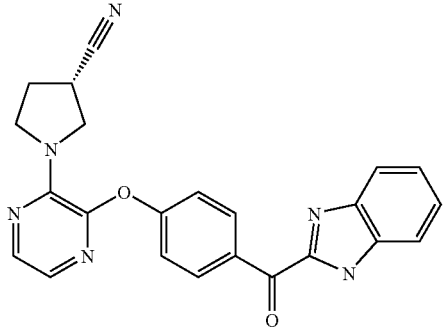 | 410.435 | 0.00132 |
| 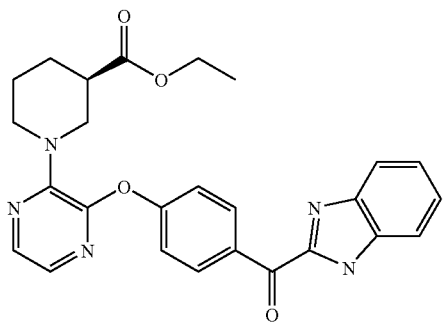 | 471.515 | 0.0108 |

TABLE XIII-continued

AVERAGE IC50 OF REPRESENTATIVE COMPOUNDS OF THE INVENTION.

| Structure | MS | Average IC50 (μM) |
|---|---|---|
| 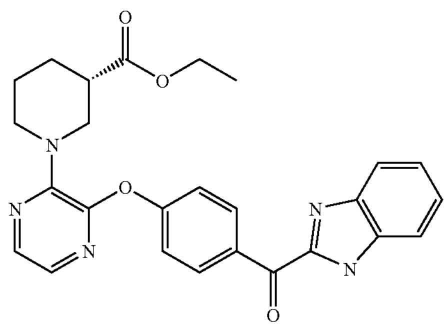 | 471.515 | 0.000843 |
|  | 372.81 | >30 |
|  | 372.81 | 0.538 |
|  | 432.506 | 0.00305 |
|  | 432.506 | 0.0171 |
|  | 372.81 | 0.614 |

TABLE XIII-continued
AVERAGE IC50 OF REPRESENTATIVE COMPOUNDS OF THE INVENTION.
| Structure | MS | Average IC50 (μM) |
|---|---|---|
| 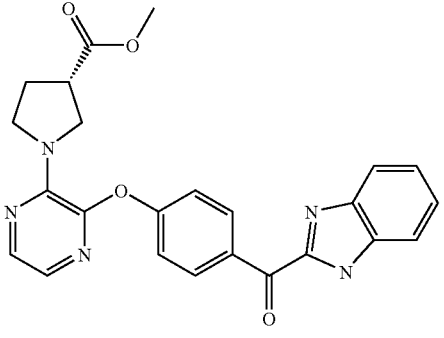 | 443.461 | 0.00421 |
| 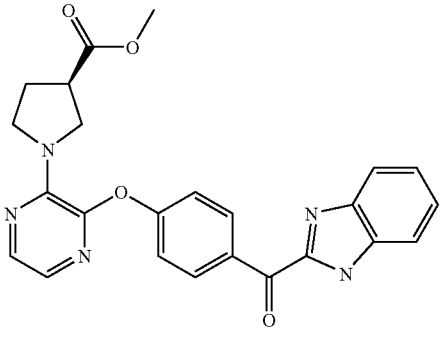 | 443.461 | 0.00135 |
| 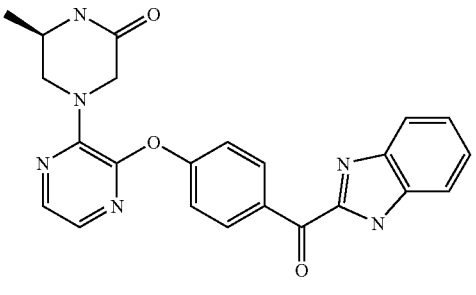 | 428.45 | 0.00257 |
| 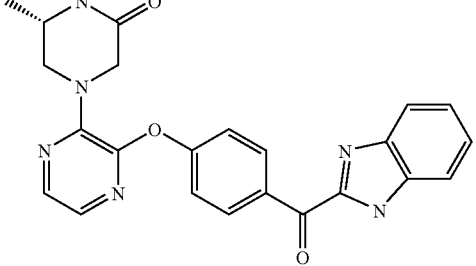 | | |

TABLE XIII-continued

AVERAGE IC50 OF REPRESENTATIVE COMPOUNDS OF THE INVENTION.

| Structure | MS | Average IC50 (μM) |
|---|---|---|
| 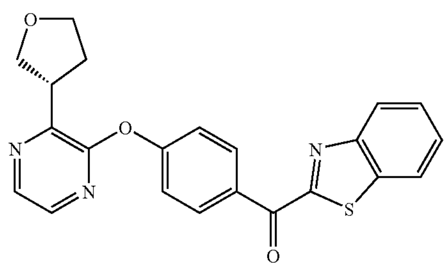 | 390.465 | 0.00203 |
| | | |
| 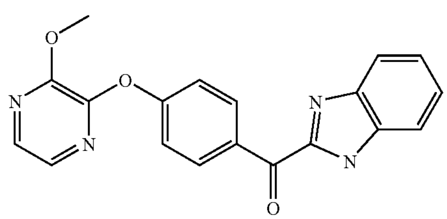 | 346.345 | 0.0436 |
| 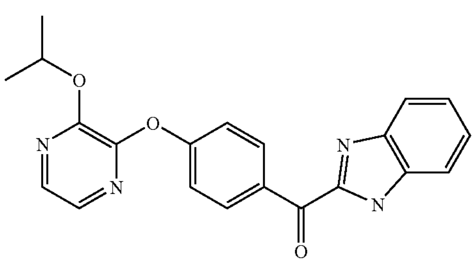 | 374.398 | 0.0566 |
| 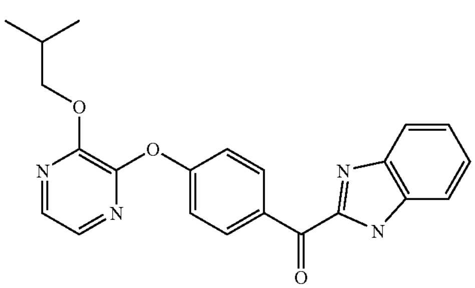 | 388.425 | 0.0262 |

TABLE XIII-continued
AVERAGE IC50 OF REPRESENTATIVE COMPOUNDS OF THE INVENTION.
| Structure | MS | Average IC50 (μM) |
|---|---|---|
| 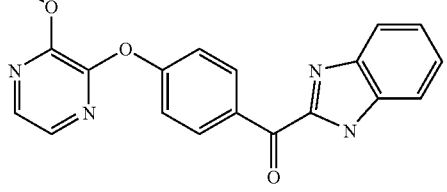 | 386.409 | 0.164 |
| 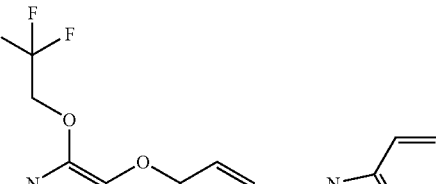 | 414.342 | 0.187 |
| 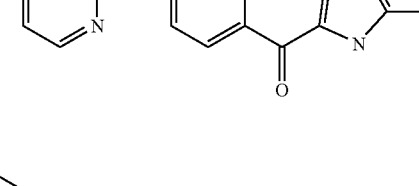 | 390.397 | 0.0291 |
| 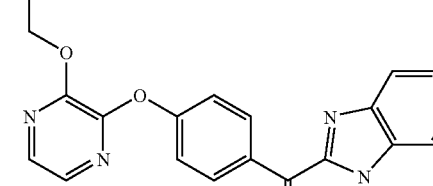 | 423.43 | 1.71 |
| 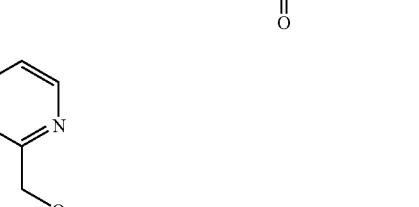 | 408.415 | 2.12 |

TABLE XIII-continued

AVERAGE IC50 OF REPRESENTATIVE COMPOUNDS OF THE INVENTION.

| Structure | MS | Average IC50 (μM) |
|---|---|---|
| 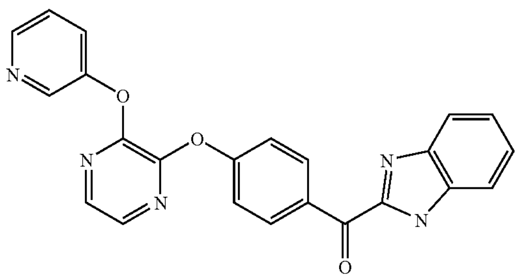 | 409.404 | 0.0515 |
| 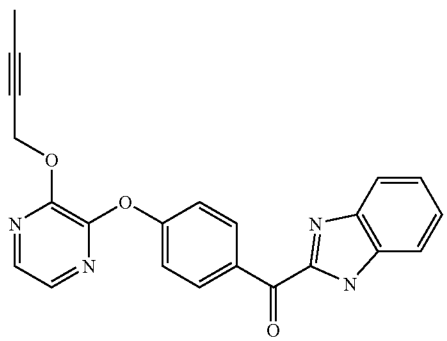 | 384.393 | 0.673 |
| 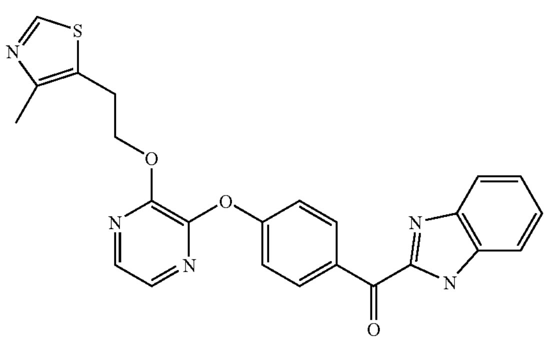 | 457.512 | 0.00186 |
| 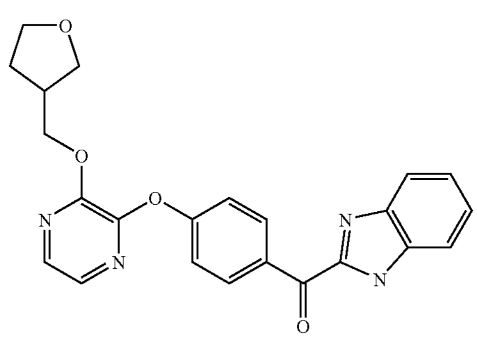 | 416.435 | 0.00556 |

TABLE XIII-continued

AVERAGE IC50 OF REPRESENTATIVE COMPOUNDS OF THE INVENTION.

| Structure | MS | Average IC50 ($\mu$M) |
|---|---|---|
| 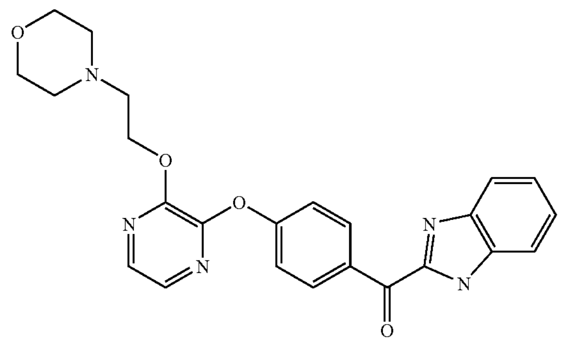 | 445.477 | 0.0895 |
| 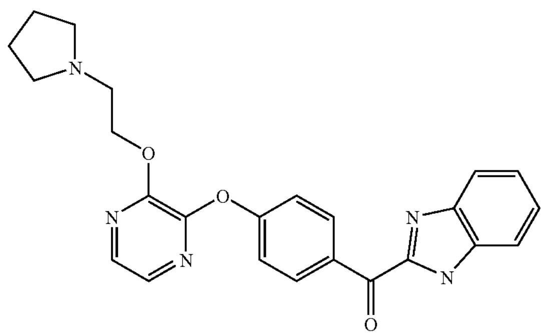 | 429.478 | 0.541 |
| 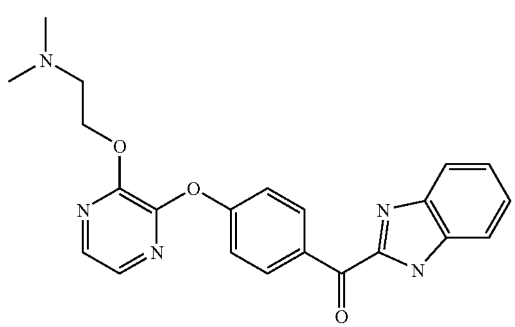 | 403.44 | 0.486 |
| 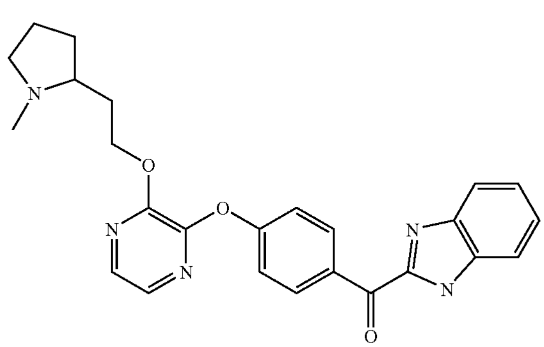 | 443.505 | 0.235 |

TABLE XIII-continued

AVERAGE IC50 OF REPRESENTATIVE COMPOUNDS OF THE INVENTION.

| Structure | MS | Average IC50 (μM) |
|---|---|---|
| 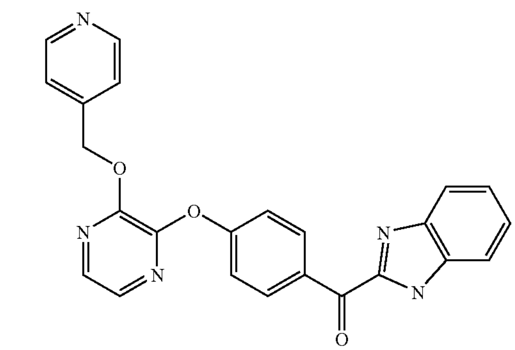 | 423.43 | 0.014 |
| 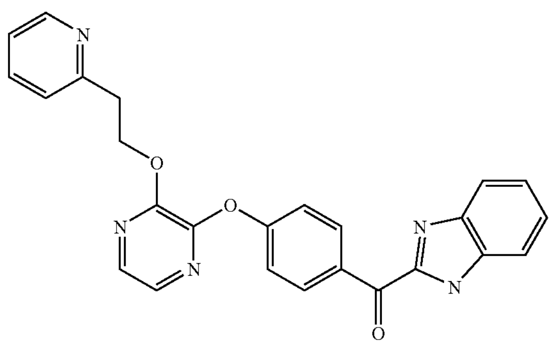 | 437.457 | 0.00805 |
| 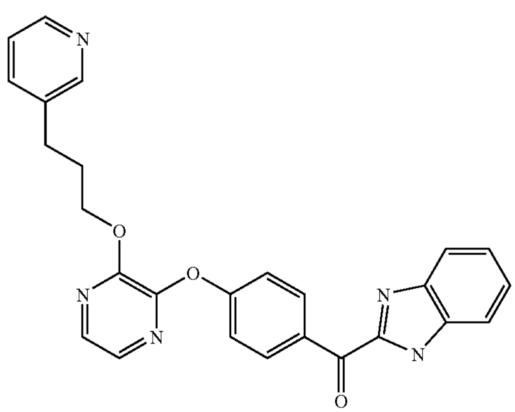 | 451.484 | 0.0109 |
| 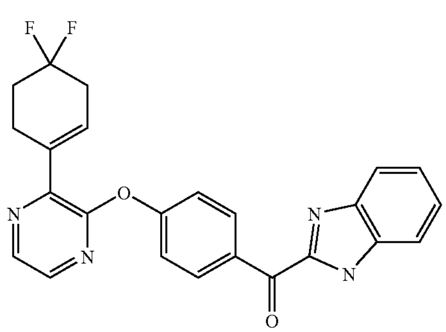 | 432.428 | 0.0142 |

TABLE XIII-continued

AVERAGE IC50 OF REPRESENTATIVE COMPOUNDS OF THE INVENTION.

| Structure | MS | Average IC50 (μM) |
|---|---|---|
| 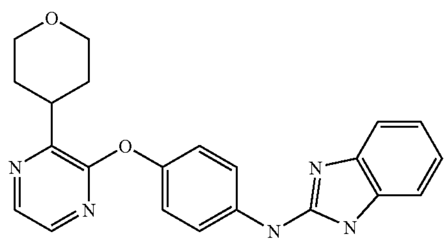 | 387.441 | 0.000101 |
| 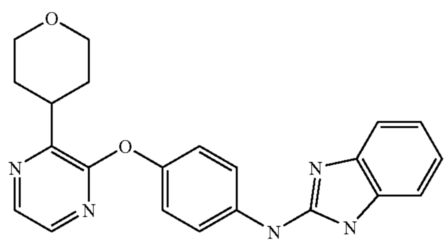 | 404.492 | 0.000606 |
| 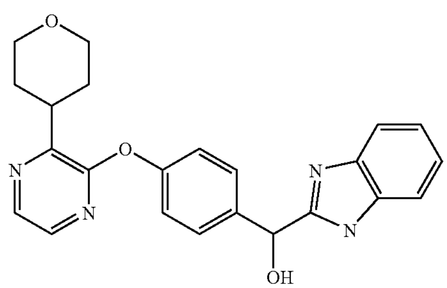 | 402.452 | 0.386 |
| 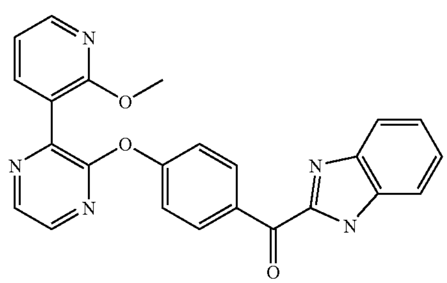 | 423.43 | 0.000321 |
| 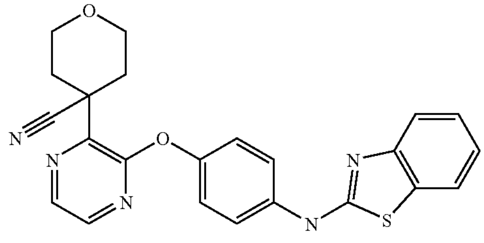 | 429.502 | 0.00446 |

TABLE XIII-continued

AVERAGE IC50 OF REPRESENTATIVE COMPOUNDS OF THE INVENTION.

| Structure | MS | Average IC50 (μM) |
|---|---|---|
| 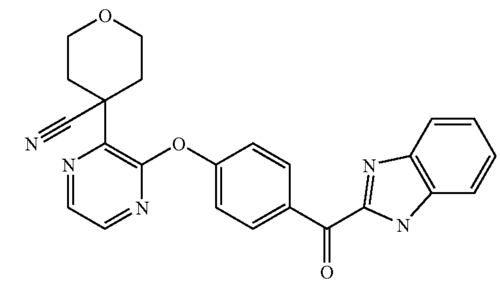 | 425.446 | 0.0025 |
| 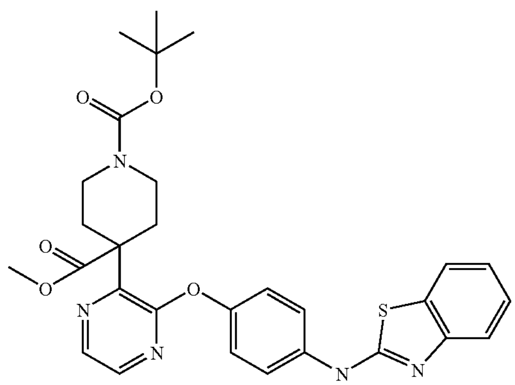 | 561.66 | 0.245 |
| 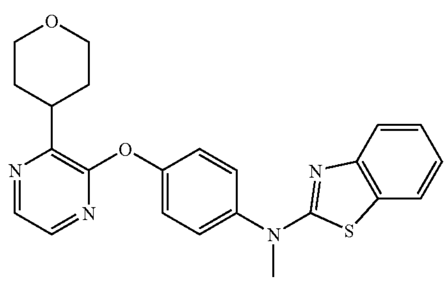 | 418.519 | 0.0118 |
| 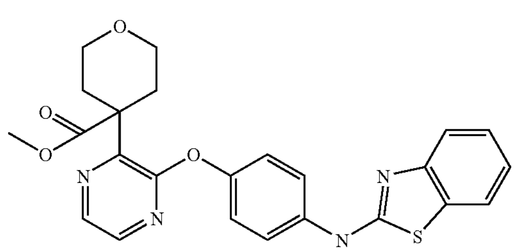 | 462.528 | 0.00628 |
| 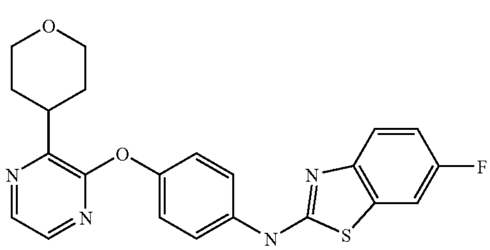 | 422.482 | 0.000661 |

TABLE XIII-continued

AVERAGE IC50 OF REPRESENTATIVE COMPOUNDS OF THE INVENTION.

| Structure | MS | Average IC50 (μM) |
|---|---|---|
| 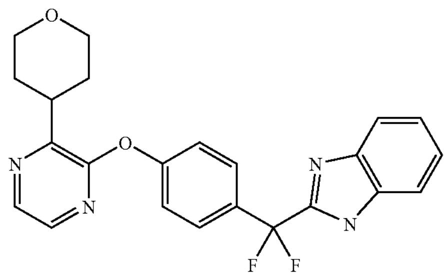 | 422.433 | 0.0529 |
| 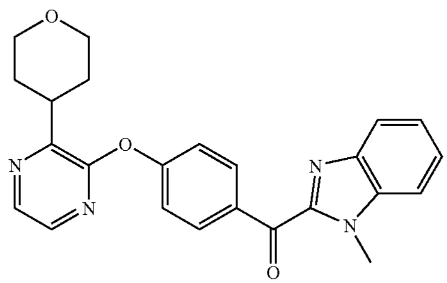 | 414.463 | 0.00131 |
| 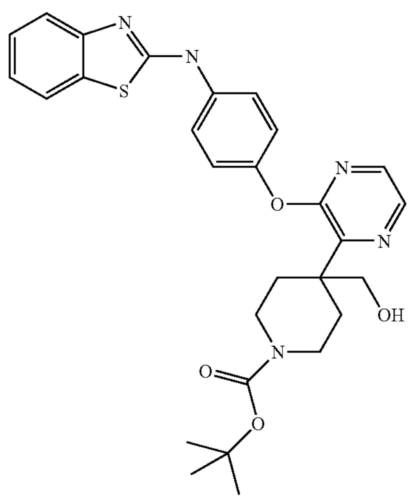 | 533.65 | 0.251 |
| 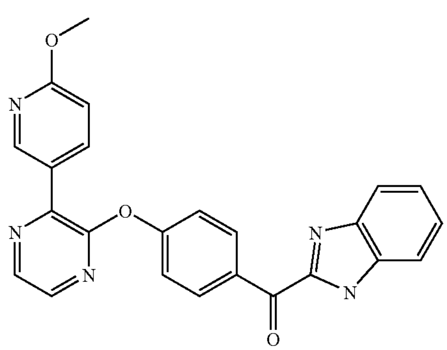 | 423.43 | 0.0142 |

TABLE XIII-continued

AVERAGE IC50 OF REPRESENTATIVE COMPOUNDS OF THE INVENTION.

| Structure | MS | Average IC50 (μM) |
|---|---|---|
| | 422.482 | 0.00264 |
| | 338.365 | 0.777 |
| 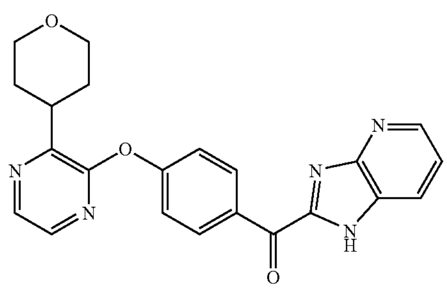 | 399.408 | 0.0317 |
| | 338.365 | 0.803 |
| | 422.482 | 0.0118 |
| | 338.365 | 12.5 |

TABLE XIII-continued

AVERAGE IC50 OF REPRESENTATIVE COMPOUNDS OF THE INVENTION.

| Structure | MS | Average IC50 (μM) |
|---|---|---|
| 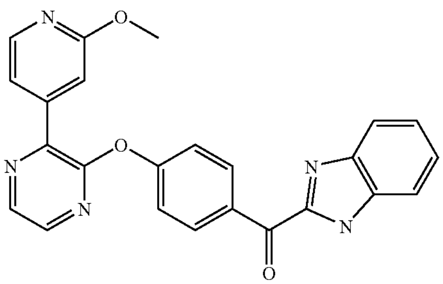 | 423.43 | 0.00756 |
| 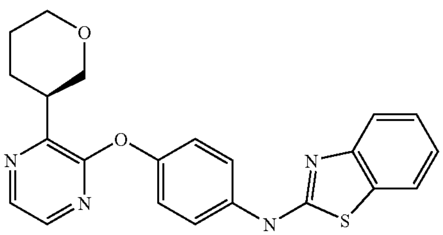 | 404.492 | 0.00243 |
| | | |
| 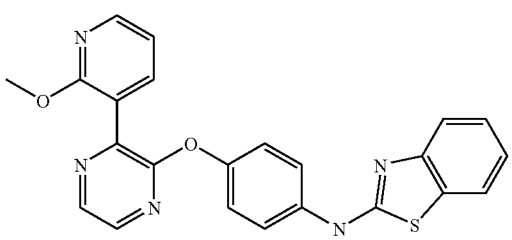 | 427.486 | 0.00367 |
| 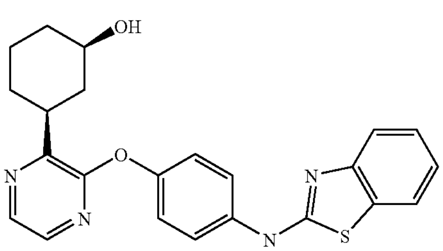 | 418.519 | 0.00232 |
| | | |

TABLE XIII-continued
AVERAGE IC50 OF REPRESENTATIVE COMPOUNDS OF THE INVENTION.
| Structure | MS | Average IC50 (μM) |
|---|---|---|
| 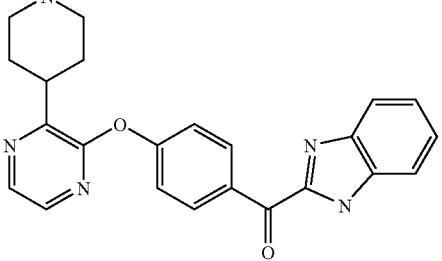 | 441.489 | 0.000182 |
| 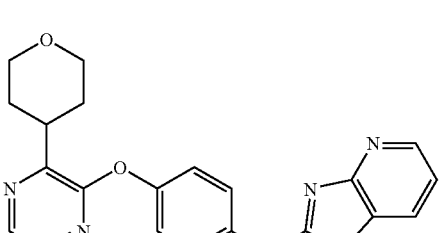 | 401.424 | 0.00772 |
| 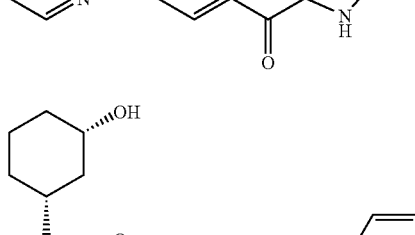 | 414.463 | 0.00102 |
| 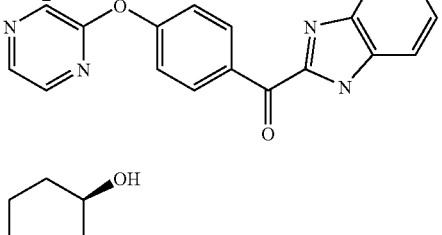 | | |
| 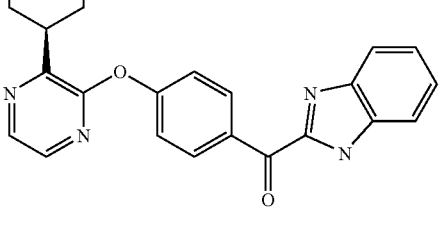 | 445.545 | 0.000059 |

TABLE XIII-continued

AVERAGE IC50 OF REPRESENTATIVE COMPOUNDS OF THE INVENTION.

| Structure | MS | Average IC50 (μM) |
|---|---|---|
| 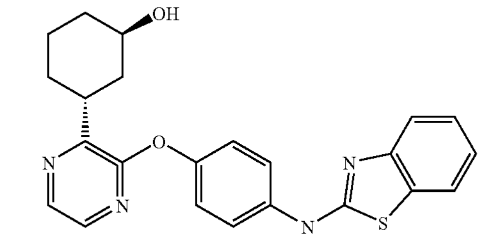 | 418.519 | 0.00157 |
| | | |
| 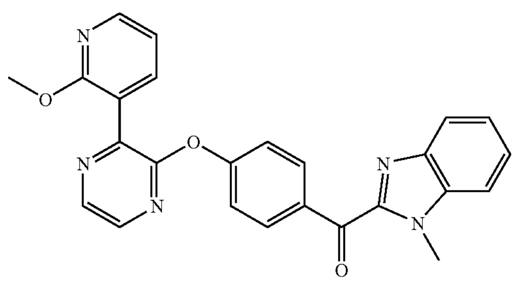 | 437.457 | 0.000594 |
| 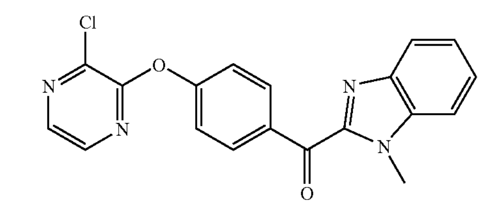 | 364.791 | 0.187 |
| 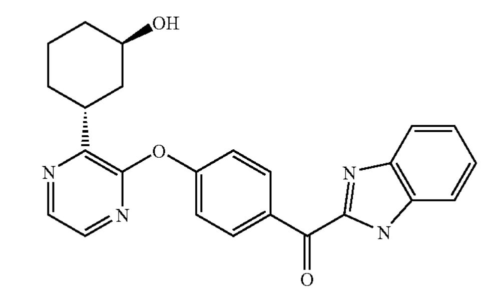 | 414.463 | 0.00125 |
| | | |

TABLE XIII-continued

AVERAGE IC50 OF REPRESENTATIVE COMPOUNDS OF THE INVENTION.

| Structure | MS | Average IC50 (μM) |
|---|---|---|
| 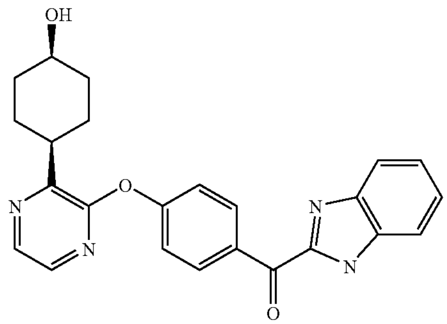 | 414.463 | 0.00136 |
| 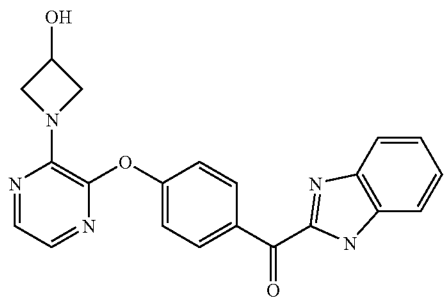 | 387.397 | 0.00694 |
| 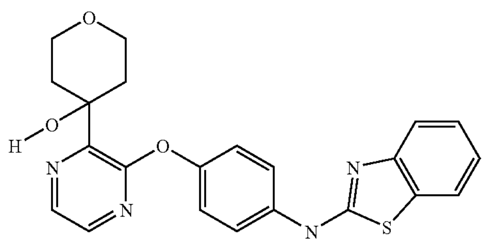 | 420.491 | 0.000902 |
| 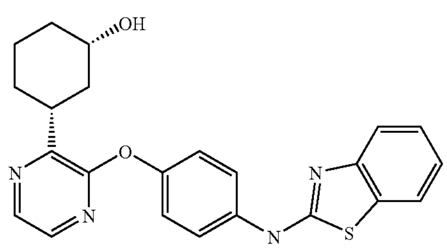 | 418.519 | 0.00133 |
| 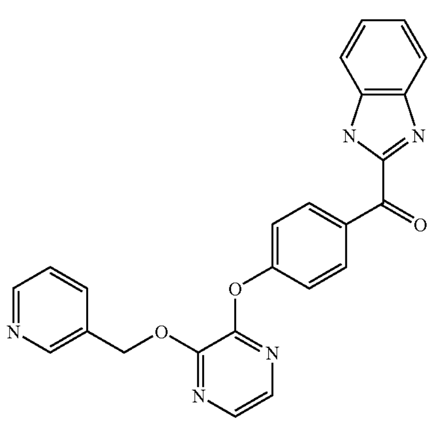 | 423.43 | 0.0388 |

TABLE XIII-continued
AVERAGE IC50 OF REPRESENTATIVE COMPOUNDS OF THE INVENTION.
| Structure | MS | Average IC50 (μM) |
|---|---|---|
| 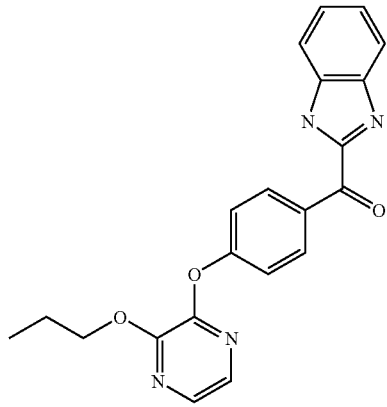 | 374.398 | 0.0252 |
| 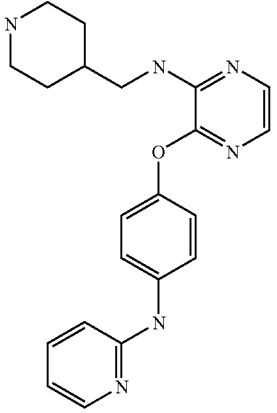 | 376.462 | 0.814 |
| 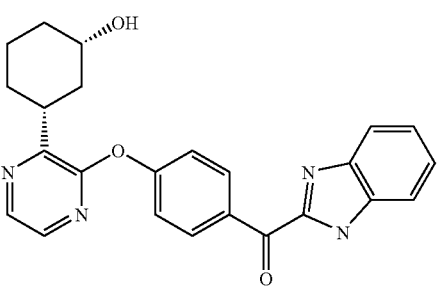 | 414.463 | 0.00116 |
| 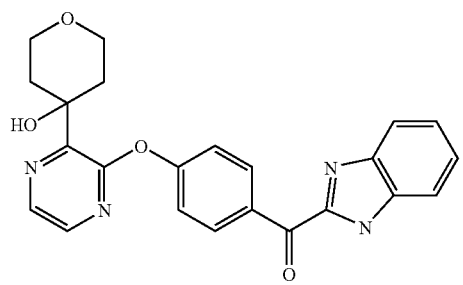 | 416.435 | 0.00216 |

TABLE XIII-continued

AVERAGE IC50 OF REPRESENTATIVE COMPOUNDS OF THE INVENTION.

| Structure | MS | Average IC50 (μM) |
|---|---|---|
| 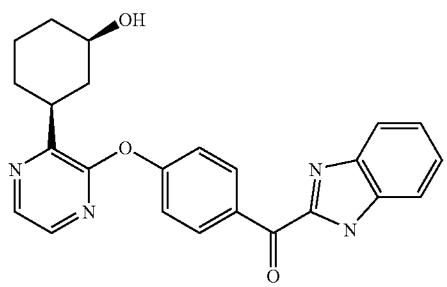 | 414.463 | 0.000961 |
| | 418.519 | 0.00222 |
| 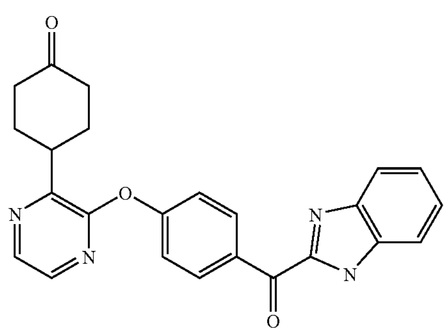 | 412.447 | 0.000199 |
| | 418.519 | 0.00254 |
| | 418.519 | 0.00134 |

TABLE XIII-continued

AVERAGE IC50 OF REPRESENTATIVE COMPOUNDS OF THE INVENTION.

| Structure | MS | Average IC50 (μM) |
|---|---|---|
| | 414.463 | 0.000992 |
| | 414.463 | 0.00112 |
| 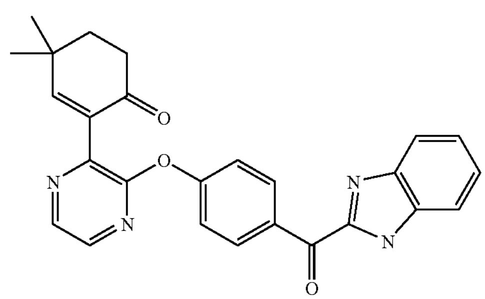 | 438.485 | 0.166 |
| 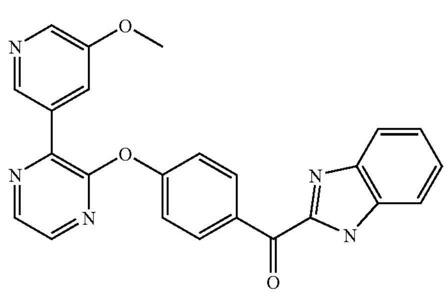 | 423.43 | 0.00542 |
| 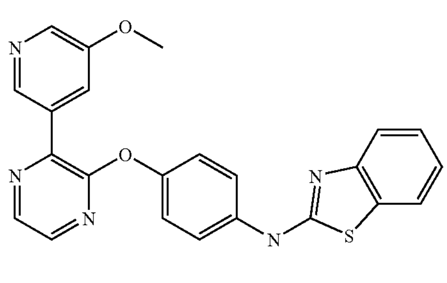 | 427.486 | 0.0122 |

TABLE XIII-continued

AVERAGE IC50 OF REPRESENTATIVE COMPOUNDS OF THE INVENTION.

| Structure | MS | Average IC50 ($\mu$M) |
|---|---|---|
| | 440.501 | 0.0418 |
| | 440.501 | 0.154 |
| 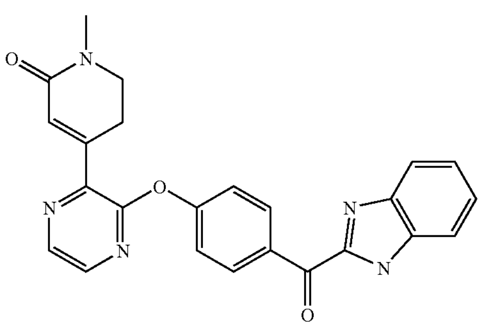 | 425.446 | 0.00186 |
| 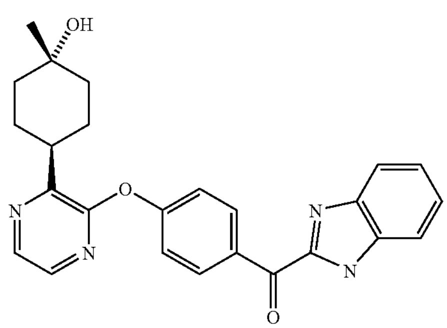 | 428.49 | 0.000748 |

TABLE XIII-continued

AVERAGE IC50 OF REPRESENTATIVE COMPOUNDS OF THE INVENTION.

| Structure | MS | Average IC50 (μM) |
|---|---|---|
| 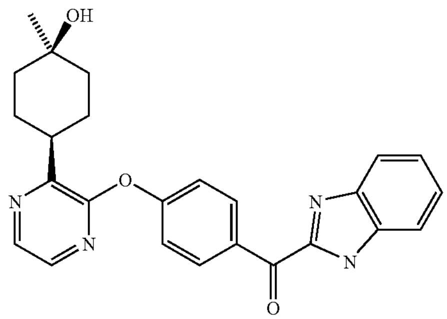 | 428.49 | 0.00142 |
| 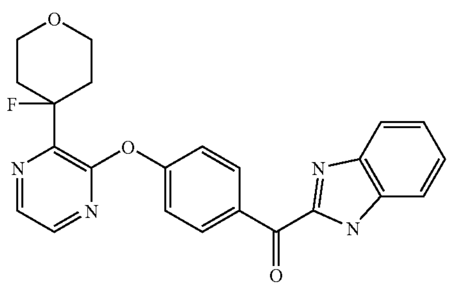 | 418.426 | 0.00183 |
| 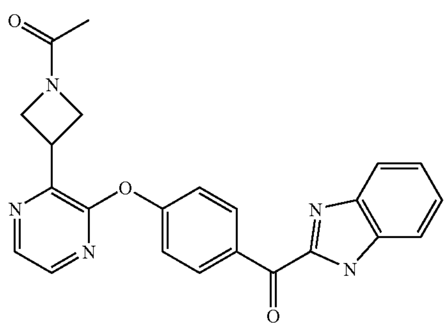 | 413.435 | 0.00271 |
| 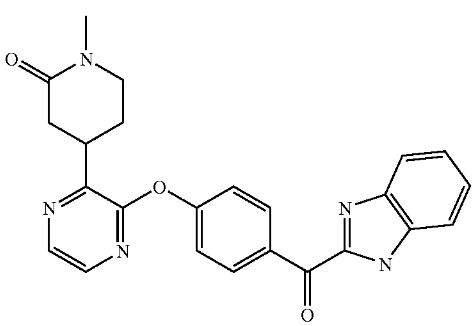 | 427.462 | 0.00602 |
| 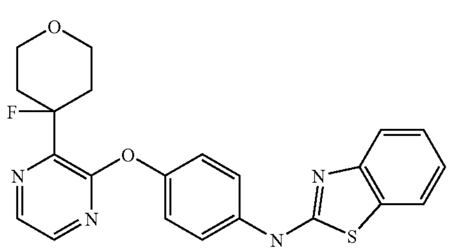 | 422.482 | 0.0122 |

TABLE XIII-continued

AVERAGE IC50 OF REPRESENTATIVE COMPOUNDS OF THE INVENTION.

| Structure | MS | Average IC50 (μM) |
|---|---|---|
| 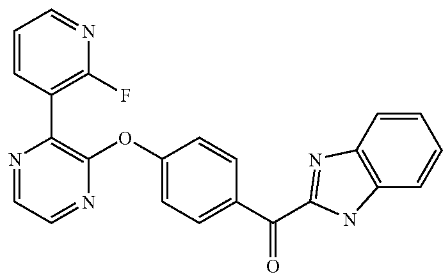 | 411.395 | 0.00353 |
| 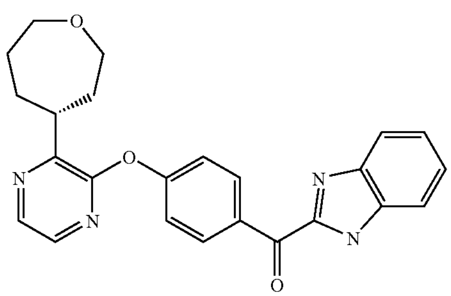 | 414.463 | 0.00122 |
| | | |
| 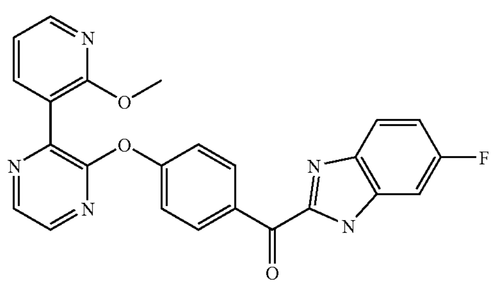 | 441.42 | 0.00584 |
| 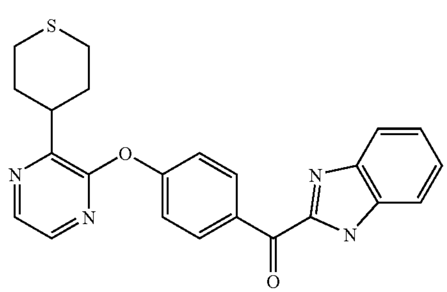 | 416.503 | 0.00185 |

TABLE XIII-continued

AVERAGE IC50 OF REPRESENTATIVE COMPOUNDS OF THE INVENTION.

| Structure | MS | Average IC50 (µM) |
|---|---|---|
| 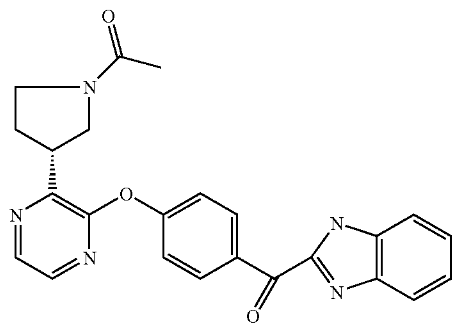 | 427.462 | 0.00763 |
| | | |
| 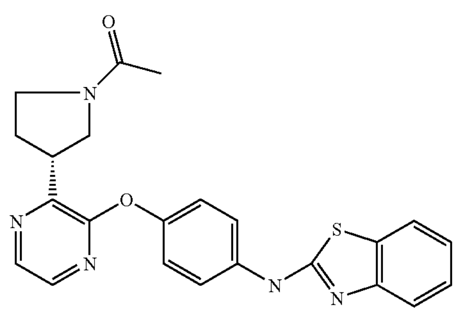 | 431.518 | 0.00182 |
| | | |

TABLE XIII-continued

AVERAGE IC50 OF REPRESENTATIVE COMPOUNDS OF THE INVENTION.

| Structure | MS | Average IC50 (μM) |
|---|---|---|
| 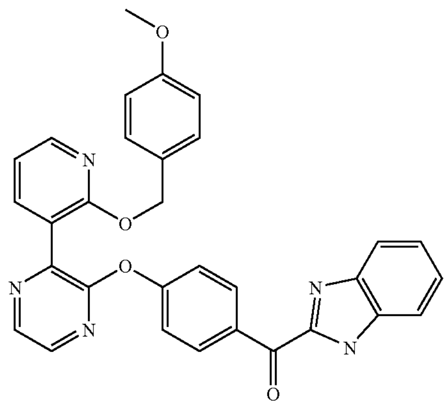 | 529.554 | 0.0109 |
| 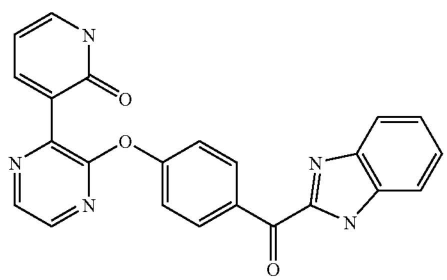 | 409.404 | 0.00708 |
| 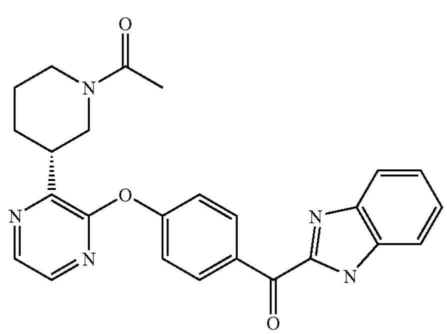 | 441.489 | 0.00296 |
| | | |

TABLE XIII-continued

AVERAGE IC50 OF REPRESENTATIVE COMPOUNDS OF THE INVENTION.

| Structure | MS | Average IC50 (μM) |
|---|---|---|
| 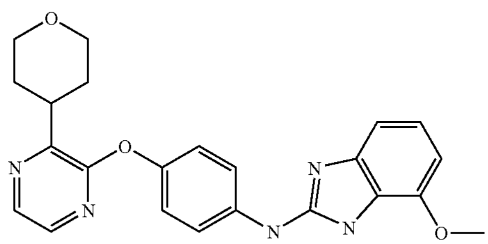 | 417.467 | 0.000186 |
| 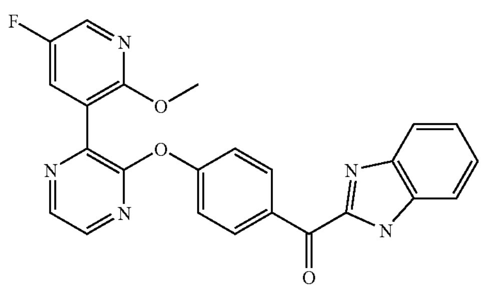 | 441.42 | 0.00295 |
| 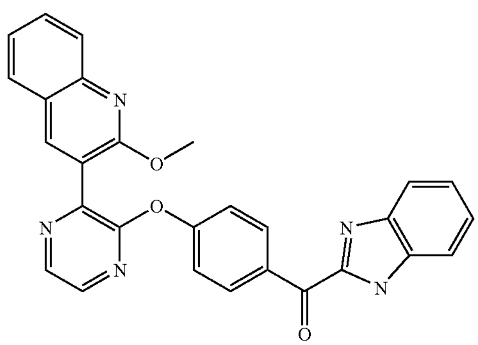 | 473.49 | 0.224 |
| 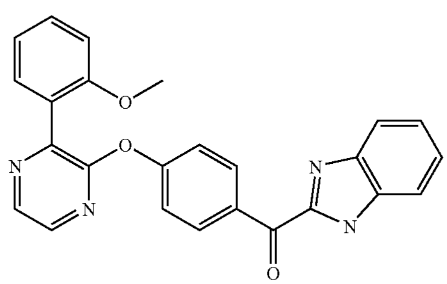 | 422.442 | 0.0029 |
| 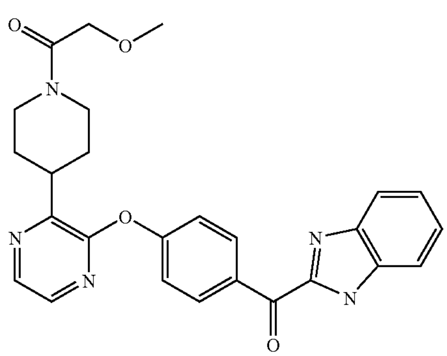 | 471.515 | 0.0000365 |

TABLE XIII-continued

AVERAGE IC50 OF REPRESENTATIVE COMPOUNDS OF THE INVENTION.

| Structure | MS | Average IC50 (μM) |
|---|---|---|
| 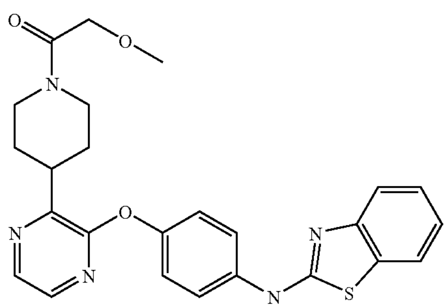 | 475.571 | 0.000024 |
| 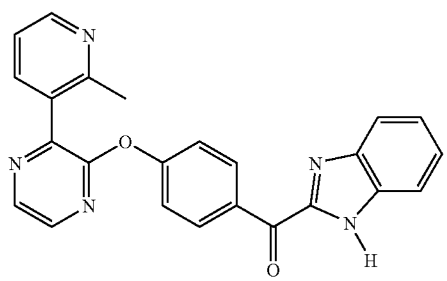 | 407.431 | 0.00207 |
| 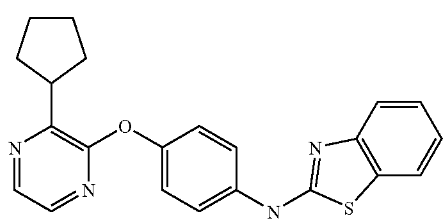 | 388.493 | 0.00496 |
| 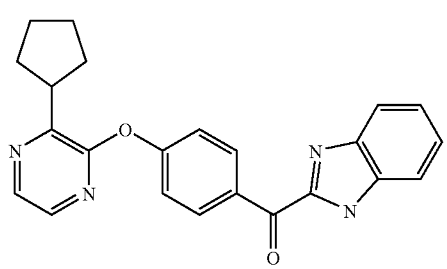 | 384.437 | 0.00176 |
| 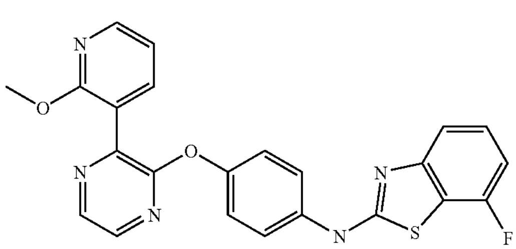 | 445.476 | 0.00776 |

TABLE XIII-continued
AVERAGE IC50 OF REPRESENTATIVE COMPOUNDS OF THE INVENTION.
| Structure | MS | Average IC50 (μM) |
|---|---|---|
| 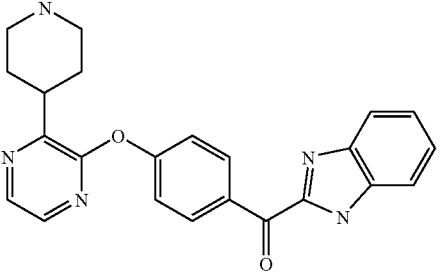 | 473.506 | 0.000132 |
| 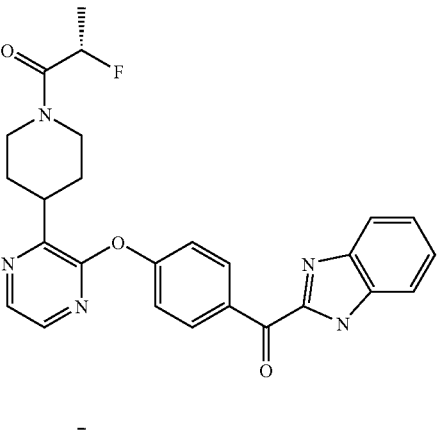 | | |
| 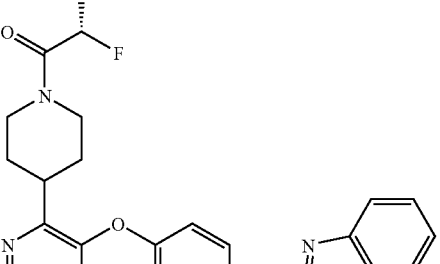 | 477.562 | 0.000178 |
| 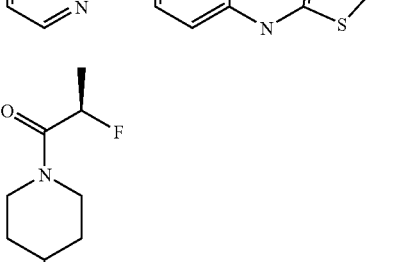 | | |

TABLE XIII-continued
AVERAGE IC50 OF REPRESENTATIVE COMPOUNDS OF THE INVENTION.
| Structure | MS | Average IC50 (μM) |
|---|---|---|
| 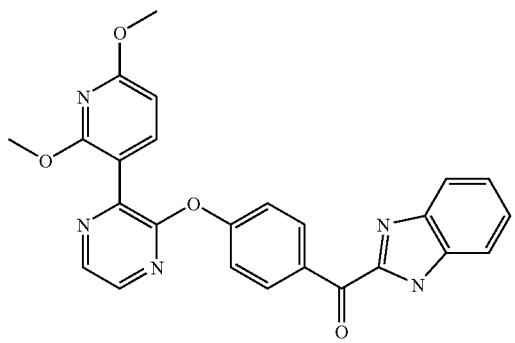 | 453.456 | 0.000577 |
| 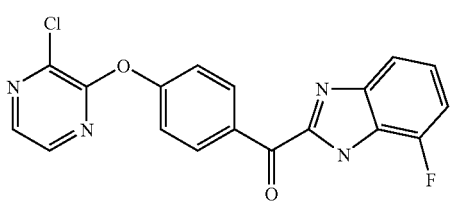 | 368.754 | 0.406 |
| 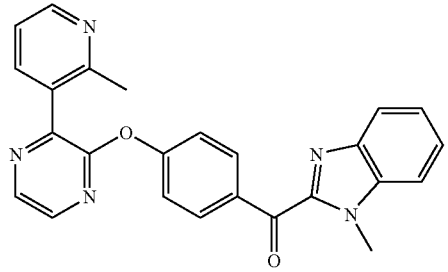 | 421.458 | 0.00878 |
| 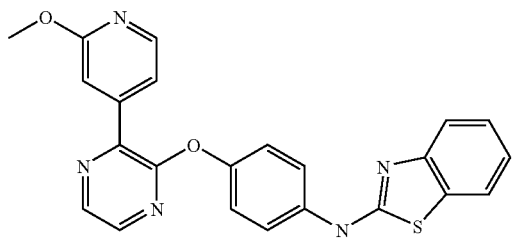 | 427.486 | 0.0464 |
| 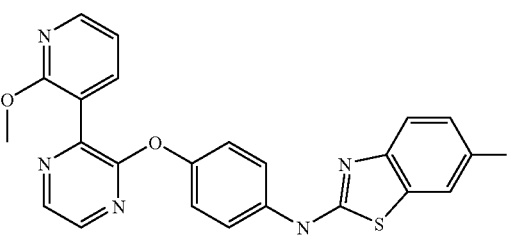 | 445.476 | 0.0072 |

TABLE XIII-continued
AVERAGE IC50 OF REPRESENTATIVE COMPOUNDS OF THE INVENTION.
| Structure | MS | Average IC50 (μM) |
|---|---|---|
| 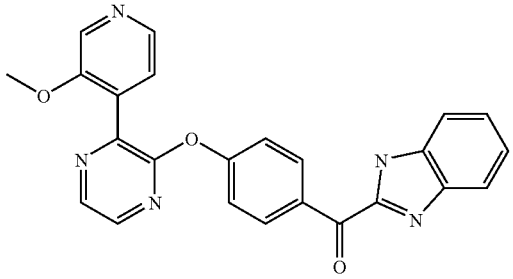 | 423.43 | 0.000489 |
| 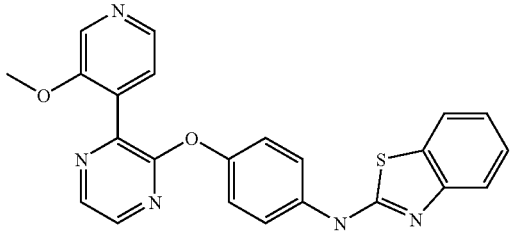 | 427.486 | 0.00191 |
| 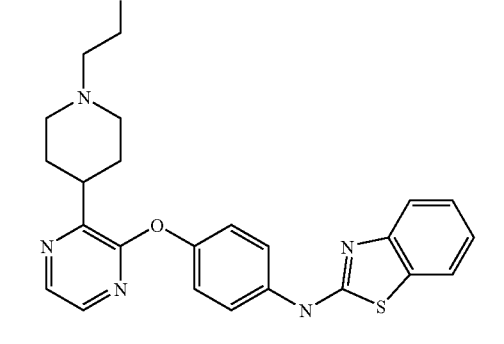 | 449.552 | 0.00324 |
| 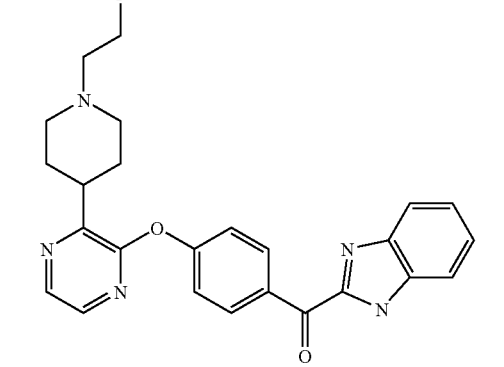 | 445.496 | 0.0025 |
| 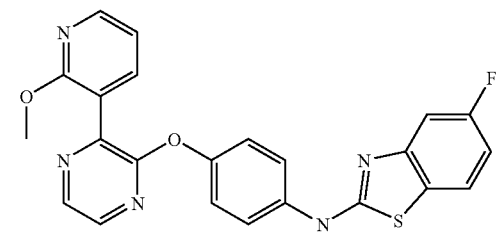 | 445.476 | 0.0497 |

TABLE XIII-continued

AVERAGE IC50 OF REPRESENTATIVE COMPOUNDS OF THE INVENTION.

| Structure | MS | Average IC50 (μM) |
|---|---|---|
| 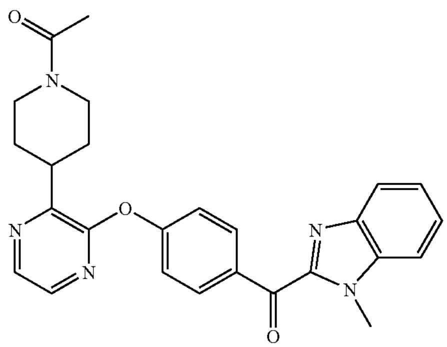 | 455.516 | 0.000174 |
| 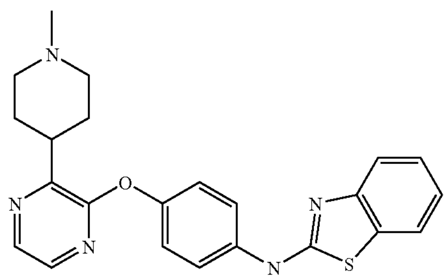 | 417.535 | 0.00592 |
| 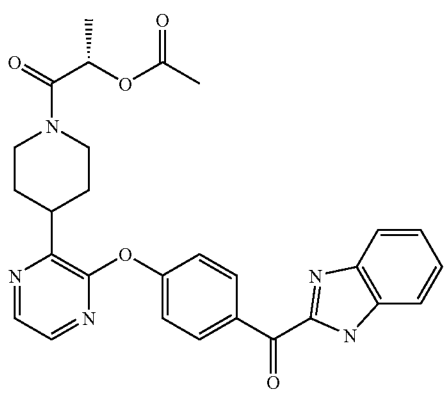 | 513.551 | 0.000119 |
| | | |

TABLE XIII-continued

AVERAGE IC50 OF REPRESENTATIVE COMPOUNDS OF THE INVENTION.

| Structure | MS | Average IC50 (μM) |
|---|---|---|
| 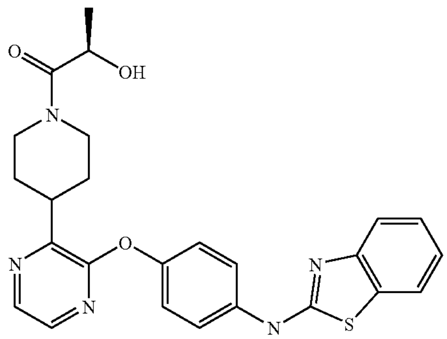 | 475.571 | 0.0000455 |
| | | |
| 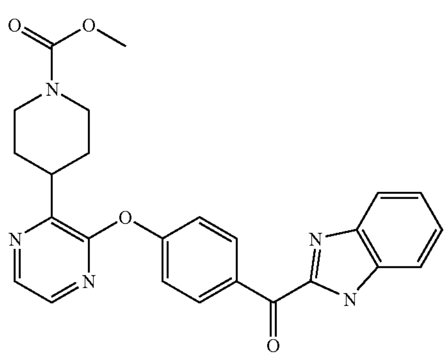 | 457.488 | 0.0000615 |
| 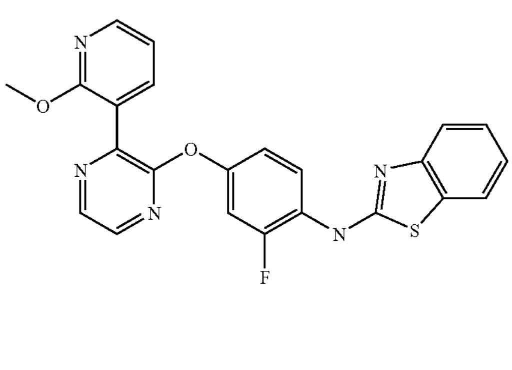 | 445.476 | 0.00268 |

TABLE XIII-continued
AVERAGE IC50 OF REPRESENTATIVE COMPOUNDS OF THE INVENTION.
| Structure | MS | Average IC50 (μM) |
|---|---|---|
| 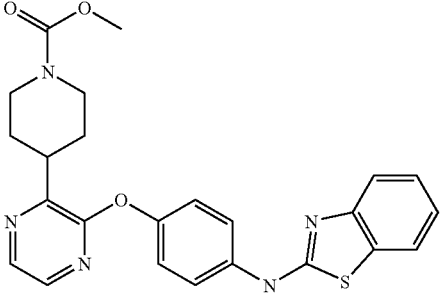 | 461.544 | 0.000206 |
| 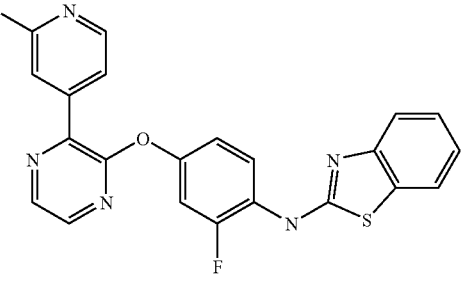 | 433.441 | 0.0631 |
| 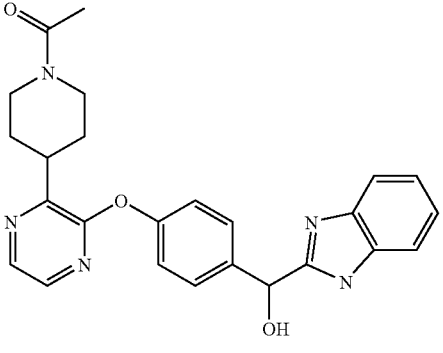 | 443.505 | 0.019 |
| 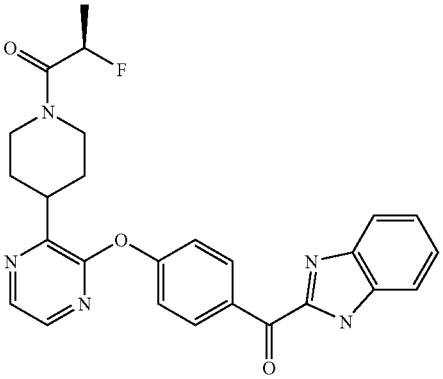 | 473.506 | 0.000005 |

TABLE XIII-continued

AVERAGE IC50 OF REPRESENTATIVE COMPOUNDS OF THE INVENTION.

| Structure | MS | Average IC50 (μM) |
|---|---|---|
| 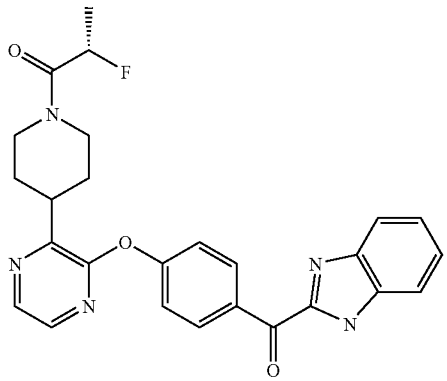 | 473.506 | 0.000137 |
| | 477.562 | 0.000031 |
| | 477.562 | 0.000156 |

TABLE XIII-continued

AVERAGE IC50 OF REPRESENTATIVE COMPOUNDS OF THE INVENTION.

| Structure | MS | Average IC50 (μM) |
|---|---|---|
| 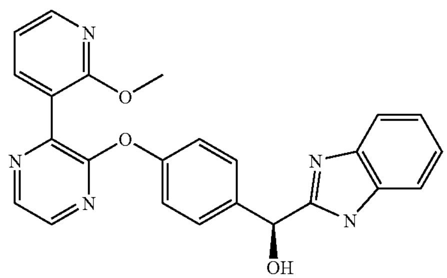 | 425.446 | 0.0149 |
| | | |
| 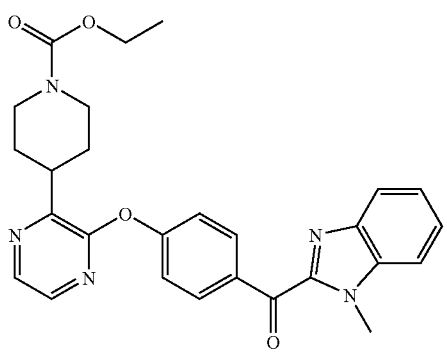 | 485.541 | 0.000521 |
| 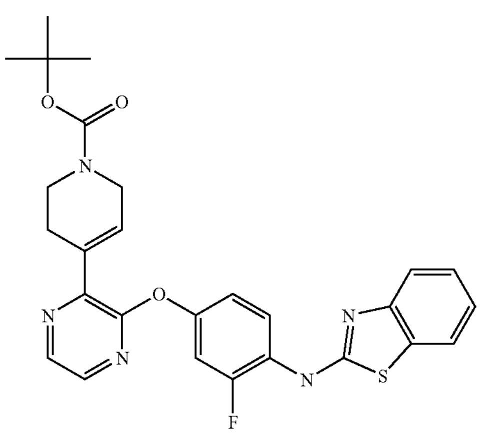 | 519.598 | 0.07 |

TABLE XIII-continued

AVERAGE IC50 OF REPRESENTATIVE COMPOUNDS OF THE INVENTION.

| Structure | MS | Average IC50 (μM) |
|---|---|---|
| 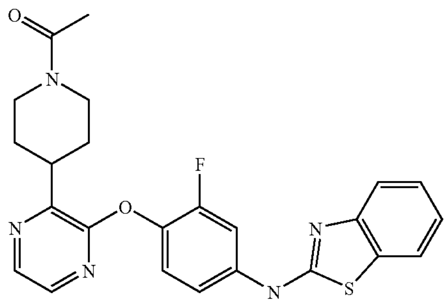 | 463.535 | 0.00112 |
| 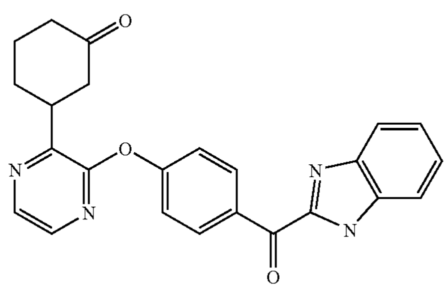 | 412.447 | 0.00133 |
| 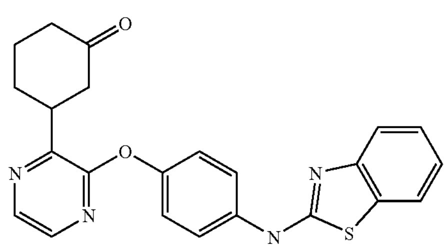 | 416.503 | 0.00121 |
| 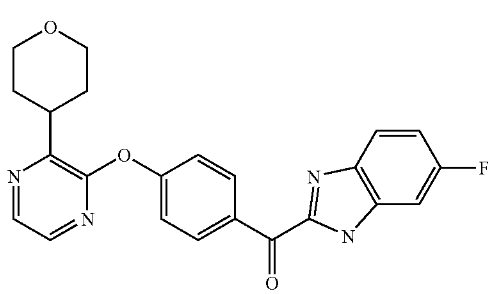 | 418.426 | 0.000593 |

TABLE XIII-continued

AVERAGE IC50 OF REPRESENTATIVE COMPOUNDS OF THE INVENTION.

| Structure | MS | Average IC50 (μM) |
|---|---|---|
| 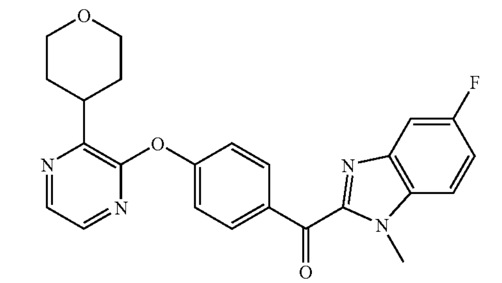 | 432.453 | 0.00465 |
| | | |
| 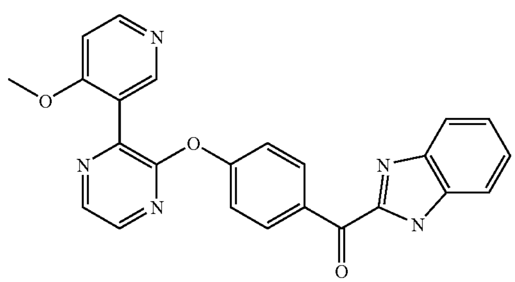 | 423.43 | 0.000533 |
| 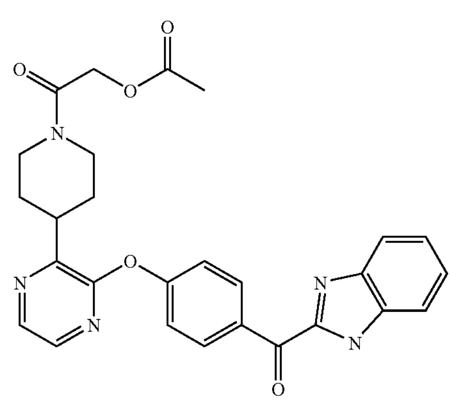 | 499.525 | 0.0000175 |
| 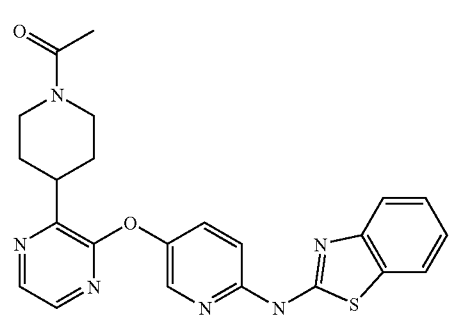 | 446.533 | 0.00059 |

TABLE XIII-continued

AVERAGE IC50 OF REPRESENTATIVE COMPOUNDS OF THE INVENTION.

| Structure | MS | Average IC50 (μM) |
|---|---|---|
| 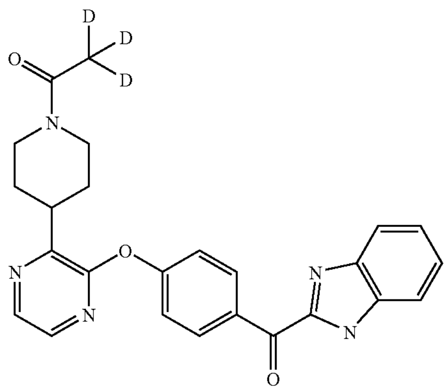 | 444.507 | 0.000105 |
| 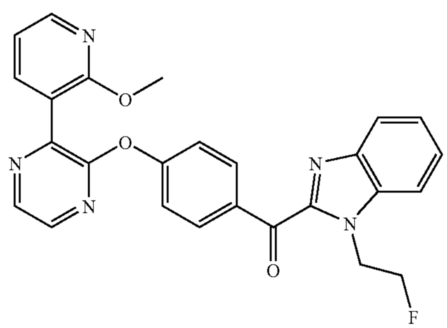 | 469.474 | 0.00583 |
| 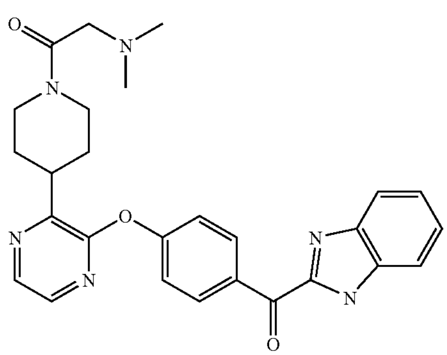 | 484.557 | 0.00143 |
| 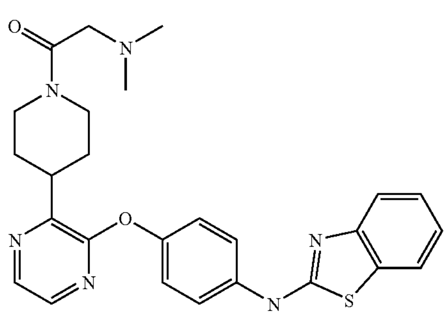 | 488.613 | 0.000705 |

TABLE XIII-continued

AVERAGE IC50 OF REPRESENTATIVE COMPOUNDS OF THE INVENTION.

| Structure | MS | Average IC50 (μM) |
|---|---|---|
| 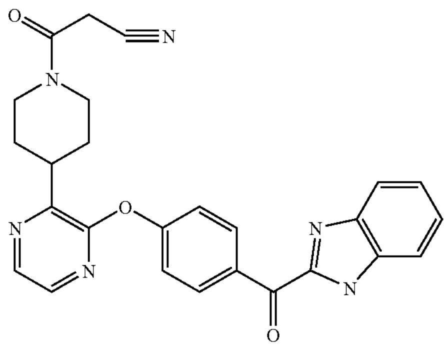 | 466.499 | 0.000025 |
| 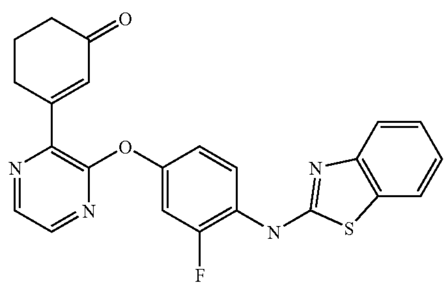 | 432.477 | 0.0221 |
| 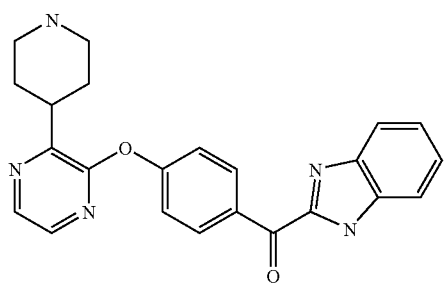 | 399.452 | 0.0077 |
| 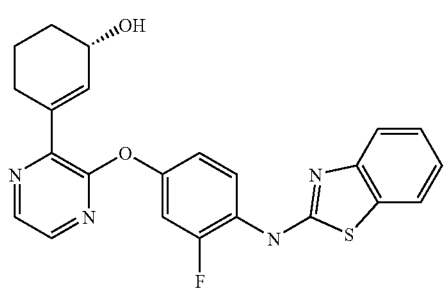 | 434.493 | 0.0079 |
|  |  |  |

TABLE XIII-continued

AVERAGE IC50 OF REPRESENTATIVE COMPOUNDS OF THE INVENTION.

| Structure | MS | Average IC50 (µM) |
|---|---|---|
| 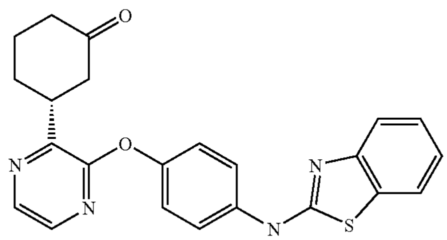 | 416.503 | 0.00112 |

Example 2

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats are exposed to a sudden burst of noise, at a level of 120 db for 40 msec, e.g., the reflex activity of the rats is measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example 3

Conditioned Avoidance Responding (Car) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal is placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal is free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training is conducted using a shuttle box (Med Associates, St. Albans, Vt.). The shuttle box is divided into 2 equal compartments that each contain a light source, a speaker that emits an 85 dB tone when activated and an electrified grid that can deliver a scrambled foot shock. Sessions consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and is recorded as an escape response. If an animal does not leave the conditioning chamber during the delivery of the shock it is recorded as an escape failure. Training is continued daily until the avoidance of 16 or more shocks out of 20 trials (80% avoidance) on 2 consecutive days is achieved. After this criterion is reached the rats are given one day of pharmacological testing. On test day, rats are randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds are injected at 1.0 ml/kg for i.p. and 10 mL/kg for p.o. administration. Compounds can be administered either acutely or chronically. For testing, each rat is placed in the shuttle box, and given 20 trials with the same parameters as described above for training trials. The number of avoidances, escapes, and escape failures are recorded.

Example 4

PCP-Induced Hyperactivity (PCP-LMA)

Equipment Used: 4×8 home cage photobeam activity system (PAS) frame from San Diego Instruments. Open PAS program and prepare an experimental session using the following variables:
Multiphase experiment
300 sec/interval (5 min)
12 intervals (1 h)
Individual on screen switches.
Start recording after first beam break.
End session after end of interval.

Cage Preparation:

Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.

Animal Preparation:

Mark rats and record their weights. Bring rats to testing room.

Phase I: Habituation

Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g½ needle or oral gavage needle) with Amgen compound solution (5 mL/kg) or risperidone (1 mL syringe with 23 g½ needle) control (1 mL/kg) s.c.

Phase II: Compound Pre-Treatment

Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.

During phase II, prepare pcp: Dissolve pcp in saline to a concentration of 5 mg/mL.

Fill syringes (1 mL syringes with 26 g3/8 needle) with pcp solution (1 mL/kg).

Phase III: Pcp Administration.

Make sure phase II is ended. Remove rat from enclosure, start the next phase using on-screen individual switch, administer pcp s.c. and place rat back in the enclosure. The computer will record for 1 h.

Clean-Up:

End-session to terminate experiment and so that computer will compile data. Export raw data to excel file for data analysis. Euthanize rats and take necessary tissue/sample for PK.

Data Generation:

Export raw data to excel file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The compounds of the present invention may be administered orally, parentally, by inhalation spray, rectally, or topically in dosage unit formulations containing conventional pharmaceutically acceptable carriers, adjuvants, and vehicles, for the treatment of PDE10-related diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating PDE10-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the formula:

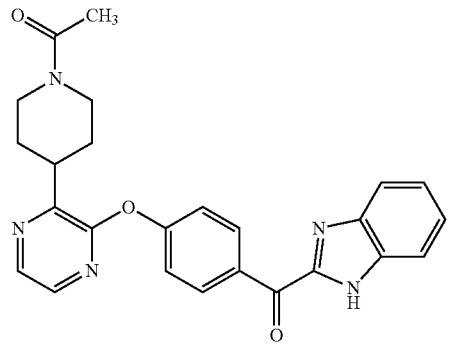

or a pharmaceutically acceptable salt thereof.

2. A compound having the formula:

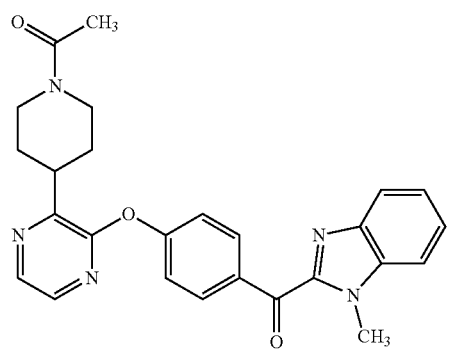

or a pharmaceutically acceptable salt thereof.

3. A compound having the formula:

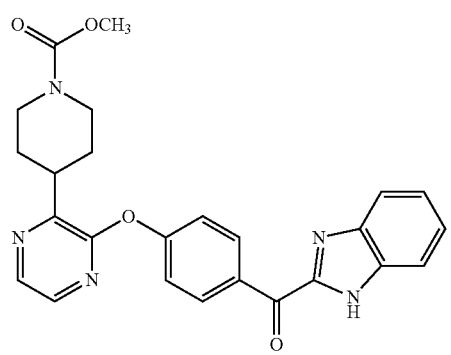

or a pharmaceutically acceptable salt thereof.

4. A compound having the formula:

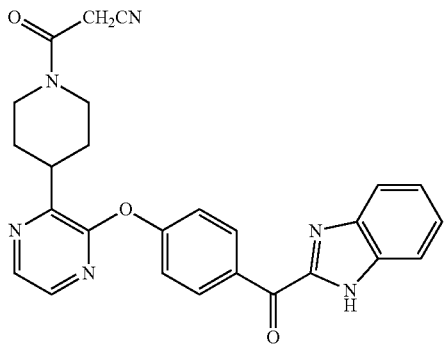

or a pharmaceutically acceptable salt thereof.

5. A compound having the formula:

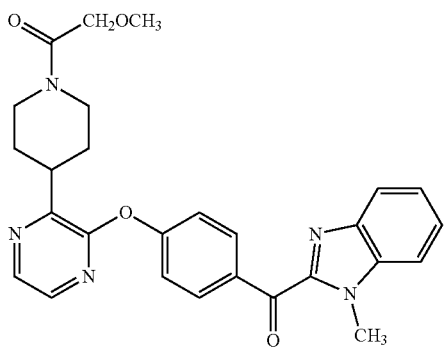

or a pharmaceutically acceptable salt thereof.

6. A compound having the formula:

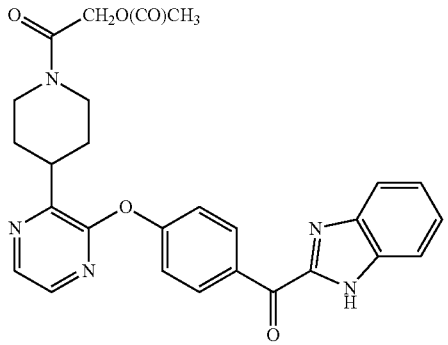

or a pharmaceutically acceptable salt thereof.

7. A compound having the formula:

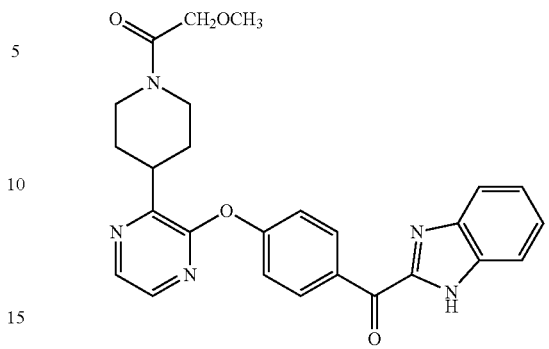

or a pharmaceutically acceptable salt thereof.

8. A compound having the formula:

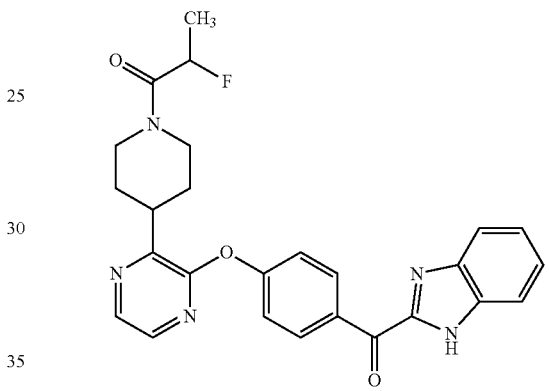

or a pharmaceutically acceptable salt thereof.

9. A pharmaceutically acceptable salt of the compound according to claim 1.

10. A pharmaceutically acceptable salt of the compound according to claim 2.

11. A pharmaceutically acceptable salt of the compound according to claim 3.

12. A pharmaceutically acceptable salt of the compound according to claim 4.

13. A pharmaceutically acceptable salt of the compound according to claim 5.

14. A pharmaceutically acceptable salt of the compound according to claim 6.

15. A pharmaceutically acceptable salt of the compound according to claim 7.

16. A pharmaceutically acceptable salt of the compound according to claim 8.

17. A pharmaceutical composition comprising an effective amount of the compound or a pharmaceutically acceptable salt thereof according to claim 1, and a pharmaceutically acceptable carrier.

18. A pharmaceutical composition comprising an effective amount of the compound or a pharmaceutically acceptable salt thereof according to claim 2, and a pharmaceutically acceptable carrier.

19. A pharmaceutical composition comprising an effective amount of the compound or a pharmaceutically acceptable salt thereof according to claim 3, and a pharmaceutically acceptable carrier.

20. A pharmaceutical composition comprising an effective amount of the compound or a pharmaceutically acceptable salt thereof according to claim 4, and a pharmaceutically acceptable carrier.

21. A pharmaceutical composition comprising an effective amount of the compound or a pharmaceutically acceptable salt thereof according to claim 5, and a pharmaceutically acceptable carrier.

22. A pharmaceutical composition comprising an effective amount of the compound or a pharmaceutically acceptable salt thereof according to claim 6, and a pharmaceutically acceptable carrier.

23. A pharmaceutical composition comprising an effective amount of the compound or a pharmaceutically acceptable salt thereof according to claim 7, and a pharmaceutically acceptable carrier.

24. A pharmaceutical composition comprising an effective amount of the compound or a pharmaceutically acceptable salt thereof according to claim 8, and a pharmaceutically acceptable carrier.

* * * * *